US012583851B2

(12) United States Patent
Turberg et al.

(10) Patent No.: US 12,583,851 B2
(45) Date of Patent: Mar. 24, 2026

(54) HETEROARYL-SUBSTITUTED PYRAZINE DERIVATIVES AS PESTICIDES

(71) Applicant: Elanco Animal Health GmbH, Monheim am Rhein (DE)

(72) Inventors: Andreas Turberg, Haan (DE); Iring Heisler, Duesseldorf (DE); Joachim Telser, Wuppertal (DE); Alexander Arlt, Cologne (DE); Peter Jeschke, Bergisch Gladbach (DE); Hans-Georg Schwarz, Dorsten (DE); Martin Fuesslein, Duesseldorf (DE); Yolanda Cancho-Grande, Leverkusen (DE); Peter Loesel, Leverkusen (DE); Ulrich Ebbinghaus-Kintscher, Dortmund (DE); Bing Ashley Liang O'Dowd, Duesseldorf (DE); Arunas Damijonaitis, Leverkusen (DE); Steffen Mueller, Muelheim (DE); Jiakang Ma, Tongzhou District Beijing (CN)

(73) Assignee: Elanco Animal Health GmbH, Monheim am Rhein (DE)

( * ) Notice: Subject to any disclaimer, the term of this patent is extended or adjusted under 35 U.S.C. 154(b) by 903 days.

(21) Appl. No.: 17/766,151

(22) PCT Filed: Oct. 8, 2020

(86) PCT No.: PCT/EP2020/078261
§ 371 (c)(1),
(2) Date: Apr. 1, 2022

(87) PCT Pub. No.: WO2021/069575
PCT Pub. Date: Apr. 15, 2021

(65) Prior Publication Data
US 2023/0023326 A1 Jan. 26, 2023

(30) Foreign Application Priority Data

Oct. 11, 2019 (WO) ................ PCT/CN2019/110528
May 11, 2020 (EP) ..................................... 20173955

(51) Int. Cl.
*C07D 417/04* (2006.01)
*C07D 403/04* (2006.01)
*C07D 413/04* (2006.01)

(52) U.S. Cl.
CPC ......... *C07D 417/04* (2013.01); *C07D 403/04* (2013.01); *C07D 413/04* (2013.01)

(58) Field of Classification Search
CPC ................................................. C07D 417/04
See application file for complete search history.

(56) References Cited

U.S. PATENT DOCUMENTS

| | | | |
|---|---|---|---|
| 8,664,228 | B2 | 3/2014 | Collingwood |
| 10,287,276 | B2 | 5/2019 | Tosatti et al. |
| 10,981,897 | B2 | 4/2021 | Tosatti et al. |
| 2018/0186778 | A1 | 7/2018 | Tosatti et al. |
| 2019/0256501 | A1 | 8/2019 | Tosatti et al. |
| 2020/0404919 | A1 | 12/2020 | Schwarz et al. |
| 2021/0147387 | A1 | 5/2021 | Arlt et al. |
| 2021/0155608 | A1 | 5/2021 | Arlt et al. |
| 2021/0386070 | A1 | 12/2021 | Arlt et al. |
| 2022/0002268 | A1 | 1/2022 | Arlt et al. |

FOREIGN PATENT DOCUMENTS

| | | |
|---|---|---|
| EA | 045353 B1 | 11/2023 |
| EP | 3725788 A1 | 10/2020 |
| JP | 2009023994 A | 2/2009 |
| JP | 2011178673 A | 9/2011 |
| JP | 2017533946 A | 11/2017 |
| JP | 2018510184 A | 4/2018 |
| JP | 2022504273 A | 1/2022 |
| JP | 2022526795 A | 5/2022 |
| JP | 2022527548 A | 6/2022 |

(Continued)

OTHER PUBLICATIONS

Popova L.M. Chemical products for plant protection: A manual. SPbGTURP. St. Petersburg, 2009, 96 p. (pp. 8-10).
Kharkevich D.A. Pharmacology. Textbook, 2010, 10th edition, p. 72-82 and M.D. Mashkovsky. Medicines, 14th edition, vol. 1. Moscow, 2001, p. 11.
Ting-Chao Chou, Drug combination studies and their synergy quantification using the Chou-Talalay method. Cancer Research, 2010, 70(2), pp. 440-446.
Chemical protection of plants. Edited by G.S. Gruzdev. 3rd edition. Moscow: AGROPROMIZDAT, 1987, 418 p. (Chapter 3, pp. 38-50).

(Continued)

*Primary Examiner* — Golam M Shameem
(74) *Attorney, Agent, or Firm* — McBee Moore & Vanik IP, LLC

(57) ABSTRACT

The present invention relates to novel heteroaryl-substituted pyrazine derivatives of the general formula (I), in which the structural elements $R^1$, $R^2$, $R^3$, $R^4$, $R^5$ and $R^6$ have the meaning given in the description, to formulations and compositions comprising such compounds and for their use in the control of animal pests including arthropods and insects in plant protection and to their use for control of ectoparasites on animals.

(I)

10 Claims, No Drawings

(56)  References Cited

FOREIGN PATENT DOCUMENTS

| | | | |
|---|---|---|---|
| JP | 2022528181 | A | 6/2022 |
| RU | 2532470 | C2 | 11/2014 |
| WO | 2006117356 | A1 | 11/2006 |
| WO | 2011017513 | A1 | 2/2011 |
| WO | 2017081290 | A1 | 5/2017 |
| WO | 2017/192385 | A1 | 11/2017 |
| WO | 2018117034 | A1 | 6/2018 |
| WO | 2018160755 | A1 | 9/2018 |
| WO | 2019075262 | A1 | 4/2019 |
| WO | 2019075265 | A1 | 4/2019 |
| WO | 2019/170626 | A1 | 9/2019 |
| WO | 2019/197468 | A1 | 10/2019 |
| WO | 2019/201835 | A1 | 10/2019 |
| WO | 2019/202077 | A1 | 10/2019 |
| WO | 2019/206799 | A1 | 10/2019 |
| WO | 2019/215198 | A1 | 11/2019 |
| WO | 2020/002563 | A1 | 1/2020 |
| WO | 2020/053364 | A1 | 3/2020 |
| WO | 2020/053365 | A2 | 3/2020 |
| WO | 2020/070049 | A1 | 4/2020 |
| WO | 2020/079198 | A1 | 4/2020 |
| WO | 2020/169445 | A1 | 8/2020 |
| WO | 2020/201398 | A1 | 10/2020 |
| WO | 2020/208036 | A1 | 10/2020 |
| WO | 2020201079 | A1 | 10/2020 |
| WO | 2021/013719 | A1 | 1/2021 |
| WO | 2021/013720 | A1 | 1/2021 |
| WO | 2021037614 | A1 | 3/2021 |

OTHER PUBLICATIONS

RN:2303389-89-9, Database Registry [Online] , Apr. 8, 2019, Retrieved from STN (and total 532 compounds).

RN:2330654-01-6, Database Registry [Online] , Jun. 12, 2019, Retrieved from STN , (and total 404 compounds).

Registry[online], Colimbus, Ohio, US, Oct. 31, 2010, 26 pages.

CAS Registry [Online], Compound RN: 1537020-06-6, Compound Name: 1-[3-(Pyridin-2-yl)pyrazin-2-yl]methanamine, Colimbus, Ohio, US, Feb. 4, 2014.

S. B. Ferreira et al., "Pyrazine derivatives: a patent review ", (2008-present) (published Aug. 6, 2012) (org/10.1517/13543776. 2012.714370), 19 pages.

International Search Report of International Application No. PCT/EP2020/078261, mailed Feb. 26, 2021.

Shvetsov, et al., "Modern computational methods evaluation of herbicidal and pesticidal activity of organic compounds", Bashkir Chemical Journal, 2013, vol. 20, No. 2, 5 pages.

Dyson, et al., "Chemistry of Synthetic Drugs", Translated by professor M. Belenky, MIR Publishing House Moscow, 1964, 19 pages.

HETEROARYL-SUBSTITUTED PYRAZINE DERIVATIVES AS PESTICIDES

CROSS-REFERENCE TO RELATED APPLICATIONS

This application is the National Stage entry of International Application No. PCT/EP2020/078261, filed 8 Oct. 2020, which claims priority to Chinese Patent Application No. PCT/CN2019/110528, filed 11 Oct. 2019 and European Patent Application No. 20173955.4, filed 11 May 2020.

BACKGROUND

Field

The present invention relates to novel heteroaryl-substituted pyrazine derivatives, to formulations and compositions comprising such compounds and to their use in the control of animal pests including arthropods and insects in plant protection and to their use for control of ectoparasites on animals.

Description of Related Art

Certain heteroaryl-triazole and heteroaryl-tetrazole compounds are disclosed for the use in controlling of ectoparasites on animals in WO 2017/192385 and for the use in controlling of animal pests in the field of plant protection in WO 2019/170626 and WO 2019/215198.

Further, the patent applications WO 2019/201835 (PCT/EP 2019/059624), WO 2019/197468 (PCT/EP 2019/059089), WO 2019/202077 (PCT/EP 2019/060081), WO 2019/206799 (PCT/EP 2019/060077), EP 19169209.4, EP 19187891.7, and EP 19187899.0 (the latter three not yet published) relate to triazole- and tetrazole-compounds and their use in crop protection and/or their use as pesticides.

WO 2020/002563, WO 2020/053364, WO 2020/053365, WO 2020/079198 and WO 2020/169445 describe azole-amide compounds whereas WO 2020/070049 relates to pyrazine compounds all of which can be used as insecticides.

Modern plant protection products and veterinary ectoparasiticides have to meet many demands, for example in relation to efficacy, persistence, spectrum and resistance breaking properties. Questions of toxicity, the combinability with other active compounds or formulation auxiliaries play a role, as well as the question of the expense that the synthesis of an active compound requires. Furthermore, resistances may occur. Resistant parasites are an increasing problem both for farm animals as well as for companion animals and also in crop pests. For all these reasons, the search for novel crop protection compositions or veterinary ectoparasiticides cannot be considered to be complete, and there is a constant need for novel compounds having properties which, compared to the known compounds, are improved at least in respect of individual aspects. It is in particular desirable to find new pesticides and parasiticides that overcome resistance.

SUMMARY

It was an object of the present invention to provide compounds which widen the spectrum of the pesticides in various aspects.

Therefore, in a first aspect (aspect 1.1) the invention relates to compounds of the general formula (I)

(I)

in which $R^1$ is hydrogen; in each case optionally substituted $C_1$-$C_6$alkyl, $C_3$-$C_6$cycloalkyl, $C_3$-$C_6$cycloalkyl$C_1$-$C_6$alkyl, $C_2$-$C_6$alkenyl, $C_2$-$C_6$haloalkenyl, $C_2$-$C_6$alkynyl, $C_2$-$C_6$haloalkynyl;

or phenyl-$C_1$-$C_6$alkyl, in which phenyl is optionally substituted with 1 to 5 substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$al-kylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

or heterocyclyl-$C_1$-$C_6$alkyl, wherein the heterocyclyl is selected from the group consisting of saturated and partially unsaturated 3- to 10-membered heterocyclyl, 5-membered heteroaryl, 6-membered heteroaryl, 9-membered heteroaryl and 10-membered heteroaryl and the heterocyclyl is optionally substituted with 1 to 5 substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$al-kylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl $R^2$ is phenyl or a 5- or 6-membered heteroaryl, each of which is optionally substituted with 1, 2 or 3 substituents independently selected from the group consisting of halogen, hydroxy, —CN, —COOH, —NO$_2$, —NH$_2$, —SF$_5$;

and in each case optionally substituted $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_1$-$C_6$alkoxy, $C_3$-$C_6$cycloalkoxy, $C_1$-$C_6$haloalkoxy, hydroxy-$C_1$-$C_6$alkyl, —CO$_2$C$_1$-$C_6$alkyl, —NH($C_1$-$C_6$alkyl), —N($C_1$-$C_6$alkyl)$_2$, S—$C_1$-$C_6$alkylsulfinimidoyl, S—$C_3$-$C_6$cycloalkylsulfinimidoyl, S—$C_2$-$C_6$alkenylsulfinimidoyl, S—$C_2$-$C_6$alkinylsulfinimidoyl, S-phenylsulfinimidoyl, S-heterocyclylsulfinimidoyl, S-heteroarylsulfinimidoyl, S—$C_1$-$C_6$alkylsulfonimidoyl, S—$C_3$-$C_6$cycloalkylsulfonimidoyl, S—$C_2$-$C_6$alkenylsulfonimidoyl, S—$C_2$-$C_6$alkinylsulfonimidoyl, S-phenylsulfonimidoyl, S-heterocyclylsulfonimidoyl, S-heteroarylsulfonimidoyl, —C(=NO$C_1$-$C_6$alkyl)H, —C(=NO$C_1$-$C_6$alkyl)-$C_1$-$C_6$alkyl, ($C_1$-$C_6$alkyl)$_3$-silyl;

and the substructures S1-S9, in which the bond to the phenyl or 5- or 6-membered heteroaryl is marked with a # and Z is CO or CS and Y is independently selected from CO or SO$_2$;

S1

$$R^{21} \diagdown {}^{Z} \diagdown {}^{N} \diagdown {}^{\#}$$
$$\underset{R^{22}}{|}$$

S2

$$\underset{R^{23}}{\overset{O}{\underset{\|}{\overset{\|}{S}}}} \diagdown {}^{N} \diagdown {}^{\#}$$
$$\underset{R^{22}}{|}$$

S3

$$R^{23} \diagdown {}^{Y} \diagdown {}^{N} \diagdown {}^{\#}$$
$$\underset{Y \diagdown R^{23}}{|}$$

S4

$$\overset{R^{21}}{\underset{R^{22} \diagdown N \diagdown Z \diagdown \#}{|}}$$

S5

$$\overset{R^{21}}{\underset{R^{22} \diagdown N \diagdown S \diagdown \#}{|}}$$
$$\overset{\|}{O}$$

S6

$$\overset{R^{22}}{\underset{R^{23} \diagdown Y \diagdown N \diagdown Y \diagdown \#}{|}}$$

S7

$$R^{24} \diagdown {}_S \diagdown {}^{\#}$$

S8

$$R^{24} \diagdown {\underset{\underset{O}{\|}}{S}} \diagdown {}^{\#}$$

S9

$$R^{24} \diagdown {\underset{\underset{O}{\|}}{S}} {=} {}^{\#}$$

$R^{21}$ is hydrogen or in each case optionally substituted $C_1$-$C_6$alkyl, $C_1$-$C_6$haloalkyl, $C_3$-$C_6$cycloalkyl, —$C_1$-$C_6$alkyl-$C_3$-$C_6$cycloalkyl, phenyl, heteroaryl and heterocyclyl;

$R^{22}$ is hydrogen or in each case optionally substituted $C_1$-$C_6$alkyl, $C_1$-$C_6$haloalkyl, —$C_1$-$C_6$alkyl-$C_3$-$C_6$cycloalkyl and $C_3$-$C_6$cycloalkyl;

$R^{23}$ is independently selected from in each case optionally substituted $C_1$-$C_6$alkyl, $C_1$-$C_6$haloalkyl, $C_3$-$C_6$cycloalkyl and phenyl;

$R^{24}$ is in each case optionally substituted $C_1$-$C_6$alkyl, $C_2$-$C_6$alkenyl, $C_2$-$C_6$alkynyl, $C_1$-$C_6$haloalkyl, $C_3$-$C_6$cycloalkyl, phenyl, heteroaryl and heterocyclyl;

or $R^{21}$ and $R^{22}$ together with the nitrogen atom to which they are attached, represent a monocyclic or polycyclic optionally substituted 3- to 12-membered saturated or unsaturated heterocyclyl which may contain further heteroatoms;

and 3- to 6-membered heterocyclyl or a 5- to 6-membered heteroaryl each containing 1 or 2 heteroatoms selected from the group consisting of N, O, and S, wherein the 3- to 6-membered heterocyclyl or the 5- to 6-membered heteroaryl substituent may optionally carry 1, 2, 3 or 4 substituents independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_3$-$C_6$cy- anocycloalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^3$ is hydrogen or $C_1$-$C_6$alkyl optionally substituted with 1 to 3 substituents selected from halogen, $C_3$-$C_6$-cycloalkyl and $C_1$-$C_6$-alkoxy;

$R^4$ is a monocyclic heterocycle selected from the group consisting of a 5-membered heteroaryl, a 6-membered heteroaryl and a 3-6 membered heterocyclyl, each of which containing 1 or 2 heteroatoms selected from the group consisting of N, O, and S, and each of which is optionally substituted by 1, 2, 3 or 4 substituents independently selected from the group consisting of halogen, hydroxy, —CN, —COOH, —NO$_2$, —NH$_2$, —SF$_5$;

and in each case optionally substituted $C_1$-$C_6$alkyl, $C_2$-$C_6$alkenyl, $C_2$-$C_6$alkynyl, $C_3$-$C_6$cycloalkyl, $C_1$-$C_6$alkyl-$C_3$-$C_6$cycloalkyl, $C_1$-$C_6$haloalkyl, $C_3$-$C_6$halocycloalkyl, $C_1$-$C_6$alkoxy, $C_3$-$C_6$cycloalkoxy, $C_1$-$C_6$haloalkoxy, hydroxy-$C_1$-$C_6$alkyl, —NH($C_1$-$C_6$alkyl), —NH($C_1$-$C_6$alkyl-$C_3$-$C_6$cycloalkyl), —N($C_1$-$C_6$alkyl)$_2$, —N($C_1$-$C_6$alkyl)($C_1$-$C_6$alkyl-$C_3$-$C_6$cycloalkyl), —CO$_2$$C_1$-$C_6$alkyl, S—$C_1$-$C_6$alkylsulfinimidoyl, S—$C_3$-$C_6$cycloalkylsulfinimidoyl, S—$C_2$-$C_6$alkenylsulfinimidoyl, S—$C_2$-$C_6$alkinylsulfinimidoyl, S-phenylsulfinimidoyl, S-heterocyclylsulfinimidoyl, S-heteroarylsulfinimidoyl, S—$C_1$-$C_6$alkylsulfonimidoyl, S—$C_3$-$C_6$cycloalkylsulfonimidoyl, S—$C_2$-$C_6$alkenylsulfonimidoyl, S—$C_2$-$C_6$alkinylsulfonimidoyl, S-phenylsulfonimidoyl, S-heterocyclylsulfonimidoyl, S-heteroarylsulfonimidoyl, —C(=NO$C_1$-$C_6$alkyl)H, —C(=NO$C_1$-$C_6$alkyl)-$C_1$-$C_6$alkyl;

and 3- to 6-membered heterocyclyl containing 1 or 2 heteroatoms selected from the group consisting of N, O, and S, wherein the 3- to 6-membered heterocyclyl substituent may optionally carry 1, 2, 3 or 4 substituents independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

and the following substructures S10-S18, in which the bond to the pyrazine is marked with a # and Z is CO or CS and Y is independently selected from CO or SO$_2$:

S10

S11

S12

S13

S14

S15

S16

S17

S18

$R^{41}$ is hydrogen or in each case optionally substituted $C_1$-$C_6$alkyl, $C_1$-$C_6$haloalkyl, $C_3$-$C_6$cycloalkyl, —$C_1$-$C_6$alkyl-$C_3$-$C_6$cycloalkyl, phenyl, heteroaryl and heterocyclyl;

$R^{42}$ is hydrogen or in each case optionally substituted $C_1$-$C_6$alkyl, $C_1$-$C_6$haloalkyl and $C_3$-$C_6$cycloalkyl;

$R^{43}$ is independently selected from in each case optionally substituted $C_1$-$C_6$alkyl, $C_1$-$C_6$haloalkyl, $C_3$-$C_6$cycloalkyl and phenyl;

$R^{44}$ is in each case optionally substituted $C_1$-$C_6$alkyl, $C_2$-$C_6$alkenyl, $C_2$-$C_6$alkynyl, $C_1$-$C_6$haloalkyl, $C_3$-$C_6$cycloalkyl, phenyl, heteroaryl and heterocyclyl;

or $R^{41}$ and $R^{42}$ together with the nitrogen atom to which they are attached, represent a monocyclic or polycyclic optionally substituted 3- to 12-membered saturated or unsaturated heterocyclyl which may contain further heteroatoms;

$R^5$ is hydrogen, halogen, —CN, or in each case optionally substituted $C_1$-$C_3$-alkyl, $C_1$-$C_3$-haloalkyl, $C_1$-$C_3$cyanoalkyl, $C_3$-$C_4$-cycloalkyl, $C_3$-$C_4$halocycloalkyl, $C_3$-$C_6$cyanocycloalkyl, $C_1$-$C_3$alkoxy, $C_1$-$C_3$haloalkoxy, $C_1$-$C_3$cyanoalkoxy, —$CO_2$($C_1$-$C_3$alkyl), —CH—($C_1$-$C_3$alkoxy)$_2$, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NOC$_1$-$C_4$alkyl)H, or —C(=NOC$_1$-$C_4$alkyl)-$C_1$-$C_4$alkyl, —NH$_2$, —NH($C_1$-$C_3$alkyl), —N($C_1$-$C_3$alkyl)$_2$, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl;

$R^6$ is hydrogen, halogen, —CN, or in each case optionally substituted $C_1$-$C_3$-alkyl, $C_1$-$C_3$-haloalkyl, $C_3$-$C_4$cycloalkyl, $C_3$-$C_4$halocycloalkyl, $C_1$-$C_3$alkoxy, $C_1$-$C_3$haloalkoxy, —$CO_2$($C_1$-$C_3$alkyl), —CH—($C_1$-$C_3$alkoxy)$_2$, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NOC$_1$-$C_4$alkyl)H, or —C(=NOC$_1$-$C_4$alkyl)-$C_1$-$C_4$alkyl, —NH$_2$, —NH($C_1$-$C_3$alkyl), —N($C_1$-$C_3$alkyl)$_2$, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl;

and salts and N-oxides thereof.

DETAILED DESCRIPTION OF A PREFERRED EMBODIMENT

The compounds of the formula (I) described anywhere herein likewise encompass any diastereomers or enantiomers and E/Z isomers which exist, and also salts and N-oxides of compounds of the formula (I).

The compounds of the formula (I) described anywhere herein may possibly also, depending on the nature of the substituents, be in the form of stereoisomers, i.e. in the form of geometric and/or optical isomers or isomer mixtures of varying composition. This invention provides both the pure stereoisomers and any desired mixtures of these isomers, even though it is generally only compounds of the formula (I) that are discussed here.

However, preference is given in accordance with the invention to using the optically active, stereoisomeric forms of the compounds of the formula (I) and salts thereof.

The invention therefore relates both to the pure enantiomers and diastereomers and to mixtures thereof.

According to an embodiment of the present invention dextrorotatory compounds of formula (I) are preferred, i.e. those isomers which rotate plane-polarized light clockwise ((+)-direction). Such enantiomers are usually designated with "(+)". Methods of separating enantiomers are well-known in the art, e.g. separation via chiral chromatography.

At the carbon atom in formula (I) which carries $R^3$ the present compounds can have R- or S-configuration (according to the Cahn-Ingold-Prelog rules). The present invention relates to compounds which have R- or S-configuration at this site as well as to mixtures of these isomers. According to a further embodiment compounds of formula (I) are preferred which have an S-configuration at the carbon atom which carries $R^3$.

If appropriate, the compounds of the formula (I) may be present in various polymorphic forms or as a mixture of various polymorphic forms. Both the pure polymorphs and the polymorph mixtures are provided by the invention and can be used in accordance with the invention.

The invention further relates to preferred embodiments as defined in the following aspects of the invention:

According to the following embodiments compounds of the formula (I) are excluded from the present invention:

(i) According to a one embodiment compounds of formula (I) are excluded, wherein $R^2$ is phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon C=O is attached, and each substituent is independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halogen, $NO_2$, $SF_5$, CN, $CONH_2$, COOH and C(S)$NH_2$.

(ii) According to a further embodiment compounds of formula (I) are excluded, wherein $R^2$ is phenyl or pyridine wherein the phenyl or pyridine is optionally substituted with one or two substituents, provided the substituent(s) are not on either carbon adjacent to the carbon C=O is attached, and each substituent is independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halogen, and —CN;

or wherein preferably each substituent is selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, and halogen.

(iii) According to a further embodiment compounds of formula (I) are excluded, wherein $R^4$ is pyridine, pyrimidine, pyrazine or pyridazine wherein the pyridine, pyrimidine, pyrazine or pyridazine is optionally substituted with one to three substituents, independently selected, from $C_1$-$C_3$alkyl, $C_1$-$C_3$haloalkyl, $C_1$-$C_3$alkoxy, $C_3$-$C_4$cycloalkyl, halogen and hydroxy.

(iv) According to a further embodiment compounds of formula (I) are excluded, wherein $R^4$ is pyridine or pyrimidine wherein the pyridine or pyrimidine is optionally substituted with one substituent selected from $C_1$-$C_3$alkyl, $C_3$-$C_4$cycloalkyl or halogen or hydroxy;

or wherein preferably the pyridine or pyrimidine is optionally substituted with one substituent selected from, $C_3$-$C_4$cycloalkyl or halogen and hydroxy;

or wherein more preferably the pyridine or pyrimidine is optionally substituted with one substituent selected from $C_3$-$C_4$cycloalkyl, F, Cl and Br.

(v) According to a further embodiment compounds of formula (I) are excluded, wherein $R^2$ is phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon C=O is attached, and each substituent is independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halogen, $NO_2$, $SF_5$, CN, $CONH_2$, COOH and C(S)$NH_2$, and at the same time $R^4$ is pyridine, pyrimidine, pyrazine or pyridazine wherein the pyridine, pyrimidine, pyrazine or pyridazine is optionally substituted with one to three substituents, independently selected, from $C_1$-$C_3$alkyl, $C_1$-$C_3$haloalkyl, $C_1$-$C_3$alkoxy, $C_3$-$C_4$cycloalkyl, halogen or hydroxy.

(vi) According to a further embodiment compounds of formula (I) are excluded wherein $R^2$ is phenyl, pyridine, pyrimidine, pyrazine or pyridazine, wherein the phenyl, pyridine, pyrimidine, pyrazine or pyridazine is optionally substituted with one to three substituents, provided the substituent(s) are not on either carbon adjacent to the carbon C=O is attached, and each substituent is independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halogen, $NO_2$, $SF_5$, CN, $CONH_2$, COOH and C(S)$NH_2$;

and at the same time $R^4$ is pyridine or pyrimidine wherein the pyridine or pyrimidine is optionally substituted with one substituent selected from $C_1$-$C_3$alkyl, $C_3$-$C_4$cycloalkyl or halogen or hydroxy;

or wherein preferably the pyridine or pyrimidine is optionally substituted with one substituent selected from, $C_3$-$C_4$cycloalkyl or halogen and hydroxy;

or wherein more preferably the pyridine or pyrimidine is optionally substituted with one substituent selected from $C_3$-$C_4$cycloalkyl, F, Cl and Br.

(vii) According to a further embodiment compounds of formula (I) are excluded wherein $R^2$ is phenyl or pyridine wherein the phenyl or pyridine is optionally substituted with one or two substituents, provided the substituent(s) are not on either carbon adjacent to the carbon C=O is attached, and each substituent is independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halogen, and —CN;

or wherein preferably each substituent is selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, and halogen;

and at the same time $R^4$ is pyridine, pyrimidine, pyrazine or pyridazine wherein the pyridine, pyrimidine, pyrazine or pyridazine is optionally substituted with one to three substituents, independently selected, from $C_1$-$C_3$alkyl, $C_1$-$C_3$haloalkyl, $C_1$-$C_3$alkoxy, $C_3$-$C_4$cycloalkyl, halogen or hydroxy.

(viii) According to a further embodiment compounds of formula (I) are excluded wherein $R^2$ is phenyl or pyridine wherein the phenyl or pyridine is optionally substituted with one or two substituents, provided the substituent(s) are not on either carbon adjacent to the carbon C=O is attached, and each substituent is independently selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, halogen, and —CN;

or wherein preferably each substituent is selected from: $C_1$-$C_3$alkyl, $C_1$-$C_3$haloalkyl, $C_1$-$C_3$thiohaloalkyl, $C_1$-$C_3$alkoxy, $C_1$-$C_3$haloalkoxy, and halogen;

and at the same time $R^4$ is pyridine or pyrimidine wherein the pyridine or pyrimidine is optionally substituted with one substituent selected from $C_1$-$C_3$alkyl, $C_3$-$C_4$cycloalkyl or halogen or hydroxy;

or wherein preferably the pyridine or pyrimidine is optionally substituted with one substituent selected from, $C_3$-$C_4$cycloalkyl or halogen and hydroxy;

or wherein more preferably the pyridine or pyrimidine is optionally substituted with one substituent selected from $C_3$-$C_4$cycloalkyl, F, Cl and Br.

In a further aspect (aspect 1.2) the invention relates to compounds of the general formula (I)

(I)

in which $R^1$ is hydrogen; in each case optionally substituted $C_1$-$C_6$alkyl, $C_3$-$C_6$cycloalkyl, $C_3$-$C_6$cycloalkyl$C_1$-$C_6$alkyl, $C_2$-$C_6$alkenyl, $C_2$-$C_6$alkynyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl, $C_1$-$C_3$haloalkyl, $C_1$-$C_6$cyanoalkyl;

or phenyl-$C_1$-$C_6$alkyl, in which phenyl is optionally substituted with 1 to 5 substituents, each independently selected from the group consisting of halogen, hydroxy, —CN, —COOH, —CONH₂, —CSNH₂, —NO₂, —Si(CH₃)₃, —SF₅, —NH₂, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^2$ is phenyl or a 5- or 6-membered heteroaryl, each of which is optionally substituted by 1, 2 or 3 substituents independently selected from the group consisting of halogen, hydroxy, CN, —COOH, —CONH₂, —NO₂, —NH₂, SF₅, $C_1$-$C_6$alkyl, $C_2$-$C_6$alkenyl, $C_2$-$C_6$alkynyl, $C_3$-$C_6$cycloalkyl, $C_1$-$C_3$haloalkyl, $C_1$-$C_3$cyanoalkyl, $C_3$-$C_6$cyanocycloalkyl, $C_1$-$C_4$alkoxy, $C_3$-$C_6$cycloalkoxy, $C_1$-$C_3$haloalkoxy, $C_1$-$C_3$cyanoalkoxy, hydroxy-$C_1$-$C_4$alkyl, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl, alkenylthio, alkynylthio, —NH($C_1$-$C_4$alkyl), —N($C_1$-$C_4$alkyl)₂, —NHCO—$C_1$-$C_4$alkyl, NHCO—$C_3$-$C_6$cycloalkyl, —NHSO₂($C_1$-$C_4$alkyl), —N($C_1$-$C_4$alkyl)CO—$C_1$-$C_4$alkyl, —N($C_1$-$C_4$alkyl)CO—$C_3$-$C_6$cycloalkyl, —N($C_1$-$C_4$alkyl)SO₂$C_1$-$C_4$alkyl, —N(SO₂$C_1$-$C_4$alkyl)₂, —CO₂$C_1$-$C_4$alkyl, —CONH($C_1$-$C_4$alkyl), —CONH($C_3$-$C_6$cycloalkyl), —CONH-phenyl, —CON($C_1$-$C_4$alkyl)₂, —CON($C_1$-$C_4$alkyl)($C_3$-$C_6$cycloalkyl), —CON($C_1$-$C_4$alkyl)-phenyl, —C(═NO$C_1$-$C_4$alkyl)H, —C(═NO$C_1$-$C_4$alkyl)-$C_1$-

$C_4$alkyl, ($C_1$-$C_4$alkyl)₃-silyl, —SO₂NH₂, —SO₂NH($C_1$-$C_4$alkyl), phenylsulfonyl, and 3- to 6-membered heterocyclyl containing 1 or 2 heteroatoms selected from the group consisting of N, O, and S, wherein phenyl groups of the substituents and the 3- to 6-membered heterocyclyl substituent may optionally carry 1, 2, 3 or 4 substituents independently selected from the group consisting of halogen, hydroxy, —CN, —COOH, —CONH₂, —CSNH₂, —NO₂, —Si(CH₃)₃, —SF₅, —NH₂, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_3$-$C_6$cyanocycloalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^3$ is hydrogen or optionally substituted $C_1$-$C_6$alkyl;

$R^4$ is a monocyclic heterocycle selected from the group consisting of a 5-membered heteroaryl, a 6-membered heteroaryl and a 3-6 membered heterocyclyl, each of which containing 1 or 2 heteroatoms selected from the group consisting of N, O, and S, and each of which is optionally substituted by 1, 2, 3 or 4 substituents independently selected from the group consisting of halogen, hydroxy, CN, —COOH, —CONH₂, —NO₂, —NH₂, SF₅, $C_1$-$C_6$alkyl, $C_2$-$C_6$alkenyl, $C_2$-$C_6$alkynyl, $C_3$-$C_6$cycloalkyl, $C_1$-$C_4$alkyl-$C_3$-$C_6$cycloalkyl, $C_1$-$C_3$haloalkyl, $C_1$-$C_3$cyanoalkyl, $C_3$-$C_6$halocycloalkyl, $C_3$-$C_6$cyanocycloalkyl, $C_1$-$C_4$alkoxy, $C_3$-$C_6$cycloalkoxy, $C_1$-$C_3$haloalkoxy, $C_1$-$C_3$cyanoalkoxy, hydroxy-$C_1$-$C_4$alkyl, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl, alkenylthio, alkynylthio, —NH($C_1$-$C_4$alkyl), —NH($C_1$-$C_4$alkyl-$C_3$-$C_6$cyclo alkyl), —N($C_1$-$C_4$alkyl)₂, —N($C_1$-$C_4$alkyl)($C_1$-$C_4$alkyl-$C_3$-$C_6$cycloalkyl), —NHCO—$C_1$-$C_4$alkyl, NHCO—$C_3$-$C_6$cycloalkyl, —NHCO($C_1$-$C_4$alkyl-$C_3$-$C_6$cycloalkyl), —NHSO₂($C_1$-$C_4$alkyl), —N($C_1$-$C_4$alkyl)CO—$C_1$-$C_4$alkyl, —N($C_1$-$C_4$alkyl)CO—$C_3$-$C_6$cycloalkyl, —N($C_1$-$C_4$alkyl)SO₂$C_1$-$C_4$alkyl, —N(SO₂$C_1$-$C_4$alkyl)₂, —CO₂$C_1$-$C_4$alkyl, —CONH($C_1$-$C_4$alkyl), —CONH($C_3$-$C_6$cycloalkyl), —CONH($C_1$-$C_4$alkyl-$C_3$-$C_6$cycloalkyl), —CONH-phenyl, —CONHSO₂($C_1$-$C_4$alkyl), —CON($C_1$-$C_4$alkyl)₂, —CON($C_1$-$C_4$alkyl)($C_3$-$C_6$cycloalkyl), —CON($C_1$-$C_4$alkyl)($C_1$-$C_4$alkyl-$C_3$-$C_6$cycloalkyl), —CON($C_1$-$C_4$alkyl)-phenyl, —CON($C_1$-$C_4$alkyl)SO₂($C_1$-$C_4$alkyl), —C(═NO$C_1$-$C_4$alkyl)H, —C(═NO$C_1$-$C_4$alkyl)-$C_1$-$C_4$alkyl, —SO₂NH₂, —SO₂NH($C_1$-$C_4$alkyl), phenylsulfonyl and 3- to 6-membered heterocyclyl containing 1 or 2 heteroatoms selected from the group consisting of N, O, and S, wherein phenyl groups of the substituents and the 3- to 6-membered heterocyclyl substituent may optionally carry 1, 2, 3 or 4 substituents independently selected from the group consisting of halogen, hydroxy, —CN, —COOH, —CONH₂, —CSNH₂, —NO₂, —Si(CH₃)₃, —SF₅, —NH₂, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^5$ is hydrogen, halogen, CN, or in each case optionally substituted $C_1$-$C_3$-alkyl, $C_1$-$C_3$-haloalkyl, $C_1$-$C_3$cyanoalkyl, $C_3$-$C_4$-cycloalkyl, $C_3$-$C_4$halocycloalkyl, $C_3$-$C_6$cyanocycloalkyl, $C_1$-$C_3$alkoxy, $C_1$-$C_3$haloalkoxy, $C_1$-$C_3$cyanoalkoxy, —C(O)—$C_1$-$C_3$alkoxy, —CH—($C_1$-$C_3$alkoxy)$_2$, —CO$_2$$C_1$-$C_4$alkyl, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NOC$_1$-$C_4$alkyl)H, or —C(=NOC$_1$-$C_4$alkyl)-$C_1$-$C_4$alkyl, $NH_2$, NH($C_1$-$C_3$alkyl), N($C_1$-$C_3$alkyl)$_2$, $C_1$-$C_3$alkylthio, $C_3$-$C_6$cycloalkylthio;

$R^6$ is hydrogen, halogen, CN, or in each case optionally substituted $C_1$-$C_3$-alkyl, $C_1$-$C_3$-haloalkyl, $C_3$-$C_4$cycloalkyl, $C_3$-$C_4$halocycloalkyl, $C_1$-$C_3$alkoxy, $C_1$-$C_3$haloalkoxy, —C(O)—$C_1$-$C_3$alkoxy, —CH—($C_1$-$C_3$alkoxy)$_2$, —CO$_2$$C_1$-$C_4$alkyl, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NOC$_1$-$C_4$alkyl)H, or —C(=NOC$_1$-$C_4$alkyl)-$C_1$-$C_4$alkyl, $NH_2$, NH($C_1$-$C_3$alkyl), N($C_1$-$C_3$alkyl)$_2$, $C_1$-$C_3$alkylthio, $C_3$-$C_6$cycloalkylthio;

and salts and N-oxides thereof.

In a further aspect (aspect 2.1) the invention relates to compounds of the formula (I) as described supra, in which $R^1$ is hydrogen; or in each case optionally substituted $C_1$-$C_6$alkyl, $C_3$-$C_6$cycloalkyl$C_1$-$C_6$alkyl, $C_2$-$C_6$alkenyl, $C_2$-$C_6$alkynyl, $C_1$-$C_6$alkoxy$C_1$-$C_6$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$ and $C_1$-$C_6$alkyl;

or phenyl-$C_1$-$C_6$alkyl, in which phenyl is optionally substituted with 1 to 5 substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cyanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

or heterocyclyl-$C_1$-$C_3$alkyl, wherein the heterocyclyl is selected from the group consisting of tetrahydropyranyl, tetrahydrofuranyl, oxetanyl and azetidinyl, or heteroaryl, wherein the heteroaryl is selected from the group consisting of pyridyl, pyrimidinyl, pyrazyl, pyridazinyl, thiophenyl, furanyl, pyrazolyl, imidazolyl, triazolyl, thiazolyl, and oxazolyl, and wherein the heteroaryl or the heterocyclyl is optionally substituted with 1 to 3 substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^2$ is selected from the group consisting of phenyl, pyridine, pyrimidine, pyrazine, pyridazine, pyrazole, pyrrole, thiazole, oxazole and thiophene, each of which is optionally substituted by 1, 2 or 3 substituents independently selected from the group consisting of halogen, hydroxy, —CN, —COOH, —NO$_2$, —NH$_2$, —SF$_5$;

and in each case optionally substituted $C_1$-$C_6$alkyl, $C_2$-$C_6$alkenyl, $C_2$-$C_6$alkynyl, $C_3$-$C_6$cycloalkyl, $C_1$-$C_3$haloalkyl, $C_1$-$C_4$alkoxy, $C_3$-$C_6$cycloalkoxy, $C_1$-$C_3$haloalkoxy, hydroxy-$C_1$-$C_4$alkyl, —CO$_2$$C_1$-$C_4$alkyl, —NH($C_1$-$C_4$alkyl), —N($C_1$-$C_4$alkyl)$_2$, —C(=NOC$_1$-$C_4$alkyl)H, —C(=NOC$_1$-$C_4$alkyl)-$C_1$-$C_4$alkyl and ($C_1$-$C_4$alkyl)$_3$-silyl, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$, $C_1$-$C_3$alkyl, $C_1$-$C_3$haloalkyl, $C_3$-$C_4$cycloalkyl, $C_3$-$C_4$halocycloalkyl, $C_1$-$C_3$alkylsulfonyl, $C_3$-$C_4$cycloalkylsulfonyl, $C_1$-$C_3$haloalkylthio and $C_1$-$C_3$haloalkylsulfonyl;

and the substructures S1, S4, S7, S8 and S9, in which the bond to the aforementioned phenyl, pyridine, pyrimidine, pyrazine, pyridazine, pyrazole, pyrrole, thiazole, oxazole or thiophene is marked with a # and Z is CO or CS;

S1

$$R^{21}\diagup Z \diagdown N \diagup \#$$
$$| \atop R^{22}$$

S4

$$R^{21} \atop | \atop R^{22}\diagup N \diagdown Z \diagup \#$$

S7

$$R^{24}\diagdown S \diagup \#$$

S8

$$R^{24}\diagdown S \diagup \# \atop \| \atop O$$

S9

$$R^{24}\diagdown S{\diagup \# \atop \Vert \diagdown O} \atop \| \atop O$$

$R^{21}$ is hydrogen or in each case optionally substituted $C_1$-$C_4$alkyl, $C_1$-$C_4$haloalkyl, $C_3$-$C_6$cycloalkyl, —$C_1$-$C_4$alkyl-$C_3$-$C_6$cycloalkyl and 3- to 6-membered heterocyclyl;

$R^{22}$ is hydrogen or in each case optionally substituted $C_1$-$C_4$alkyl, $C_1$-$C_4$haloalkyl, —$C_1$-$C_4$alkyl-$C_3$-$C_6$cycloalkyl and $C_3$-$C_6$cycloalkyl;

$R^{24}$ is in each case optionally substituted $C_1$-$C_4$alkyl, $C_2$-$C_6$alkenyl, $C_2$-$C_6$alkynyl, $C_1$-$C_4$haloalkyl, $C_3$-$C_6$cycloalkyl, phenyl, heteroaryl and 3- to 6-membered heterocyclyl;

wherein the aforementioned optionally substituted radicals in the definitions of $R^{21}$, $R^{22}$ and $R^{24}$ are optionally substituted with up to 3 substituents independently selected from the group consisting of halogen, hydroxy, —CN, —NO$_2$, —Si(CH$_3$)$_3$, —NH$_2$, $C_1$-$C_3$alkyl, $C_1$-$C_3$haloalkyl, $C_3$-$C_4$cycloalkyl, $C_3$-$C_4$halocycloalkyl, $C_1$-$C_4$alkoxy, $C_1$-$C_4$haloalkoxy, $C_1$-$C_3$alkylsulfonyl, $C_3$-$C_4$cycloalkylsulfonyl, $C_1$-$C_3$haloalkylthio and $C_1$-$C_3$haloalkylsulfonyl;

or $R^{21}$ and $R^{22}$ together with the nitrogen atom to which they are attached, represent a 4- to 12-membered saturated or unsaturated heterocyclyl which may contain up to two further heteroatoms selected from the group of oxygen, nitrogen and sulfur and which is optionally substituted with one to three substituents selected from the group consisting of halogen, =O (oxo), =S (thiono), hydroxy, —CN, —NO$_2$, —SF$_5$, and —NH$_2$;

and $C_1$-$C_4$alkyl, $C_3$-$C_6$cycloalkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_3$-$C_6$cycloalkylsulfanyl, $C_3$-$C_6$cycloalkylsulfinyl, $C_3$-$C_6$cycloalkylsulfonyl, $C_1$-$C_4$haloalkylthio, $C_1$-$C_4$haloalkylsulfinyl, $C_1$-$C_4$haloalkylsulfonyl;

and 3- to 6-membered heterocyclyl or a 5- to 6-membered heteroaryl each containing 1 or 2 heteroatoms selected from the group consisting of N, O, and S, wherein the 3- to 6-membered heterocyclyl or the 5- to 6-membered heteroaryl substituent may optionally carry 1, 2 or 3 substituents independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl;

$R^3$ is hydrogen or $C_1$-$C_6$alkyl optionally substituted with halogen, cyano, $C_3$-$C_6$cycloalkyl or $C_1$-$C_4$alkoxy;

$R^4$ is selected from the group consisting of pyridine, pyrimidine, pyrazine, pyridazine, and thiazole, pyrazole, pyrrole, oxazole, isothiazole, isoxazole, thiophene and imidazole, each of which is optionally substituted by 1, 2 or 3 substituents independently selected from the group consisting of halogen, hydroxy, —CN, —COOH, —NO$_2$, —NH$_2$, —SF$_5$;

and in each case optionally substituted $C_1$-$C_6$alkyl, $C_2$-$C_6$alkenyl, $C_2$-$C_6$alkynyl, $C_3$-$C_6$cycloalkyl, $C_1$-$C_3$haloalkyl, $C_1$-$C_4$alkoxy, $C_3$-$C_6$cycloalkoxy, $C_1$-$C_3$haloalkoxy, hydroxy-$C_1$-$C_4$alkyl, —CO$_2$$C_1$-$C_4$alkyl, —NH($C_1$-$C_4$alkyl), —N($C_1$-$C_4$alkyl)$_2$, —C(=NO$C_1$-$C_4$alkyl)H, —C(=NO$C_1$-$C_4$alkyl)-$C_1$-$C_4$alkyl and ($C_1$-$C_4$alkyl)$_3$-silyl, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$, $C_1$-$C_3$alkyl, $C_1$-$C_3$haloalkyl, $C_3$-$C_4$cycloalkyl, $C_3$-$C_4$halocycloalkyl, $C_1$-$C_4$alkoxy, $C_1$-$C_4$haloalkoxy, $C_1$-$C_3$alkylsulfonyl, $C_3$-$C_4$cycloalkylsulfonyl, $C_1$-$C_3$haloalkylthio and $C_1$-$C_3$haloalkylsulfonyl;

and the substructures S10, S11, S13, S14, S16, S17 and S18, in which the bond to the aforementioned pyridine, pyrimidine, pyrazine, pyridazine, thiazole, pyrazole, pyrrole, oxazole, isothiazole, isoxazole, thiophene or imidazole is marked with a # and Z is CO or CS;

S10

S11

S13

S14

S16

S17

S18

$R^{41}$ is hydrogen or in each case optionally substituted $C_1$-$C_4$alkyl, $C_1$-$C_4$haloalkyl, $C_3$-$C_6$cycloalkyl, —$C_1$-$C_4$alkyl-$C_3$-$C_6$cycloalkyl and 3- to 6-membered heterocyclyl;

$R^{42}$ is hydrogen or in each case optionally substituted $C_1$-$C_4$alkyl, $C_1$-$C_4$haloalkyl, —$C_1$-$C_4$alkyl-$C_3$-$C_6$cycloalkyl and $C_3$-$C_6$cycloalkyl;

$R^{43}$ is independently selected from in each case optionally substituted $C_1$-$C_4$alkyl, $C_1$-$C_4$haloalkyl and $C_3$-$C_6$cycloalkyl;

$R^{44}$ is in each case optionally substituted $C_1$-$C_4$alkyl, $C_1$-$C_4$haloalkyl, $C_3$-$C_6$cycloalkyl, phenyl, heteroaryl and 3- to 6-membered heterocyclyl;

wherein the aforementioned optionally substituted radicals in the definitions of $R^{41}$, $R^{42}$, $R^{43}$ and $R^{24}$ are optionally substituted with up to 3 substituents independently selected from the group consisting of halogen, hydroxy, —CN, —NO$_2$, —Si(CH$_3$)$_3$, —NH$_2$, $C_1$-$C_3$alkyl, $C_1$-$C_3$haloalkyl, $C_3$-$C_4$cycloalkyl, $C_3$-$C_4$halocycloalkyl, $C_1$-$C_4$alkoxy, $C_1$-$C_4$haloalkoxy, $C_1$-$C_3$alkylsulfonyl, $C_3$-$C_4$cycloalkylsulfonyl, $C_1$-$C_3$haloalkylthio and $C_1$-$C_3$haloalkylsulfonyl;

or $R^{41}$ and $R^{42}$ together with the nitrogen atom to which they are attached, represent a 4- to 12-membered saturated or unsaturated heterocyclyl which may contain up to two further heteroatoms selected from the group of oxygen, nitrogen, sulfur and silicon and which is optionally substituted with one to three substituents selected from the group consisting of halogen, =O (oxo), =S (thiono), hydroxy, —CN, —NO$_2$, —SF$_5$, and —NH$_2$;

and $C_1$-$C_4$alkyl, $C_3$-$C_6$cycloalkyl, $C_3$-$C_6$cycloalkyl-$C_1$-$C_6$alkyl, $C_1$-$C_4$haloalkyl, $C_1$-$C_4$alkoxy, $C_1$-$C_4$haloalkoxy, $C_1$-$C_4$alkoxy-$C_1$-$C_6$alkyl, $C_1$-$C_4$alkylthio, $C_1$-$C_4$alkylsu- lfinyl, $C_1$-$C_4$alkylsulfonyl, $C_3$-$C_6$cycloalkyls- ulfanyl, $C_3$-$C_6$cycloalkylsulfinyl, $C_3$-$C_6$cycl- oalkylsulfonyl, $C_1$-$C_4$haloalkylthio, $C_1$-$C_4$hal- oalkylsulfinyl, $C_1$-$C_4$haloalkylsulfonyl;

and 3- to 6-membered heterocyclyl or a 5- to 6-membered heteroaryl each containing 1 or 2 heteroatoms selected from the group consisting of N, O, and S, wherein the 3- to 6-membered heterocyclyl or the 5- to 6-membered heteroaryl substituent may optionally carry 1, 2 or 3 substituents independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$alkylthio, $C_1$-$C_3$alkylsulfi- nyl, $C_1$-$C_3$alkylsulfonyl, $C_1$-$C_3$haloalkylthio, $C_1$-$C_3$haloalkylsulfinyl, $C_1$-$C_3$haloalkylsulfonyl;

$R^5$ is hydrogen, halogen, —CN, —NH$_2$, or in each case optionally substituted $C_1$-$C_3$-alkyl, $C_3$-$C_4$-cycloalkyl, $C_1$-$C_3$alkoxy, —CO$_2$($C_1$-$C_3$alkyl), —CH—($C_1$-$C_3$alkoxy)$_2$, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NOC$_1$-$C_4$alkyl)H, or —C(=NOC$_1$-$C_4$alkyl)-$C_1$-$C_4$alkyl, —NH($C_1$-$C_3$alkyl), —N($C_1$-$C_3$alkyl)$_2$, $C_1$-$C_3$-alkylthio, $C_3$-$C_6$cycloalkylthio, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$ and $C_1$-$C_3$alkyl;

$R^6$ is hydrogen, halogen, —CN, —NH$_2$, or in each case optionally substituted $C_1$-$C_3$-alkyl, $C_3$-$C_4$-cycloalkyl, $C_1$-$C_3$alkoxy, —CO$_2$($C_1$-$C_3$alkyl), —CH—($C_1$-$C_3$alkoxy)$_2$, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NOC$_1$-$C_4$alkyl)H, or —C(=NOC$_1$-$C_4$alkyl)-$C_1$-$C_4$alkyl, —NH($C_1$-$C_3$alkyl), —N($C_1$-$C_3$alkyl)$_2$, $C_1$-$C_3$-alkylthio, $C_3$-$C_6$cycloalkylthio, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$ and $C_1$-$C_3$alkyl;

and salts and N-oxides thereof.

In a further aspect (aspect 2.2) the invention relates to compounds or the formula (I) as described supra, in which

$R^1$ is hydrogen; or in each case optionally substituted $C_1$-$C_6$alkyl, $C_3$-$C_6$cycloalkylC$_1$-$C_6$alkyl, $C_2$-$C_6$al- kenyl, $C_2$-$C_6$alkynyl, $C_1$-$C_3$alkoxyC$_1$-$C_3$alkyl, $C_1$-$C_3$alkylthioC$_1$-$C_3$alkyl, $C_1$-$C_3$haloalkyl, $C_1$-$C_6$cyanoalkyl;

or phenyl-$C_1$-$C_6$alkyl, in which phenyl is optionally substituted with 1 to 5 substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkyl- thio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^2$ is selected from the group consisting of phenyl, pyri- dine, pyrimidine, pyrazine, pyridazine, pyrazole, pyr- role, thiazole, oxazole, isothiazole, isoxazole, thio- phene and imidazole, each of which is optionally substituted by 1, 2 or 3 substituents independently selected from the group consisting of halogen, hydroxy, CN, —COOH, —CONH$_2$, —NO$_2$, —NH$_2$, SF$_5$, $C_1$-$C_6$alkyl, $C_3$-$C_6$cycloalkyl, $C_1$-$C_3$haloalkyl, $C_1$-$C_3$cyanoalkyl, $C_3$-$C_6$cyanocycloalkyl, $C_1$-$C_4$al- koxy, $C_1$-$C_3$haloalkoxy, $C_1$-$C_3$cyanoalkoxy, hydroxy- $C_1$-$C_4$alkyl, $C_1$-$C_3$alkylthio, $C_1$-$C_3$alkylsulfinyl, $C_1$-$C_3$alkylsulfonyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl, —NH($C_1$-$C_4$alkyl), —N($C_1$-$C_4$alkyl)$_2$, —NHCO—$C_1$- $C_4$alkyl, NHCO—$C_3$-$C_6$cyclo alkyl, —NHSO$_2$($C_1$- $C_4$alkyl), —N($C_1$-$C_4$alkyl)CO—$C_1$-$C_4$alkyl, —N($C_1$- $C_4$alkyl)CO—$C_3$-$C_6$cycloalkyl, —N($C_1$-$C_4$alkyl) SO$_2$$C_1$-$C_4$alkyl, —N(SO$_2$$C_1$-$C_4$alkyl)$_2$, —CO$_2$$C_1$- $C_4$alkyl, —CONH($C_1$-$C_4$alkyl), —CONH($C_3$- $C_6$cycloalkyl), —CONH-phenyl, —CON($C_1$-$C_4$ alkyl)$_2$, —CON($C_1$-$C_4$alkyl) ($C_3$-$C_6$cycloalkyl), —CON($C_1$-$C_4$alkyl)-phenyl, —C(=NOC$_1$-$C_4$alkyl)H, —C(=NOC$_1$-$C_4$alkyl)-$C_1$-$C_4$alkyl, ($C_1$-$C_4$alkyl)$_3$-si- lyl, —SO$_2$NH$_2$, —SO$_2$NH($C_1$-$C_4$alkyl), phenylsulfo- nyl, and 3- to 6-membered heterocyclyl containing 1 or 2 heteroatoms selected from the group consisting of N, O, and S, wherein phenyl groups of the substituents and the 3- to 6-membered heterocyclyl substituent may optionally carry 1, 2, 3 or 4 substituents independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkyl- thio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^3$ is hydrogen or optionally substituted $C_1$-$C_6$alkyl;

$R^4$ is selected from the group consisting of pyridine, pyrimidine, pyrazine, pyridazine and thiazole, each of which is optionally substituted by 1, 2, 3 or 4 substitu- ents independently selected from the group consisting of halogen, hydroxy, CN, —COOH, —CONH$_2$, —$NO_2$, —$NH_2$, $SF_5$, $C_1$-$C_6$alkyl, $C_3$-$C_6$cyclo alkyl, $C_1$-$C_4$alkyl-$C_3$-$C_6$cycloalkyl, $C_1$-$C_3$haloalkyl, $C_1$-$C_3$cyanoalkyl, $C_3$-$C_6$halocycloalkyl, $C_3$-$C_6$cyano-cycloalkyl, $C_1$-$C_4$alkoxy, $C_1$-$C_3$haloalkoxy, $C_1$-$C_3$cyanoalkoxy, hydroxy-$C_1$-$C_4$alkyl, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl, —$NH$($C_1$-$C_4$alkyl), —$NH$($C_1$-$C_4$alkyl-$C_3$-$C_6$cyclo alkyl), —$N$($C_1$-$C_4$alkyl)$_2$, —$N$($C_1$-$C_4$alkyl)($C_1$-$C_4$alkyl-$C_3$-$C_6$cycloalkyl), —$NHCO$—$C_1$-$C_4$alkyl, $NHCO$—$C_3$-$C_6$cycloalkyl, —$NHCO$($C_1$-$C_4$alkyl-$C_3$-$C_6$cycloalkyl), —$NHSO_2$($C_1$-$C_4$alkyl), —$N$($C_1$-$C_4$alkyl)$CO$—$C_1$-$C_4$alkyl, —$N$($C_1$-$C_4$alkyl)$CO$—$C_3$-$C_6$cycloalkyl, —$N$($C_1$-$C_4$alkyl)$SO_2C_1$-$C_4$alkyl, —$N$($SO_2C_1$-$C_4$alkyl)$_2$, —$CO_2C_1$-$C_4$alkyl, —$CONH$($C_1$-$C_4$alkyl), —$CONH$($C_3$-$C_6$cycloalkyl), —$CONH$($C_1$-$C_4$alkyl-$C_3$-$C_6$cycloalkyl), —$CONH$-phenyl, —$CONHSO_2$($C_1$-$C_4$alkyl), —$CON$($C_1$-$C_4$alkyl)$_2$, —$CON$($C_1$-$C_4$alkyl)($C_3$-$C_6$cycloalkyl), —$CON$($C_1$-$C_4$alkyl)($C_1$-$C_4$alkyl-$C_3$-$C_6$cycloalkyl), —$CON$($C_1$-$C_4$alkyl)-phenyl, —$CON$($C_1$-$C_4$alkyl)$SO_2$($C_1$-$C_4$alkyl), —$C$(=$NOC_1$-$C_4$alkyl)$H$, —$C$(=$NOC_1$-$C_4$alkyl)-$C_1$-$C_4$alkyl, —$SO_2NH_2$, —$SO_2NH$($C_1$-$C_4$alkyl), phenylsulfonyl and 3- to 6-membered heterocyclyl containing 1 or 2 heteroatoms selected from the group consisting of N, O, and S, wherein phenyl groups of the substituents and the 3- to 6-membered heterocyclyl substituent may optionally carry 1, 2, 3 or 4 substituents independently selected from the group consisting of halogen, hydroxy, —$CN$, —$COOH$, —$CONH_2$, —$CSNH_2$, —$NO_2$, —$Si$($CH_3$)$_3$, —$SF_5$, —$NH_2$, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkyl sulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^5$ is hydrogen, halogen, CN, or in each case optionally substituted $C_1$-$C_3$-alkyl, $C_1$-$C_3$-haloalkyl, $C_1$-$C_3$cyanoalkyl, $C_3$-$C_4$-cycloalkyl, $C_3$-$C_4$halocycloalkyl, $C_3$-$C_6$cyanocycloalkyl, $C_1$-$C_3$alkoxy, $C_1$-$C_3$haloalkoxy, $C_1$-$C_3$cyanoalkoxy, —$C(O)$—$C_1$-$C_3$alkoxy, —$CH$—($C_1$-$C_3$alkoxy)$_2$, —$CO_2C_1$-$C_4$alkyl, —$CONH$($C_1$-$C_4$alkyl), —$CON$($C_1$-$C_4$alkyl)$_2$, —$NHCO$—$C_1$-$C_4$alkyl, —$N$($C_1$-$C_4$alkyl)$CO$—$C_1$-$C_4$alkyl, —$C$(=$NOC_1$-$C_4$alkyl)$H$, or —$C$(=$NOC_1$-$C_4$alkyl)-$C_1$-$C_4$alkyl, $NH_2$, $NH$($C_1$-$C_3$alkyl), $N$($C_1$-$C_3$alkyl)$_2$, $C_1$-$C_3$alkylthio, $C_3$-$C_6$cycloalkylthio;

$R^6$ is hydrogen, halogen, CN, or in each case optionally substituted $C_1$-$C_3$-alkyl, $C_1$-$C_3$-haloalkyl, $C_1$-$C_3$cyanoalkyl, $C_3$-$C_4$cycloalkyl, $C_3$-$C_4$halocycloalkyl, $C_3$-$C_6$cyanocycloalkyl, $C_1$-$C_3$alkoxy, $C_1$-$C_3$halo alkoxy, $C_1$-$C_3$cyanoalkoxy, —$C(O)$—$C_1$-$C_3$alkoxy, —$CH$—($C_1$-$C_3$alkoxy)$_2$, —$CO_2C_1$-$C_4$alkyl, —$CONH$($C_1$-$C_4$alkyl), —$CON$($C_1$-$C_4$alkyl)$_2$, —$NHCO$—$C_1$-$C_4$alkyl, —$N$($C_1$-$C_4$alkyl)$CO$—$C_1$-$C_4$alkyl, —$C$(=$NOC_1$-$C_4$alkyl)$H$, or —$C$(=$NOC_1$-$C_4$alkyl)-$C_1$-$C_4$alkyl, $NH_2$, $NH$($C_1$-$C_3$alkyl), $N$($C_1$-$C_3$alkyl)$_2$, $C_1$-$C_3$alkylthio, $C_3$-$C_6$cycloalkylthio;

and salts and N-oxides thereof.

In a further aspect (aspect 3.1) the invention relates to compounds of the formula (I) as described supra, in which $R^1$ is hydrogen; or $C_1$-$C_6$alkyl, $C_3$-$C_6$cycloalkyl$C_1$-$C_6$alkyl, $C_2$-$C_6$alkenyl, $C_2$-$C_6$haloalkenyl, $C_2$-$C_6$alkynyl, $C_2$-$C_6$haloalkynyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl, $C_1$-$C_6$haloalkyl, $C_1$-$C_6$cyanoalkyl;

$R^2$ is selected from the group consisting of pyrazole, phenyl, pyridine, pyrimidine, pyrazine, and pyridazine, each of which is optionally substituted by a total of 1, 2 or 3 substituents, wherein 1, 2 or 3 of the optional substituents are independently selected from group A consisting of halogen, hydroxy, —$CN$, —$COOH$, —$NO_2$, —$NH_2$, —$SF_5$;

and $C_1$-$C_4$alkyl, $C_1$-$C_3$haloalkyl, $C_1$-$C_3$cyanoalkyl, $C_3$-$C_4$cycloalkyl, $C_3$-$C_4$halocycloalkyl, $C_3$-$C_4$cyanocycloalkyl, $C_1$-$C_3$alkoxy, $C_1$-$C_3$haloalkoxy, $C_3$-$C_4$cycloalkoxy, $C_1$-$C_3$cyanoalkoxy, —$CO_2C_1$-$C_4$alkyl and ($C_1$-$C_3$alkyl)$_3$-silyl;

and optionally 1 of the optional substituents may be selected from group B consisting of the substructures S1, S4, S7, S8 and S9, in which the bond to the phenyl, pyridine, pyrimidine, pyrazine, or pyridazine is marked with a # and Z is CO;

S1

S4

S7

S8

S9

$R^{21}$ is hydrogen or in each case optionally substituted $C_1$-$C_3$alkyl, $C_1$-$C_3$haloalkyl, $C_3$-$C_4$cycloalkyl;

$R^{22}$ is hydrogen or in each case optionally substituted $C_1$-$C_3$alkyl, $C_1$-$C_3$haloalkyl and $C_3$-$C_4$cycloalkyl;

$R^{24}$ is in each case optionally substituted $C_1$-$C_3$alkyl, $C_1$-$C_3$haloalkyl, $C_3$-$C_4$cycloalkyl and phenyl;

wherein the aforementioned optionally substituted radicals in the definitions of $R^{21}$, $R^{22}$ and $R^{24}$ are optionally substituted with up to 3 substituents independently selected from the group consisting of halogen, —$CN$, —$NO_2$, —$Si$($CH_3$)$_3$, $C_1$-$C_3$alkyl, $C_1$-$C_3$haloalkyl;

$R^3$ is hydrogen or $C_1$-$C_6$alkyl;

$R^4$ is selected from the group consisting of pyridine, pyrimidine, pyrazine, pyridazine, pyrazole, pyrrole, thiazole, oxazole, isothiazole, isoxazole, thiophene and imidazole, wherein the aforementioned 6-membered heteroaryl are each optionally substituted by 1, 2 or 3 substituents and the aforementioned 5-membered heteroaryl are each optionally substituted by 1 or 2 substituents, wherein in each case up to all of the optional substituents are independently selected from group D consisting of halogen, hydroxy, —CN, —COOH, —NO$_2$, —NH$_2$, —SF$_5$;

and C$_1$-C$_3$alkyl, C$_3$-C$_4$cycloalkyl, C$_1$-C$_3$haloalkyl, C$_1$-C$_3$cyanoalkyl, C$_3$-C$_4$cyanocycloalkyl, C$_1$-C$_3$alkoxy, C$_3$-C$_4$cycloalkoxy, C$_1$-C$_3$haloalkoxy, C$_1$-C$_3$cyanoalkoxy, hydroxy-C$_1$-C$_3$alkyl, —CO$_2$C$_1$-C$_3$alkyl, —NH(C$_1$-C$_3$alkyl), —N(C$_1$-C$_3$alkyl)$_2$, —C(=NOC$_1$-C$_3$alkyl)H, —C(=NOC$_1$-C$_3$alkyl)-C$_1$-C$_3$alkyl and (C$_1$-C$_3$alkyl)$_3$-silyl;

and optionally 1 of the optional substituents may be selected from group E consisting of the substructures S10, S13, S16, S17 and S18, in which the bond to the aforementioned pyridine, pyrimidine, pyrazine, pyridazine, pyrazole, pyrrole, thiazole, oxazole, isothiazole, isoxazole, thiophene or imidazole is marked with a # and Z is CO;

S10

$$R^{41}\diagdown Z \diagdown N(R^{42}) \diagup \#$$

S13

$$R^{42}\diagdown N(R^{41}) \diagdown Z \diagup \#$$

S16

$$R^{44}\diagdown S \diagup \#$$

S17

$$R^{44}\diagdown \underset{O}{\overset{}{S}}(=O) \diagup \#$$

S18

$$R^{44}\diagdown \underset{O}{\overset{}{S}}(=O)(=O) \diagup \#$$

R$^{41}$ is hydrogen or in each case optionally substituted C$_1$-C$_3$alkyl, C$_1$-C$_3$haloalkyl, C$_3$-C$_4$cycloalkyl, —C$_1$-C$_2$alkyl-C$_3$-C$_4$cycloalkyl and 3- to 6-membered heterocyclyl containing 1 heteroatoms selected from the group consisting of N, O, and S;

R$^{42}$ is hydrogen or in each case optionally substituted C$_1$-C$_3$alkyl, C$_1$-C$_3$haloalkyl, —C$_1$-C$_2$alkyl-C$_3$-C$_4$cycloalkyl and C$_3$-C$_4$cycloalkyl;

R$^{44}$ is in each case optionally substituted C$_1$-C$_3$alkyl, C$_1$-C$_3$haloalkyl, C$_3$-C$_4$cycloalkyl;

wherein the aforementioned optionally substituted radicals defined for R$^{41}$, R$^{42}$ and R$^{44}$ are optionally substituted with up to 2 substituents independently selected from the group consisting of halogen, —CN, —NO$_2$, —Si(CH$_3$)$_3$, C$_1$-C$_3$alkyl, C$_1$-C$_3$haloalkyl;

or

R$^{41}$ and R$^{42}$ together with the nitrogen atom to which they are attached, represent a monocyclic 4- to 8-membered saturated heterocyclyl which may contain up to one further heteroatom selected from the group of oxygen, nitrogen, sulfur and silicon and which is optionally substituted with one to three substituents selected from the group consisting of halogen, =O (oxo), =S (thiono), hydroxy, —CN, —NO$_2$, and —NH$_2$;

and C$_1$-C$_3$alkyl, C$_3$-C$_4$cycloalkyl, C$_1$-C$_3$haloalkyl, C$_1$-C$_3$alkoxy, C$_1$-C$_3$haloalkoxy;

R$^5$ is hydrogen, halogen, —CN, C$_1$-C$_3$-alkyl, C$_1$-C$_3$-haloalkyl, C$_3$-C$_4$-cycloalkyl, C$_1$-C$_3$alkoxy, C$_1$-C$_3$haloalkoxy;

R$^6$ is hydrogen, halogen, —CN, C$_1$-C$_3$-alkyl, C$_1$-C$_3$-haloalkyl, C$_3$-C$_4$cycloalkyl, C$_1$-C$_3$alkoxy, C$_1$-C$_3$haloalkoxy;

and salts and N-oxides thereof.

In a further aspect (aspect 3.2) the invention relates to compounds of the formula (I) as described supra, in which R$^1$ is hydrogen; or C$_1$-C$_6$alkyl, C$_3$-C$_6$cycloalkylC$_1$-C$_6$alkyl, C$_2$-C$_6$alkenyl, C$_2$-C$_6$haloalkenyl, C$_2$-C$_6$alkynyl, C$_2$-C$_6$haloalkynyl, C$_1$-C$_3$alkoxyC$_1$-C$_3$alkyl, C$_1$-C$_3$alkylthioC$_1$-C$_3$alkyl, C$_1$-C$_3$alkylsulfinylC$_1$-C$_3$alkyl, C$_1$-C$_3$alkylsulfonylC$_1$-C$_3$alkyl, C$_1$-C$_6$haloalkyl, C$_1$-C$_6$cyanoalkyl;

R$^2$ is selected from the group consisting of phenyl, pyridine, pyrimidine, pyrazine, and pyridazine, each of which is optionally substituted by a total of 1, 2 or 3 substituents, wherein 1, 2 or 3 of the optional substituents are independently selected from group A consisting of halogen, hydroxy, —CN, —COOH, —NO$_2$, —NH$_2$, —SF$_5$;

and C$_1$-C$_4$alkyl, C$_1$-C$_3$haloalkyl, C$_1$-C$_3$cyanoalkyl, C$_3$-C$_4$cycloalkyl, C$_3$-C$_4$halocycloalkyl, C$_3$-C$_4$cyanocycloalkyl, C$_1$-C$_3$alkoxy, C$_1$-C$_3$haloalkoxy, C$_3$-C$_4$cycloalkoxy, C$_1$-C$_3$cyanoalkoxy, —CO$_2$C$_1$-C$_4$alkyl and (C$_1$-C$_3$alkyl)$_3$-silyl;

and optionally 1 of the optional substituents may be selected from group B consisting of the substructures S1, S4, S7, S8 and S9, in which the bond to the phenyl, pyridine, pyrimidine, pyrazine, or pyridazine is marked with a # and Z is CO;

S1

$$R^{21}\diagdown Z \diagdown N(R^{22}) \diagup \#$$

S4

$$R^{22}\diagdown N(R^{21}) \diagdown Z \diagup \#$$

S7

$$R^{24}\diagdown S \diagup \#$$

S8

$$R^{24}\diagdown \underset{O}{\overset{}{S}}(=O) \diagup \#$$

S9

$$R^{24}\diagdown \underset{O}{\overset{}{S}}(=O)(=O) \diagup \#$$

$R^{21}$ is hydrogen or in each case optionally substituted $C_1$-$C_3$alkyl, $C_1$-$C_3$haloalkyl, $C_3$-$C_4$cycloalkyl;

$R^{22}$ is hydrogen or in each case optionally substituted $C_1$-$C_3$alkyl, $C_1$-$C_3$haloalkyl and $C_3$-$C_4$cycloalkyl;

$R^{24}$ is in each case optionally substituted $C_1$-$C_3$alkyl, $C_1$-$C_3$haloalkyl, $C_3$-$C_4$cycloalkyl and phenyl;

wherein the aforementioned optionally substituted radicals in the definitions of $R^{21}$, $R^{22}$ and $R^{24}$ are optionally substituted with up to 3 substituents independently selected from the group consisting of halogen, —CN, —NO$_2$, —Si(CH$_3$)$_3$, $C_1$-$C_3$alkyl, $C_1$-$C_3$haloalkyl;

$R^3$ is hydrogen or $C_1$-$C_6$alkyl;

$R^4$ is selected from the group consisting of pyridine, pyrimidine, pyrazine, pyridazine, pyrazole, pyrrole, thiazole, oxazole, isothiazole, isoxazole, thiophene and imidazole, wherein the aforementioned 6-membered heteroaryl are each optionally substituted by 1, 2 or 3 substituents and the aforementioned 5-membered heteroaryl are each optionally substituted by 1 or 2 substituents, wherein in each case up to all of the optional substituents are independently selected from group D consisting of halogen, hydroxy, —CN, —COOH, —NO$_2$, —NH$_2$, —SF$_5$;

and $C_1$-$C_3$alkyl, $C_3$-$C_4$cycloalkyl, $C_1$-$C_3$haloalkyl, $C_1$-$C_3$cyanoalkyl, $C_3$-$C_4$cyanocycloalkyl, $C_1$-$C_3$alkoxy, $C_3$-$C_4$cycloalkoxy, $C_1$-$C_3$haloalkoxy, $C_1$-$C_3$cyanoalkoxy, hydroxy-$C_1$-$C_3$alkyl, —CO$_2$$C_1$-$C_3$alkyl, —NH($C_1$-$C_3$alkyl), —N($C_1$-$C_3$alkyl)$_2$, —C(=NO$C_1$-$C_3$alkyl)H, —C(=NO$C_1$-$C_3$alkyl)-$C_1$-$C_3$alkyl and ($C_1$-$C_3$alkyl)$_3$-silyl;

and optionally 1 of the optional substituents may be selected from group E consisting of the substructures S10, S13, S16, S17 and S18, in which the bond to the aforementioned pyridine, pyrimidine, pyrazine, pyridazine, pyrazole, pyrrole, thiazole, oxazole, isothiazole, isoxazole, thiophene or imidazole is marked with a # and Z is CO;

S10

R$^{41}$—Z—N—#
|
R$^{42}$

S13

R$^{41}$
|
R$^{42}$—N—Z—#

S16

R$^{44}$—S—#

S17

R$^{44}$—S(=O)—#

S18

R$^{44}$—S(=O)$_2$—#

$R^{41}$ is hydrogen or in each case optionally substituted $C_1$-$C_3$alkyl, $C_1$-$C_3$haloalkyl, $C_3$-$C_4$cycloalkyl, —$C_1$-$C_2$alkyl-$C_3$-$C_4$cycloalkyl and 3- to 6-membered heterocyclyl containing 1 heteroatoms selected from the group consisting of N, O, and S;

$R^{42}$ is hydrogen or in each case optionally substituted $C_1$-$C_3$alkyl, $C_1$-$C_3$haloalkyl, —$C_1$-$C_2$alkyl-$C_3$-$C_4$cycloalkyl and $C_3$-$C_4$cycloalkyl;

$R^{44}$ is in each case optionally substituted $C_1$-$C_3$alkyl, $C_1$-$C_3$haloalkyl, $C_3$-$C_4$cycloalkyl.

wherein the aforementioned optionally substituted radicals defined for $R^{41}$, $R^{42}$ and $R^{44}$ are optionally substituted with up to 2 substituents independently selected from the group consisting of halogen, —CN, —NO$_2$, —Si(CH$_3$)$_3$, $C_1$-$C_3$alkyl, $C_1$-$C_3$haloalkyl;

or $R^{41}$ and $R^{42}$ together with the nitrogen atom to which they are attached, represent a monocyclic 4- to 8-membered saturated heterocyclyl which may contain up to one further heteroatom selected from the group of oxygen, nitrogen, sulfur and silicon and which is optionally substituted with one to three substituents selected from the group consisting of halogen, =O (oxo), =S (thiono), hydroxy, —CN, —NO$_2$, and —NH$_2$;

and $C_1$-$C_3$alkyl, $C_3$-$C_4$cycloalkyl, $C_1$-$C_3$haloalkyl, $C_1$-$C_3$alkoxy, $C_1$-$C_3$haloalkoxy;

$R^5$ is hydrogen, halogen, —CN, $C_1$-$C_3$-alkyl, $C_1$-$C_3$-haloalkyl, $C_3$-$C_4$-cycloalkyl, $C_1$-$C_3$alkoxy, $C_1$-$C_3$haloalkoxy;

$R^6$ is hydrogen, halogen, —CN, $C_1$-$C_3$-alkyl, $C_1$-$C_3$-haloalkyl, $C_3$-$C_4$cycloalkyl, $C_1$-$C_3$alkoxy, $C_1$-$C_3$haloalkoxy;

and salts and N-oxides thereof.

In a further aspect (aspect 3.3) the invention relates to compounds of the formula (I) as described supra, in which $R^1$ is hydrogen; or in each case optionally substituted $C_1$-$C_6$alkyl, $C_3$-$C_6$cycloalkyl$C_1$-$C_6$alkyl, $C_2$-$C_6$alkenyl, $C_2$-$C_6$alkynyl, $C_1$-$C_3$alkoxy$C_1$-$C_3$alkyl, $C_1$-$C_3$alkylthio$C_1$-$C_3$alkyl, $C_1$-$C_6$cyanoalkyl;

$R^2$ is selected from the group consisting of phenyl, pyridine, pyrimidine, pyrazine, and pyridazine, each of which is optionally substituted by 1, 2 or 3 substituents independently selected from the group consisting of halogen, hydroxy, CN, —COOH, —CONH$_2$, —NO$_2$, —NH$_2$, SF$_5$, $C_1$-$C_6$alkyl, $C_3$-$C_6$cycloalkyl, $C_1$-$C_3$haloalkyl, $C_1$-$C_3$cyanoalkyl, $C_3$-$C_6$cyanocycloalkyl, $C_1$-$C_4$alkoxy, $C_1$-$C_3$haloalkoxy, $C_1$-$C_3$cyanoalkoxy, hydroxy-$C_1$-$C_4$alkyl, $C_1$-$C_3$alkylthio, $C_1$-$C_3$alkylsulfinyl, $C_1$-$C_3$alkyl-sulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cyclo alkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cycloalkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CON($C_1$-$C_4$alkyl)$_2$, —CON($C_1$-$C_4$alkyl)($C_3$-$C_6$cycloalkyl), —CON($C_1$-$C_4$alkyl)-phenyl, —C(=NO$C_1$-$C_4$alkyl)H, —C(=NO$C_1$-$C_4$alkyl)-$C_1$-$C_4$alkyl, ($C_1$-$C_4$alkyl)$_3$-silyl, —SO$_2$NH$_2$, —SO$_2$NH($C_1$-$C_4$alkyl), phenylsulfonyl, and 3- to 6-membered heterocyclyl containing 1 or 2 heteroatoms selected from the group consisting of N, O, and S, wherein phenyl groups of the substituents and the 3- to 6-membered heterocyclyl substituent may optionally carry 1, 2 or 3 substituents independently selected from the group consisting of halogen, $C_1$-$C_6$alkyl and $C_1$-$C_3$cyanoalkyl;

$R^3$ is hydrogen or optionally substituted $C_1$-$C_6$alkyl;

$R^4$ is selected from the group consisting of pyridine, pyrimidine, pyrazine, pyridazine and thiazole, each of which is optionally substituted by 1, 2, 3 or 4 substituents independently selected from the group consisting of halogen, hydroxy, CN, —COOH, —CONH$_2$, —NO$_2$, —NH$_2$, SF$_5$, $C_1$-$C_6$alkyl, $C_3$-$C_6$cycloalkyl, $C_1$-$C_4$alkyl-$C_3$-$C_6$cycloalkyl, $C_1$-$C_3$haloalkyl, $C_1$-$C_3$cyanoalkyl, $C_3$-$C_6$halocycloalkyl, $C_3$-$C_6$cyanocycloalkyl, $C_1$-$C_4$alkoxy, $C_1$-$C_3$haloalkoxy, $C_1$-$C_3$cyanoalkoxy, hydroxy-$C_1$-$C_4$alkyl, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —NH($C_1$-$C_4$alkyl-$C_3$-$C_6$cycloalkyl), —N($C_1$-$C_4$alkyl)$_2$, —N($C_1$-$C_4$alkyl)($C_1$-$C_4$alkyl-$C_3$-$C_6$cycloalkyl), —NHCO—$C_1$-$C_4$alkyl, NHCO—$C_3$-$C_6$cycloalkyl, —NHCO($C_1$-$C_4$alkyl-$C_3$-$C_6$cycloalkyl), —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cycloalkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH($C_1$-$C_4$alkyl-$C_3$-$C_6$cycloalkyl), —CONH-phenyl, —CONHSO$_2$($C_1$-$C_4$alkyl), —CON($C_1$-$C_4$alkyl)$_2$, —CON($C_1$-$C_4$alkyl)($C_3$-$C_6$cycloalkyl), —CON($C_1$-$C_4$alkyl)($C_1$-$C_4$alkyl-$C_3$-$C_6$cycloalkyl), —CON($C_1$-$C_4$alkyl)-phenyl, —CON($C_1$-$C_4$alkyl)SO$_2$($C_1$-$C_4$alkyl), —C(=NOC$_1$-$C_4$alkyl)H, —C(=NOC$_1$-$C_4$alkyl)-$C_1$-$C_4$alkyl, —SO$_2$NH$_2$, —SO$_2$NH($C_1$-$C_4$alkyl), phenylsulfonyl and 3- to 6-membered heterocyclyl containing 1 or 2 heteroatoms selected from the group consisting of N, O, and S, wherein phenyl groups of the substituents and the 3- to 6-membered heterocyclyl substituent may optionally carry 1, 2 or 3 substituents independently selected from the group consisting of halogen, $C_1$-$C_6$alkyl and $C_1$-$C_3$cyanoalkyl;

$R^5$ is hydrogen, halogen, CN, or in each case optionally substituted $C_1$-$C_3$-alkyl, $C_1$-$C_3$-haloalkyl, $C_1$-$C_3$cyanoalkyl, $C_3$-$C_4$-cycloalkyl, $C_3$-$C_4$halocycloalkyl, $C_3$-$C_6$cyanocycloalkyl, $C_1$-$C_3$alkoxy, $C_1$-$C_3$haloalkoxy, $C_1$-$C_3$cyanoalkoxy, —C(O)—$C_1$-$C_3$alkoxy, —CH—($C_1$-$C_3$alkoxy)$_2$, —CO$_2$$C_1$-$C_4$alkyl, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NOC$_1$-$C_4$alkyl)H, or —C(=NOC$_1$-$C_4$alkyl)-$C_1$-$C_4$alkyl;

$R^6$ is hydrogen, halogen, CN, or in each case optionally substituted $C_1$-$C_3$-alkyl, $C_1$-$C_3$-haloalkyl, $C_1$-$C_3$cyanoalkyl, $C_3$-$C_4$cycloalkyl, $C_3$-$C_4$halocycloalkyl, $C_3$-$C_6$cyanocycloalkyl, $C_1$-$C_3$alkoxy, $C_1$-$C_3$haloalkoxy, $C_1$-$C_3$cyanoalkoxy, —C(O)—$C_1$-$C_3$alkoxy, —CH—($C_1$-$C_3$alkoxy)$_2$, —CO$_2$$C_1$-$C_4$alkyl, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NOC$_1$-$C_4$alkyl)H, or —C(=NOC$_1$-$C_4$alkyl)-$C_1$-$C_4$alkyl;

and salts and N-oxides thereof.

In a further aspect (aspect 4.1) the invention relates to compounds of the formula (I) as described supra, in which $R^1$ is hydrogen; methyl, ethyl, n-propyl, isopropyl, cyanomethyl, cyclopropylmethyl, methoxymethyl, ethoxymethyl, methylthiomethyl, ethylthiomethyl, methylthioethyl, ethylthioethyl, methylsulfonylethyl, ethylsulfonylethyl;

$R^2$ is selected from the group consisting of pyrazole, phenyl and pyridine each of which is optionally substituted by 1 or 2 substituents independently selected from the group consisting of fluorine, chlorine, bromine, iodine, hydroxy, —CN, —COOH, —CONH$_2$, —NO$_2$, —NH$_2$, —SF$_5$, methyl, ethyl, n-propyl, isopropyl, butyl, tert-butyl, cyclopropyl, cyclobutyl, 1-cyanocyclopropyl, difluoromethyl, trifluoromethyl, pentafluoroethyl, cyanomethyl, 1-cyano-1-methyleth-1-yl, methoxy, ethoxy, difluoromethoxy, trifluoromethoxy, cyanomethoxy, methylthio, methylsulfinyl, methylsulfonyl, ethylsulfonyl, cyclopropylsulfonyl, difluoromethylthio, trifluoromethylthio, difluoromethylsulfinyl, trifluoromethylsulfinyl, difluoromethylsulfonyl, trifluoromethylsulfonyl, (CH$_3$)$_3$-silyl, phenylsulfonyl which may carry a fluorine, chlorine or methyl substituent;

$R^3$ is hydrogen, methyl, ethyl, n-propyl, or isopropyl;

$R^4$ is selected from the group consisting of pyridin-2-yl, pyrimidin-2-yl, pyrimidin-4-yl, pyrazin-3-yl, and 1,3-thiazol-2-yl, 1,3-oxazol-2-yl, 1,2-oxazol-3-yl, 1,2-thiazol-3-yl, 1H-pyrazol-1-yl, 1H-pyrazol-3-yl, 1H-imidazol-4-yl, each of which is optionally substituted by 1 substituent selected from the group consisting of fluorine, chlorine, bromine, —CN, —COOH, methyl, ethyl, n-propyl, isopropyl, cyclopropyl, cyclobutyl, difluoromethyl, trifluoromethyl, pentafluoroethyl, cyanomethyl, methoxy, ethoxy, difluoromethoxy, trifluoromethoxy, cyanomethoxy, methylthio, methylsulfinyl, methylsulfonyl, ethylsulfonyl, cyclopropylsulfonyl, difluoromethylthio, trifluoromethylthio, difluoromethylsulfinyl, trifluoromethylsulfinyl, difluoromethylsulfonyl, trifluoromethylsulfonyl, —COOCH$_3$, —COOCH$_2$CH$_3$, and the substructures S13, in which the bond to the aforementioned pyridin-2-yl, pyrimidin-2-yl, pyrimidin-4-yl, pyrazin-3-yl, and 1,3-thiazol-2-yl, 1,3-oxazol-2-yl, 1,2-oxazol-3-yl, 1,2-thiazol-3-yl, 1H-pyrazol-1-yl, 1H-pyrazol-3-yl, 1H-imidazol-4-yl, is marked with a # and Z is CO;

S13

$R^{41}$ is hydrogen, methyl, ethyl, n-propyl, propane-2-yl, butane-2-yl, 2,2,2-trifluoroethyl, 2-trifluoromethoxyethyl, cyanomethyl, cyclopropyl, cyclopropylmethyl, or 2-methyl-n-propyl;

$R^{42}$ is hydrogen, methyl, ethyl, n-propyl, propane-2-yl, butane-2-yl, 2,2,2-trifluoroethyl, 2-trifluoromethoxyethyl, cyanomethyl, cyclopropyl, cyclopropylmethyl, or 2-methyl-n-propyl;

$R^{41}$ and $R^{42}$ together with the nitrogen atom to which they are attached, represent pyrrolidine, piperidine, azepane, morpholine, oxazepane, azasilolidine, azasilinane, azasilepane each of which is optionally substituted with 1 or 2 methyl groups;

$R^5$ is hydrogen, fluorine, chlorine, bromine, iodine, —CN, methyl, ethyl, n-propyl, isopropyl, butyl, tert-butyl, difluoromethyl, trifluoromethyl, pentafluoroethyl, cyanomethyl, cyclopropyl, cyclobutyl, methoxy, ethoxy, difluoromethoxy, trifluoromethoxy or cyanomethoxy;

$R^6$ is hydrogen, fluorine, chlorine, bromine, iodine, —CN, methyl, ethyl, n-propyl, isopropyl, butyl, tert-butyl, difluoromethyl, trifluoromethyl, pentafluoroethyl, cyanomethyl, cyclopropyl, cyclobutyl, methoxy, ethoxy, difluoromethoxy, trifluoromethoxy or cyanomethoxy; and salts and N-oxides thereof.

In a further aspect (aspect 4.2) the invention relates to compounds of the formula (I) as described supra, in which $R^1$ is hydrogen; methyl, ethyl, n-propyl, isopropyl, cyanomethyl, cyclopropylmethyl, methoxymethyl, ethoxymethyl, methylthiomethyl, ethylthiomethyl, methylthioethyl, ethylthioethyl, methylsulfonylethyl, ethylsulfonylethyl;

$R^2$ is selected from the group consisting of phenyl and pyridine each of which is optionally substituted by 1 or 2 substituents independently selected from the group consisting of fluorine, chlorine, bromine, iodine, hydroxy, —CN, —COOH, —CONH$_2$, —NO$_2$, —NH$_2$, —SF$_5$, methyl, ethyl, n-propyl, isopropyl, butyl, tert-butyl, cyclopropyl, cyclobutyl, 1-cyanocyclopropyl, difluoromethyl, trifluoromethyl, pentafluoroethyl, cyanomethyl, 1-cyano-1-methyleth-1-yl (also referred to as 1-methyl-1-cyanoethyl), methoxy, ethoxy, difluoromethoxy, trifluoromethoxy, cyanomethoxy, methylthio, methylsulfinyl, methylsulfonyl, ethylsulfonyl, cyclopropylsulfonyl, difluoromethylthio, trifluoromethylthio, difluoromethylsulfinyl, trifluoromethylsulfinyl, difluoromethylsulfonyl, trifluoromethylsulfonyl, (CH$_3$)$_3$-silyl, phenylsulfonyl which may carry a fluorine, chlorine or methyl substituent;

$R^3$ is hydrogen, methyl, ethyl, n-propyl, or isopropyl;

$R^4$ is selected from the group consisting of pyridin-2-yl, pyrimidin-2-yl, pyrimidin-4-yl, pyrazin-3-yl, and 1,3-thiazol-2-yl, 1,3-oxazol-2-yl, 1,2-oxazol-3-yl, 1,2-thiazol-3-yl, 1H-pyrazol-1-yl, 1H-pyrazol-3-yl, 1H-imidazol-4-yl, each of which is optionally substituted by 1 substituent selected from the group consisting of fluorine, chlorine, bromine, —CN, —COOH, methyl, ethyl, n-propyl, isopropyl, cyclopropyl, cyclobutyl, difluoromethyl, trifluoromethyl, pentafluoroethyl, cyanomethyl, methoxy, ethoxy, difluoromethoxy, trifluoromethoxy, cyanomethoxy, methylthio, methylsulfinyl, methylsulfonyl, ethylsulfonyl, cyclopropylsulfonyl, difluoromethylthio, trifluoromethylthio, difluoromethylsulfinyl, trifluoromethylsulfinyl, difluoromethylsulfonyl, trifluoromethylsulfonyl, —COOCH$_3$, —COOCH$_2$CH$_3$, and the substructures S13, in which the bond to the aforementioned pyridin-2-yl, pyrimidin-2-yl, pyrimidin-4-yl, pyrazin-3-yl, and 1,3-thiazol-2-yl, 1,3-oxazol-2-yl, 1,2-oxazol-3-yl, 1,2-thiazol-3-yl, 1H-pyrazol-1-yl, 1H-pyrazol-3-yl, 1H-imidazol-4-yl, is marked with a # and Z is CO;

S13

$R^{41}$ is hydrogen, methyl, ethyl, n-propyl, propane-2-yl, butane-2-yl, 2,2,2-trifluoroethyl, 2-trifluoromethoxyethyl, cyanomethyl, cyclopropyl, cyclopropylmethyl, or 2-methyl-n-propyl;

$R^{42}$ is hydrogen, methyl, ethyl, n-propyl, propane-2-yl, butane-2-yl, 2,2,2-trifluoroethyl, 2-trifluoromethoxyethyl, cyanomethyl, cyclopropyl, cyclopropylmethyl, or 2-methyl-n-propyl;

$R^{41}$ and $R^{42}$ together with the nitrogen atom to which they are attached, represent pyrrolidine, piperidine, azepane, morpholine, oxazepane, azasilolidine, azasilinane, azasilepane each of which is optionally substituted with 1 or 2 methyl groups $R^5$ is hydrogen, fluorine, chlorine, bromine, iodine, —CN, methyl, ethyl, n-propyl, isopropyl, butyl, tert-butyl, difluoromethyl, trifluoromethyl, pentafluoroethyl, cyanomethyl, cyclopropyl, cyclobutyl, methoxy, ethoxy, difluoromethoxy, trifluoromethoxy or cyanomethoxy;

$R^6$ is hydrogen, fluorine, chlorine, bromine, iodine, —CN, methyl, ethyl, n-propyl, isopropyl, butyl, tert-butyl, difluoromethyl, trifluoromethyl, pentafluoroethyl, cyanomethyl, cyclopropyl, cyclobutyl, methoxy, ethoxy, difluoromethoxy, trifluoromethoxy or cyanomethoxy; and salts and N-oxides thereof.

In a further aspect (aspect 4.3) the invention relates to compounds of the formula (I) as described supra, in which $R^1$ is hydrogen; methyl, ethyl, n-propyl, isopropyl, cyanomethyl, cyclopropylmethyl, methoxymethyl, ethoxymethyl, methylthiomethyl, ethylthiomethyl;

$R^2$ is selected from the group consisting of phenyl, pyridine, pyrimidine, pyrazine, and pyridazine, each of which is optionally substituted by 1, 2 or 3 substituents independently selected from the group consisting of fluorine, chlorine, bromine, iodine, hydroxy, CN, —COOH, —CONH$_2$, —NO$_2$, —NH$_2$, SF$_5$, methyl, ethyl, n-propyl, isopropyl, butyl, tert-butyl, cyclopropyl, cyclobutyl, cyclopentyl, cyclohexyl, difluoromethyl, trifluoromethyl, pentafluoroethyl, cyanomethyl, methoxy, ethoxy, difluoromethoxy, trifluoromethoxy, cyanomethoxy, isopropan-2-ol, methylthio, methylsulfinyl, methylsulfonyl, ethylsulfonyl, cyclopropylsulfonyl, difluoromethylthio, trifluoromethylthio, difluoromethylsulfinyl, trifluoromethylsulfinyl, difluoromethylsulfonyl, trifluoromethylsulfonyl, (CH$_3$)$_3$-silyl, —SO$_2$NH$_2$, phenylsulfonyl which may carry a fluorine, chlorine or methyl substituent, and oxetane, tetrahydropyrane and piperazine which each may carry a methyl substituent;

$R^3$ is hydrogen, methyl, ethyl, n-propyl, or isopropyl;

$R^4$ is selected from the group consisting of pyridine, pyrimidine, pyrazine, pyridazine and thiazole, each of which is optionally substituted by 1, 2, or 3 substituents independently selected from the group consisting of fluorine, chlorine, bromine, iodine, hydroxy, CN, —COOH, —CONH$_2$, —NO$_2$, —NH$_2$, SF$_5$, methyl, ethyl, n-propyl, isopropyl, butyl, tert-butyl, cyclopropyl, cyclobutyl, cyclopentyl, cyclohexyl, difluoromethyl, trifluoromethyl, pentafluoroethyl, cyanomethyl, methoxy, ethoxy, difluoromethoxy, trifluoromethoxy, cyanomethoxy, isopropan-2-ol, methylthio, methylsulfinyl, methylsulfonyl, ethylsulfonyl, cyclopropylsulfonyl, difluoromethylthio, trifluoromethylthio, difluoromethylsulfinyl, trifluoromethylsulfinyl, difluoromethylsulfonyl, trifluoromethylsulfonyl, —NH (CH$_3$), —N(CH$_3$)$_2$, —NHCO—CH$_3$, NHCO-cyclopropyl, —CON(CH$_3$)(CH$_3$-cyclopropyl), —SO$_2$NH$_2$, and phenylsulfonyl which may carry a fluorine, chlorine, methyl or cyanomethyl substituent;

$R^5$ is hydrogen, fluorine, chlorine, bromine, iodine, CN, methyl, ethyl, n-propyl, isopropyl, butyl, tert-butyl, difluoromethyl, trifluoromethyl, pentafluoroethyl, cyanomethyl, cyclopropyl, cyclobutyl, methoxy, ethoxy, difluoromethoxy, trifluoromethoxy or cyanomethoxy;

$R^6$ is hydrogen, fluorine, chlorine, bromine, iodine, CN, methyl, ethyl, n-propyl, isopropyl, butyl, tert-butyl, difluoromethyl, trifluoromethyl, pentafluoroethyl, cyanomethyl, cyclopropyl, cyclobutyl, methoxy, ethoxy, difluoromethoxy, trifluoromethoxy or cyanomethoxy; and salts and N-oxides thereof.

In a further aspect (aspect 5.1) the invention relates to compounds of the formula (I) as described supra, in which $R^1$ is hydrogen, or cyclopropylmethyl;

$R^2$ is selected from the group consisting of pyrazol, phenyl and pyridine, each of which is optionally substituted by 1 or 2 substituents independently selected from the group consisting of fluorine, chlorine, bromine, iodine, —CN, —SF$_5$, methyl, ethyl, n-propyl, isopropyl, tert-butyl, 1-cyano-1-methyleth-1-yl, cyclopropyl, 1-cyanocyclopropyl, difluoromethyl, trifluoromethyl, methoxy, ethoxy, difluoromethoxy, difluoromethoxy, trifluoromethoxy, methylsulfonyl, ethylsulfonyl, cyclopropylsulfonyl, trifluoromethylsulfonyl, 4-fluorophenylsulfonyl, difluoromethylsulfonyl;

$R^3$ is methyl;

$R^4$ is selected from the group consisting of pyridine-2-yl, pyrimidin-2-yl, 1,3-thiazol-2-yl, 1H-pyrazol-1-yl each of which is optionally substituted by 1 substituent selected from the group consisting of fluorine, chlorine, bromine, —CN, methyl, ethyl, trifluoromethyl, methoxy, ethoxy, —COOH, —COOCH$_3$, —COOCH$_2$CH$_3$, and the substructure S13, in which the bond marked with # is connected to the C-5-position of the aforementioned pyridin-2-yl, pyrimidin-2-yl, 1,3-thiazol-2-yl-, or to the C-4-position in the above mentioned 1H-pyrazol-1-yl, and Z is CO;

S13

$R^{41}$ is hydrogen, methyl, ethyl, propane-2-yl, 2,2,2-trifluoroethyl, cyanomethyl, cyclopropylmethyl, 2-methyl-n-propyl, cyclopropyl;

$R^{42}$ is hydrogen, methyl, ethyl, propane-2-yl, 2,2,2-trifluoroethyl, cyanomethyl, cyclopropylmethyl, 2-methyl-n-propyl;

$R^{41}$ and $R^{42}$ together with the nitrogen atom to which they are attached, represent pyrrolidine, piperidine, morpholine, 2,6-dimethylmorpholine, oxazepane, or (Si,Si-dimethyl)azasilinane;

$R^5$ is hydrogen or methyl;

$R^6$ is hydrogen or methyl;

and salts and N-oxides thereof.

In a further aspect (aspect 5.2) the invention relates to compounds of the formula (I) as described supra, in which $R^1$ is hydrogen, or cyclopropylmethyl;

$R^2$ is selected from the group consisting of phenyl and pyridine, each of which is optionally substituted by 1 or 2 substituents independently selected from the group consisting of fluorine, chlorine, bromine, iodine, —CN, —SF$_5$, methyl, ethyl, n-propyl, isopropyl, tert-butyl, cyclopropyl, trifluoromethyl, methoxy, ethoxy, difluoromethoxy, trifluoromethoxy, methylsulfonyl, ethylsulfonyl, cyclopropylsulfonyl, trifluoromethylsulfonyl;

$R^3$ is methyl;

$R^4$ is selected from the group consisting of pyridine-2-yl, pyrimidin-2-yl, 1,3-thiazol-2-yl, 1H-pyrazol-1-yl each of which is optionally substituted by 1 substituent selected from the group consisting of fluorine, chlorine, bromine, —CN, methyl, ethyl, trifluoromethyl, methoxy, ethoxy, —COOH, —COOCH$_3$, —COOCH$_2$CH$_3$, and the substructure S13, in which the bond marked with # is connected to the C-5-position of the aforementioned pyridin-2-yl, pyrimidin-2-yl, 1,3-thiazol-2-yl-, or to the C-4-position in the above mentioned 1H-pyrazol-1-yl, and Z is CO;

S13

$R^{41}$ is hydrogen, methyl, ethyl, propane-2-yl, 2,2,2-trifluoroethyl, cyanomethyl, cyclopropylmethyl, 2-methyl-n-propyl;

$R^{42}$ is hydrogen, methyl, ethyl, propane-2-yl, 2,2,2-trifluoroethyl, cyanomethyl, cyclopropylmethyl, 2-methyl-n-propyl;

$R^{41}$ and $R^{42}$ together with the nitrogen atom to which they are attached, represent pyrrolidine, piperidine, morpholine, 2,6-dimethylmorpholine, oxazepane, (Si,Si-dimethyl)azasilinane, $R^5$ is hydrogen or methyl;

$R^6$ is hydrogen or methyl;

and salts and N-oxides thereof.

In a further aspect (aspect 5.3) the invention relates to compounds of the formula (I) as described supra, in which $R^1$ is hydrogen, methyl, cyclopropylmethyl, ethoxymethyl or ethylthiomethyl;

$R^2$ is selected from the group consisting of phenyl and pyridine, each of which is optionally substituted by 1, 2 or 3 substituents independently selected from the group consisting of fluorine, chlorine, bromine, CN, SF$_5$, methyl, ethyl, n-propyl, isopropyl, butyl, tert-butyl, cyclopropyl, trifluoromethyl, cyanomethyl, methoxy, ethoxy, difluoromethoxy, trifluoromethoxy, cyanomethoxy, isopropan-2-ol, (CH$_3$)$_3$-silyl, methylsulfonyl, ethylsulfonyl, cyclopropylsulfonyl, trifluoromethylsulfonyl, —SO$_2$NH$_2$, phenylsulfonyl which may carry a fluorine substituent, and oxetane, tetrahydropyrane and piperazine which each may carry a methyl substituent;

$R^3$ is methyl;

$R^4$ is selected from the group consisting of pyridine, pyrimidine, pyrazine, pyridazine and thiazole, each of which is optionally substituted by 1 or 2 substituents independently selected from the group consisting of fluorine, chlorine, bromine, CN, methyl, ethyl, n-propyl, isopropyl, butyl, tert-butyl, cyclopropyl, trifluoromethyl, cyanomethyl, methoxy, ethoxy, difluoromethoxy, trifluoromethoxy, cyanomethoxy, isopropan-2-ol, —NHCO—CH$_3$, NHCO-cyclopropyl, —CON(CH$_3$)(CH$_3$-cyclopropyl), and methylsulfonyl;

$R^5$ is hydrogen, fluorine, chlorine, bromine, iodine, CN, methyl, ethyl, n-propyl, isopropyl, butyl, tert-butyl, difluoromethyl, trifluoromethyl, pentafluoroethyl, cyclopropyl, cyclobutyl, methoxy, ethoxy, difluoromethoxy, or trifluoromethoxy;

$R^6$ is hydrogen, fluorine, chlorine, bromine, iodine, CN, methyl, ethyl, n-propyl, isopropyl, butyl, tert-butyl, difluoromethyl, trifluoromethyl, pentafluoroethyl, cyclopropyl, cyclobutyl, methoxy, ethoxy, difluoromethoxy, or trifluoromethoxy;
and salts and N-oxides thereof.

In a further aspect (aspect 6) the invention relates to compounds of the formula (I) as described supra, in which $R^2$ is phenyl which may be substituted as defined anywhere supra, and wherein the remaining substituents may have the meaning as defined anywhere supra, and salts and N-oxides thereof.

In one preferred embodiment of aspect 6 of the invention supra $R^2$ is the following substructure Q1, in which the bond to the C═O-group is marked with a #:

Q1 wherein $R^{25}$ is hydroxy, —NH$_2$, —SO$_2$NH$_2$, C$_4$-C$_6$alkyl, C$_4$alkoxy, C$_1$-C$_3$cyanoalkyl, C$_3$-C$_6$cycloalkyl, C$_3$-C$_6$halocycloalkyl, C$_3$-C$_6$cyanocycloalkyl, C$_1$-C$_3$alkylthio, C$_1$-C$_3$alkylsulfinyl, C$_1$-C$_3$alkylsulfonyl, C$_3$-C$_6$cycloalkylsulfanyl, C$_3$-C$_6$cycloalkylsulfinyl, C$_3$-C$_6$cycloalkylsulfonyl, C$_1$-C$_3$haloalkylsulfinyl, C$_1$-C$_3$haloalkylsulfonyl, C$_1$-C$_3$cyanoalkoxy, hydroxy-C$_1$-C$_4$alkyl, —NH(C$_1$-C$_4$alkyl), —N(C$_1$-C$_4$alkyl)$_2$, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cycloalkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CON(C$_1$-C$_4$alkyl)$_2$, —CON(C$_1$-C$_4$alkyl)(C$_3$-C$_6$cycloalkyl), —CON(C$_1$-C$_4$alkyl)-phenyl, —C(═NOC$_1$-C$_4$alkyl)H, —C(═NOC$_1$-C$_4$alkyl)-C$_1$-C$_4$alkyl, (C$_1$-C$_4$alkyl)$_3$-silyl, —SO$_2$NH(C$_1$-C$_4$alkyl), phenylsulfonyl, or 3- to 6-membered heterocyclyl containing 1 or 2 heteroatoms selected from the group consisting of N, O, and S,
wherein phenyl groups of the aforementioned substituents and the 3- to 6-membered heterocyclyl substituent may optionally carry 1, 2 or 3 substituents independently selected from the group consisting of halogen, CN, C$_1$-C$_6$alkyl, C$_1$-C$_6$haloalkyl and C$_1$-C$_3$cyanoalkyl; and $R^{26}$ is halogen, —CN, —COOH, —CONH$_2$, —NO$_2$, —SF$_5$, C$_1$-C$_3$alkyl, C$_1$-C$_3$haloalkyl, C$_1$-C$_3$alkoxy, C$_1$-C$_3$haloalkoxy, C$_1$-C$_3$haloalkylthio, C$_1$-C$_3$alkylthio, C$_1$-C$_3$alkylsulfinyl, C$_1$-C$_3$-alkylsulfonyl, C$_1$-C$_3$haloalkylsulfinyl, C$_1$-C$_3$haloalkylsulfonyl, C$_3$-C$_6$cycloalkylsulfanyl, C$_3$-C$_6$cycloalkylsulfinyl, C$_3$-C$_6$cycloalkylsulfonyl, C$_3$-C$_6$cycloalkyl, C$_1$-C$_3$cyanoalkyl, C$_3$-C$_6$cyanocycloalkyl.

$R^{25}$ and $R^{26}$ are preferably defined as follows:

$R^{25}$ is —SO$_2$NH$_2$, methylsulfonyl, ethylsulfonyl, cyclopropylsulfonyl, difluoromethylsulfonyl, trifluoromethylsulfonyl, (CH$_3$)$_3$-silyl, cyanomethoxy, tert-butyl, cyclopropyl, cyanomethyl, 1-cyano-1-methyleth-1-yl, 1-cyanocyclopropyl, isopropan-2-ol, phenylsulfonyl which may optionally carry a fluorine substituent; or is oxetane, tetrahydropyrane or piperazine which each may optionally carry a methyl substituent;

$R^{26}$ is fluorine, chlorine, bromine, CN, SF$_5$, methyl, ethyl, n-propyl, isopropyl, butyl, difluoromethyl, trifluoromethyl, methoxy, ethoxy, difluoromethoxy, trifluoromethoxy, methylsulfonyl, ethylsulfonyl, cyclopropylsulfonyl, trifluoromethylsulfonyl, cyclopropyl.

According to a further embodiment $R^{25}$ and $R^{26}$ are preferably defined as follows:

$R^{25}$ is —SO$_2$NH$_2$, methylsulfonyl, ethylsulfonyl, cyclopropylsulfonyl, trifluoromethylsulfonyl, (CH$_3$)$_3$-silyl, cyanomethoxy, tert-butyl, cyclopropyl, cyanomethyl, isopropan-2-ol, phenylsulfonyl which may optionally carry a fluorine substituent; or is oxetane, tetrahydropyrane or piperazine which each may optionally carry a methyl substituent;

$R^{26}$ is fluorine, chlorine, bromine, CN, SF$_5$, methyl, ethyl, n-propyl, isopropyl, butyl, trifluoromethyl, methoxy, ethoxy, difluoromethoxy, trifluoromethoxy, methylsulfonyl, ethylsulfonyl, cyclopropylsulfonyl, trifluoromethylsulfonyl, cyclopropyl.

$R^{25}$ and $R^{26}$ are particularly preferably defined as follows:

$R^{25}$ is methylsulfonyl, ethylsulfonyl, cyclopropylsulfonyl, trifluoromethylsulfonyl, tert-butyl, cyclopropyl, 1-cyano-1-methyleth-1-yl, 1-cyanocyclopropyl, 4-fluorophenylsulfonyl; and $R^{26}$ is fluorine, chlorine, bromine, iodine, CN, SF$_5$, methyl, ethyl, isopropyl, tert.-butyl, difluoromethyl, trifluoromethyl, methoxy, ethoxy, difluoromethoxy, trifluoromethoxy, methylsulfonyl, ethylsulfonyl, cyclopropylsulfonyl, trifluoromethylsulfonyl, cyclopropyl.

According to a further embodiment $R^{25}$ and $R^{26}$ are particularly preferably defined as follows:

$R^{25}$ is methylsulfonyl, ethylsulfonyl, cyclopropylsulfonyl, trifluoromethylsulfonyl, tert-butyl, cyclopropyl; and $R^{26}$ is fluorine, chlorine, bromine, CN, SF$_5$, methyl, ethyl, isopropyl, tert.-butyl, trifluoromethyl, methoxy, ethoxy, difluoromethoxy, trifluoromethoxy, methylsulfonyl, ethylsulfonyl, cyclopropylsulfonyl, trifluoromethylsulfonyl, cyclopropyl.

In further embodiment of aspect 6 of the invention supra $R^2$ is the following substructure Q2, in which the bond to the C═O-group is marked with a # and

Q2 wherein $R^{27}$ is halogen, —CN, —COOH, —CONH$_2$, —NO$_2$, —SF$_5$, C$_1$-C$_3$alkyl, C$_1$-C$_3$haloalkyl, C$_1$-C$_3$alkoxy, C$_1$-C$_3$haloalkoxy or C$_1$-C$_3$haloalkylthio; and $R^{28}$ is halogen, —CN, —COOH, —CONH$_2$, —NO$_2$, —SF$_5$, C$_1$-C$_3$alkyl, C$_1$-C$_3$haloalkyl, C$_1$-C$_3$alkoxy, C$_1$-C$_3$haloalkoxy, or C$_1$-C$_3$haloalkylthio.

$R^{27}$ and $R^{28}$ are preferably defined as follows:

$R^{27}$ is fluorine, chlorine, bromine, —CN, —SF$_5$, methyl, ethyl, n-propyl, isopropyl, butyl, trifluoromethyl, methoxy, ethoxy, difluoromethoxy, trifluoromethoxy;

$R^{28}$ is fluorine, chlorine, bromine, —CN, —SF$_5$, methyl,
ethyl, n-propyl, isopropyl, butyl, trifluoromethyl,
methoxy, ethoxy, difluoromethoxy, trifluoromethoxy.

In a further aspect (aspect 7) the invention relates to
compounds of the formula (I) as described supra, in which
$R^2$ is thiophene, pyrazole or imidazole, each of which may
be substituted as defined anywhere supra, and wherein the
remaining substituents may have the meaning as defined
anywhere supra, and salts and N-oxides thereof.

In a preferred embodiment of aspect 7 of the invention
supra $R^2$ is selected from an optionally substituted thiophene
and a pyrazole group:

wherein $R^9$ is selected from halogen, preferably fluorine, chlorine
and bromine, $C_1$-$C_3$alkyl, preferably methyl,
$C_1$-$C_3$haloalkyl, preferably trifluoromethyl, and pen-
tafluorosulfanyl;

n is an integer of 0, 1 or 2, preferably 1 or 2; and

Y represents hydrogen, $C_1$-$C_3$alkyl, preferably methyl and
ethyl, cycloalkyl, preferably cyclopropyl,
$C_1$-$C_3$haloalkyl, preferably trifluoromethyl.

Preferred examples of such groups $R^2$ are represented by
the following formulae:

In a further aspect (aspect 8) the invention relates to
compounds of the formula (I) as described supra, in which
$R^4$ is selected from the group consisting of pyridine, pyrimi-
dine, thiazole, pyrazol and pyrazine each of which may be
substituted as defined anywhere supra, and wherein the
remaining substituents may have the meaning as defined
anywhere supra, and salts and N-oxides thereof.

In a preferred embodiment of the aspect 8 of the invention
supra $R^4$ is selected from the group consisting of pyridine,
pyrimidine and thiazole, each of which may be substituted
as defined anywhere supra, and wherein the remaining
substituents may have the meaning as defined anywhere
supra, and salts and N-oxides thereof.

In a preferred embodiment of the aspect 8 of the invention
supra the compounds of the formula (I) are characterized by
having a structure according to formula (I-i), (I-ii) or (I-iii)

(I-i)

(I-ii)

(I-iii)

wherein $R^1$, $R^2$, $R^3$, $R^5$ and $R^6$ have the meaning as defined in any
of the aspects described supra; and $R^8$ represents 0, 1, 2, 3 or 4 same or different substituents
as defined in any of the aspects described anywhere
supra for $R^4$, preferably $R^8$ represents 0, 1 or 2 sub-
stituents, more preferably 0 or 1 substituents;

and salts and N-oxides thereof.

In a further preferred embodiment of the aspect 8 of the
invention supra the compounds of the formula (I) are
characterized by having a structure according to formula
(I-i) supra, and $R^1$, $R^2$, $R^3$, $R^5$, $R^6$ have the meaning as
defined in any of the aspects described supra and $R^8$ repre-
sents 0, 1 or 2, preferably 0 or 1, same or different substitu-
ents selected from fluorine, chlorine, bromine, cyano,
methyl, trifluormethyl, CONHcyclopropyl, CO—N-mor-
pholinyl, CON(CH$_3$(cyclopropylmethyl), CO—N-pyrrolidi-
nyl, CON(CH$_3$(CH$_2$CN); and salts and N-oxides thereof.

In a further preferred embodiment of the aspect 8 of the
invention supra the compounds of the formula (I) are
characterized by having a structure according to formula
(I-i) supra, and $R^1$, $R^2$, $R^3$, $R^5$, $R^6$ have the meaning as
defined in any of the aspects described supra and $R^8$ repre-
sents 0, 1 or 2, preferably 0 or 1, same or different substitu-
ents selected from the group consisting of —CN, —COOH,
—COOCH$_3$, —COOCH$_2$CH$_3$, and the substructure S13, in
which the bond marked with # is connected to the pyridine,
preferably in C-5-position, and Z is CO;

S13

$R^{41}$ is hydrogen, methyl, ethyl, propane-2-yl, 2,2,2-trif-
luoroethyl, cyanomethyl, cyclopropylmethyl,
2-methyl-n-propyl or cyclopropyl;

$R^{42}$ is hydrogen, methyl, ethyl, propane-2-yl, 2,2,2-trif-
luoroethyl, cyanomethyl, cyclopropylmethyl,
2-methyl-n-propyl;

$R^{41}$ and $R^{42}$ together with the nitrogen atom to which they
are attached, represent pyrrolidine, piperidine, morpho-
line, 2,6-dimethylmorpholine, oxazepane, (Si,Si-dim-
ethyl)azasilinane, and salts and N-oxides thereof.

In a further preferred embodiment of the aspect 8 of the
invention supra the compounds of the formula (I) are
characterized by having a structure according to formula
(I-ii) supra, and $R^1$, $R^2$, $R^3$, $R^5$, $R^6$ have the meaning as
defined in any of the aspects described supra and $R^8$ repre-
sents 0, 1 or 2, preferably 0 or 1, same or different substitu-
ents selected from fluorine, chlorine, bromine, cyano,
methyl, trifluormethyl, CONHcyclopropyl, CO—N-mor-
pholinyl, CON(CH₃(cyclopropylmethyl), CO—N-pyrrolidi-
nyl, CON(CH₃(CH₂CN); and salts and N-oxides thereof.

In a further preferred embodiment of the aspect 8 of the
invention supra the compounds of the formula (I) are
characterized by having a structure according to formula
(I-ii) supra, and $R^1$, $R^2$, $R^3$, $R^5$, $R^6$ have the meaning as
defined in any of the aspects described supra and $R^8$ repre-
sents 0, 1 or 2, preferably 0 or 1, same or different substitu-
ents selected from the group consisting of —CN, —COOH,
—COOCH₃, —COOCH₂CH₃, and the substructure S13, in
which the bond marked with # is connected to the pyrimi-
dine, preferably in C-5-position, and Z is CO;

S13

$R^{41}$ is hydrogen, methyl, ethyl, propane-2-yl, 2,2,2-trif-
luoroethyl, cyanomethyl, cyclopropylmethyl,
2-methyl-n-propyl, or cyclopropyl;

$R^{42}$ is hydrogen, methyl, ethyl, propane-2-yl, 2,2,2-trif-
luoroethyl, cyanomethyl, cyclopropylmethyl,
2-methyl-n-propyl;

$R^{41}$ and $R^{42}$ together with the nitrogen atom to which they
are attached, represent pyrrolidine, piperidine, morpho-
line, 2,6-dimethylmorpholine, oxazepane, (Si,Si-dim-
ethyl)azasilinane, and salts and N-oxides thereof.

In a further preferred embodiment of the aspect 8 of the
invention supra the compounds of the formula (I) are
characterized by having a structure according to formula
(I-iii) supra, and $R^1$, $R^2$, $R^3$, $R^5$, $R^6$ have the meaning as
defined in any of the aspects described supra and $R^8$ repre-
sents 0, 1 or 2, preferably 0 or 1, 0, 1 or 2, preferably 0 or
1, same or different substituents selected from fluorine,
chlorine, bromine, cyano, methyl, trifluormethyl, CONHcy-
clopropyl, CO—N-morpholinyl, CON(CH₃(cyclopropylm-
ethyl), CO—N-pyrrolidinyl, CON(CH₃(CH₂CN); and salts
and N-oxides thereof.

In a further preferred embodiment of the aspect 8 of the
invention supra the compounds of the formula (I) are
characterized by having a structure according to formula
(I-iii) supra, and $R^1$, $R^2$, $R^3$, $R^5$, $R^6$ have the meaning as
defined in any of the aspects described supra and $R^8$ repre-
sents 0, 1 or 2, preferably 0 or 1, 0, 1 or 2, preferably 0 or
1, same or different substituents selected from the group
consisting of fluorine, chlorine, bromine, —CN, methyl,
ethyl, trifluoromethyl, methoxy, ethoxy, —COOH,
—COOCH₃, —COOCH₂CH₃, and the substructure S13, in
which the bond marked with # is connected to the thiazole,
preferably to the C-5-position, and Z is CO;

S13

$R^{41}$ is hydrogen, methyl, ethyl, propane-2-yl, 2,2,2-trif-
luoroethyl, cyanomethyl, cyclopropylmethyl,
2-methyl-n-propyl or cyclopropyl;

$R^{42}$ is hydrogen, methyl, ethyl, propane-2-yl, 2,2,2-trif-
luoroethyl, cyanomethyl, cyclopropylmethyl,
2-methyl-n-propyl;

$R^{41}$ and $R^{42}$ together with the nitrogen atom to which they
are attached, represent pyrrolidine, piperidine, morpho-
line, 2,6-dimethylmorpholine, oxazepane, (Si,Si-dim-
ethyl)azasilinane, and salts and N-oxides thereof.

In a further preferred embodiment of the aspect 8 of the
invention supra the compounds of the formula (I) are
characterized by having a structure according to formula
(I-iv)

(I-iv)

wherein $R^1$, $R^2$, $R^3$, $R^5$ and $R^6$ have the meaning as defined in any
of the aspects described supra; and $R^8$ represents 0, 1, 2 or 3 same or different substituents as
defined in any of the aspects described anywhere supra
for $R^4$, preferably $R^8$ represents 0, 1 or 2 substituents,
more preferably 0 or 1 substituents;

and salts and N-oxides thereof.

In a further preferred embodiment of the aspect 8 of the
invention supra the compounds of the formula (I) are
characterized by having a structure according to formula
(I-iv) supra, and $R^1$, $R^2$, $R^3$, $R^5$, $R^6$ have the meaning as
defined in any of the aspects described supra and $R^8$ repre-
sents 0, 1 or 2, preferably 0 or 1, 0, 1 or 2, preferably 0 or
1, same or different substituents selected from fluorine,
chlorine, bromine, cyano, methyl, trifluormethyl, CONHcyclopropyl, CO—N-morpholinyl, CON(CH$_3$(cyclopropylm-ethyl), CO—N-pyrrolidinyl, CON(CH$_3$(CH$_2$CN); and salts and N-oxides thereof.

In a further preferred embodiment of the aspect 8 of the invention supra the compounds of the formula (I) are characterized by having a structure according to formula (I-iv) supra, and R$^1$, R$^2$, R$^3$, R$^5$, R$^6$ have the meaning as defined in any of the aspects described supra and R$^8$ represents 0, 1 or 2, preferably 0 or 1, 0, 1 or 2, preferably 0 or 1, same or different substituents selected from the group consisting of fluorine, chlorine, bromine, —CN, methyl, ethyl, trifluoromethyl, methoxy, ethoxy, —COOH, —COOCH$_3$, —COOCH$_2$CH$_3$, and the substructure S13, in which the bond marked with # is connected to the thiazole, preferably to the C-5-position, and Z is CO;

S13

R$^{41}$ is hydrogen, methyl, ethyl, propane-2-yl, 2,2,2-trif-luoroethyl, cyanomethyl, cyclopropylmethyl, 2-methyl-n-propyl, cyclopropyl;

R$^{42}$ is hydrogen, methyl, ethyl, propane-2-yl, 2,2,2-trif-luoroethyl, cyanomethyl, cyclopropylmethyl, 2-methyl-n-propyl;

R$^{41}$ and R$^{42}$ together with the nitrogen atom to which they are attached, represent pyrrolidine, piperidine, morpho-line, 2,6-dimethylmorpholine, oxazepane, (Si,Si-dim-ethyl)azasilinane, and salts and N-oxides thereof.

In a further aspect (aspect 9) the invention relates to compounds of the formula (I) as described in any of the aspects supra, which are characterized by having a structure according to formula (I-v), (I-vi) or (I-vii)

-continued (I-vii)

in which

R$^1$, R$^3$, R$^5$ and R$^6$ have the meaning as defined in any of the aspects described supra;

R$^7$ represents same or different substituents of R$^2$ as defined in any of the aspects described supra;

R$^8$ represents same or different substituents of R$^4$ as defined in any of the aspects described supra;

n represents an integer of 0, 1 or 2, preferably 0 or 1;

m represents an integer of 0, 1 or 2, preferably of 1 or 2;

and salts and N-oxides thereof.

According to a preferred embodiment of the aspect 9 the invention is directed to compounds of formula (I-v) as defined above.

According to a further preferred embodiment of the aspect 9 the invention is directed to compounds of formula (I-vi) as defined above.

According to a preferred embodiment of the aspect 9 the invention is directed to compounds of formula (I-vii) as defined above.

In a further aspect (aspect 10) the invention relates to compounds of the formula (I) as described in any of the aspects supra, which are characterized by having a structure according to one of the formulae (I-viii), (I-ix), (I-x), (I-xi) and (I-xii)

(I-v)

(I-viii)

(I-vi)

(I-ix)

-continued (I-x)

(I-xi)

in which

R$^1$, R$^3$, R$^5$ and R$^6$ have the meaning as defined in any of the aspects described supra;

R$^7$ represents same or different substituents of R$^2$ as defined in any of the aspects described supra;

R$^8$ represents same or different substituents of R$^4$ as defined in any of the aspects described supra;

n represents an integer of 0, 1 or 2, preferably 0 or 1;

m represents an integer of 0, 1 or 2, preferably of 1 or 2;

and salts and N-oxides thereof.

According to a preferred embodiment of aspect 10 the invention is directed to compounds of formula (I-viii) as defined above.

According to a further preferred embodiment of the aspect 10 the invention is directed to compounds of formula (I-ix) as defined above.

According to a preferred embodiment of the aspect 10 the invention is directed to compounds of formula (I-x) as defined above.

According to a preferred embodiment of the aspect 10 the invention is directed to compounds of formula (I-xi) as defined above.

According to a preferred embodiment the aspect 10 of the invention relates to compounds of formulae (I-xii), (I-xiii), (I-xiv), (I-xv), (I-xvi), (I-xvii), (I-xviii) or (I-xix)

(I-xii)

-continued (I-xiii)

(I-xiv)

(I-xv)

(I-xvi)

(I-xvii)

-continued (I-xviii)

(I-xix)

in which $R^1$, $R^3$, $R^5$ and $R^6$ have the meaning as defined in any of the aspects described supra;

$R^7$ represents same or different substituents of $R^2$ as defined in any of the aspects described supra;

$R^8$ represents same or different substituents of $R^4$ as defined in any of the aspects described supra;

$R^{81}$ represents in each case optionally substituted $C_1$-$C_6$alkyl, $C_2$-$C_6$alkenyl, $C_2$-$C_6$alkynyl, $C_3$-$C_6$cycloalkyl, $C_1$-$C_3$haloalkyl, hydroxy-$C_2$-$C_4$alkyl, —$CO_2C_1$-$C_4$alkyl, —$C(=NOC_1$-$C_4$alkyl)H, —$C(=NOC_1$-$C_4$alkyl)-$C_1$-$C_4$alkyl, wherein the aforementioned optionally substituted radicals are optionally substituted with up to 3 substituents independently selected from the group consisting of halogen, hydroxy, —CN, —$NO_2$, —$Si(CH_3)_3$, —$NH_2$, $C_1$-$C_3$alkyl, $C_1$-$C_3$haloalkyl, $C_3$-$C_4$cycloalkyl, $C_3$-$C_4$halocycloalkyl, $C_1$-$C_4$alkoxy, $C_1$-$C_4$haloalkoxy, $C_1$-$C_3$alkylsulfonyl, $C_3$-$C_4$cycloalkylsulfonyl, $C_1$-$C_3$haloalkylthio and $C_1$-$C_3$haloalkylsulfonyl;

or represents 3- to 6-membered heterocyclyl containing 1 or 2 heteroatoms selected from the group consisting of N, O, and S, wherein the 3- to 6-membered heterocyclyl may optionally carry 1, 2, 3 or 4 substituents independently selected from the group consisting of halogen, hydroxy, CN, —COOH, —$CONH_2$, —$CSNH_2$, —$NO_2$, —$Si(CH_3)_3$, —$SF_5$, —$NH_2$, $C_1$-$C_6$alkyl, $C_3$-$C_6$cycloalkyl, $C_3$-$C_6$cyanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, $C_1$-$C_3$cyanoalkylsulfonyl;

$R^{81}$ preferably represents $C_1$-$C_3$alkyl, $C_3$-$C_4$cycloalkyl, $C_1$-$C_3$haloalkyl, $C_1$-$C_3$cyanoalkyl, $C_3$-$C_4$cyanocycloalkyl, hydroxy-$C_2$-$C_3$alkyl, —$CO_2C_1$-$C_3$alkyl, —$NH(C_1$-$C_3$alkyl), —$N(C_1$-$C_3$alkyl)_2, —$C(=NOC_1$-$C_3$alkyl)H, or —$C(=NOC_1$-$C_3$alkyl)-$C_1$-$C_3$alkyl;

$R^{81}$ more preferably represents methyl, ethyl, n-propyl, isopropyl, cyclopropyl, cyclobutyl, difluoroethyl, trifluoroethyl, cyanomethyl, cyanoethyl, 2-hydroxyethyl, —$COOCH_3$, or —$COOCH_2CH_3$, $R^{81}$ particularly preferably represents methyl or ethyl, m represents an integer of 0, 1 or 2, preferably of 1 or 2;

and salts and N-oxides thereof.

According to a preferred embodiment of the aspect 10 the invention is directed to compounds of formula (I-xii) as defined above.

According to a further preferred embodiment of the aspect 10 the invention is directed to compounds of formula (I-xiii) as defined above.

According to a preferred embodiment of the aspect 10 the invention is directed to compounds of formula (I-xiv) as defined above.

According to a preferred embodiment of the aspect 10 the invention is directed to compounds of formula (I-xv) as defined above.

According to a further preferred embodiment of the aspect 10 the invention is directed to compounds of formula (I-xvi) as defined above.

According to a preferred embodiment of the aspect 10 the invention is directed to compounds of formula (I-xvii) as defined above.

According to a preferred embodiment of the aspect 10 the invention is directed to compounds of formula (I-xviii) as defined above.

According to a preferred embodiment of the aspect 10 the invention is directed to compounds of formula (I-xix) as defined above.

According to one embodiment the invention is directed to compounds of formula (I) as described in the various aspects and embodiments herein, wherein $R^5$ represents hydrogen and the other substituents may have any of the meanings described herein.

According to one embodiment the invention is directed to compounds of formula (I) as described in the various aspects and embodiments herein, wherein $R^6$ does not represent hydrogen and the other substituents may have any of the meanings described herein.

A further aspect (aspect 11) of the invention relates to the Intermediate Compounds according to formula IX-1, X or XIII wherein $R^3$, $R^4$, $R^5$ and $R^6$ have the meaning as defined in any of the aspects of the invention supra.

IX-1

-continued

IX-2

X

XIII

Particularly preferred are the compounds according to the Examples infra.

DEFINITIONS

The person skilled in the art is aware that, if not stated explicitly, the expressions "a" or "an" as used in the present application may, depending on the situation, mean "one (1)", "one (1) or more" or "at least one (1)".

For all the structures described herein, such as ring systems and groups, adjacent atoms must not be —O—O— or —O—S—.

Structures having a variable number of possible carbon atoms (C atoms) may be referred to in the present application as $C_{lower\ limit\ of\ carbon\ atoms}$-$C_{upper\ limit\ of\ carbon\ atoms}$ structures ($C_{LL}$-$C_{UL}$, structures), in order thus to be stipulated more specifically. Example: an alkyl group may consist of 3 to 10 carbon atoms and in that case corresponds to $C_3$-$C_{10}$alkyl. Ring structures composed of carbon atoms and heteroatoms may be referred to as "LL- to UL-membered" structures. One example of a 6-membered ring structure is toluene (a 6-membered ring structure substituted by a methyl group).

If a collective term for a substituent, for example $C_{LL}$-$C_{UL}$alkyl, is at the end of a composite substituent, for example $C_{LL}$-$C_{UL}$cycloalkyl-$C_{LL}$-$C_{UL}$alkyl, the constituent at the start of the composite substituent, for example the $C_{LL}$-$C_{UL}$cycloalkyl, may be mono- or polysubstituted identically or differently and independently by the latter substituent, for example $C_{LL}$-$C_{UL}$alkyl. All the collective terms used in this application for chemical groups, cyclic systems and cyclic groups can be stipulated more specifically through the addition "$C_{LL}$-$C_{UL}$" or "LL- to UL-membered".

In the definitions of the symbols given in the above formulae, collective terms which are generally representative of the following substituents were used:

Halogen relates to elements of the 7th main group, preferably fluorine, chlorine, bromine and iodine, more preferably fluorine, chlorine and bromine, and even more preferably fluorine and chlorine.

Examples of heteroatom are N, O, S, P, B, Si. Preferably, the term "heteroatom" relates to N, S and O.

According to the invention, "alkyl"—on its own or as part of a chemical group—represents straight-chain or branched hydrocarbons preferably having 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is also given to alkyls having 1 to 4 carbon atoms such as, inter alia, methyl, ethyl, ethyl, n-propyl, isopropyl, n-butyl, isobutyl, s-butyl or t-butyl. The inventive alkyls may be substituted by one or more identical or different radicals.

According to the invention, "alkenyl"—on its own or as part of a chemical group—represents straight-chain or branched hydrocarbons preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is also given to alkenyls having 2 to 4 carbon atoms such as, inter alia, 2-propenyl, 2-butenyl or 1-methyl-2-propenyl. The inventive alkenyls may be substituted by one or more identical or different radicals.

According to the invention, "alkynyl"—on its own or as part of a chemical group—represents straight-chain or branched hydrocarbons preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is also given to alkynyls having 2 to 4 carbon atoms such as, inter alia, ethynyl, 2-propynyl or 2-butynyl-2-propenyl. The inventive alkynyls may be substituted by one or more identical or different radicals.

According to the invention, "cycloalkyl"—on its own or as part of a chemical group—represents mono-, bi- or tricyclic hydrocarbons preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2]

octyl or adamantyl. Preference is also given to cycloalkyls having 3, 4, 5, 6 or 7 carbon atoms such as, inter alia, cyclopropyl or cyclobutyl. The inventive cycloalkyls may be substituted by one or more identical or different radicals.

According to the invention, "alkylcycloalkyl" represents mono-, bi- or tricyclic alkylcycloalkyl preferably having 4 to 10 or 4 to 7 carbon atoms, for example methylcyclopropyl, ethylcyclopropyl, isopropylcyclobutyl, 3-methylcyclopentyl and 4-methylcyclohexyl. Preference is also given to alkyl-cycloalkyls having 4, 5 or 7 carbon atoms such as, inter alia, ethylcyclopropyl or 4-methylcyclohexyl. The inventive alkylcycloalkyls may be substituted by one or more identical or different radicals.

According to the invention, "cycloalkylalkyl" represents mono-, bi- or tricyclic cycloalkylalkyl preferably having 4 to 10 or 4 to 7 carbon atoms, for example cyclopropylmethyl, cyclobutylmethyl, cycloheptylmethyl, cyclohexylmethyl and cyclopentylethyl. Preference is also given to cycloalky-lalkyls having 4, 5 or 7 carbon atoms such as, inter alia, cyclopropylmethyl or cyclobutylmethyl. The inventive cycloalkylalkyls may be substituted by one or more identical or different radicals.

According to the invention, "hydroxyalkyl" represents a straight-chain or branched alcohol preferably having 1 to 6 carbon atoms, for example methanol, ethanol, n-propanol, isopropanol (isopropan-2-ol), n-butanol, isobutanol, s-buta-nol and t-butanol. Preference is also given to hydroxyalkyl groups having 1 to 4 carbon atoms. The inventive hydroxy-alkyl groups may be substituted by one or more identical or different radicals.

According to the invention, "alkoxy" represents a straight-chain or branched O-alkyl preferably having 1 to 6 carbon atoms, for example methoxy, ethoxy, n-propoxy, isopropoxy, n-butoxy, isobutoxy, s-butoxy and t-butoxy. Preference is also given to alkoxy groups having 1 to 4 carbon atoms. The inventive alkoxy groups may be substi-tuted by one or more identical or different radicals.

According to the invention, "cycloalkoxy" represents a —O-cycloalkyl group, wherein cycloalkyl has the meaning as defined supra. Preference is given to cycloalkyls having 3, 4, 5, 6 or 7 carbon atoms, i.e. inter alia, —O-cyclopropyl, —O-cyclobutyl, —O-cyclopentyl, —O-cyclohexyl, —O-cycloheptyl. The inventive cycloalkoxy groups may be substituted by one or more identical or different radicals, preferably optional substituents are selected from halogens.

According to the invention, "alkylthio", or "alkylsulfa-nyl", represents straight-chain or branched S-alkyl prefer-ably having 1 to 6 carbon atoms, for example methylthio, ethylthio, n-propylthio, isopropylthio, n-butylthio, isobutyl-thio, s-butylthio and t-butylthio. Preference is also given to alkylthio groups having 1 to 4 carbon atoms. The inventive alkylthio groups may be substituted by one or more identical or different radicals.

According to the invention, "alkylsulfinyl" represents straight-chain or branched alkylsulfinyl preferably having 1 to 6 carbon atoms, for example methylsulfinyl, ethylsulfinyl, n-propylsulfinyl, isopropylsulfinyl, n-butylsulfinyl, isobu-tylsulfinyl, s-butylsulfinyl and t-butylsulfinyl. Preference is also given to alkylsulfinyl groups having 1 to 4 carbon atoms. The inventive alkylsulfinyl groups may be substi-tuted by one or more identical or different radicals.

According to the invention, "alkylsulfonyl" represents straight-chain or branched alkylsulfonyl preferably having 1 to 6 carbon atoms, for example methylsulfonyl, ethylsulfo-nyl, n-propylsulfonyl, isopropylsulfonyl, n-butylsulfonyl, isobutylsulfonyl, s-butylsulfonyl and t-butylsulfonyl. Pref-erence is also given to alkylsulfonyl groups having 1 to 4 carbon atoms. The inventive alkylsulfonyl groups may be substituted by one or more identical or different radicals.

According to the invention, "cycloalkylsulfonyl" repre-sents mono-, bi- or tricyclic cycloalkylsulfonyl preferably having 4 to 10 or 4 to 7 carbon atoms, for example cyclopropylsulfonyl, cyclobutylsulfonyl, cyclopentylsulfo-nyl and cyclohexylsulfonyl. Preference is also given to cycloalkylsulfonyls having 4, 5 or 7 carbon atoms such as, inter alia, cyclopropylsulfonyl or cyclobutylsulfonal. The inventive cycloalkylsulfonyls may be substituted by one or more identical or different radicals.

If used herein, the term "alkylcarbonyl" represents straight-chain or branched alkyl-C(═O) preferably having 2 to 7 carbon atoms such as methylcarbonyl, ethylcarbonyl, n-propylcarbonyl, isopropylcarbonyl, s-butylcarbonyl and t-butylcarbonyl. Preference is also given to alkylcarbonyls having 1 to 4 carbon atoms. Alkylcarbonyls may be substi-tuted by one or more identical or different radicals.

If used herein, the term "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety, for example methoxycarbonyl, ethoxycarbonyl, n-propoxy-carbonyl, isopropoxycarbonyl, s-butoxycarbonyl and t-bu-toxycarbonyl. Alkoxycarbonyl groups may be substituted by one or more identical or different radicals.

If used herein, the term "alkylaminocarbonyl" represents straight-chain or branched alkylaminocarbonyl having pref-erably 1 to 6 carbon atoms or 1 to 4 carbon atoms in the alkyl moiety, for example methylaminocarbonyl, ethylaminocar-bonyl, n-propylaminocarbonyl, isopropylaminocarbonyl, s-butylaminocarbonyl and t-butylaminocarbonyl. Alkylami-nocarbonyl groups may be substituted by one or more identical or different radicals.

If used herein, the term "N,N-dialkylaminocarbonyl" rep-resents straight-chain or branched N,N-dialkylaminocarbo-nyl having preferably 1 to 6 carbon atoms or 1 to 4 carbon atoms in the alkyl moiety, for example N,N-dimethylami-nocarbonyl, N,N-diethylaminocarbonyl, N,N-di(n-propy-lamino)carbonyl, N,N-di(isopropylamino)carbonyl and N,N-di-(s-butylamino)carbonyl. N,N-dialkylaminocarbonyl groups may be substituted by one or more identical or different radicals.

Generally, the term "aryl" represents a mono-, bi- or polycyclic aromatic system having preferably 6 to 14, espe-cially 6 to 10, ring carbon atoms, for example phenyl, naphthyl, anthryl, phenanthrenyl, preferably phenyl. Aryl may also represent polycyclic systems, including fused polycyclic systems, such as tetrahydronaphthyl, indenyl, indanyl, fluorenyl, biphenyl, where the bonding site is on the aromatic system. A fused polycyclic system has at least two fused rings, wherein these two fused rings share two adja-cent atoms (or, iIn other words, the rings share one covalent bond). Preference is given to phenyl. The inventive aryl groups, in particular phenyl groups, may be substituted by one or more identical or different radicals.

According to the invention the term "polycyclic" ring refers to fused, bridged and spirocyclic carbocyclic and heterocyclic rings as well as ring systems linked through single or double bonds.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted, where the bonding site is on a ring atom. Unless defined differently, the heterocyclic ring contains 3 to 12 ring atoms, preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulphur atoms. Non-aromatic heterocycles herein are usually referred to as "saturated or unsaturated heterocycle". When the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo[3.2.1]octanyl, 1-azabicyclo[2.2.1]heptyl, 1-oxa-5-azaspiro[2.3]hexyl or 2,3-dihydro-1H-indole. In the case of optionally substituted heterocyclyl, the invention also embraces spirocyclic systems, for example 1-oxa-5-azaspiro[2.3]hexyl.

Preferred heterocyclyl groups of the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl. Most preferred is oxetanyl, tetrahydropyranyl and piperazinyl.

Of particular significance are heteroaryls, i.e. heteroaromatic systems. According to the invention, the term heteroaryl represents heteroaromatic compounds, i.e. completely unsaturated aromatic heterocyclic compounds which fall under the above definition of heterocycles. For clarification, if the definition of a substituent herein includes "heterocycle" (or "heterocyclyl") as well as "heteroaryl" (or "heteroaromatic") this means that the term "heterocycle" (or "heterocyclyl") does not include "heteroaryl" (or "heteroaromatic") groups in order to avoid an overlap of definitions. Preference is given to 5- to 7-membered rings, more preferably 6- or 6-membered rings, having 1 to 3, preferably 1 or 2, identical or different heteroatoms from the groups above. Inventive heteroaryls are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. Preference is given to pyridinyl, pyrimidinyl, pyrazinyl, pyridazinyl, pyrazolyl, pyrrolyl, thiazolyl, oxazolyl, isothiazolyl, and isoxazolyl. More preferred are pyridinyl, pyrimidinyl, pyrazinyl, pyridazinyl, pyrazolyl, pyrrolyl, and thiazolyl. The inventive heteroaryl groups may also be substituted by one or more identical or different radicals.

The term "in each case optionally substituted" means that a group/substituent, such as a alkyl, alkenyl, alkynyl, alkoxy, alkylthio, alkylsulfinyl, alkylsulfonyl, cycloalkyl, aryl, phenyl, benzyl, heterocyclyl and heteroaryl radical etc., may be substituted, meaning, for example, a substituted radical derived from the unsubstituted base structure, where the substituents, for example, one (1) substituent or a plurality of substituents, preferably 1, 2, 3, 4, 5, 6 or 7, more preferably 1, 2, 3 or 4 substituents, more preferably 1, 2 or 3 substituents, even more preferred 1 or 2 substituents, are independently selected from a group consisting of amino, hydroxyl, halogen, nitro, cyano, isocyano, mercapto, isothiocyanato, $C_1$-$C_4$carboxyl, carbonamide, $SF_5$, aminosulphonyl, $C_1$-$C_4$alkyl, $C_1$-$C_4$haloalkyl $C_3$-$C_4$cycloalkyl, $C_2$-$C_4$alkenyl, $C_5$-$C_6$cycloalkenyl, $C_2$-$C_4$alkynyl, N-mono-$C_1$-$C_4$alkylamino, N,N-di-$C_1$-$C_4$alkylamino, N—$C_1$-$C_4$alkanoylamino, $C_1$-$C_4$alkoxy, $C_1$-$C_4$haloalkoxy, $C_2$-$C_4$alkenyloxy, $C_2$-$C_4$alkynyloxy, $C_3$-$C_4$cycloalkoxy, $C_5$-$C_6$cycloalkenyloxy, $C_1$-$C_4$alkoxycarbonyl, $C_2$-$C_4$alkenyloxycarbonyl, $C_2$-$C_4$alkynyloxycarbonyl, $C_6$-, $C_{10}$-,$C_{14}$-aryloxycarbonyl, $C_1$-$C_4$alkanoyl, $C_2$-$C_4$alkenylcarbonyl, $C_2$-$C_4$alkynylcarbonyl, $C_6$-,$C_{10}$-, $C_{14}$-arylcarbonyl, $C_1$-$C_4$alkylthio, $C_1$-$C_4$haloalkylthio, $C_3$-$C_4$cycloalkylthio, $C_2$-$C_4$alkenylthio, $C_5$-$C_6$cycloalkenylthio, $C_2$-$C_4$alkynylthio, $C_1$-$C_4$alkylsulfinyl, including both enantiomers of the $C_1$-$C_4$alkylsulfinyl group, $C_1$-$C_4$haloalkylsulfinyl, including both enantiomers of the $C_1$-$C_4$haloalkylsulfinyl group, $C_1$-$C_4$alkylsulfonyl, $C_1$-$C_4$haloalkylsulfonyl, N-mono-$C_1$-$C_4$alkylaminosulfonyl, N,N-di-$C_1$-$C_4$alkylaminosulfonyl, $C_1$-$C_4$alkylphosphonyl, $C_1$-$C_4$alkylphosphonyl, including both enantiomers of $C_1$-$C_4$alkylphosphonyl and $C_1$-$C_4$alkylphosphonyl, N—$C_1$-$C_4$alkylaminocarbonyl, N,N-di-$C_1$-$C_4$alkylaminocarbonyl, N—$C_1$-$C_4$alkanoylaminocarbonyl, N—$C_1$-$C_4$alkanoyl-N—$C_1$-$C_4$alkylaminocarbonyl, $C_6$-,$C_{10}$-,$C_{14}$-aryl, $C_6$-,$C_{10}$-,$C_{14}$-aryloxy, benzyl, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl (($C_1$-$C_4$alkyl)$_3$-silyl), substituents bonded via a double bond, such as $C_1$-$C_4$alkylidene (e.g. methylidene or ethylidene), an oxo group, an imino group and a substituted imino group. When two or more radicals form one or more rings, these may be carbocyclic, heterocyclic, saturated, partly saturated, unsaturated, for example including aromatic rings and with further substitution. The substituents mentioned by way of example ("first substituent level") may, if they contain hydrocarbonaceous components, optionally have further substitution therein ("second substituent level"), for example by one or more of the substituents each independently selected from halogen, hydroxyl, $C_1$-$C_6$alkyl, amino, nitro, cyano, isocyano, azido, acylamino, an oxo group and an imino group. The term "(optionally) substituted" group preferably embraces just one or two substituent levels.

The inventive halogen-substituted chemical groups or halogenated groups (for example alkyl, cycloalkyl, alkoxy, alkylthio, alkylsulfinyl, or alkylsulfonyl etc.) are mono- or polysubstituted by halogen up to the maximum possible number of substituents. Such groups are also referred to as halo groups (for example haloalkyl, halocycloalkyl, haloalkoxy, haloalkylthio, haloalkylsulfinyl, or haloalkylsulfonyl etc.). In the case of polysubstitution by halogen, the halogen atoms may be the same or different, and may all be bonded to one carbon atom or may be bonded to a plurality of carbon atoms. Halogen is especially fluorine, chlorine, bromine or iodine, preferably fluorine, chlorine or bromine and more preferably fluorine or chlorine, even more preferred is fluorine. More particularly, halogen-substituted groups are monohalocycloalkyl such as 1-fluorocyclopropyl, 2-fluorocyclopropyl or 1-fluorocyclobutyl, monohaloalkyl such as 2-chloroethyl, 2-fluoroethyl, 1-chloroethyl, 1-fluoroethyl, chloromethyl, or fluoromethyl; perhaloalkyl such as trichloromethyl or trifluoromethyl or $CF_2CF_3$, polyhaloalkyl such as difluoromethyl, 2-fluoro-2-chloroethyl, dichloromethyl, 1,1,2,2-tetrafluoroethyl or 2,2,2-trifluoroethyl. Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2, 2-difluoroethyl, pentafluoroethyl, 3,3,3-trifluoropropyl and pentafluoro-t-butyl. Preference is given to haloalkyls having 1 to 4 carbon atoms and 1 to 9, preferably 1 to 5, identical or different halogen atoms selected from fluorine, chlorine and bromine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoro-ethyl. Further examples of halogen-substituted compounds are haloalkoxy such as $OCF_3$, $OCHF_2$, $OCH_2F$, $OCF_2CF_3$, $OCH_2CF_3$, $OCH_2CHF_2$ and $OCH_2CH_2Cl$; haloalkylsulfa-nyls such as difluoromethylthio, trifluoromethylthio, trichlo-romethylthio, chlorodifluoromethylthio, 1-fluoroethylthio, 2-fluoroethylthio, 2,2-difluoroethylthio, 1,1,2,2-tetrafluoro-ethylthio, 2,2,2-trifluoroethylthio or 2-chloro-1,1,2-trifluo-roethylthio; haloalkylsulfinyls such as difluoromethylsulfi-nyl, trifluoromethylsulfinyl, trichloromethylsulfinyl, chlorodifluoromethylsulfinyl, 1-fluoroethylsulfinyl, 2-fluo-roethylsulfinyl, 2,2-difluoroethylsulfinyl, 1,1,2,2-tetrafluo-roethylsulfinyl, 2,2,2-trifluoroethylsulfinyl and 2-chloro-1,1, 2-trifluoroethylsulfinyl; haloalkylsulfonyl groups such as difluoromethylsulfonyl, trifluoromethylsulfonyl, trichlo-romethylsulfonyl, chlorodifluoromethylsulfonyl, 1-fluoro-ethylsulfonyl, 2-fluoroethylsulfonyl, 2,2-difluoroethylsulfo-nyl, 1,1,2,2-tetrafluoroethylsulfonyl, 2,2,2-trifluoroethylsulfonyl and 2-chloro-1,1,2-trifluoroethylsulfonyl.

The inventive cyano-substituted chemical groups (for example alkyl, cycloalkyl, alkoxy, alkylthio, alkylsulfinyl, or alkylsulfonyl etc.) are preferably monosubstituted by cyano. Such cyano-substituted groups are also referred to as cyano groups (for example cyanoalkyl, cyanocycloalkyl, cyanoalkoxy, cyanoalkylthio, cyanoalkylsulfinyl, cyanoal-kylsufonyl etc.). If the number of carbon atoms is specified in such cyano groups, for example $C_{LL-UL}$cyanoalkyl, the carbon atom of the cyano group will not be counted; e.g. $C_{1-3}$cyanoalkyl includes cyanopropyl groups.

In the case of radicals having carbon atoms, preference is given to those having 1 to 4 carbon atoms, especially 1 or 2 carbon atoms. Preference is generally given to substituents from the group of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine, chlorine, bromine and cyano.

Substituted amino such as mono- or disubstituted amino means a radical from the group of the substituted amino radicals which are N-substituted, for example, by one or two identical or different radicals from the group of alkyl, hydroxy, amino, alkoxy, acyl and aryl; preferably N-mono- and N,N-dialkylamino, (for example methylamino, ethyl-amino, N,N-dimethylamino, N,N-diethylamino, N,N-di-n-propylamino, N,N-diisopropylamino or N,N-dibutylamino), N-mono- or N,N-dialkoxyalkylamino groups (for example N-methoxymethylamino, N-methoxyethylamino, N,N-di (methoxymethyl)amino or N,N-di(methoxyethyl)amino), N-mono- and N,N-diarylamino, such as optionally substi-tuted anilines, acylamino, N,N-diacylamino, N-alkyl-N-ary-lamino, N-alkyl-N-acylamino and also saturated N-hetero-cycles; preference is given here to alkyl radicals having 1 to 4 carbon atoms; here, aryl is preferably phenyl or substituted phenyl; for acyl, the definition given further below applies, preferably $(C_1-C_4)$-alkanoyl. The same applies to substituted hydroxylamino or hydrazino.

Substituted amino also includes quaternary ammonium compounds (salts) having four organic substituents on the nitrogen atom.

Optionally substituted phenyl is preferably phenyl which is unsubstituted or mono- or polysubstituted, preferably up to trisubstituted, by identical or different radicals from the group of halogen, $SF_5$, $(C_1-C_4)$alkyl, $C_3-C_6$cycloalkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, hydroxy-$C_1-C_4$alkyl, $(C_1-C_4)$alkylthio, $(C_1-C_4)$haloalkyl-thio, $(C_1-C_4)$alkylsulfinyl $(C_1-C_4)$haloalkylsulfinyl, $(C_1-C_4)$alkylsulfonyl $(C_1-C_4)$haloalkylsulfonyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and 4-trichloromethylphenyl, 2,4-, 3,5-, 2,5- and 2,3-dichlorophenyl, o-, m- and p-methoxy-phenyl, 4-heptafluorophenyl.

Optionally substituted cycloalkyl is preferably cycloalkyl which is unsubstituted or mono- or polysubstituted, prefer-ably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl and $(C_1-C_4)$haloalkoxy, espe-cially by one or two $(C_1-C_4)$alkyl radicals.

Inventive compounds may occur in preferred embodi-ments. Individual embodiments described herein may be combined with one another. Not included are combinations which contravene the laws of nature and which the person skilled in the art would therefore rule out on the basis of his/her expert knowledge. Ring structures having three or more adjacent oxygen atoms, for example, are excluded.

Isomers

Depending on the nature of the substituents, the com-pounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Prefer-ably excluded herefrom are methods for the surgical or therapeutic treatment of the human or animal body and diagnostic methods carried out on the human or animal body.

The invention furthermore relates to the use of the com-pounds of the formula (I) as pesticides, in particular crop protection agents.

In the context of the present application, the term "pes-ticide" in each case also always comprises the term "crop protection agent".

The compounds of the formula (I), having good plant tolerance, favourable homeotherm toxicity and good envi-ronmental compatibility, are suitable for protecting plants and plant organs against biotic and abiotic stressors, for increasing harvest yields, for improving the quality of the harvested material and for controlling animal pests, espe-cially insects, arachnids, helminths, in particular nematodes, and molluscs, which are encountered in agriculture, in horticulture, in animal husbandry, in aquatic cultures, in forests, in gardens and leisure facilities, in the protection of stored products and of materials, and in the hygiene sector.

Within the context of the present patent application, the term "hygiene" is understood to mean any and all measures, procedures and practices which aim to prevent disease, in particular infectious disease, and which serve to protect the health of humans and animals and/or to protect the environment, and/or which maintain cleanliness. In accordance with the invention, this especially includes measures for cleaning, disinfection and sterilisation of, for example, textiles or hard surfaces, especially surfaces of glass, wood, concrete, porcelain, ceramics, plastic or also of metal(s), and for ensuring that these are kept free of hygiene pests and/or their excretions. Preferably excluded from the scope of the invention in this regard are surgical or therapeutic treatment procedures applicable to the human body or to the bodies of animals and diagnostic procedures which are carried out on the human body or on the bodies of animals.

The term "hygiene sector" thus covers all areas, technical fields and industrial applications in which these hygiene measures, procedures and practices are important, in relation for example to hygiene in kitchens, bakeries, airports, bathrooms, swimming pools, department stores, hotels, hospitals, stables, animal husbandries, etc.

The term "hygiene pest" is therefore understood to mean one or more animal pests whose presence in the hygiene sector is problematic, in particular for health reasons. It is therefore a primary objective to avoid or minimize the presence of hygiene pests, and/or exposure to them, in the hygiene sector. This can be achieved in particular through the application of a pesticide that can be used both to prevent infestation and to tackle an infestation which is already present. Preparations which avoid or reduce exposure to pests can also be used. Hygiene pests include, for example, the organisms mentioned below.

The term "hygiene protection" thus covers all actions to maintain and/or improve these hygiene measures, procedures and practices.

The compounds of the formula (I) can preferably be used as pesticides. They are active against normally sensitive and resistant species and against all or some stages of development. The abovementioned pests include:

pests from the phylum of the Arthropoda, in particular from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli,*

*Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agrilus* spp., for example *Agrilus planipennis, Agrilus coxalis, Agrilus bilineatus, Agrilus anxius, Agriotes* spp., for example *Agriotes linneatus, Agriotes mancus, Alphitobius diaperinus, Amphimallon solstitialis, Anobium punctatum, Anoplophora* spp., for example *Anoplophora glabripennis, Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dendroctonus* spp., for example *Dendroctonus ponderosae, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Limonius ectypus, Lissorhoptrus oryzophilus, Listronotus (=Hyperodes)* spp., *Lixus* spp., *Luperodes* spp., *Luperomorpha xanthodera, Lyctus* spp., *Megacyllene* spp., for example *Megacyllene robiniae, Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., for example *Scolytus multistriatus, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;*
from the order of the Dermaptera, for example *Anisolabis maritime, Forficula auricularia, Labidura riparia;*
from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;*
from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma pini, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni (=Parthenolecanium corni), Lepidosaphes* spp., for example *Lepidosaphes ulmi, Lipaphis erysimi, Lopholeucaspis japonica, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp.,

*Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., for example *P*aratrioza *cockerelli, Parlatoria* spp., *Pemphigus* spp., for example *Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Megacopta cribraria, Miridae, Monalonion atratum, Nezara* spp., for example *Nezara viridula, Nysius* spp., *Oebalus* spp., *Pentomidae, Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Camponotus* spp., *Dolichovespula* spp.,

*Diprion* spp., for example *Diprion similis, Hoplocampa* spp., for example *Hoplocampa cookei, Hoplocampa testudinea, Lasius* spp., *Linepithema* (Iridiomyrmex) *humile, Monomorium pharaonis, Paratrechina* spp., *Paravespula* spp., *Plagiolepis* spp., *Sirex* spp., for example *Sirex noctilio, Solenopsis invicta, Tapinoma* spp., *Technomyrmex albipes, Urocerus* spp., *Vespa* spp., for example *Vespa crabro, Wasmannia auropunctata, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diparopsis* spp., *Diatraea saccharalis, Dioryctria* spp., for example *Dioryctria zimmermani, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., for example *Ostrinia nubilalis, Panolis flammea, Parnara* spp., *Pectinophora* spp., for example *Pectinophora gos-*

*sypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Podesia* spp., for example *Podesia syringae, Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., for example *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp., and also from the class of the Gastropoda, for example *Anion* spp., for example *Anion* ater *rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

plant pests from the phylum of the Nematoda, i.e. phytoparasitic nematodes, in particular *Aglenchus* spp., for example *Aglenchus agricola, Anguina* spp., for example *Anguina tritici, Aphelenchoides* spp., for example *Aphelenchoides arachidis, Aphelenchoides*

*fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hirschmaniella* spp., *Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Paratylenchus* spp., *Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index.*

The compounds of the formula (I) can optionally, at certain concentrations or application rates, also be used as herbicides, safeners, growth regulators or agents to improve plant properties, as microbicides or gametocides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active compounds.

Formulations

The present invention further relates to formulations, compositions and use forms comprising at least one compound of the formula (I) as defined anywhere supra. Such formulations and compositions are in particular prepared as pesticides, for example drench, drip and spray liquors, comprising at least one compound of the formula (I). Such formulations may further comprise at least one further compound selected from auxiliaries, excipients, solvents and/or additional pharmaceutically active agents. In some cases, the formulations or use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are prepared either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), the esters (including fats and oils) and (poly)ethers, the unsubstituted and substituted amines, amides, lactams (such as N-alkypyrrolidones) and lactones, the sulphones and sulphoxides (such as dimethyl sulphoxide), the carbonates and the nitriles.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, carbonates such as propylene carbonate, butylene carbonate, diethyl carbonate or dibutyl carbonate, or nitriles such as acetonitrile or propanenitrile.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, carbonates such as propylene carbonate, butylene carbonate, diethyl carbonate or dibutyl carbonate, nitriles such as acetonitrile or propanenitrile, and also water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam-formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), isethionate derivatives, phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

It is possible to use colorants such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc as further auxiliaries in the formulations and the use forms derived therefrom.

Additional components may be stabilizers, such as low-temperature stabilizers, preservatives, antioxidants, light stabilizers or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001 and 98% by weight of the compound of the formula (I) or, with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms is usually between 0.00000001 and 95% by weight of the compound of the formula (I), preferably between 0.00001 and 1% by weight, based on the weight of the use form. The compounds are employed in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, such active compound combinations may improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used to improve plant properties such as, for example, growth, yield and quality of the harvested material.

In a particular embodiment according to the invention, the compounds of the formula (I) are present in formulations or the use forms prepared from these formulations in a mixture with further compounds, preferably those as described below.

If one of the compounds mentioned below can occur in different tautomeric forms, these forms are also included even if not explicitly mentioned in each case. Further, all named mixing partners can, if their functional groups enable this, optionally form salts with suitable bases or acids.

Insecticides/Acaricides/Nematicides

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides). The classification is based on the current IRAC Mode of Action Classification Scheme at the time of filing of this patent application.

(1) Acetylcholinesterase (AChE) inhibitors, preferably carbamates selected from alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb, or organophosphates selected from acephate, azamethiphos, azinphosethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, preferably cyclodiene-organochlorines selected from chlordane and endosulfan, or phenylpyrazoles (fiproles) selected from ethiprole and fipronil.

(3) Sodium channel modulators, preferably pyrethroids selected from acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, preferably neonicotinoids selected from acetamiprid, clothianidin, dinotefuran, imidacloprid, nitenpyram, thiacloprid and thiamethoxam, or nicotine, or sulfoximines selected from sulfoxaflor, or butenolids selected from flupyradifurone, or mesoionics selected from triflumezopyrim.

(5) Nicotinic acetylcholine receptor (nAChR) allosteric modulators, preferably spinosyns selected from spinetoram and spinosad.

(6) Glutamate-gated chloride channel (GluCl) allosteric modulators, preferably avermectins/milbemycins selected from abamectin, emamectin benzoate, lepimectin and milbemectin.

(7) Juvenile hormone mimics, preferably juvenile hormone analogues selected from hydroprene, kinoprene and methoprene, or fenoxycarb or pyriproxyfen.

(8) Miscellaneous non-specific (multi-site) inhibitors, preferably alkyl halides selected from methyl bromide and other alkyl halides, or chloropicrine or sulphuryl fluoride or borax or tartar emetic or methyl isocyanate generators selected from diazomet and metam.

(9) Chordotonal organ TRPV channel modulators selected from pymetrozine and pyrifluquinazone.

(10) Mite growth inhibitors selected from clofentezine, hexythiazox, diflovidazin and etoxazole.

(11) Microbial disruptors of the insect gut membrane selected from *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis,* and B.t. plant proteins selected from Cry1Ab, Cry1Ac, Cry1Fa, Cry1A.105, Cry2Ab, Vip3A, mCry3A, Cry3Ab, Cry3Bb and Cry34Ab1/35Ab1.

(12) Inhibitors of mitochondrial ATP synthase, preferably ATP disruptors selected from diafenthiuron, or organotin compounds selected from azocyclotin, cyhexatin and fenbutatin oxide, or propargite or tetradifon.

(13) Uncouplers of oxidative phosphorylation via disruption of the proton gradient selected from chlorfenapyr, DNOC and sulfluramid.

(14) Nicotinic acetylcholine receptor channel blockers selected from bensultap, cartap hydrochloride, thiocylam and thiosultap-sodium.

(15) Inhibitors of chitin biosynthesis, type 0, selected from bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1 selected from buprofezin.

(17) Moulting disruptor (in particular for Diptera, i.e. dipterans) selected from cyromazine.

(18) Ecdysone receptor agonists selected from chromafenozide, halofenozide, methoxyfenozide and tebufenozide.

(19) Octopamine receptor agonists selected from amitraz.

(20) Mitochondrial complex III electron transport inhibitors selected from hydramethylnone, acequinocyl and fluacrypyrim.

(21) Mitochondrial complex I electron transport inhibitors, preferably METI acaricides selected from fenazaquin, fenpyroximate, pyrimidifen, pyridaben, tebufenpyrad and tolfenpyrad, or rotenone (Derris).

(22) Voltage-dependent sodium channel blockers selected from indoxacarb and metaflumizone.

(23) Inhibitors of acetyl CoA carboxylase, preferably tetronic and tetramic acid derivatives selected from spirodiclofen, spiromesifen and spirotetramat.

(24) Mitochondrial complex IV electron transport inhibitors, preferably phosphines selected from aluminium phosphide, calcium phosphide, phosphine and zinc phosphide, or cyanides selected from calcium cyanide, potassium cyanide and sodium cyanide.

(25) Mitochondrial complex II electron transport inhibitors, preferably beta-ketonitrile derivatives selected from cyenopyrafen and cyflumetofen, and carboxanilides selected from pyflubumide.

(28) Ryanodine receptor modulators, preferably diamides selected from chlorantraniliprole, cyantraniliprole and flubendiamide.

(29) Chordotonal organ Modulators (with undefined target site) selected from flonicamid.

(30) further active compounds selected from Acynonapyr, Afidopyropen, Afoxolaner, Azadirachtin, Benclothiaz, Benzoximate, Benzpyrimoxan, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, Dimpropyridaz, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Flupyrimin, Fluralaner, Fluxametamide, Fufenozide, Guadipyr, Heptafluthrin, Imidaclothiz, Iprodione, Isocycloseram, kappa-Bifenthrin, kappa-Tefluthrin, Lotilaner, Meperfluthrin, Oxazosulfyl, Paichongding, Pyridalyl, Pyrifluquinazon, Pyriminostrobin, Spirobudiclofen, Spiropidion, Tetramethylfluthrin, Tetraniliprole, Tetrachlorantraniliprole, Tigolaner, Tioxazafen, Thiofluoximate iodomethane; furthermore preparations based on *Bacillus firmus* (1-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1)

(CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl) sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridi-nyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-meth-ylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl) [4-[(trifluoromethyl)thio] phenyl]amino]carbonyl]-indeno[1,2-e][1,3,4]oxadiazine-4a (3H)-carboxylic acid methyl ester (known from CN 102391261 A) (CAS 1370358-69-2); 6-deoxy-3-O-ethyl-2, 4-di-O-methyl-, 1-[N-[4-[1-[4-(1,1,2,2,2-pentafluoroeth-oxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluorom-ethyl-phenoxy)-3-(6-trifluoromethyl-pyridazin-3-yl)-3-aza-bicyclo[3.2.1]octane (CAS 1253850-56-4), (8-anti)-8-(2-cy-clopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methyl-amino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluo-romethyl)phenyl]methoxy]-pyrimidine (known from WO 2013/115391 A1) (CAS 1449021-97-9), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), 4-[(5S)-5-(3,5-Dichloro-4-fluorophenyl)-4,5-dihydro-5-(trifluoromethyl)-3-isoxazolyl]-N-[(4R)-2-ethyl-3-oxo-4-isoxazolidinyl]-2-methyl-benzamide (bekannt aus WO 2011/067272, WO2013/050302) (CAS 1309959-62-3).

Fungicides

The active ingredients specified herein by their Common Name are known and described, for example, in The Pesti-cide Manual (16th Ed. British Crop Protection Council) or can be searched in the internet (e.g. www.alanwood.net/pesticides).

All named fungicidal mixing partners of the classes (1) to (15) can, if their functional groups enable this, optionally form salts with suitable bases or acids. All named mixing partners of the classes (1) to (15) can include tautomeric forms, where applicable.

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) Pyrisoxazole, (1.020) spiroxamine, (1.021) tebu-conazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-tri-azol-1-ylmethyl)-cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyflphenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl] (pyridin-3-yl)methanol, (1.035) (S)-[3-(4-chloro-2-fluorophenyl)-5-(2,4-difluorophenyl)-1,2-oxazol-4-yl] (pyridin-3-yl)methanol, (1.036) [3-(4-chloro-2-fluorophenyl)-5-(2,4-difluorophenyl)-1,2-oxazol-4-yl] (pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl}methyl]-1H-1,2,4-triazol-5-yl thiocyanate, (1.041) 1-{[rel(2R,3S)-3-(2-chlorophenyl)-2-(2,4-difluorophenyl)oxi-ran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hy-droxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2, 4-dihydro-3H-1,2,4-triazole-3-thione, (1.045) 2-[(2R,4S, 5S)-1-(2,4-dichlorophenyl)-5-hydroxy-2,6,6-trimethyl-heptan-4-yl]-2,4-dihydro-3H-1,2,4-triazole-3-thione, (1.046) 2-[(2S,4R,5R)-1-(2,4-dichlorophenyl)-5-hydroxy-2, 6,6-trimethylheptan-4-yl]-2,4-dihydro-3H-1,2,4-triazole-3-thione, (1.047) 2-[(2S,4R,5S)-1-(2,4-dichlorophenyl)-5-hy-droxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyflphenyl]-1-(1H-1,2,4-triazol-1-yl)butan-2-ol, (1.054) 2-[4-(4-chlorophenoxy)-2-(trifluoromethyflphenyl]-1-(1H-1,2,4-triazol-1-yl)pentan-2-ol, (1.055) Mefentrifluconazole, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)-oxiran-2-yl]methyl}-2,4-dihydro-3H-1,2,4-triazole-3-thione, (1.059) 5-(4-chlorobenzyl)-2-(chloro-methyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Ipfentrifluconazole.

2) Inhibitors of the respiratory chain at complex I or II, for example (2.001) benzovindiflupyr, (2.002) bixafen, (2.003)

boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) Fluindapyr, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}-phenyl) ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) isoflucypram, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoro-methyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl) benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carbox-amide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl- 1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide, (2.057) pyrapropoyne.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) mandestrobin, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate, (3.030) metyltetraprole, (3.031) florylpicoxamid.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019)

4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defence, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds capable to act as an uncoupler, for example (14.001) fluazinam, (14.002) meptyldinocap.

15) Further compounds, for example (15.001) Abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) dipymetitrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) Ipflufenoquin, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) quinofumelin, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6- [({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one, (15.063) aminopyrifen.

Biological Pesticides as Mixing Components

The compounds of the formula (I) can be combined with biological pesticides.

Biological pesticides comprise in particular bacteria, fungi, yeasts, plant extracts and products formed by microorganisms, including proteins and secondary metabolites.

Biological pesticides comprise bacteria such as sporeforming bacteria, root-colonising bacteria and bacteria which act as biological insecticides, fungicides or nematicides.

Examples of such bacteria which are employed or can be used as biological pesticides are:

*Bacillus amyloliquefaciens*, strain FZB42 (DSM 231179), or *Bacillus cereus*, in particular *B. cereus* strain CNCM I-1562 or *Bacillus firmus*, strain 1-1582 (Accession number CNCM I-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. kurstaki strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Acession Number NRRL 30232).

Examples of fungi and yeasts which are employed or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, Metarhizium anisopliae, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accesion No. ATCC 20874), *Paecilomyces lilacinus*, in particular *P. lilacinus* strain 251 (AGAL 89/030550), *Talaromyces flavus*, in particular strain V117b, *Trichoderma* atroviride, in particular strain SC1 (Accession Number CBS 122089), *Trichoderma harzianum*, in particular *T. harzianum rifai* T39. (Accession Number CNCM I-952).

Examples of viruses which are employed or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans*, *Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., in particular *Rhizobium trifolii*, *Rhizopogon* spp., *Scleroderma* spp., *Suillus* spp., *Streptomyces* spp.

Examples of plant extracts and products formed by microorganisms including proteins and secondary metabolites which are employed or can be used as biological pesticides are:

*Allium sativum, Artemisia absinthium*, azadirachtin, Bio-keeper WP, *Cassia nigricans, Celastrus angulatus, Chenopodium anthelminticum*, chitin, Armour-Zen, Dryopteris filix-mas, Equisetum *arvense*, Fortune Aza, Fungastop, Heads Up (*Chenopodium quinoa* saponin extract), Pyrethrum/Pyrethrins, *Quassia amara, Quercus, Quillaja, Regalia*, "Requiem™ Insecticide", rotenone, ryania/ryanodine, Symphytum *officinale, Tanacetum vulgare*, thymol, Triact 70, TriCon, *Tropaeulum majus, Urtica dioica, Veratrin, Viscum album, Brassicaceae* extract, in particular oilseed rape powder or mustard powder.

Safener as Mixing Components

The compounds of the formula (I) can be combined with safeners such as, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Here, plants are to be understood to mean all plants and plant parts such as wanted and unwanted wild plants or crop plants (including naturally occurring crop plants), for example cereals (wheat, rice, triticale, barley, rye, oats), maize, soya bean, potato, sugar beet, sugar cane, tomatoes, pepper, cucumber, melon, carrot, watermelon, onion, lettuce, spinach, leek, beans, *Brassica oleracea* (e.g. cabbage) and other vegetable species, cotton, tobacco, oilseed rape, and also fruit plants (with the fruits apples, pears, citrus fruits and grapevines). Crop plants can be plants which can be obtained by conventional breeding and optimization methods or by biotechnological and genetic engineering methods or combinations of these methods, including the transgenic plants and including the plant varieties which can or cannot be protected by varietal property rights. Plants should be understood to mean all developmental stages, such as seeds, seedlings, young (immature) plants up to mature plants. Plant parts should be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested plants or harvested plant parts and vegetative and generative propagation material, for example seedlings, tubers, rhizomes, cuttings and seeds.

Treatment according to the invention of the plants and plant parts with the compounds of the formula (I) is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

Transgenic Plant, Seed Treatment and Integration Events

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), furthermore increased resistance of the plants against phytopathogenic fungi, bacteria and/or viruses owing, for example, to systemic acquired resistance (SAR), systemin, phytoalexins, elicitors and also resistance genes and correspondingly expressed proteins and toxins, and also increased tolerance of the plants to certain herbicidally active compounds, for example imidazolinones, sulphonylureas, glyphosate or phosphinothricin (for example the "PAT" gene). The genes which impart the desired traits in question may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This may be done, for example, by drenching, or by mixing into the soil or the nutrient solution, i.e. the locus of the plant (e.g. soil or hydroponic systems) is impregnated with a liquid form of the compounds of the formula (I), or by soil application, i.e. the compounds of the formula (I) according to the invention are introduced in solid form (e.g. in the form of granules) into the locus of the plants, or by drip application (often also referred to as "chemigation"), i.e. the liquid application of the compounds of the formula (I) according to the invention from surface or sub-surface driplines over a certain period of time together with varying amounts of water at defined locations in the vicinity of the plants. In the case of paddy rice crops, this can also be done by metering the compound of the formula (I) in a solid application form (for example as granules) into a flooded paddy field.

Treatment of Seed

The control of animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is furthermore desirable to optimize the amount of active compound employed in such a way as to provide optimum protection for the seed and the germinating plant from attack by animal pests, but without damaging the plant itself by the active compound employed. In particular, methods for the treatment of seed should also take into consideration the intrinsic insecticidal or nematicidal properties of pest-resistant or -tolerant transgenic plants in order to achieve optimum protection of the seed and also the germinating plant with a minimum of pesticides being employed.

The present invention therefore in particular also relates to a method for the protection of seed and germinating plants, from attack by pests, by treating the seed with one of the compounds of the formula (I). The method according to the invention for protecting seed and germinating plants against attack by pests furthermore comprises a method where the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

Furthermore, the invention relates to seed which has been treated with a compound of the formula (I) according to the invention so as to afford protection from animal pests. The invention also relates to seed which has been treated simultaneously with a compound of the formula (I) and a mixing component. The invention furthermore relates to seed which has been treated at different times with a compound of the formula (I) and a mixing component. In the case of seed which has been treated at different points in time with a compound of the formula (I) and a mixing component, the individual substances may be present on the seed in different layers. Here, the layers comprising a compound of the formula (I) and mixing components may optionally be separated by an intermediate layer. The invention also relates to seed where a compound of the formula (I) and a mixing component have been applied as component of a coating or as a further layer or further layers in addition to a coating.

Furthermore, the invention relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this manner, the immediate treatment of the crop at the time of sowing or shortly thereafter can be dispensed with.

It has to be considered a further advantage that by treatment of the seed with a compound of the formula (I), germination and emergence of the treated seed may be enhanced.

It is likewise to be considered advantageous that compounds of the formula (I) can be used in particular also for transgenic seed.

Furthermore, compounds of the formula (I) can be employed in combination with compositions or compounds of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. In particular, this takes the form of seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, bean, cruciferous vegetables, onions and lettuce, fruit plants, lawns and ornamental plants. The treatment of the seed of cereals (such as wheat, barley, rye and oats), maize, soya beans, cotton, canola, oilseed rape, vegetables and rice is of particular importance.

As already mentioned above, the treatment of transgenic seed with a compound of the formula (I) is also of particular importance. This takes the form of seed of plants which, as a rule, comprise at least one heterologous gene which governs the expression of a polypeptide with in particular insecticidal and/or nematicidal properties. The heterologous genes in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. It is particularly preferably a heterologous gene derived from *Bacillus thuringiensis*.

In the context of the present invention, the compound of the formula (I) is applied to the seed. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water to a certain stage of the rice embryo ('pigeon breast stage'), stimulating the germination and a more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

In general, the compounds of the formula (I) are applied to the seed in a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of agrochemically active compounds. Preference is given to using alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions. Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel", vol. 2, Springer Verlag, 1970, pp. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom by adding water, all mixing units usable customarily for the seed dressing are useful. Specifically, the procedure in the seed dressing is to place the seed into a mixer, operated batch-wise or continously, to add the particular desired amount of seed dressing formulations, either as such or after prior dilution with water, and to mix everything until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. in the field of veterinary medicine, the compounds of the formula (I) are active against animal parasites, in particular ectoparasites or endoparasites. Ectoparasites are typically and preferably arthropods, in particular insects or acarids.

In the field of veterinary medicine the compounds of the formula (I) are suitable, with favourable toxicity in warm blooded animals, for controlling parasites which occur in animal breeding and animal husbandry in livestock, breeding, zoo, laboratory, experimental and domestic animals (companion animals). They are active against all or specific stages of development of the parasites.

Agricultural livestock (farm animals) include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture; or, as the case may be, insects such as bees.

Domestic animals or companion animals include, for example, mammals, such as hamsters, guinea pigs, rats, mice, chinchillas, ferrets or in particular dogs, cats; cage birds; reptiles; amphibians or aquarium fish.

According to a particular embodiment, the compounds of the formula (I) are administered to mammals.

According to another particular embodiment, the compounds of the formula (I) are administered to birds, namely cage birds or in particular poultry.

According to another particular embodiment, the compounds of the formula (I) are administered to farm animals or companion animals, in particular to companion animals such as cats and dogs.

By using the compounds of the formula (I) to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the formula (I) are effective in reducing the incidence of the respective parasite in an animal infected with such parasites to innocuous levels. More specifically, "controlling", as used herein, means that the compounds of the formula (I) are effective in killing the respective parasite, inhibiting its growth, or inhibiting its proliferation.

Exemplary arthropods include, without any limitation from the order of the Anoplurida, for example, *Haematopinus* spp., *Linognathus* spp., *Pediculus* spp., *Phtirus* spp., *Solenopotes* spp.;

from the order of the Mallophagida and the suborders Amblycerina and Ischnocerina, for example *Bovicola* spp., *Damalina* spp., *Felicola* spp., *Lepikentron* spp., *Menopon* spp., *Trichodectes* spp., *Trimenopon* spp., *Trinoton* spp., *Werneckiella* spp.;

from the order of the Diptera and the suborders Nematocerina and Brachycerina, for example *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.

from the order of the Siphonapterida, for example *Ceratophyllus* spp.; *Ctenocephalides* spp., *Pulex* spp., *Tunga* spp., *Xenopsylla* spp.;

from the order of the Heteropterida, for example *Cimex* spp., *Panstrongylus* spp., *Rhodnius* spp., *Triatoma* spp.; as well as nuisance and hygiene pests from the order of the Blattarida.

Further, among the arthropods, the following acari may be mentioned by way of example, without any limitation:

from the subclass of the Acari (Acarina) and the order of the Metastigmata, for example, from the family of argasidae like *Argas* spp., *Ornithodorus* spp., *Otobius* spp., from the family of Ixodidae like *Amblyomma* spp., *Dermacentor* spp., *Haemaphysalis* spp., *Hyalomma* spp., *Ixodes* spp., *Rhipicephalus* (*Boophilus*) spp, *Rhipicephalus* spp. (the original genus of multi host ticks); from the order of mesostigmata like *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

In a particular aspect the compounds of the formula (I) are effective in reducing the incidence of parasites selected from arthropods, more particularly from the subclass of the Acari and insects, in an animal infected with such parasites to innocuous levels.

In the veterinary field and in animal keeping, the administration of the compounds of the formula (I) is carried out by methods generally known in the art, such as enterally, parenterally, dermally or nasally, in the form of suitable preparations Administration can be carried out prophylactically, methaphylactically or therapeutically.

Thus, one embodiment of the present invention refers to the compounds of the formula (I) for use as a medicament.

Another aspect refers to the compounds of the formula (I) for use as an antiendoparasitical agent.

Another aspect refers to the compounds of the formula (I) for use as an antiectoparasitical agent, in particular an arthropodicidal agent, more particular an insecticidal agent or acaricidal agent.

Further aspects of the invention are veterinary formulations, comprising an effective amount of at least one compound of the formula (I) and at least one of the following: pharmaceutically acceptable excipient (e.g. solid or liquid diluents), pharmaceutically acceptable auxiliary (e.g. surfactants), in particular a pharmaceutically acceptable excipient and/or pharmaceutically acceptable auxiliary which is normally used in veterinary formulations.

A related aspect of the invention is a method for preparing a veterinary formulation as described herein, comprising the step of mixing at least one compound of the formula (I) with pharmaceutically acceptable excipients and/or auxiliaries, in particular with pharmaceutically acceptable excipients and/or auxiliaries which are normally used in veterinary formulations.

Another particular aspect of the invention are veterinary formulations, selected from the group of ectoparasiticidal and endoparasiticidal formulations, more particular an arthropodicidal formulations, even more particular selected from the group of nematicidal, platyhelminthicidal, acanthocephalicidal, pentastomicidal, insecticidal, and acaricidal formulations, in accordance with the mentioned aspects, as well as their methods for preparation.

Another aspect refers to a method for treatment of a parasitic infection, in particular an infection by a parasite selected from the group of ectoparasites and endoparasites mentioned herein, by applying an effective amount of a compound of the formula (I) to an animal, in particular a non-human animal, in need thereof.

Another aspect refers to a method for treatment of a parasitic infection, in particular an infection by a parasite selected from the group of ectoparasites and endoparasites mentioned herein, by applying a veterinary formulation as defined herein to an animal, in particular a non-human animal, in need thereof.

Another aspect refers to the use of the compounds of the formula (I) in the treatment of a parasitic infection, in particular an infection by a parasite selected from the group of ectoparasites and endoparasites mentioned herein, in an animal, in particular a non-human animal.

In the present context of the animal health or veterinary field, the term "treatment" includes prophylactic, metaphylactic or therapeutical treatment.

In a particular embodiment, mixtures of at least one compound of the formula (I) with other active ingredients, particularly with endo- and ectoparasiticides, for the veterinary field are provided herewith.

In the field of animal health "mixture" not only means that two (or more) different active ingredients are formulated in a joint formulation and are accordingly applied together but also refers to products which comprise separate formulations for each active compound. Accordingly, if more than two active compounds are to be applied, all active compounds may be formulated in a joint formulation or all active compounds may be formulated in separate formulations; also feasible are mixed forms where some of the active compounds are formulated jointly and some of the active compounds are formulated separately. Separate formulations allow the separate or successive application of the active compounds in question.

The active compounds specified herein by their common names are known and described, for example, in the Pesticide Manual (see above) or can be searched in the internet (e.g. http://www.alanwood.net/pesticides).

Exemplary active ingredients from the group of ectoparasiticides, as mixing partners, include, without limitation insecticides and acaricides listed in detail above. Further active ingredients which may be used are listed below following the aforementioned classification which is based on the current IRAC Mode of Action Classification Scheme: (1) Acetylcholinesterase (AChE) inhibitors; (2) GABA-gated chloride channel blockers; (3) Sodium channel modulators; (4) Nicotinic acetylcholine receptor (nAChR) competitive modulators; (5) Nicotinic acetylcholine receptor (nAChR) allosteric modulators; (6) Glutamate-gated chloride channel (GluCl) allosteric modulators; (7) Juvenile hormone mimics; (8) Miscellaneous non-specific (multisite) inhibitors; (9) Modulators of Chordotonal Organs; (10) Mite growth inhibitors; (12) Inhibitors of mitochondrial ATP synthase, such as, ATP disruptors; (13) Uncouplers of oxidative phosphorylation via disruption of the proton gradient; (14) Nicotinic acetylcholine receptor channel blockers; (15) Inhibitors of chitin biosynthesis, type 0; (16) Inhibitors of chitin biosynthesis, type 1; (17) Moulting disruptor (in particular for Diptera, i.e. dipterans); (18) Ecdysone receptor agonists; (19) Octopamine receptor agonists; (21) Mitochondrial complex I electron transport inhibitors; (25) Mitochondrial complex II electron transport inhibitors; (20) Mitochondrial complex III electron transport inhibitors; (22) Voltage-dependent sodium channel blockers; (23) Inhibitors of acetyl CoA carboxylase; (28) Ryanodine receptor modulators;

Active compounds with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

Compounds from other classes, e.g. butacarb, dimetilan, cloethocarb, phosphocarb, pirimiphos (-ethyl), parathion (-ethyl), methacrifos, isopropyl o-salicylate, trichlorfon, tigolaner, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;

organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

Biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz Bee hive varroa acaricides, for example organic acids, e.g. formic acid, oxalic acid.

Exemplary active ingredients from the group of endoparasiticides, as mixing partners, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;

from the class of imidazothiazoles, for example: butamisole, levamisole, tetramisole;

from the class of aminophenylamidines, for example: amidantel, deacylated amidantel (dAMD), tribendimidine;

from the class of aminoacetonitriles, for example: monepantel;

from the class of paraherquamides, for example: paraherquamide, derquantel;

from the class of salicylanilides, for example: tribromsalan, bromoxanide, brotianide, clioxanide, closantel, niclosamide, oxyclozanide, rafoxanide;

from the class of substituted phenols, for example: nitroxynil, bithionol, disophenol, hexachlorophene, niclofolan, meniclopholan;

from the class of organophosphates, for example: trichlorfon, naphthalofos, dichlorvos/DDVP, crufomate, coumaphos, haloxon;

from the class of piperazinones/quinolines, for example: praziquantel, epsiprantel;

from the class of piperazines, for example: piperazine, hydroxyzine;

from the class of tetracyclines, for example: tetracyclin, chlorotetracycline, doxycyclin, oxytetracyclin, rolitetracyclin;

from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active compounds, including, without limitation, the following active compounds:

from the class of triazines, for example: diclazuril, ponazuril, letrazuril, toltrazuril;

from the class of polylether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis* rossi, *Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named mixing partners can, if their functional groups enable this, optionally form salts with suitable bases or acids.

Vector Control

The compounds of the formula (I) can also be used in vector control. For the purpose of the present invention, a vector is an arthropod, in particular an insect or arachnid, capable of transmitting pathogens such as, for example, viruses, worms, single-cell organisms and bacteria from a reservoir (plant, animal, human, etc.) to a host. The pathogens can be transmitted either mechanically (for example trachoma by non-stinging flies) to a host, or by injection (for example malaria parasites by mosquitoes) into a host.

Examples of vectors and the diseases or pathogens they transmit are:

1) Mosquitoes

Anopheles: malaria, filariasis;

Culex: Japanese encephalitis, other viral diseases, filariasis, transmission of other worms;

Aedes: yellow fever, dengue fever, other viral diseases, filariasis;

Simuliidae: transmission of worms, in particular *Onchocerca volvulus;*

Psychodidae: transmission of leishmaniasis

2) Lice: skin infections, epidemic typhus;

3) Fleas: plague, endemic typhus, cestodes;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borellioses such as *Borrelia burgdorferi* sensu lato., *Borrelia duttoni*, tick-borne encephalitis, Q fever (*Coxiella burnetii*), babesioses (*Babesia canis canis*), ehrlichiosis.

Examples of vectors in the sense of the present invention are insects, for example aphids, flies, leafhoppers or thrips, which are capable of transmitting plant viruses to plants. Other vectors capable of transmitting plant viruses are spider mites, lice, beetles and nematodes.

Further examples of vectors in the sense of the present invention are insects and arachnids such as mosquitoes, in particular of the genera *Aedes, Anopheles*, for example *A. gambiae, A. arabiensis, A. funestus, A. dirus* (malaria) and *Culex*, psychodids such as *Phlebotomus, Lutzomyia*, lice, fleas, flies, mites and ticks capable of transmitting pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protecting wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. Likewise, the compounds of the formula (I), alone or in combinations with other active compounds, can be used as antifouling agents.

Control of Animal Pests in the Hygiene Sector

The compounds of the formula (I) are suitable for controlling animal pests in the hygiene sector. In particular, the invention can be applied in the domestic sector, in the hygiene sector and in the protection of stored products, especially for controlling insects, arachnids, ticks and mites encountered in enclosed spaces such as dwellings, factory halls, offices, vehicle cabins, animal husbandries. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Abbreviations and Symbols

AcOH: acetic acid
aq.: aqueous
BINAP 2,2'-Bis(diphenylphosphino)-1,1'-binaphthyl
br.: broad
d: doublet
dppf 1,1'-Bis(diphenylphosphino)ferrocene
DCC: N,N'-dicyclohexylcarbodiimide
DCM dichloromethane
DIPEA: diisopropylethylamine
DIAD Diisopropylazodicarboxylate
DMF: N,N-dimethylformamide
DMSO: dimethylsulfoxide
ee: enantiomeric excess
eq.: equivalent
ES: electrospray ionization
EtOAc: ethyl acetate
HATU: 1-[bis(dimethylamino)methylene]-1H-1,2,3-triazolo[4,5-b]pyridinium-3-oxid hexafluorophosphate
HOBt: 1-hydroxybenzotriazole hydrate
HPLC: high performance liquid chromatography
iPrOH: isopropanol
J: coupling constant
LCMS: liquid chromatography-mass spectrometry
m/z: mass-to-charge ratio
M: molarity
m: multiplet
MeCN acetonitrile
MeOH: methanol
MTBE tert-butyl methyl ether
NMR: nuclear magnetic resonance
q: quartet
r. t.: room temperature $R_t$: retention time
s: singlet
sat.: saturated
T: temperature
TMP 2,2,6,6-tetramethylpiperidine
t: triplet
T3P®: propylphosphonic anhydride
THF: tetrahydrofuran
wt.: weight
XantPHOS 4,5-Bis(diphenylphosphino)-9,9-dimethylxanthene (CAS RN 161265-03-8)
δ: chemical shift
λ: wavelength Description of the Processes and Intermediates Compounds of formula (I) may be prepared as illustrated in the following scheme 1 where $R^1$, $R^2$, $R^3$, $R^4$, $R^5$, $R^6$ are as previously defined.

Scheme 1

-continued (Ib)

The synthesis starts with a pyrazine of formula (II) which carries residues $R^5$ and $R^6$, as well as one group $X^1$ which can be chlorine, bromine or iodine. These compounds are commercially available or can be made according to methods described in the art. In a first transformation, the hydrogen atom next to $X^1$ is abstracted and replaced by a metal fragment consisting of a main group metal such as Li, Mg, Zn and appropriate ligands L. An example for such a transformation is given by F. Buron, N. Pié, A. Turck, G, Quéguigner, *J. Org. Chem.* 2005, 70, 2616-2621, showing the lithiation of 2-chloropyrazine with Li-TMP (2,2,6,6-tetramethylpiperidyl-lithium base) in THF. Other TMP based reagents are summarized in a review by T. Klatt, J. T. Markiewicz, C. Samann, P. Knochel, *J. Org. Chem.* 2014, 79, 4253-4269. The metalated intermediate (III) is then trapped in situ with an aldehyde (IV) to give the secondary alcohol (V). Metalation and reaction with the aldehyde are typically carried out in one pot in a polar, nonprotic solvent such as THF, diethyl ether, dioxane. The temperature in the metalation step is typically below 0° C., preferably at −78° C. in a dry ice bath. After the addition of the aldehyde, the temperature may be raised to 0° C. or even room temperature. Instead of the one-pot procedure, the organometal intermediate may also be prepared in advance and then be added to a solution of the aldehyde in a suitable nonprotic solvent such as, for instance, THF, ether or toluene.

The subsequent step consists in the replacement of the hydroxy group from intermediate (V) by a fully protected nitrogen resulting in intermediates of formula (VII). $PG^1$ and $PG^2$ may be either two independent protecting groups or may be joined to form one cyclic protecting group. Depending on the respective reaction and the protecting group used the other of $PG^1$ and $PG^2$ may also represent hydrogen. Examples for protecting groups suitable for the protection of amino functionalities can be found in T. W. Greene, P. G. M. Wuts "Protective Groups in Organic Chemistry" 3$^{rd}$ edition, Wiley Interscience, New York 1999, e.g. the Boc-group. Preferentially, the phthalimide protecting group is used. The replacement of the hydroxy group may be carried out either by converting the alcohol into a halogenide by a method known in the art, e.g. Appel reaction, treatment with sulfuryl chloride etc and subsequent nucleophilic substitution by phthalimide, or, preferably, by direct conversion of intermediate (V) with phthalimide in a Mitsunobu reaction with DIAD and triphenylphosphine a in a suitable solvent such as THF at temperature ranging from −40° C. to 100° C., preferentially from 0° C. to room temperature.

Introduction of $R^4$ occurs in the next step using a cross coupling reaction with reagent (VIII) which carries the leaving group $X^2$. $X^2$ may be a trialkyl stannyl residue, a boronic acid, a boronic ester or a metal fragment $M(L_n)$ with a metal such as Ni, Zn, Mg and appropriate ligands L. The cross coupling reaction is typically catalyzed by a transition metal catalyst such as a palladium or copper catalyst with appropriate ligands. A broad survey on cross coupling reactions is available in F. Diederich, A. de Meijere, "Metal catalyzed Cross Coupling Reactions, Second Edition", Wiley Online Library, online ISBN: 9783527619535.

A variation of the cross coupling reaction could be to replace the moiety $X^1$ from intermediate (VII) by a trialkyl trialkyl stannyl residue, a boronic acid, a boronic ester or a metal fragment $M(L_n)$ with a metal such as Ni, Zn, Mg and appropriate ligands L. In this case, intermediate (VIII) would have to carry a group $X^2$ chosen from, for instance, Cl, Br, I, triflate or similar.

Suitable conditions for a coupling of $X^1$=Cl, Br or I and $X^2$=trialkyl stannyl, boronic acid or boronic ester may involve the use of 0.01-0.5 equivalents of a palladium source such as $PdCl_2$(dppf)×DCM, palldium diacetate, tetrakistriphenylphosphine palladium or other compounds together with a ligand. Ligands can be chosen from phosphine ligands or N-heterocyclic carbene ligands, an overview of some ligands is given in R. Martin, S. L. Buchwald, *Acc. Chem. Res.* 2008, 61, 1461-1473.

The product (IX) of the cross coupling reaction has to be deprotected in the next step. In case a phthalimide protecting group is used, this can be achieved by reacting (IX) with hydrazine hydrate in an appropriate solvent such as ethanol at room temperature or above room temperature.

Compounds of formula (I) can be obtained by reacting intermediates (X) with carboxylic acid derivatives (XI) wherein $X^3$ is Cl, O-acyl or OH. In cases where X is Cl or O-acyl, (X) and (XI) are directly reacted in the presence of a base such as, for instance, DIPEA, triethylamine or N-methylmorpholine in a solvent such as DMF, THF or similar. In cases where X is OH, the acid (XI) needs to be activated using a coupling agent such as HATU, TBTU, TCTU, PyBOP etc or, alternatively, converting it into the corresponding acid chloride or an anhydride prior to react it with (X) as described above. The resulting products (Ia) are compounds of the invention where R' is H. In order to achieve compounds with $R^1$ other than hydrogen, an alkylation reaction with alkylating agent (XII) may be used. Examples of leaving groups LG are Cl, Br, I, tosylate, mesylate or triflate groups. The reaction may be carried out by mixing the reagents (Ia) and (XII) together with a base, such as $K_2CO_3$ or DIPEA in a suitable solvent, such as acetonitrile or DMF and letting them react at a temperature in the range 20 to 100° C. Compounds of formula (Ib) may then be isolated and, if necessary and desired, purified using techniques well known in the art, such as chromatography.

If in the compounds (I) $R^4$ is a pyridine-group, then it is preferred that in the Scheme 1 supra $X^1$ is Cl, $X^2$ is Zn—Cl, the Pd-catalyst is a $Pd_2$(dba)$_3$ catalyst and the ligand L is X-Phos.

If in the compounds (I) $R^4$ is a pyrimidine-group, then it is preferred that in the Scheme 1 supra $X^1$ is Cl, $X^2$ is SnBu$_3$, the Pd-catalyst is a $PdCl_2$*2APhos catalyst and ZnCl$_2$ is added as an additive.

If in the compounds (I) $R^4$ is a thiazole-group, then it is preferred that in the Scheme 1 supra $X^1$ is Cl, $X^2$ is SnBu$_3$, the Pd-catalyst is a $PdCl_2$*2PPh$_3$ catalyst and the ligand L is PPh$_3$.

Scheme 2

V

87

-continued

XIII + VI →

IX

In a variant of the above described synthetic pathway, the Mitsunobu reaction and the cross coupling reaction may be applied in inverse order as displayed in Scheme 2. In this case, the introduction of $R^4$ by one of the cross coupling methods described above results in intermediate XIII which is then further converted into intermediate IX by a Mitsunobu reaction as described above. In certain cases, this may give an advantage in terms of yield or practicability. Regarding the meaning of the group $PG^1$ and $PG^2$ reference is made to the definition supra.

In cases where $R^4$ is bound to the pyrazine moiety by a nitrogen atom, $X^1$ of intermediates V and VII is preferentially halogen (in particular Cl, Br or I), and $X^2$ is hydrogen bound to a nitrogen atom within $R^4$. Specifically, this applies to cases where $R^4$ is optionally substituted pyrazole or imidazole. The general strategy for these molecules may follow the order of steps displayed in either Scheme 1 or Scheme 2. Preferentially, the introduction of a pyrazole or imidazole is carried out prior to the introduction of the amine as shown in Scheme 2. The actual cross coupling step is carried out using a metal catalyst, optionally ligands, a base and a solvent. Metal catalysts useful in this step comprise copper(I) and copper(II) salts, preferentially copper(I) halides such as, for instance, copper(I) iodide. The use of a ligand may be beneficial, the choice of a suitable ligand depends on the metal catalyst. In the case of copper(I) salts, 1,2-diamines such as TMEDA or trans-N,N,N',N'-tetramethylcyclohexane-1,2-diamine are used. A catalytic amount of the metal catalyst and the ligand is used, typically in the range of 0.01-0.5 molar equivalents of each of them. As a base, alkali or earth alkali carbonates may be used such as, for instance, calcium carbonate, sodium carbonate, potassium carbonate or cesium carbonate. Solvents include DMF, THF, 1,4-dioxane toluene, chlorobenzene or other organic solvents usually employed for cross coupling reactions. The reaction is performed at room temperature or above, preferrably at 100-120° C.

If $R^4$ is a pyrazole, the preferred conditions for cross coupling comprise using 0.3 equiovalents of copper(I) iodide, 0.3 eqivalents of trans-N,N,N',N'-tetramethylcyclohexane-1,2-diamine, an excess of potassium carbonate in toluene under reflux.

In certain cases, compounds of the invention are accessible via modifications of the substituents in the aftermath of the introduction of $R^4$. These operations can be carried out either in the presence of the $R^2$ moiety or, as an alternative, prior to the introduction of $R^2$ using a suitably protected intermediate according to formula IX (see Scheme I). For instance, an ester group placed on $R^4$ may be saponified by standard methodology. Preferred methods for the saponification of esters comprise lithium hydroxide or sodium hydroxide in a mixture of solvents such as methanol and THF with water at a temperature ranging from room temperature to reflux, or lithium iodide in pyridine at a temperature above 100° C. The resulting carboxylic acid can be converted into carboxamides by the use of coupling agents such as TBTU, HATU, EDCI or other reagents known in the art. Carboxylic esters can also be converted into cyanides using Burgess reagent. Alternatively, carboxylic acids can be converted into amines using a Curtius rearrangement, and the resulting amino group can then be acylated to give a carboxamide linked to $R^4$ via a nitrogen atom by the use of coupling agents such as TBTU, HATU, EDCI or other reagents known in the art.

The processes according to the invention for the preparation of compounds of the formula (I) are preferably performed using a diluent. Useful diluents for performance of the processes according to the invention are, as well as water, all inert solvents. Examples include: halohydrocarbons (for example chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (for example methanol, ethanol, isopropanol, butanol), ethers (for example ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (for example trimethyl-, triethyl-, tripropyl-, tributylamine, N-methylmorpholine, pyridine and tetramethylenediamine), nitrohydrocarbons (for example nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (for example dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (for example pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, benzene, toluene, xylene, esters (for example methyl, ethyl, butyl and isobutyl acetate, dimethyl, dibutyl and ethylene carbonate); amides (for example hexamethylphosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (for example acetone, acetophenone, methyl ethyl ketone, methyl butyl ketone).

It is also possible to perform the process according to the invention in mixtures of the solvents and diluents mentioned.

When performing the process according to the invention, the reaction temperatures can be varied within a relatively wide range. In general, the temperatures employed are between −30° C. and +150° C., preferably between −10° C. and +100° C.

The process according to the invention is generally performed under atmospheric pressure. However, it is also possible to perform the process according to the invention under elevated or reduced pressure—generally at absolute pressures between 0.1 bar and 15 bar.

To perform the process according to the invention, the starting materials are generally used in approximately equimolar amounts. However, it is also possible to use one of the components in a relatively large excess. The reaction is generally carried out in a suitable diluent in the presence of a reaction auxiliary, optionally also under a protective gas atmosphere (for example under nitrogen, argon or helium) and the reaction mixture is generally stirred at the temperature required for several hours. The workup is performed by customary methods (cf. the preparation examples).

The basic reaction auxiliaries used to perform the process according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, 2-picoline, 3-picoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine). The acidic reaction auxiliaries used to perform the process according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

The following Examples further illustrate and describe the invention without limiting it.

Preparation Examples

Analytical Methods
Method 1 (LC-MS)

Instrument: Agilent MS Quad 6150; HPLC: Agilent 1290; column: Waters Acquity UPLC HSS T3 1.8 µm 50×2.1 mm; Eluent A: 1 L water+0.25 mL 99% formic acid, Eluent B: 1 L acetonitrile+0.25 mL 99% formic acid; gradient: 0.0 min 90% A→0.3 min 90% A→1.7 min 5% A→3.0 min 5% A oven temp: 50° C.; flow: 1.20 mL/min; UV-detection: 205-305 nm.
Method 2 (LC-MS)

Instrument MS: Thermo Scientific FT-MS; instrument for UHPLC+: Thermo Scientific UltiMate 3000; column: Waters, HSST3, 2.1×75 mm, C18 1.8 µm; eluent A: 1 L water+0.01% formic acid; eluent B: 1 L acetonitrile+0.01% formic acid; gradient: 0.0 min 10% B→2.5 min 95% B→3.5 min 95% B; oven temp: 50° C.; flow: 0.90 mL/min; UV-Detektion: 210 nm/Optimum Integration Path 210-300 nm
Method 3 (LC-MS)

Instrument: Waters Single Quad MS System; Instrument Waters UPLC Acquity; column: Waters BEH C18 1.7µ 50×2.1 mm; Eluent A: 1 L water+1.0 mL 25% ammonia, Eluent B: 1 L acetonitrile; gradient: 0.0 min 92% A→0.1 min 92% A→1.8 min 5% A→3.5 min 5% A; oven temp: 50° C.; flow: 0.45 mL/min; UV-detection: 210 nm.
Method 4 (LC-MS) Analytical Method E Instrument: SHIMADZU LCMS-UFLC 20-AD-LCMS 2020 MS detector; Column: Ascentis Express C18 2.7 µm, 50×3.0 mm; eluent A: water+0.05 vol % trifluoroacetic acid, eluent B: acetonitrile+0.05 vol % trifluoroacetic acid; gradient: assigned for each compound; flow 1.2 mL/min; temperature: 40° C.; PDA scan: 190-400 nm.
Method 5 (LC-MS) Analytical Method E1

Instrument: SHIMADZU LCMS-UFLC 20-AD-LCMS 2020 MS detector; Column: Ascentis Express C18 2.7 µm, 50×2.1 mm; eluent A: water+0.1 vol % formic acid, eluent B: acetonitrile+0.1 vol % formic acid; gradient: assigned for each compound; flow 1.5 mL/min; temperature: 40° C.; PDA scan: 190-400 nm.
Method 6 (LC-MS) Analytical Method F Instrument: SHIMADZU LCMS-UFLC 20-AD-LCMS 2020 MS detector; Column: Shim-pack XR-ODS, 2.2 µm, 3.0×50 mm; eluent A: water+0.05 vol % trifluoroacetic acid, eluent B: acetonitrile+0.05 vol % trifluoroacetic acid; gradient: assigned for each compound; flow 1.5 mL/min; temperature: 40° C.; PDA scan: 190-400 nm.
Method 7 (chiral HPLC)

Column: Daicel Chiralpak ID, 5 µm 250×4.6 mm; Eluent A: iso-hexane, Eluent B: 2-propanol, isocratic at A:B=1:1, 40° C.; flow: 1.0 mL/min; UV-detection: 220 nm.
Method 8 (Optical Rotation)
Device: Anton Paar Polarimeter MCP200

Specific rotation $[\alpha]$ (depending wavelength, temperature, optical pathway, solvent and concentration).
Method 9 (HPLC-MS)

System MS: Waters TOF instrument; System UPLC: Waters Acquity I-CLASS; Column: Waters Acquity UPLC HSS T3 1.8 µm 50×1 mm; Eluent A: 1 l Water+0.100 ml 99% ige Formic acid, Eluent B: 1 l Acetonitrile+0.100 ml 99% ige Formic acid; Gradient: 0.0 min 90% A→1.2 min 5% A→2.0 min 5% A Oven: 50° C.; Flow: 0.40 ml/min; UV-Detection: 210 nm.
Method 10 (HPLC-MS)

System MS: Waters TOF instrument; System UPLC: Waters Acquity I-CLASS; Column: Waters Acquity UPLC HSS T3 1.8 µm 50×1 mm; Eluent A: 1 l Water+0.100 ml 99% ige Formic acid, Eluent B: 1 l Acetonitrile+0.100 ml 99% ige Formic acid; Gradient: 0.0 min 95% A→6.0 min 5% A→7.5 min 5% A Oven: 50° C.; Flow: 0.35 ml/min; UV-Detection: 210 nm.
Method 11 (HPLC-MS)

Instrument: Waters ACQUITY SQD UPLC System; Column: Waters Acquity UPLC HSS T3 1.8 µm 50×1 mm; Eluent A: 1 l Water+0.25 ml 99% ige Formic acid, Eluent B:

1 l Acetonitrile+0.25 ml 99% ige Formic acid; Gradient: 0.0 min 90% A→1.2 min 5% A→2.0 min 5% A Oven: 50° C.; Flow: 0.40 ml/min; UV-Detection: 210 nm.

General Synthetic Methods

General Synthetic Method 1

Synthesis of MIDA Boronates

MIDA boronates were synthesised according to the method described in the literature: G. R. Dick, D. M. Knapp, E. P. Gillis, M. D. Burke, *Org. Lett.* 2010, 12, 2314-2317.

On a scale of approximately 100 mmol (calculated on the basis of the 2-bromopyridine derivative), the procedure worked as described here. A 2-bromopyridine derivative (1 equivalent) and tripropan-2-yl borate (1.4 equivalents) were dissolved in THF (200 mL) and this solution was cooled to −78° C. n-Butyllithium (2.5 M in hexanes, 1.2 equivalents) was slowly added over 90 min. Stirring at −78° C. was maintained for another 60 min, then the cooling bath was removed and the mixture was left to warm to ambient temperature. In a separate 3-neck round bottom flask with a distillation device and an internal thermometer mounted, a solution of 2,2'-(methylimino)diacetic acid (1.6 equivalents) in DMSO (dried over 3 Å molecular sieves, 150 mL) was heated to 125-130° C. The suspension of the boronate in THF was slowly added over approximately 2 h distilling off the THF and keeping the temperature in a range between 115-125° C. Eventually, the mixture was stirred another 20 min and then left sitting over night. The DMSO was distilled under vacuum and the residue was adsorbed onto diatomaceous earth and chromatographed over 340 g of silica using a ternary gradient of dichloromethane-ethyl acetate and then etyl acetate-THF.

General Synthetic Method 2

Cross-Coupling of MIDA Boronates with Halogenated Pyrazines (rac)-1-(3-bromopyrazin-2-yl)ethan-1-ol (1 equivalent), a MIDA boronate (1.2 equivalents) and diethanolamine (1.0 equivalents) were dissolved in DMF (ca 4 mL/mmol of halogenated pyrazine) under argon. XPhos Pd G2 (0.1 equivalent), copper(II) acetate (0.5 equivalents) and potassium phosphate (3.0 equivalents) were added. The mixture was heated to 110° C. in a single mode microwave reactor. Then it was poured into water and extracted with 3 portions of MTBE. The organic extract was dried over anhydrous sodium sulfate, evaporated and purified by chromatography on silica gel with a gradient of cyclohexane-ethyl acetate to give the title compound.

General Synthetic Method 3

Mitsunobu Reaction

A substituted (pyrazin-2-yl)ethan-1-ol (1 equivalent) was dissolved in THF (ca 3.0 mL/mmol), 1H-isoindole-1,3(2H)-dione (1.50 equivalents) and triphenylphosphine (1.50 equivalents) were added. The mixture was cooled to 0° C., then DIAD (1.50 equivalents) was slowly added and the mixture was left stirring for another 30 min. The solvent was distilled and the crude product was purified by preparative HPLC (RP C-18, water acetonitrile gradient with 0.1% TFA) to give the title compound.

General Synthetic Method 4

Hydrazinolysis of Phthalimide Group

A phthalimide protected amine (1 equivalent) was dissolved in ethanol (ca 10 mL/mmol) and hydrazine hydrate (80% in water, 5 equivalents) was added. The mixture was heated to reflux for 1 h, then poured into water and extracted with 3 portions of dichloromethane. The organic phases were combined, dried over anhydrous sodium sulfate and evaporated. Optionally, the crude product was purified by flash chromatography to give the pure title compound.

General Synthetic Method 5

Amide Coupling

An amine (1.0 equivalents), a carboxylic acid (1.3 equivalents) and DIPEA (3.0 equivalents) were dissolved in DMF (ca 0.17 mmol amine per mL of DMF). The solution was cooled on an ice-water bath to 0° C. and HATU (1.5 equivalents) was added. The cooling bath was removed and mixture was stirred for 30 min. Then water was added. The precipitated product was collected on a filter funnel, dried under vacuum and eventually purified by preparative HPLC (RP-C18, water-acetonitril gradient with 0.1% TFA).

General Synthetic Method 6

Copper Catalysed Coupling of Azoles (rac)-1-(3-Bromopyrazin-2-yl)ethan-1-ol (intermediate 22A, 1 equivalent) was dissolved in toluene (3.0 mL/1.0 mmol of bromopyrazine), an azole (1.5 equivalents), potassium carbonate (2.5 equivalents), copper(I) iodide (0.3 equivalents) and trans-N,N,N',N'-tetramethylcyclohexane-1, 2-diamine (0.3 equivalents) were added. The mixture was heated to reflux for 1 h and then poured into water. It was extracted with three portions of ethyl acetate, the combined organic extracts were washed twice with 20% aqueous ammonia, once with water and eventually once with brine. The organic phase was dried over anhydrous sodium sulfate, evaporated and the residue was purified on silica gel with a gradient of cyclohexane-ethyl acetate. Optionally, the crude product was once more purified by preparative HPLC (RP-C18 column with a water-acetonitrile gradient with 0.1% TFA) to give the title compound.

Synthetic Intermediates

Intermediate 1A (rac)1-(3-Chloropyrazin-2-yl)ethan-1-ol

The reaction was carried out under dry argon, in flame-dried glassware. 2,2,6,6-Tetramethylpiperidine (11 mL, 65 mmol) was dissolved in THF and cooled to −78° C. on an acetone-dry ice bath. n-Butyllithium (2.5 M in hexane, 25 mL, 64 mmol) was added dropwise so that the temperature did not exceed −70° C. Afterwards, stirring was maintained at −78° C. for 30 min. Then, 2-chloropyrazine (5.73 g, 50.0 mmol) was added dropwise and the mixture was stired for 1 h. After this time, acetaldehyde (5.6 mL, 100 mmol) was added and the mixture was allowed to warm to room temperature and stirred for another 4 h. The reaction mixture was poured into water and extracted with ethyl acetate. The organic extract was washed with brine, dried over anhydrous sodium sulfate, filtered and concentrated under vacuum. The crude product was purified by chromatography on silica gel using a gradient of cyclohexane and 0-40% ethyl acetate. 4.60 g (100% purity, 58% yield) of the title compound were obtained.

LC-MS (method 1): $R_f$=0.51 min; low ionization observed.

$^1$H-NMR (400 MHz, DMSO-d$_6$) δ [ppm]: 1.415 (15.85), 1.431 (16.00), 1.989 (0.55), 5.076 (0.46), 5.092 (1.88), 5.108 (2.88), 5.124 (1.97), 5.140 (0.51), 5.399 (4.89), 5.414 (4.45), 8.436 (3.29), 8.442 (3.57), 8.661 (3.47), 8.667 (3.40).

Intermediate 2A (rac)-2-[1-(3-Chloropyrazin-2-yl)ethyl]-1H-isoin-dole-1,3(2)-dione (rac) 1-(3-Chloropyrazin-2-yl)ethan-1-ol (intermediate 1A, 4.60 g, 29.0 mmol) was dissolved in THF (110 mL), 1H-isoindole-1,3(2H)-dione (6.40 g, 43.5 mmol) and triphenylphosphine (11.4 g, 43.5 mmol) were added at room temperature, then the mixture was cooled on an ice bath and DIAD (7.8 mL, 95% purity, 44 mmol) was slowly added. The reaction was allowed to warm to ambient temperature and was stirred for 2 h. The solvent was distilled and the residue was directly charged onto a silica gel column (100 g of silica gel) and chromatographed using a gradient of cyclohexane and 0-35% ethyl acetate. 5.37 g (98% purity, 63% yield) of the title compound were obtained.

LC-MS (method 2): $R_t$=1.69 min; MS (ESIpos): m/z=288 [M+H]$^+$ $^1$H-NMR (600 MHz, DMSO-d$_6$) δ [ppm]: 1.208 (0.56), 1.219 (0.86), 1.231 (0.50), 1.793 (5.84), 1.805 (5.93), 5.696 (0.41), 5.708 (1.33), 5.720 (1.34), 5.731 (0.43), 7.868 (16.00), 8.490 (2.02), 8.494 (2.14), 8.702 (2.31), 8.706 (2.29).

Intermediate 3A (rac)-2-{1-[3-(Pyridin-2-yl)pyrazin-2-yl]ethyl}-1-isoindole-1,3(2H)-dione The reaction was carried out under dry argon, in flame-dried glassware. Preparation of the organozinc reagent (solution A) was carried out as described in M. R. Luzung, J. S. Patel, J. Yin, *J. Org. Chem.* 2010, 75, 8330-8332.

Solution A: A three-neck round-bottom flask with a stirbar was charged with isopropylmagnesium chloride (2.0 M in THF, 2.75 mL, 5.5 mmol). To this mixture was added neat 2-bromopyridine (0.476 mL, 5.0 mmol, 1.0 equiv) dropwise with the temperature not exceeding 30° C. The mixture was stirred at room temperature for 3 h. Then, zinc chloride (1.9 M in THF, 3.16 mL, 6.0 mmol) was added dropwise with the temperature not exceeding 30° C. and stirring was continued at room temperature for another 60 min. This solution was used as is for the subsequent cross coupling reaction.

Solution B: Pd$_2$(dba)$_3$ (18.3 mg, 20.0 μmol) and dicyclohexyl[2',4',6'-tri(propan-2-yl)biphenyl-2-yf]phosphane (XPhos, 38.1 mg, 80.0 μmol) were dissolved in THF (2.0 mL). This mixture was heated to 65° C. for 10 min, then (rac)-2-[1-(3-chloropyrazin-2-yl)ethyl]-1H-isoindole-1,3 (2H)-dione (intermediate 2A, 288 mg, 1.00 mmol) was added and stirring at 65° C. was continued for another 15 min.

Eventually, an aliquot of solution A (2.0 mL, 1.5 mmol) was added at once to solution B and the mixture was stirred at 65° C. for 7 h. Water (3.0 mL) and conc.aqueous sodium hydrogen carbonate (3.0 mL) were added, the mixture was extracted with ethyl acetate, the organic extract was washed with brine, dried over anhydrous sodium sulfate and evaporated. The crude product was purified by preparative HPLC using RP C-18 10 μm material and a gradient of water (+0.1% TFA)-acetonitrile (+0.1% TFA) 90:10->5:95). 219 mg (99% purity, 66% yield) of the title compound were obtained.

LC-MS (method 2): $R_t$=1.51 min; MS (ESIpos): m/z=331 [M+H]$^+$ $^1$H-NMR (600 MHz, DMSO-d$_6$) δ [ppm]: 1.700 (15.91), 1.712 (16.00), 5.747 (3.09), 6.358 (1.15), 6.369 (3.78), 6.381 (3.73), 6.393 (1.13), 7.345 (2.24), 7.358 (2.63), 7.366 (2.41), 7.714 (4.89), 7.719 (5.36), 7.723 (6.03), 7.728 (7.85), 7.735 (1.21), 7.757 (3.00), 7.773 (10.68), 7.778 (6.32), 7.782 (5.81), 7.787 (5.19), 7.796 (2.95), 7.809 (3.67), 7.822 (1.46), 8.542 (3.70), 8.550 (3.71), 8.666 (4.22), 8.669 (8.32), 8.677 (7.99).

Intermediate 4A (rac)-1-[3-(Pyridin-2-yl)pyrazin-2-yl]ethan-1-amine (rac)-2-{1-[3-(Pyridin-2-yl)pyrazin-2-yl]ethyl}-1H-isoin-dole-1,3(2H)-dione (intermediate 3A, 218 mg, 660 μmol) was dissolved in ethanol (3.3 mL), hydrazine hydrate (160 μl, 3.3 mmol) was added and the mixture was heated to reflux for 2 h. The solvent was evaporated, ethyl acetate was added and the mixture was stirred at room temperature for 30 min. The precipitate was filtered off and the filtrate was evaporated. The crude title compound (143 mg (87% purity, 94% yield) was used in the next step without further purification.

LC-MS (method 3): $R_t$=0.92 min; MS (ESIneg): m/z=199 [M−H]−

¹H-NMR (600 MHz, DMSO-d₆) δ[ppm]: 1.035 (0.48), 1.046 (0.48), 1.107 (1.71), 1.177 (0.45), 1.188 (0.44), 1.416 (15.78), 1.428 (16.00), 1.745 (4.66), 2.070 (3.46), 3.078 (0.63), 3.309 (1.12), 3.395 (0.61), 4.898 (0.98), 4.909 (3.05), 4.920 (3.04), 4.931 (1.00), 7.529 (1.82), 7.533 (1.81), 7.537 (1.96), 7.540 (2.67), 7.544 (2.03), 7.548 (1.92), 7.552 (1.89), 8.016 (0.84), 8.019 (0.84), 8.030 (3.14), 8.033 (3.26), 8.041 (7.28), 8.043 (6.99), 8.052 (0.99), 8.709 (6.08), 8.713 (7.38), 8.725 (2.35), 8.727 (3.04), 8.729 (2.35), 8.733 (2.36), 8.735 (3.49), 8.737 (2.14), 8.749 (6.63), 8.753 (5.60).

Intermediate 5A (rac)-2-(1-(3-(Thiazol-2-yl)pyrazin-2-yl)ethyl)isoin-doline-1,3-dione To a solution of (rac)-2-[1-(3-chloropyrazin-2-yl)ethyl]-1H-isoindole-1,3(2)-dione (intermediate 2A, 1.2 g, 4.17 mmol), dichlorobis(triphenylphosphine)palladium(II) (293 mg, 0.42 mmol) in N,N-dimethylformamide (24 mL) was added 2-(tributylstannyl)thiazole (1.9 g, 5.01 mmol) at room temperature under N₂ atmosphere. The resulting mixture was stirred at 85° C. overnight under N₂ atmosphere. After cooled to room temperature, the reaction mixture was poured into water and extracted with ethyl acetate. The organic layers were combined, dried over anhydrous sodium sulfate, filtered and concentrated under vacuum. The residue was purified by silica gel chromatography (ethyl acetate: petroluem ether=1:3) to afford 512 mg (31% purity) of the product as a white solid.

LC-MS (method 6, gradient 0.01-1.50 min 5-100% B): $R_t$=0.873 min; MS (ESIpos): m/z=337 [M+H]+.

Intermediate 6A (rac)-1-(3-(Thiazol-2-yl)pyrazin-2-yl)ethan-1-amine

To a solution of (rac)-2-(1-(3-(thiazol-2-yl)pyrazin-2-yl)ethyl)isoindoline-1,3-dione (intermediate 5A, 520 mg, 0.48 mmol, 31% purity) in ethanol (8 mL) was added hydrazine monohydrate (120 mg, 2.40 mmol). The resulting mixture was stirred at 95° C. for 2 h. After cooled to the room temperature, the solvent was removed in vacuo, ethyl acetate was added and the solution was stirring for 30 min. Then the solid was filtered out, the filtrate was concentrated to give 300 mg of the crude product as a yellow solid.

LC-MS (method 6, gradient 0.01-1.50 min 5-100% B): $R_t$=0.572 min; MS (ESIpos): m/z=207 [M+H]+.

Intermediate 7A 5-tert-Butylnicotinic acid

To a solution of 5-bromonicotinic acid (4.0 g, 19.99 mmol) and copper(I) iodide (380 mg, 2.00 mmol) in tetrahydrofuran (100 mL) was added a solution of tert-butylmagnesium chloride in tetrahydrofuran (1.7 M, 29.4 mL, 50.0 mmol) dropwise at −70° C. under N₂ atmosphere. Then the mixture was stirred overnight at room temperature. The reaction was quenched by careful addition of ammonium chloride solution. The resulting mixture was concentrated and poured into water, then extracted with ethyl acetate. The organic layers were combined, dried over anhydrous sodium sulfate and concentrated. The residue was purified by silica gel chromatography to give 80 mg of desired product as a white solid.

LC-MS (method 4, gradient 0.01-2.50 min 5-100% B): $R_t$=0.718 min; MS (ESIpos): m/z=180 [M+H]+.

Intermediate 8A (rac)-2-(1-(3-(Pyrimidin-2-yl)pyrazin-2-yl)ethyl) isoindoline-1,3-dione To a solution of (rac)-2-[1-(3-Chloropyrazin-2-yl)ethyl]-1H-isoindole-1,3(2)-dione (intermediate 2A, 1.3 g, 4.52 mmol) in N,N-dimethylformamide (39 mL) was added Pd(AMPhos)$_2$Cl$_2$ (CAS RN 887919-35-9, 0.3 g, 0.45 mmol), ZnCl2 (0.6 g, 4.52 mmol) and 2-(tributylstannyl) pyrimidine (2.5 g, 6.78 mmol) under N$_2$ atmosphere. The resulting mixture was stirred overnight at 120° C. After cooled to room temperature, the reaction mixture was poured into water and extracted with ethyl acetate. The organic layers were combined and concentrated under vacuum. The residue was purified by silica gel chromatography (ethyl acetate:petroleum ether=1:5) to afford 600 mg of the product (40% yield) as a white solid.

Intermediate 9A

(rac)-1-(3-(Pyrimidin-2-yl)pyrazin-2-yl)ethan-1-amine

To a solution of rac-2-(1-(3-(pyrimidin-2-yl)pyrazin-2-yl) ethyl)isoindoline-1,3-dione (intermediate 8A, 600 mg, 1.81 mmol) in ethanol (8 mL), was added hydrazine monohydrate (453 mg, 9.05 mmol). The resulting mixture was stirred at 95° C. for 2 h. After cooled to the room temperature, the solvent was removed in vacuo, Ethyl acetate was added and the solution was stirring for 30 min. Then the solid filtered out, the filtrated was concentrated to give 312 mg (85%) of the crude product as a yellow solid.

LC-MS (method 4, gradient 0.01-1.80 min 5-100% B): R$_t$=0.457 min; MS (ESIpos): m/z=202 [M+H]$^+$.

Intermediate 10A

2-(5-Chloropyridin-2-yl)-6-methyl-1,3,6,2-dioxaza-borocane-4,8-dione

According to General Synthetic Method 1, 13.6 g (100% purity, 49% yield) of the title compound were synthesized from 2-bromo-5-chloropyridine (20.0 g, 104 mmol) obtained as crystalline solid.

LC-MS (method 2): R$_t$=0.96 min; MS (ESIpos): m/z=269 [M+H]$^+$ $^1$H-NMR (400 MHz, DMSO-d6) δ[ppm]: 1.106 (16.00), 1.122 (0.51), 2.823 (0.67), 3.077 (4.92), 4.060 (2.24), 4.102 (2.85), 4.376 (2.77), 4.419 (2.18), 7.572 (1.12), 7.592 (1.29), 7.862 (0.88), 7.868 (0.88), 7.882 (0.78), 7.888 (0.77), 8.724 (1.09), 8.729 (1.07).

Other MIDA boronates prepared by General Synthetic Method 1:

Intermediate 11A

6-Methyl-2-[5-(trifluoromethyl)pyridin-2-yl]-1,3,6,2-dioxazaborocane-4,8-dione According to General Synthetic Method 1, 2.56 g (100% purity, 38% yield) of the title compound were synthesized from 2-bromo-5-trifluoromethylpyridine (5.00 g, 22.1 mmol) obtained as crystalline solid.

LC-MS (method 2): R$_t$=1.19 min; MS (ESIpos): m/z=303 [M+H]$^+$ $^1$H-NMR (600 MHz, DMSO-d6) δ[ppm]: 0.871 (0.42), 0.884 (0.42), 1.107 (3.20), 1.121 (1.66), 2.575 (16.00), 2.783 (1.36), 2.800 (0.66), 2.826 (0.55), 2.919 (2.76), 3.078 (0.89), 3.995 (0.46), 4.024 (0.68), 4.103 (5.55), 4.132 (6.70), 4.157 (0.77), 4.167 (1.28), 4.187 (0.57), 4.196 (1.58), 4.342 (1.31), 4.370 (0.96), 4.417 (6.51), 4.445 (5.50), 7.790 (2.61), 7.804 (2.83), 8.142 (2.22), 8.155 (2.13), 9.052 (3.80).

Intermediate 12A

2-(5-Methoxypyridin-2-yl)-6-methyl-1,3,6,2-di-oxazaborocane-4,8-dione

According to General Synthetic Method 1, 3.25 g (95% purity, 22% yield) of the title compound were synthesized from 2-bromo-5-methoxypyridine (10.0 g, 53.2 mmol) obtained as crystalline solid.

LC-MS (method 3): R$_t$=0.88 min; MS (ESIpos): m/z=265 [M+H]$^+$ $^1$H-NMR (600 MHz, DMSO-d6) δ[ppm]: 2.514 (13.24), 2.663 (1.41), 3.823 (16.00), 3.824 (15.35), 3.844 (1.76), 4.032 (4.59), 4.061 (5.40), 4.333 (5.36), 4.362 (4.47), 4.392 (0.52), 4.420 (0.44), 7.305 (1.32), 7.308 (1.37), 7.318 (1.53), 7.322 (1.56), 7.474 (0.57), 7.488 (2.76), 7.502 (2.35), 8.140 (0.56), 8.407 (2.61), 8.411 (2.53).

Intermediate 13A (rac)-1-[3-(5-Chloropyridin-2-yl)pyrazin-2-yl]ethan-1-ol

According to General Synthetic Method 2, 410 mg (96% purity, 17% yield) of the title compound were obtained from (rac)-1-(3-bromopyrazin-2-yl)ethan-1-ol (2.00 g, 9.85 mmol) and 2-(5-chloropyridin-2-yl)-6-methyl-1,3,6,2-dioxazaborocane-4,8-dione (intermediate 10A, 3.31 g, 96% purity, 11.8 mmol).

LC-MS (method 9): $R_t$=0.72 min; MS (ESIpos): m/z=236 [M+H]$^+$ $^1$H-NMR (600 MHz, DMSO-d6) δ[ppm]: 1.439 (5.75), 1.449 (5.77), 3.289 (16.00), 5.164 (1.86), 5.175 (2.20), 5.283 (0.97), 5.294 (1.39), 5.304 (0.88), 8.005 (1.56), 8.019 (1.94), 8.132 (1.18), 8.136 (1.20), 8.146 (0.99), 8.150 (0.99), 8.666 (1.85), 8.670 (2.07), 8.728 (2.02), 8.732 (1.83), 8.771 (1.74), 8.775 (1.72).

Intermediate 14A (rac)-1-{3-[5-(Trifluoromethyl)pyridin-2-yl]pyrazin-2-yl}ethan-1-ol According to General Synthetic Method 2, 736 mg (98% purity, 35% yield) of the title compound were obtained from (rac)-1-(3-bromopyrazin-2-yl)ethan-1-ol (1.55 g, 7.63 mmol) and 6-Methyl-2-[5-(trifluoromethyOpyridin-2-yl]-1,3,6,2-dioxazaborocane-4,8-dione (intermediate 11A, 2.65 g, 8.78 mmol).

LC-MS (method 2): $R_t$=1.46 min; MS (ESIpos): m/z=270 [M+H]$^+$ $^1$H-NMR (600 MHz, DMSO-d6) δ[ppm]: 1.463 (16.00), 1.474 (16.00), 4.337 (0.42), 5.296 (1.07), 5.307 (3.14), 5.318 (3.12), 5.328 (1.05), 8.175 (2.20), 8.189 (2.47), 8.412 (2.79), 8.415 (2.76), 8.426 (2.55), 8.428 (2.50), 8.713 (3.36), 8.780 (3.42), 9.116 (3.28).

Intermediate 15A (rac)-1-[3-(5-Methoxypyridin-2-yl)pyrazin-2-yl]ethan-1-ol

According to General Synthetic Method 2, 480 mg (100% purity, 44% yield) of the title compound were obtained from (rac)-1-(3-bromopyrazin-2-yl)ethan-1-ol (961 mg, 4.73 mmol) and 2-(5-Methoxypyridin-2-yl)-6-methyl-1,3,6,2-dioxazaborocane-4,8-dione (intermediate 12A, 1.50 g, 5.68 mmol).

LC-MS (method 2): $R_t$=1.12 min; MS (ESIpos): m/z=232 [M+H]$^+$ $^1$H-NMR (500 MHz, DMSO-d6) δ[ppm]: 1.434 (6.13), 1.447 (6.14), 3.824 (0.47), 3.927 (16.00), 5.244 (0.96), 5.256 (1.47), 5.269 (0.99), 5.504 (2.39), 5.517 (2.16), 7.614 (1.28), 7.620 (1.29), 7.632 (1.38), 7.638 (1.39), 8.016 (2.04), 8.033 (1.85), 8.439 (1.91), 8.444 (1.84), 8.633 (2.32), 8.638 (3.22), 8.659 (2.97), 8.664 (2.08).

Intermediate 16A (rac)-2-{1-[3-(5-Chloropyridin-2-yl)pyrazin-2-yl]ethyl}-1H-isoindole-1,3(2H)-dione According to General Synthetic Method 3, 458 mg (100% purity, 72% yield) of the title compound were obtained from (rac)-1-[3-(5-chloropyridin-2-yl)pyrazin-2-yl]ethan-1-ol (intermediate 13A, 410 mg, 1.74 mmol).

LC-MS (method 2): $R_t$=1.91 min; MS (ESIpos): m/z=365 [M+H]$^+$ $^1$H-NMR (400 MHz, DMSO-d6) δ[ppm]: 1.171 (0.62), 1.187 (0.72), 1.201 (0.57), 1.217 (0.50), 1.709 (15.98), 1.727 (16.00), 1.739 (0.74), 1.757 (0.48), 2.072 (0.99), 6.275 (1.08), 6.292 (4.05), 6.310 (4.02), 6.327 (1.07), 7.726 (4.85), 7.733 (5.58), 7.740 (4.92), 7.747 (9.26), 7.757 (1.56), 7.778 (2.12), 7.788 (9.71), 7.797 (5.84), 7.801 (9.05), 7.809

(5.73), 7.821 (5.58), 7.830 (0.77), 7.924 (4.64), 7.931 (4.68), 7.946 (3.38), 7.952 (3.50), 8.571 (3.68), 8.577 (3.67), 8.698 (15.93), 8.704 (2.65).

Intermediate 17A

(rac)-2-[1-{3-[5-(Trifluoromethyl)pyridin-2-yl]pyrazin-2-yl}ethyl]-1H-isoindole-1,3(2H)-dione According to General Synthetic Method 3, 897 mg (100% purity, 82% yield) of the title compound were obtained from (rac)-1-{3-[5-(trifluoromethyl)pyridin-2-yl]pyrazin-2-yl}ethan-1-ol (intermediate 14A, 736 mg, 2.73 mmol).

LC-MS (method 2): $R_t$=1.99 min; MS (ESIpos): m/z=399 [M+H]$^+$

Intermediate 18A

(rac)-2-{1-[3-(5-methoxypyridin-2-yl)pyrazin-2-yl]ethyl}-1H-isoindole-1,3(2H)-dione According to General Synthetic Method 3, 325 mg (97% purity, 88% yield) of the title compound were obtained from (rac)-1-[3-(5-methoxypyridin-2-yl)pyrazin-2-yl]ethan-1-ol (intermediate 15A, 230 mg, 1.00 mmol).

LC-MS (method 2): $R_t$=1.65 min; MS (ESIpos): m/z=361 [M+H]$^+$ $^1$H-NMR (600 MHz, DMSO-d6) δ[ppm]: 1.164 (0.74), 1.176 (2.18), 1.188 (2.01), 1.709 (6.41), 1.721 (6.32), 1.988 (1.52), 3.820 (16.00), 6.399 (0.46), 6.411 (1.51), 6.423 (1.49), 6.435 (0.44), 7.399 (1.31), 7.404 (1.33), 7.414 (1.41), 7.419 (1.40), 7.550 (0.84), 7.555 (0.69), 7.562 (0.69), 7.567 (0.58), 7.606 (0.87), 7.611 (0.49), 7.618 (0.69), 7.625 (1.26), 7.639 (0.82), 7.741 (1.97), 7.746 (2.26), 7.750 (2.33), 7.755 (3.40), 7.762 (0.55), 7.781 (0.63), 7.788 (3.47), 7.793 (2.38), 7.797 (2.30), 7.802 (2.07), 7.807 (2.62), 7.822 (2.27), 8.259 (2.29), 8.263 (2.25), 8.588 (2.48), 8.592 (2.89), 8.631 (2.64), 8.635 (2.25).

Intermediate 19A

(rac)-1-[3-(5-Chloropyridin-2-yl)pyrazin-2-yl]ethan-1-amine

According to General Procedure 4, 285 mg (100% purity, 97% yield) of the title compound were obtained from (rac)-2-{1-[3-(5-chloropyridin-2-yl)pyrazin-2-yl]ethyl}-1-isoindole-1,3(2H)-dione (intermediate 16A, 457 mg, 1.25 mmol).

LC-MS (method 2): $R_t$=0.69 min; MS (ESIpos): m/z=235 [M+H]$^+$ $^1$H-NMR (600 MHz, DMSO-d6) δ[ppm]: 1.178 (1.08), 1.188 (1.03), 1.235 (0.56), 1.335 (15.63), 1.346 (16.00), 1.542 (0.57), 1.554 (0.54), 3.239 (2.07), 4.581 (0.99), 7.880 (0.43), 7.995 (9.27), 8.009 (11.43), 8.061 (0.42), 8.070 (0.50), 8.127 (7.67), 8.131 (7.76), 8.141 (6.36), 8.146 (6.35), 8.633 (4.91), 8.667 (0.45), 8.671 (0.50), 8.724 (2.87), 8.769 (10.46), 8.773 (10.19).

Intermediate 20A

(rac)-1-{3-[5-(Trifluoromethyl)pyridin-2-yl]pyrazin-2-yl}ethan-1-amine

According to General Procedure 4, 600 mg (94% purity, 94% yield) of the title compound were obtained from (rac)-2-[1-{3-[5-(trifluoromethyl)pyridin-2-yl]pyrazin-2-yl]ethyl}-1H-isoindole-1,3(2H)-dione (intermediate 17A, 895 mg, 2.25 mmol).

LC-MS (method 2): $R_t$=0.83 min; MS (ESIpos): m/z=269 [M+H]$^+$ $^1$H-NMR (400 MHz, DMSO-d6) δ[ppm]: −0.149 (0.45), 0.146 (0.47), 1.150 (0.53), 1.157 (0.64), 1.174 (1.96), 1.188 (1.70), 1.338 (15.76), 1.355 (16.00), 1.988 (1.27), 2.082 (1.11), 2.710 (0.40), 4.485 (0.83), 4.502 (2.44), 4.518 (2.42), 4.534 (0.82), 8.166 (3.45), 8.187 (4.18), 8.410 (2.44), 8.416 (2.48), 8.431 (2.19), 8.436 (2.21), 8.664 (5.15), 8.669 (5.67), 8.767 (5.57), 8.773 (5.03), 9.121 (3.56), 9.123 (3.60).

Intermediate 21A (rac)-1-[3-(5-Methoxypyridin-2-yl)pyrazin-2-yl]ethan-1-amine According to General Procedure 4, 220 mg (60% purity, 64% yield) of the title compound were obtained from (rac)-2-[1-{3-[5-(methoxy)pyridin-2-yl]pyrazin-2-yl}ethyl]-1H-isoindole-1,3(2H)-dione (intermediate 18A, 325 mg, 0.90 mmol).

LC-MS (method 2): $R_t$=0.60 min; MS (ESIpos): m/z=321 [M+H]$^+$

Intermediate 22A (rac)-1-(3-Bromopyrazin-2-yl)ethan-1-ol

A solution of 2,2,6,6-tetramethylpiperidine (21 mL, 120 mmol) in THF (260 mL) was cooled to −78° C. A solution of n-butyllithium (2.5 M in hexanes, 48 mL, 120 mmol) was slowly added and stirring was maintained for 30 min at −78° C. Then, 2-bromopyrazine (8.5 mL, 94 mmol) was added dropwise keeping the temperature at −70° C. Stirring was continued at −78° C. for one hour. Acetaldehyde (11 mL, 190 mmol) was added dropwise, the cooling bath was removed and the mixture was allowed to slowly warm to room temperature. The reaction mixture was poured into water (500 mL), acidified with 1 M hydrochloric acid and extracted with 6 portions of ethyl acetate. The combined organic extracts were dried over anhydrous sodium sulfate, the solvent was carefully distilled (40° C. bath temperature, 140 mbar) on the rotatory evaporator and eventually purified by flash chromatography on silica gel with a gradient of cyclohexane-ethyl acetateto yield 12.6 g (61% of theory) of the title compound.

LC-MS (method 2): $R_t$=0.81 min; MS (ESIpos): m/z=203 [M+H]$^+$ $^1$H-NMR (600 MHz, DMSO-d6) δ[ppm]: 1.164 (2.79), 1.176 (5.67), 1.187 (2.84), 1.407 (15.63), 1.418 (16.00), 1.907 (0.49), 1.987 (10.52), 4.013 (0.83), 4.025 (2.50), 4.037 (2.49), 4.049 (0.82), 5.076 (0.53), 5.087 (2.14), 5.097

(3.28), 5.108 (2.23), 5.119 (0.58), 5.353 (5.76), 5.363 (5.33), 5.744 (1.31), 8.400 (4.78), 8.404 (4.96), 8.670 (4.87), 8.674 (4.75).

Intermediate 23A (rac)-2-[1-(3-bromopyrazin-2-yl)ethyl]-1H-isoindole-1,3(2H)-dione According to General synthetic method 3, 12.8 g (98% purity, 77% yield) was obtained from (rac)-1-(3-bromopyrazin-2-yl)ethan-1-ol (intermediate 22A, 10.0 g, 49.3 mmol).

LC-MS (method 2): $R_t$=1.75 min; MS (ESIpos): m/z=332 [M+H]$^+$ $^1$H-NMR (600 MHz, DMSO-d6) δ[ppm]: 1.179 (0.88), 1.189 (0.84), 1.786 (5.16), 1.798 (5.17), 5.655 (1.17), 5.667 (1.14), 7.867 (16.00), 8.452 (1.85), 8.457 (1.83), 8.708 (2.09), 8.712 (1.94).

Intermediate 24A (rac)-Methyl 6-{3-[−1-(1,3-dioxo-1,3-dihydro-2H-isoindol-2-yl)ethyl]pyrazin-2-yl}pyridine-3-carboxylate Solution A—chlorido[5-(methoxycarbonyl)pyridin-2-yl] zinc in THF: In a flame-dried 3-neck round bottom flask, methyl 6-iodopyridine-3-carboxylate (1.88 g, 7.15 mmol) was suspended in THF (8.0 mL) and then cooled to −30° C. A solution of isopropylmagnesium chloridexlithium chloride (1.3 M in THF, 7.1 mL, 9.3 mmol) was added dropwise and the mixture was stirred for 5 min. Then, zinc dichloride (4.5 mL, 1.9 M in methyl-THF, 8.6 mmol) was added. This solution was then directly used for the cross coupling reaction.

To this end, (rac)-2-[–(3-bromopyrazin-2-yl)ethyl]-1H-isoindole-1,3(2H)-dione (intermediate 23A, 780 mg, 2.34 mmol) and 1,1-bis(diphenylphosphino)-ferrocenedichloropalladium(II) (192 mg, 234 µmol) were put in two separate microwave reactor vials under argon, solution A was added and the mixture was heated to 110° C. in a single mode microwave device for 90 min. After cooling, the mixture was charged upon silica gel, evaporated and then purified by flash chromatography with a gradient of cyclohexane-ethyl acetate to give 97.0 mg (97% purity, 11% yield) of the title compound.

LC-MS (method 9): $R_f$=0.92 min; MS (ESIpos): m/z=389 [M+H]$^+$ $^1$H-NMR (600 MHz, DMSO-d6) δ[ppm]: 1.719 (4.11), 1.731 (4.05), 2.069 (0.45), 3.289 (16.00), 3.901 (9.08), 3.934 (0.75), 6.306 (1.05), 6.318 (1.04), 7.690 (1.45), 7.696 (1.59), 7.699 (1.63), 7.705 (1.97), 7.764 (2.09), 7.769 (1.71), 7.773 (1.54), 7.778 (1.40), 7.912 (1.49), 7.926 (1.61), 8.247 (0.99), 8.250 (0.93), 8.260 (0.92), 8.264 (0.85), 8.726 (2.04), 8.738 (2.11), 8.742 (1.29), 8.985 (1.57), 8.987 (1.53).

Intermediate 25A (rac)-Methyl 6-{3-[1-aminoethyl]pyrazin-2-yl}pyridine-3-carboxylate According to General synthetic method 4, 115 mg (79% purity, 85% yield) were obtained from (rac)-methyl 6-{3-[1-(1,3-dioxo-1,3-dihydro-2H-isoindol-2-yl)ethyl]pyrazin-2-yl}pyridine-3-carboxylate (intermediate 24A, 160 mg, 412 µmol)

LC-MS (method 2): $R_f$=0.76 min; MS (ESIpos): m/z=259 [M+H]$^+$

Intermediate 26A (rac)-(6-{3-[1-Aminoethyl]pyrazin-2-yl}pyridin-3-yl)(morpholin-4-yl)methanone LC-MS (method 2): $R_f$=0.46 min; MS (ESIpos): m/z=314 [M+H]$^+$

Intermediate 27A (rac)-Methyl 2-{3-[1-(1,3-dioxo-1,3-dihydro-2H-isoindol-2-yl)ethyl]pyrazin-2-yl}-1,3-thiazole-5-carboxylate Solution A: Methyl 2-bromo-1,3-thiazole-5-carboxylate (2.00 g, 9.00 mmol) was dissolved in THF (9.0 mL). The mixture was cooled to –40° C. and isopropylmagnesium chloride×lithium chloride (8.3 mL, 1.3 M in THF, 11 mmol) was added. The temperature was adjusted to –70° C. and a solution of zinc dichloride (5.2 mL, 1.9 M in methyl-THF, 9.9 mmol) was added keeping the temperature in a range between –50 and –70° C. This solution was immediately used in the cross coupling reaction.

(rac)-2-[1-(3-bromopyrazin-2-yl)ethyl]-1H-isoindole-1,3(2H)-dione (intermediate 23A, 950 mg, 2.86 mmol) was dissolved in THF (17.0 mL). 1,1-Bis(diphenylphosphino)-ferrocenedichloropalladium(II): (117 mg, 143 µmol) and solution A were added. The resulting mixture was distributed into 20 mL microwave reactor vials under an argon atmosphere. Each vial was crimp-capped and heated to 120° C. for 2 h in a single mode microwave device. After cooling, the aliquots were combined, diluted with water (20 mL) and conc. aq. sodium hydrogen carbonate (20 mL) and extracted with ethyl acetate. The organic extract was dried over anhydrous sodium sulfate, filtered and evaporated. The crude product was first purified by column chromatography (silica gel, cyclohexane ethyl acetate gradient with 0-35% etyl acetate) and eventually by preparative HPLC (RP-C18 column, water-acetonitril gradient with 0.1% TFA) to give 510 mg (100% purity, 45% yield) of the title compound.

LC-MS (method 2): $R_f$=2.04 min; MS (ESIpos): m/z=395 [M+H]$^+$ $^1$H-NMR (600 MHz, DMSO-d6) δ[ppm]: 1.106 (5.49), 1.892 (4.85), 1.904 (4.85), 3.077 (1.74), 3.886 (10.87), 6.653 (1.27), 6.665 (1.27), 7.839 (16.00), 8.610 (3.63), 8.730 (0.78), 8.735 (5.05), 8.740 (0.86).

Intermediate 28A (rac)-Methyl 2-{3-[1-aminoethyl]pyrazin-2-yl}-1,3-thiazole-5-carboxylate According to General synthetic method 4, (rac)-methyl 2-{3-[1-(1,3-dioxo-1,3-dihydro-2H-isoindol-2-yl)ethyl]pyrazin-2-yl}-1,3-thiazole-5-carboxylate (intermediate 27A, 730 mg, 1.85 mmol) was converted into 300 mg (96% purity, 59% yield) of the title compound.

LC-MS (method 3): $R_t$=1.32 min; MS (ESIpos): m/z=265 [M+H]$^+$ $^1$H-NMR (600 MHz, DMSO-d6) δ[ppm]: 1.164 (0.49), 1.176 (0.98), 1.188 (0.50), 1.345 (7.54), 1.356 (7.35), 1.987 (1.84), 3.895 (16.00), 3.906 (0.60), 4.025 (0.43), 4.037 (0.43), 5.271 (0.52), 5.281 (1.71), 5.292 (1.70), 5.303 (0.52), 8.649 (5.41), 8.653 (3.03), 8.657 (3.10), 8.799 (2.80), 8.803 (2.77).

Intermediate 29A (rac)-Ethyl 1-{3-[1-hydroxyethyl]pyrazin-2-yl}-1H-pyrazole-4-carboxylate (rac)-1-(3-Bromopyrazin-2-yl)ethan-1-ol (intermediate 22A, 500 mg, 2.46 mmol) was dissolved in toluene (5.0 mL), ethyl 1H-pyrazole-4-carboxylate (518 mg, 3.69 mmol), potassium carbonate (851 mg, 6.16 mmol), copper(I) iodide (141 mg, 0.74 mmol) and trans-N,N,N',N'-tetramethylcyclohexane-1,2-diamine (120 µl, 740 µmol) were added. The mixture was heated to reflux for 1 h and then poured into water. It was extracted with three portions of ethyl acetate, the combined organic extracts were washed twice with 20% aqueous ammonia, once with water and eventually once with brine. The organic phase was dried over anhydrous sodium sulfate, evaporated and the residue was purified on silica gel with a gradient of cyclohexane-ethyl acetate. The crude product was once more purified by preparative HPLC (RP-C18 column with a water-acetonitrile gradient with 0.1% TFA) to give 389 mg (100% purity, 60% yield) of the title compound.

LC-MS (method 2): $R_t$=1.34 min; MS (ESIpos): m/z=263 [M+H]$^+$ $^1$H-NMR (600 MHz, DMSO-d6) δ[ppm]: 1.298 (7.89), 1.309 (16.00), 1.321 (7.95), 1.430 (14.41), 1.441 (14.34), 2.073 (1.32), 4.273 (2.53), 4.285 (7.54), 4.297 (7.46), 4.309 (2.39), 5.225 (1.14), 5.235 (3.55), 5.246 (3.47), 5.257 (1.07), 8.247 (7.91), 8.595 (5.44), 8.598 (5.53), 8.830 (5.44), 8.834 (5.22), 8.872 (8.46).

In analogy, the following intermediates were synthesized according to General synthetic method 6:

| Inter-mediate | Structure IUPAC-Name LC-MS (method): Retention time; Mass found $^1$H-NMR |
|---|---|
| 30A | (rac)-1-{3-[4-(Trifluoromethyl)-1H-pyrazol-1-yl]pyrazin-2-yl}ethan-1-ol LC-MS (method 1): $R_t$ = 1.20 min; MS (ESIneg): m/z = 257 [M – H]$^-$ $^1$H-NMR (600 MHz, DMSO-d6) δ [ppm]: 1.440 (15.77), 1.450 (16.00), 5.185 (2.86), 5.196 (6.01), 5.201 (1.32), 5.211 (3.04), 5.221 (3.73), 5.232 (2.15), 5.242 (0.49), 8.332 (7.25), 8.605 (5.25), 8.609 (5.80), 8.850 (5.64), 8.854 (5.72), 9.047 (5.94). |
| 31A | (rac)-1-[3-(4-Chloro-1H-pyrazol-1-yl)pyrazin-2-yl]ethan-1-ol LC-MS (method 2): $R_t$ = 1.36 min; MS (ESIpos): m/z = 225 [M + H]$^+$ $^1$H-NMR (600 MHz, DMSO-d6) δ [ppm]: 1.429 (16.00), 1.440 (15.87), 5.283 (1.18), 5.294 (3.57), 5.304 (3.52), 5.315 (1.12), 8.017 (8.27), 8.552 (6.09), 8.556 (6.31), 8.666 (8.83), 8.776 (5.98), 8.780 (5.81). |
| 32A | (rac)-1-{3-[1-hydroxyethyl]pyrazin-2-yl}-1H-pyrazole-4-carbonitrile LC-MS (method 2): $R_t$ = 0.96 min; MS (ESIpos): m/z = 216 [M + H]$^+$ $^1$H-NMR (600 MHz, DMSO-d6) δ [ppm]: 1.433 (1.56), 1.439 (15.57), 1.450 (16.00), 1.458 (1.17), 5.185 (3.48), 5.188 (3.33), 5.193 (13.48), 5.195 (10.23), 5.201 (4.93), 5.212 (2.31), 5.222 (0.53), 8.456 (12.86), 8.615 (9.05), 8.620 (9.53), 8.866 (9.19), 8.870 (9.10), 9.235 (13.67). |

Intermediate 33A

(rac)-Ethyl 1-{3-[1-(1,3-dioxo-1,3-dihydro-2H-isoindol-2-yl)ethyl]pyrazin-2-yl}-1H-pyrazole-4-carboxylate According to General synthetic method 3, (rac)-Ethyl 1-{3-[1-hydroxyethyl]pyrazin-2-yl}-1H-pyrazole-4-carboxylate (intermediate 29A, 385 mg, 1.47 mmol) was converted into the title compound (500 mg, 100% purity, 87% yield).

LC-MS (method 2): $R_t$=1.91 min; MS (ESIpos): m/z=392 [M+H]$^+$ $^1$H-NMR (600 MHz, DMSO-d6) δ[ppm]: 1.165 (0.45), 1.177 (0.84), 1.189 (0.54), 1.260 (7.86), 1.271 (16.00), 1.283 (7.88), 1.397 (2.89), 1.666 (13.05), 1.678 (12.95), 1.989 (1.24), 4.212 (2.54), 4.224 (7.65), 4.236 (7.48), 4.248 (2.42), 5.747 (0.48), 6.202 (0.98), 6.214 (3.19), 6.226 (3.17), 6.237 (0.93), 7.789 (2.91), 7.795 (3.67), 7.799 (4.33), 7.804 (8.09), 7.811 (3.87), 7.818 (8.03), 7.824 (4.11), 7.827 (3.93), 7.832 (3.07), 8.100 (8.47), 8.633 (4.91), 8.637 (5.10), 8.776 (5.51), 8.780 (5.40), 8.790 (9.02).

According to General synthetic method 3, the following intermediates were obtained:

| Inter-mediate | Structure IUPAC-Name LC-MS (method): Retention time; Mass found $^1$H-NMR |
| --- | --- |
| 34A | (rac)-2-[1-{3-[4-(trifluoromethyl)-1H-pyrazol-1-yl]pyrazin-2-yl}ethyl]-1H-isoindole-1,3(2H)-dione<br>LC-MS (method 2): $R_t$ = 2.04 min; MS (ESIpos): m/z = 388 [M + H]$^+$ 1H-NMR (600 MHz, DMSO-d6) δ [ppm]: 1.681 (16.00), 1.693 (15.90), 1.988 (0.50), 3.256 (0.56), 6.141 (1.15), 6.153 (3.78), 6.164 (3.74), |

-continued

| Inter-mediate | Structure IUPAC-Name LC-MS (method): Retention time; Mass found $^1$H-NMR |
| --- | --- |
|  | 6.176 (1.11), 7.767 (5.04), 7.772 (5.93), 7.776 (6.04), 7.781 (8.59), 7.788 (1.48), 7.806 (1.56), 7.813 (8.88), 7.818 (6.09), 7.822 (5.62), 7.827 (5.03), 8.155 (8.78), 8.656 (6.20), 8.660 (6.21), 8.827 (7.12), 8.831 (6.51), 8.955 (7.09). |
| 35A | (rac)-2-{1-[3-(4-chloro-1H-pyrazol-1-yl)pyrazin-2-yl]ethyl}-1H-isoindole-1,3(2H)-dione<br>LC-MS (method 2): $R_t$ = 1.98 min; MS (ESIpos): m/z = 354 [M + H]$^+$ 1H-NMR (600 MHz, DMSO-d6) δ [ppm]: 1.176 (0.55), 1.398 (16.00), 1.679 (4.56), 1.691 (4.59), 1.987 (1.03), 6.257 (1.13), 6.269 (1.13), 7.801 (1.03), 7.807 (1.49), 7.810 (1.57), 7.812 (1.70), 7.815 (3.26), 7.820 (2.04), 7.826 (3.44), 7.830 (2.10), 7.833 (1.61), 7.835 (1.48), 7.841 (1.10), 7.866 (0.44), 7.900 (2.88), 8.589 (1.81), 8.593 (1.88), 8.606 (2.99), 8.713 (1.98), 8.717 (1.80). |
| 36A | (rac)-1-{3-[1-(1,3-dioxo-1,3-dihydro-2H-isoindol-2-yl)ethyl]pyrazin-2-yl}-1H-pyrazole-4-carbonitrile<br>LC-MS (method 2): $R_t$ = 1.70 min; MS (ESIpos): m/z = 345 [M + H]$^+$ 1H-NMR (500 MHz, DMSO-d6) δ [ppm]: 1.176 (0.82), 1.189 (0.79), 1.677 (8.23), 1.691 (8.17), 2.500 (12.11), 2.504 (16.00), 2.507 (12.46), 6.126 (0.61), 6.140 (2.09), 6.154 (2.06), 6.168 (0.60), 7.796 (2.02), 7.802 (2.59), 7.805 (2.42), 7.807 (2.92), 7.813 (5.22), 7.824 (1.78), 7.832 (5.14), 7.839 (2.72), 7.843 (2.56), 7.849 (1.98), 8.337 (5.84), 8.667 (3.44), 8.672 (3.43), 8.838 (3.73), 8.843 (3.53), 9.207 (6.06). |

<table>
<tr><td>

Intermediate 37A

(rac)-Ethyl 1-{3-[1-aminoethyl]pyrazin-2-yl}-1H-pyrazole-4-carboxylate

According to General synthetic method 4, (rac)-ethyl 1-{3-[1-(1,3-dioxo-1,3-dihydro-2H-isoindol-2-yl)ethyl]pyrazin-2-yl}-1H-pyrazole-4-carboxylate (500 mg, 1.28 mmol) was transformed into 330 mg (96% purity, 95% yield) of the title compound.

LC-MS (method 2): $R_t$=0.76 min; MS (ESIpos): m/z=262 [M+H]$^+$ $^1$H-NMR (600 MHz, DMSO-d6) δ[ppm]: 1.296 (5.40), 1.308 (16.00), 1.321 (13.65), 2.001 (0.56), 4.272 (1.75), 4.283 (5.36), 4.295 (5.41), 4.307 (1.94), 4.396 (0.71), 4.407 (2.18), 4.418 (2.21), 4.429 (0.79), 8.246 (5.19), 8.539 (3.55), 8.543 (3.95), 8.806 (3.51), 8.810 (3.73), 8.853 (5.63).

The following intermediates were synthesized according to General synthetic method 4:

| Inter-mediate | Structure IUPAC-Name LC-MS (method): Retention time; Mass found $^1$H-NMR |
|---|---|
| 38A | <br>(rac)-1-{3-[4-(Trifluoromethyl)-1H-pyrazol-1-yl]pyrazin-2-yl}ethan-1-amine<br>LC-MS (method 3): $R_t$ = 1.38 min; MS (ESIpos):<br>m/z = 258 [M + H]$^+$ $^1$H-NMR (600 MHz, DMSO-d6)<br>δ [ppm]: 1.177 (0.45), 1.324 (16.00), 1.335 (15.73),<br>1.988 (1.56), 1.993 (0.82), 4.366 (1.25), 4.377 (3.82),<br>4.388 (3.74), 4.399 (1.12), 8.337 (7.20), 8.552 (5.99),<br>8.556 (5.99), 8.827 (5.99), 8.831 (5.68), 9.033 (5.90). |
| 39A | <br>(rac)-1-[3-(4-Chloro-1H-pyrazol-1-yl)pyrazin-2-yl]ethan-1-amine<br>LC-MS (method 3): $R_t$ = 1.28 min; MS (ESIpos):<br>m/z = 224 [M + H]$^+$ $^1$H-NMR (600 MHz, DMSO-d6)<br>δ [ppm]: 1.314 (16.00), 1.325 (16.00), 1.964 (1.26), |

</td><td>

-continued

| Inter-mediate | Structure IUPAC-Name LC-MS (method): Retention time; Mass found $^1$H-NMR |
|---|---|
| | 1.987 (0.98), 4.465 (1.19), 4.476 (3.74), 4.487 (3.70),<br>4.498 (1.14), 8.012 (7.88), 8.499 (5.83), 8.503 (6.03),<br>8.642 (8.35), 8.753 (5.80), 8.757 (5.78). |
| 40A | <br>(rac)-1-{3-[1-Aminoethyl]pyrazin-2-yl}-1H-pyrazole-4-carbonitrile<br>LC-MS (method 2): $R_t$ = 0.54 min; MS (ESIpos):<br>m/z = 215 [M + H]$^+$ $^1$H-NMR (600 MHz, DMSO-d6)<br>δ [ppm]: 1.059 (0.41), 1.120 (0.57), 1.155 (0.70),<br>1.179 (4.39), 1.189 (4.09), 1.327 (16.00), 1.338 (15.88),<br>1.747 (0.84), 4.372 (1.19), 4.382 (3.73), 4.394 (3.68),<br>4.405 (1.12), 4.775 (0.48), 7.551 (0.53), 7.556 (0.43),<br>7.563 (0.44), 7.607 (0.56), 7.619 (0.46), 7.626 (0.84),<br>7.640 (0.55), 8.466 (8.22), 8.565 (5.88), 8.569 (6.27),<br>8.842 (6.12), 8.846 (6.34), 9.239 (8.73). |

Intermediate 41A

(rac)-Methyl 2-(3-{1-[(tert-Butoxycarbonyl)amino]ethyl}pyrazin-2-yl)-1,3-thiazole-5-carboxylate (rac)-Methyl 2-{3-[1-Aminoethyl]pyrazin-2-yl}-1,3-thiazole-5-carboxylate (intermediate 28A, 1.40 g, 5.30 mmol) was suspended in THF (30.0 mL), triethylamine (5.9 ml, 42.0 mmol) and di-tert-butyl dicarbonate (4.62 g, 21.2 mmol) were added at room temperature and the mixture was stirred for 1 h. The mixture was poured into water and extracted with three portions of ethyl acetate. The organic phase was dried over sodium sulfate and evaporated. The solid residue was triturated with MTBE, collected on a filter funnel and dried to give a first crop of the title compound 1.30 g (97% purity, 65% yield). The filtrate was evaporated and the residue purified by chromatography on silica gel (cyclohexane-ethyl acetate gradient) to yield a second crop 490 mg (100% purity, 25% yield) of the desired product.

LC-MS (Method 2): $R_t$=2.08 min; MS (ESIpos): m/z=365 [M+H]$^+$ $^1$H-NMR (600 MHz, DMSO-d6) δ[ppm]: 0.940 (1.20), 1.299 (13.37), 1.320 (0.58), 1.332 (0.45), 1.374 (3.69), </td></tr>
</table>

1.385 (3.89), 1.466 (1.76), 3.273 (0.43), 3.897 (16.00), 6.011 (1.33), 6.023 (1.99), 6.035 (1.36), 7.298 (0.73), 7.310 (0.69), 8.669 (7.68), 8.677 (3.66), 8.681 (3.76), 8.790 (1.45).

Intermediate 42A

(+)-Methyl 2-(3-{(1S)-1-[(tert-Butoxycarbonyl) amino]ethyl}pyrazin-2-yl)-1,3-thiazole-5-carboxylate Both crops were combined and submitted to chiral pre-parative HPLC (stationary phase: Daicel Chiralpak IC 5 µm 250×20 mm; mobile phase: n-heptane/ethanol 4:1; flow 25 mL/min.

Isomer 1: 0.75 g (39% of theory)
Analytical chiral HPLC (Method 14): $R_t$=1.80 min.
Isomer 2: 0.73 g (37% of theory)
Analytical chiral HPLC (Method 14): $R_t$=2.48 min.
$[\alpha]_D^{20}$=+92.4° (c=0.37, CHCl$_3$)
Isomer 2 was further processed into the following synthetic steps.

Intermediate 43A

(+)-2-(3-{(1S)-1-[(tert-Butoxycarbonyl)amino] ethyl}pyrazin-2-yl)-1,3-thiazole-5-carboxylic acid (+)-Methyl 2-(3-{(1S)-1-[(tert-Butoxycarbonyl)amino] ethyl}pyrazin-2-yl)-1,3-thiazole-5-carboxylate (intermediate 42A, 730 mg, 2.00 mmol) was dissolved in THF (20.0 mL). Water (5.0 mL) was added, the mixture was cooled to 0° C. and lithium hydroxide (240 mg, 10.0 mmol) was added. The mixture was stirred 105 min at 0° C., then it was diluted with water, acidified with 1M hydrochloric acid to pH 5 and extracted with 5 portions of ethyl acetate. The combined organic extracts were washed with brine, dried over sodium sulfate and evaporated. The residue was dried under vacuum to give 709 mg (100% purity, quant. yield) of the title compound.

$[\alpha]_D^{20}$=+92.3° (c=0.35, CHCl$_3$)

LC-MS (Method 2): $R_t$=1.53 min; MS (ESIpos): m/z=351 [M+H]$^+$ $^1$H-NMR (600 MHz, DMSO-d6) δ[ppm]: 0.954 (1.65), 1.165 (0.95), 1.177 (1.85), 1.188 (0.97), 1.307 (16.00), 1.357 (2.33), 1.375 (4.46), 1.386 (4.67), 1.750 (0.66), 1.756 (0.80), 1.761 (1.77), 1.767 (0.72), 1.772 (0.61), 1.990 (3.32), 3.403 (0.72), 3.592 (1.08), 3.614 (0.99), 4.025 (0.85), 4.037 (0.85), 6.020 (1.51), 6.032 (2.21), 6.044 (1.51), 7.256 (0.94), 7.268 (0.87), 8.435 (2.93), 8.657 (4.83), 8.661 (4.96), 8.750 (1.97).

Intermediate 44A

(+)-tert-Butyl [(1S)-1-(3-{5-[Ethyl(methyl)carbamoyl]-1,3-thiazol-2-yl}pyrazin-2-yl)ethyl]carbamate (+)-2-(3-{(1S)-1-[(tert-Butoxycarbonyl)amino] ethyl}pyrazin-2-yl)-1,3-thiazole-5-carboxylic acid (intermediate 43A, 825 mg, 2.35 mmol) was dissolved in DMF (19.0 mL) and the solution was cooled to 0° C. N-Methyl-ethanamine (300 µl, 3.5 mmol) and DIPEA (1.6 ml, 9.4 mmol) were added followed by HATU (1.79 g, 4.71 mmol), the mixture was allowed to warm to ambient temperature and stirred for 40 min. The mixture was directly charged upon a RP-18 HPLC column and chromatographed (RP C-18 10 µm ACN:water+0.1% TFA 10:90->95:5) to yield 880 mg (100% purity, 95% yield) of the title compound.

$[\alpha]_D^{20}$=+72.6° (c=0.22, CHCl$_3$)

LC-MS (Method 2): $R_t$=1.84 min; MS (ESIpos): m/z=392 [M+H]$^+$ $^1$H-NMR (400 MHz, DMSO-d6) δ[ppm]: 0.952 (1.46), 1.176 (1.74), 1.307 (16.00), 1.380 (5.16), 1.397 (5.30), 3.011 (0.61), 3.218 (0.75), 3.502 (1.77), 3.519 (1.72), 6.022 (1.07), 6.040 (1.66), 6.058 (1.15), 7.282 (0.81), 7.300 (0.77), 8.652 (3.72), 8.658 (4.27), 8.753 (1.91).

Structure
IUPAC-Name
LC-MS (method): Retention time; Mass found
Example ¹H-NMR

Intermediate 45A (+)-tert-Butyl[(1S)-1-(3-{5-[(cis)-2,6-Dimethylmorpholine-4-carbonyl]-1,3-thiazol-2-yl}pyrazin-2-yl)ethyl]carbamate $[\alpha]_D^{20}$ = +77.7° (c = 0.29, CHCl₃)

LC-MS (Method 2): R$_t$ = 1.96 min; MS (ESIpos):
m/z = 448 [M + H]⁺ ¹H-NMR (600 MHz, DMSO-d6)

δ [ppm]: 0.960 (1.38), 1.051 (0.49), 1.061 (0.56), 1.122 (4.84), 1.308 (16.00), 1.389 (4.84), 1.400 (4.92), 2.074 (1.80), 2.087 (0.80), 2.726 (0.63), 2.856 (1.00), 2.864 (1.04), 2.880 (0.95), 2.971 (0.97), 3.603 (1.47), 6.026 (0.86), 6.037 (1.28), 6.049 (0.89), 7.278 (0.92), 7.290 (0.87), 8.346 (6.20), 8.655 (3.29), 8.659 (3.28), 8.754 (1.78).

Intermediate 46A (+)-tert-Butyl[(1S)-1-{3-[5-(Dimethylcarbamoyl)-1,3-thiazol-2-yl]pyrazin-2-yl}ethyl]carbamate $[\alpha]_D^{20}$ = +86.1° (c = 0.35, CHCl₃)

LC-MS (Method 2): R$_t$ = 1.70 min; MS (ESIpos):
m/z = 378 [M + H]⁺ ¹H-NMR (600 MHz, DMSO-d6)

δ [ppm]: 0.957 (1.00), 1.308 (10.95), 1.386 (3.34), 1.397 (3.43), 2.074 (0.53), 2.870 (0.98), 3.042 (1.39), 3.237 (1.23), 3.286 (0.63), 3.315 (16.00), 6.029 (0.75), 6.041 (1.12), 6.053 (0.76), 7.272 (0.62), 7.284 (0.58), 8.391 (4.50), 8.652 (2.42), 8.656 (2.53), 8.750 (1.24).

-continued

Structure
IUPAC-Name
LC-MS (method): Retention time; Mass found
Example ¹H-NMR

Intermediate 47A (+)-2-(3-{(1S)-1-[3,5-Bis(trifluoromethyl)benzamido]ethyl}pyrazin-2-yl)-N-ethyl-1,3-thiazole-5-carboxamide $[\alpha]_D^{20}$ = +100.4° (c = 0.28, CHCl₃)

LC-MS (Method 2): R$_t$ = 2.08 min; MS (ESIpos):
m/z = 518 [M + H]⁺ ¹H-NMR (600 MHz, DMSO-d6)

δ [ppm]: 1.150 (8.59), 1.162 (15.53), 1.174 (8.39), 1.233 (0.97), 1.610 (14.28), 1.621 (14.06), 2.074 (6.47), 6.514 (2.67), 6.526 (3.79), 6.537 (2.62), 8.303 (7.15), 8.529 (16.00), 8.558 (9.56), 8.677 (7.41), 8.744 (7.45), 8.798 (4.56), 9.541 (4.47), 9.553 (4.25).

Intermediate 48A (−)-2-{3-[(1S)-1-Aminoethyl]pyrazin-2-yl}-N-Ethyl-N-methyl-1,3-thiazole-5-carboxamide hydrogen chloride x HCl (+)-tert-Butyl [(1S)-1-(3-{5-[Ethyl(methyl)carbamoyl]-1,3-thiazol-2-yl}pyrazin-2-yl)ethyl]carbamate (intermediate 44A, 875 mg, 2.24 mmol) was dissolved in a solution of hydrogen chloride (4.0 m in 1,4-dioxane, 9.6 mL, 38 mmol) and the mixture was stirred at room temperature for 30 min. Then volatile components were distilled and the residue was dried under vacuum. 729 mg (100% purity, 99% yield) of the title compound were obtained.

$[\alpha]_D^{20}$=−43.8° (c=0.21, water)

LC-MS (Method 2): R$_t$=0.72 min; MS (ESIpos): m/z=292 [M+H]⁺

¹H-NMR (400 MHz, DMSO-d6) δ[ppm]: −0.149 (0.44), 0.146 (0.44), 1.179 (3.64), 1.560 (15.78), 1.576 (16.00), 2.368 (0.52), 2.712 (0.52), 3.014 (1.48), 3.213 (2.00), 3.482 (2.41), 3.500 (7.02), 3.518 (6.88), 3.536 (2.34), 3.568 (2.45), 5.761 (1.73), 5.776 (2.28), 5.791 (1.72), 8.480 (6.02), 8.837 (6.80), 8.843 (9.10), 8.877 (8.80), 8.883 (7.02).

| Example | Structure<br>IUPAC-Name<br>LC-MS (method): Retention time; Mass found<br>$^1$H-NMR |
|---|---|
| Inter-mediate 49A | <br>(rac)-6-{3-[1-(1,3-Dioxo-1,3-dihydro-2H-isoindol-2-yl)ethyl]pyrazin-2-yl}-N,N-diethylpyridine-3-carboxamide<br>MS (ESIpos): m/z = 430 [M + H]$^+$ |
| Inter-mediate 50A | <br>(rac)-6-{3-[1-Aminoethyl]pyrazin-2-yl}-N,N-diethylpyridine-3-carboxamide |
| Inter-mediate 51A | <br>(−)-(2-{3-[(1S)-1-Aminoethyl]pyrazin-2-yl}-1,3-thiazol-5-yl)[(cis)-2,6-dimethylmorpholin-4-yl]methanone hydrogen chloride<br>LC-MS (Method 2): R$_t$ = 0.82 min; MS (ESIpos):<br>m/z = 348 [M + H]$^+$<br>[α]$_D^{20}$ = −15.4° (c = 0.29, CHCl$_3$)<br>$^1$H-NMR (600 MHz, DMSO-d6) δ [ppm]:<br>1.103 (1.52), 1.113 (2.17), 1.121 (2.08), 1.573 (4.70),<br>1.584 (4.55), 2.725 (0.42), 2.859 (0.63), 2.868 (0.63),<br>2.883 (0.59), 2.975 (0.63), 3.568 (16.00), 3.600 (0.68),<br>3.608 (0.76), 5.755 (0.46), 5.765 (0.57), 5.775 (0.43),<br>8.395 (4.58), 8.642 (1.70), 8.832 (2.14), 8.836 (2.44),<br>8.875 (2.46), 8.879 (2.05). |

| Example | Structure<br>IUPAC-Name<br>LC-MS (method): Retention time; Mass found<br>$^1$H-NMR |
|---|---|
| Inter-mediate 52A | <br>(−)-2-{3-[(1S)-1-Aminoethyl]pyrazin-2-yl}-N,N-dimethyl-1,3-thiazole-5-carboxamide<br>hydrogen chloride<br>LC-MS (Method 2): R$_t$ = 0.58 min; MS (ESIpos):<br>m/z = 278 [M + H]$^+$<br>[α]$_D^{20}$ = −45.6° (c = 0.26, water)<br>$^1$H-NMR (600 MHz, DMSO-d6) δ [ppm]:<br>1.566 (16.00), 1.577 (15.78), 2.386 (0.51), 2.425 (1.19),<br>2.580 (0.70), 2.615 (0.59), 2.653 (1.19), 2.871 (2.27),<br>3.044 (5.18), 3.231 (5.26), 3.568 (6.98), 5.766 (2.04),<br>5.776 (2.55), 5.786 (1.89), 8.437 (13.17), 8.543 (6.47),<br>8.833 (6.98), 8.836 (7.82), 8.874 (7.93), 8.878 (6.58). |
| Inter-mediate 53A | <br>(−)-2-{3-[(1S)-1-Aminoethyl]pyrazin-2-yl}-N-ethyl-1,3-thiazole-5-carboxamide hydrogen chloride<br>LC-MS (Method 2): R$_t$ = 0.65 min; MS (ESIpos):<br>m/z = 278 [M + H]$^+$<br>[α]$_D^{20}$ = −43.8° (c = 0.26, water)<br>$^1$H-NMR (600 MHz, DMSO-d6) δ [ppm]:<br>1.143 (7.67), 1.155 (16.00), 1.167 (7.63), 1.554 (11.09),<br>1.565 (10.97), 2.896 (0.67), 3.285 (1.55), 3.297 (4.05),<br>3.306 (5.55), 3.309 (6.28), 3.330 (1.60), 3.391 (0.46),<br>3.464 (0.41), 3.473 (0.40), 3.568 (2.73), 3.668 (0.42),<br>3.711 (0.42), 5.769 (1.10), 8.527 (3.98), 8.642 (7.80),<br>8.834 (5.13), 8.838 (6.14), 8.869 (6.00), 8.873 (4.87),<br>8.951 (1.07), 8.960 (1.96), 8.968 (1.08). |

EXAMPLES

Example I-1

(rac)-3-Chloro-N-{1-[3-(pyridin-2-yl)pyrazin-2-yl]
ethyl}-5-(trifluoromethyl)benzamide (rac)-1-[3-(Pyridin-2-yl)pyrazin-2-yl]ethan-1-amine (intermediate 4A, 66.1 mg, 330 µmol) was dissolved in DMF (3.5 mL), HATU (188 mg, 495 µmol), 3-chloro-5-(trifluoromethyl)benzoic acid (81.5 mg, 363 µmol) and DIPEA (170 µl, 990 µmol) were added and the mixture was stirred at room temperature for 45 min. The reaction mixture was directly charged onto a preparative HPLC and purified using RP C-18 10 µm material and a gradient water (+0.1% TFA)-acetonitrile (+0.1% TFA) 90:10->5:95). 67.0 mg (94% purity, 47% yield) of the title compound were obtained.

LC-MS (method 1): $R_t$=1.37 min; MS (ESIpos): m/z=407 [M+H]$^+$ $^1$H-NMR (400 MHz, DMSO-d6) δ[ppm]: 1.640 (15.92), 1.657 (16.00), 2.328 (0.59), 2.367 (0.88), 2.671 (0.57), 2.711 (0.89), 5.802 (0.55), 5.819 (2.55), 5.837 (3.96), 5.854 (2.52), 5.871 (0.53), 7.488 (2.24), 7.499 (4.50), 7.509 (4.34), 7.521 (2.44), 7.994 (8.18), 7.998 (9.32), 8.007 (8.65), 8.010 (5.11), 8.019 (4.70), 8.070 (5.99), 8.125 (5.81), 8.189 (0.88), 8.645 (7.54), 8.651 (9.96), 8.686 (9.02), 8.692 (6.94), 8.709 (2.63), 8.712 (4.56), 8.715 (2.62), 8.721 (2.72), 8.724 (4.10), 8.727 (2.43), 9.221 (3.27), 9.239 (3.22).

Example I-2

(rac)-N-(1-(3-(Thiazol-2-yl)pyrazin-2-yl)ethyl)-5-
(trifluoromethyl)nicotinamide To a solution of (rac)-1-(3-(thiazol-2-yl)pyrazin-2-yl)ethan-1-amine (intermediate 6A, 100 mg, 0.49 mmol) in N,N-dimethylformamide (8 mL) was added 5-(trifluoromethyl)nicotinic acid (93 mg, 0.49 mmol), HATU (277 mg, 0.73 mmol), and N,N-diisopropylethylamine (188 mg, 1.45 mmol). The resulting mixture was stirred at room temperature overnight. Water was added and the resulting mixture was extracted with ethyl acetate. The combined organic layer was washed with brine and concentrate under vacuum. The residue was purified by Prep-HPLC with the following conditions [Column: Mobile Phase A: Water (10 mmol/L NH$_4$HCO$_3$+0.1% NH$_3$·H$_2$O), Mobile Phase B: ACN; Flow rate: 20 mL/min; Gradient: 60 B to 80 B in 7 min] to give 9.9 mg (98% purity, 5.28% yield) of the product as a white solid.

$^1$H-NMR (400 MHz, DMSO-d$_6$): δ [ppm]=1.60-1.62 (d, 3H), 6.53-6.60 (m, 1H), 8.02-8.03 (d, 1H), 8.16-8.17 (d, 1H), 8.64-8.66 (m, 2H), 8.70-8.71 (d, 1H), 9.12-9.13 (d, 1H), 9.24-9.25 (d, 1H), 9.48-9.50 (d, 1H).

LC-MS (method 4, gradient 0.01-2.00 min 5-100% B, 2.00-2.70 min 100-100% B): $R_t$=1.340 min; MS (ESIpos): m/z=380 [M+H]$^+$.

Example I-3

(rac)-3-Chloro-N-(1-(3-(thiazol-2-yl)pyrazin-2-yl)
ethyl)-5-(trifluoromethyl)benzamide To a solution of (rac)-1-(3-(thiazol-2-yl)pyrazin-2-yl) ethan-1-amine (intermediate 6A, 100 mg, 0.49 mmol) in N,N-dimethylformamide (8 mL) was added 3-chloro-5-(trifluoromethyl)benzoic acid (109 mg, 0.49 mmol), HATU (277 mg, 0.73 mmol), and N,N-diisopropylethylamine (188 mg, 1.45 mmol). The resulting mixture was stirred at room temperature overnight. Water was added and the resulting mixture was extracted with ethyl acetate. The combined organic layer was washed with brine and concentrated under vacuum. The residue was purified by Prep-HPLC with the following conditions [Column: Mobile Phase A: Water (10 mmol/L NH$_4$HCO$_3$+0.1% NH$_3$·H$_2$O), Mobile Phase B: ACN; Flow rate: 20 mL/min; Gradient: 65 B to 95 B in 7 min] to give 16.50 mg (99% purity, 8.2% yield) of the product as a white solid.

$^1$H-NMR (400 MHz, DMSO-d$_6$): δ [ppm]=1.59-1.61 (d, 3H), 6.49-6.56 (m, 1H), 8.02-8.03 (d, 1H), 8.07 (d, 1H), 8.15-8.16 (d, 1H), 8.19 (d, 1H), 8.24 (d, 1H), 8.64-8.66 (d, 1H), 8.69-8.70 (d, 1H), 9.40-9.42 (d, 1H).

LC-MS (method 5, gradient 0.01-2.00 min 5-100% B, 2.00-2.70 min 100-100% B): R$_t$=1.848 min; MS (ESIpos): m/z=413 [M+H]$^+$.

Example I-4

(rac)-3-Fluoro-N-(1-(3-(thiazol-2-yl)pyrazin-2-yl)
ethyl)-5-(trifluoromethyl)benzamide To a solution of (rac)-1-(3-(thiazol-2-yl)pyrazin-2-yl) ethan-1-amine (intermediate 6A, 160 mg, 0.23 mmol) in dichloromethane (8 mL) was added 3-fluoro-5-(trifluoromethyl)benzoyl chloride (58 mg, 0.26 mmol), and triethylamine (71 mg, 0.70 mmol). The resulting mixture was stirred at room temperature overnight. Water was added and the resulting mixture was extracted with ethyl acetate. The combined organic layer was washed with brine and concentrated under vacuum. The residue was purified by Prep-HPLC with the following conditions [Column: Mobile Phase A: Water (0.1% FA), Mobile Phase B: ACN; Flow rate: 60 mL/min; Gradient: 52 B to 69 B in 8 min] to give 17.80 mg (97% purity, 18.7% yield) of the product as a white solid.

$^1$H-NMR (400 MHz, DMSO-d$_6$): δ [ppm]=1.59-1.61 (d, 3H), 6.51-6.55 (m, 1H), 7.90-7.92 (m, 1H), 7.99-8.04 (m, 2H), 8.14-8.16 (m, 2H), 8.64-8.70 (m, 2H), 9.37-9.39 (d, 1H).

LC-MS (method 4, gradient 0.02-3.25 min 5-70% B, 3.25-3.70 min 70-95% B, 3.70-4.10 min 95-95% B): R$_t$=3.086 min; MS (ESIpos): m/z=397 [M+H]$^+$.

Example I-5

(rac)-N-(1-(3-(Thiazol-2-yl)pyrazin-2-yl)ethyl)-3,5-
bis(trifluoromethyl)benzamide To a solution of (rac)-1-(3-(thiazol-2-yl)pyrazin-2-yl)ethan-1-amine (intermediate 6A, 180 mg, 0.26 mmol) in dichloromethane (8 mL) was added 3,5-bis(trifluoromethyl)benzoyl chloride (80 mg, 0.29 mmol), and triethylamine (79 mg, 0.79 mmol). The resulting mixture was stirred at room temperature overnight. Water was added and the resulting mixture was extracted with ethyl acetate. The combined organic layer was washed with brine and concentrated. The residue was purified by Prep-HPLC with the following conditions [Column: Mobile Phase A: Water (10 mmol/L NH$_4$HCO$_3$+0.1% NH$_3$·H$_2$O), Mobile Phase B: ACN; Flow rate: 20 mL/min; Gradient: 65 B to 95 B in 7 min] to give 38.80 mg (96% purity, 31.9% yield) of the product as a white solid.

$^1$H-NMR (400 MHz, DMSO-d$_6$): δ [ppm]=1.61-1.63 (d, 3H), 6.55-6.59 (m, 1H), 8.03-8.04 (d, 1H), 8.16-8.17 (d, 1H), 8.32 (s, 1H), 8.54 (m, 2H), 8.65-8.66 (d, 1H), 8.69-8.70 (d, 1H), 9.57-9.59 (d, 1H).

LC-MS (method 4, gradient 0.01-3.20 min 30-70% B, 3.20-3.50 min 70-95% B, 3.50-4.25 min 95-95% B): R$_t$=2.442 min; MS (ESIpos): m/z=447 [M+H]$^+$.

Example I-6

(rac)-5-(tert-Butyl)-N-(1-(3-(thiazol-2-yl)pyrazin-2-yl)ethyl)nicotinamide

To a solution of 5-tert-butylnicotinic acid (intermediate 7A, 40 mg, 0.22 mmol) in N,N-dimethylformamide (5 mL) was added (rac)-1-(3-(thiazol-2-yl)pyrazin-2-yl)ethan-1-amine (intermediate 6A, 46 mg, 0.22 mmol), HATU (127 mg, 0.34 mmol), and N,N-diisopropylethylamine (87 mg, 0.67 mmol). The resulting mixture was stirred at room temperature for 1 h. Water was added and the resulting mixture was extracted with ethyl acetate. The combined organic layer was washed with brine and concentrated under vacuum. The residue was purified by prep-HPLC with the following conditions [Column: Mobile Phase A: Water (10 mmol/L NH$_4$HCO$_3$+0.1% NH$_3$·H$_2$O), Mobile Phase B: ACN; Flow rate: 20 mL/min; Gradient: 35 B to 80 B in 7 min] to give 17.80 mg (95% purity, 20.6% yield) of the product as a white solid.

$^1$H-NMR (400 MHz, DMSO-d$_6$): δ [ppm]=1.34 (s, 9H), 1.58-1.59 (d, 3H), 6.47-6.53 (m, 1H), 8.00-8.01 (d, 1H), 8.14-8.15 (d, 2H), 8.62-8.63 (d, 1H), 8.67-8.68 (d, 1H), 8.74 (d, 1H), 8.82 (d, 1H), 9.20-9.22 (d, 1H).

LC-MS (method 4, gradient 0.01-3.25 min 5-50% B, 3.25-3.80 min 50-95% B, 3.80-4.20 min 95-95% B): R$_t$=2.269 min; MS (ESIpos): m/z=368 [M+H]$^+$.

Example I-7

(rac)-3-Fluoro-N-(1-(3-(pyrimidin-2-yl)pyrazin-2-yl)ethyl)-5-(trifluoromethyl)benzamide To a solution of (rac)-1-(3-(pyrimidin-2-yl)pyrazin-2-yl)ethan-1-amine (intermediate 9A, 80 mg, 0.40 mmol) in dichloromethane (4 mL) was added 3-fluoro-5-(trifluoromethyl)benzoyl chloride (99 mg, 0.44 mmol), and triethylamine (121 mg, 1.19 mmol). The resulting mixture was stirred at room temperature for 1 h. Water was added and the resulting mixture was extracted with ethyl acetate. The combined organic layer was washed with brine and concentrated under vacuum. The residue was purified by prep-HPLC with the following conditions [Column: Mobile Phase A: Water (10 mmol/L NH$_4$HCO$_3$+0.1% NH$_3$H$_2$O), Mobile Phase B: ACN; Flow rate: 20 mL/min; Gradient: 30 B to 90 B in 7 min] to give 99.20 mg (98% purity, 62.5% yield) of the product as a white solid.

$^1$H-NMR (400 MHz, DMSO-d$_6$): δ [ppm]=1.60-1.62 (d, 3H), 5.59-5.62 (m, 1H), 7.58-7.60 (t, 1H), 7.83-7.88 (t, 2H), 7.95 (s, 1H), 8.69-8.70 (d, 1H), 8.77-8.78 (d, 1H), 8.97-8.98 (d, 2H), 9.16-9.18 (d, 1H).

LC-MS (method 4, gradient 0.01-2.00 min 5-100% B, 2.00-2.70 min 100-100% B): R$_t$=1.284 min; MS (ESIpos): m/z=392 [M+H]$^+$.

Example I-8

(rac)-N-(1-(3-(Pyrimidin-2-yl)pyrazin-2-yl)ethyl)-3,5-bis(trifluoromethyl)benzamide To a solution of (rac)-1-(3-(pyrimidin-2-yl)pyrazin-2-yl)ethan-1-amine (intermediate 9A, 80 mg, 0.40 mmol) in dichloromethane (4 mL) was added 3,5-bis(trifluoromethyl)benzoyl chloride (121 mg, 0.44 mmol), and triethylamine (121 mg, 1.19 mmol). The resulting mixture was stirred at room temperature for 1 h. Water was added and the resulting mixture was extracted with dichloromethane. The combined organic layer was washed with brine and concentrated under vacuum. The residue was purified by prep-HPLC with the following conditions [Column: Mobile Phase A: Water (10 mmol/L $NH_4HCO_3$+0.1% $NH_3 \cdot H_2O$), Mobile Phase B: ACN; Flow rate: 20 mL/min; Gradient: 32 B to 95 B in 7 min] to give 105.90 mg (98% purity, 59% yield) of the product as a white solid.

$^1$H-NMR (400 MHz, DMSO-d$_6$): δ [ppm]=1.63-1.64 (d, 3H), 5.62-5.65 (m, 1H), 7.57-7.60 (t, 1H), 8.29 (s, 1H), 8.36 (d, 2H), 8.70-8.71 (d, 1H), 8.78-8.79 (d, 1H), 8.96-8.98 (d, 2H), 9.36-9.37 (d, 1H).

LC-MS (method 4, gradient 0.01-2.00 min 5-100% B, 2.00-2.70 min 100-100% B): R$_t$=1.425 min; MS (ESIpos): m/z=442 [M+H]$^+$.

Example I-9

(rac)-N-(1-(3-(Pyrimidin-2-yl)pyrazin-2-yl)ethyl)-5-(trifluoromethyl)nicotinamide To a solution of (rac)-1-(3-(pyrimidin-2-yl)pyrazin-2-yl)ethan-1-amine (intermediate 9A, 80 mg, 0.40 mmol) in dichloromethane (4 mL), was added 5-(trifluoromethyl)nicotinoyl chloride (92 mg, 0.44 mmol), and triethylamine (453 mg, 1.19 mmol). The resulting mixture was stirred at room temperature for 1 h. Water was added and the resulting mixture was extracted with dichloromethane. The combined organic layer was washed with brine and concentrated under vacuum. The residue was purified by Prep-HPLC with the following conditions [Column: Mobile Phase A: Water (10 mmol/L $NH_4HCO_3$+0.1% $NH_3 \cdot H_2O$), Mobile Phase B: ACN; Flow rate: 20 mL/min; Gradient: 20 B to 70 B in 7 min] to give 98.10 mg (98% purity, 64.6% yield) of the product as an off-white solid.

$^1$H-NMR (400 MHz, DMSO-d$_6$): δ [ppm]=1.61-1.63 (d, 3H), 5.60-5.67 (m, 1H), 7.59-7.61 (t, 1H), 8.46 (m, 1H), 8.70-8.71 (d, 1H), 8.78-8.79 (d, 1H), 8.98-9.00 (d, 2H), 9.09-9.11 (m, 2H), 9.27-9.29 (d, 1H).

LC-MS (method 5, gradient 0.01-2.00 min 5-100% B, 2.00-2.70 min 100-100% B): R$_t$=1.173 min; MS (ESIpos): m/z=375 [M+H]$^+$.

Example I-10

(rac)-3-Chloro-N-(1-(3-(pyrimidin-2-yl)pyrazin-2-yl)ethyl)-5-(trifluoromethyl)benzamide To a solution of (rac)-1-(3-(pyrimidin-2-yl)pyrazin-2-yl)ethan-1-amine (intermediate 9A, 80 mg, 0.40 mmol) in dichloromethane (4 mL), was added 3-chloro-5-(trifluoromethyl)benzoyl chloride (106 mg, 0.44 mmol), and triethylamine (121 mg, 1.19 mmol). The resulting mixture was stirred at room temperature for 1 h. Water was added and the resulting mixture was extracted with dichloromethane. The combined organic layer was washed with brine and concentrated under vacuum. The residue was purified by Prep-HPLC with the following conditions [Column: Mobile Phase A: Water (10 mmol/L $NH_4HCO_3$+0.1% $NH_3H_2O$), Mobile Phase B: ACN; Flow rate: 20 mL/min; Gradient: 40 B to 60 B in 7 min] to give 114.2 mg (99% purity, 69.7% yield) of the product as a white solid.

$^1$H-NMR (400 MHz, DMSO-d$_6$): δ [ppm]=1.60-1.61 (d, 3H), 5.59-5.62 (m, 1H), 7.58-7.60 (t, 1H), 8.01-8.06 (m, 3H), 8.69-8.70 (d, 1H), 8.77-8.78 (d, 1H), 8.96-9.00 (m, 2H), 9.19-9.20 (d, 1H).

LC-MS (method 4, gradient 0.01-2.00 min 5-100% B, 2.00-2.70 min 100-100% B): R$_t$=1.384 min; MS (ESIpos): m/z=408 [M+H]$^+$.

Example I-11

(rac)-5-(tert-Butyl)-N-(1-(3-(pyrimidin-2-yl)pyrazin-2-yl)ethyl)nicotinamide

To a solution of 5-tert-butylnicotinic acid (40 mg, 0.22 mmol) in N,N-dimethylformamide (5 mL), was added (rac)-1-(3-(pyrimidin-2-yl)pyrazin-2-yl)ethan-1-amine (intermediate 9A, 45 mg, 0.22 mmol), HATU (127 mg, 0.34 mmol), and N,N-diisopropylethylamine (87 mg, 0.67 mmol). The resulting mixture was stirred at room temperature for 1 h. Water was added and the resulting mixture was extracted with dichloromethane. The combined organic layer was washed with brine and concentrated under vacuum. The residue was purified by Prep-HPLC with the following conditions [Column: Mobile Phase A: Water (10 mmol/L NH$_4$HCO$_3$+0.1% NH$_3$·H$_2$O), Mobile Phase B: ACN; Flow rate: 25 mL/min; Gradient: 20 B to 35 B in 7 min] to give 17.70 mg (95% purity, 20.8% yield) of the product as a light yellow solid.

$^1$H-NMR (400 MHz, DMSO-d$_6$): δ [ppm]=1.29-1.31 (s, 9H), 1.60-1.62 (d, 3H), 5.56-5.63 (m, 1H), 7.55-7.58 (t, 1H), 7.97-7.98 (t, 1H), 8.66-8.72 (m, 3H), 8.77-8.78 (d, 1H), 8.96-8.98 (m, 3H).

LC-MS (method 4, gradient 0.01-2.00 min 5-100% B, 2.00-2.70 min 100-100% B): R$_t$=0.900 min; MS (ESIpos): m/z=363 [M+H]$^+$.

The following examples were synthesized in analogy to example I-1 starting from intermediate 4A:

| Example | Structure | NMR Peaklist[1] | LC-MS[1] |
|---|---|---|---|
| I-12 | | $^1$H-NMR (600 MHz, DMSO-d$_6$) δ [ppm]: 1.628 (16.00), 1.639 (16.00), 3.319 (0.49), 5.805 (0.61), 5.817 (2.63), 5.828 (4.05), 5.840 (2.60), 5.851 (0.60), 7.487 (1.94), 7.494 (4.63), 7.502 (4.48), 7.509 (2.10), 7.684 (5.27), 7.711 (4.91), 7.925 (7.21), 7.992 (8.61), 7.998 (8.38), 8.641 (6.67), 8.645 (8.01), 8.680 (7.84), 8.684 (6.47), 8.708 (4.04), 8.716 (3.93), 9.100 (3.24), 9.112 (3.21). | LC-MS (method 2): R$_t$ = 2.08 min; MS (ESIpos): m/z = 423 [M + H]$^+$ |
| I-13 | | $^1$H-NMR (600 MHz, DMSO-d$_6$) δ [ppm]: 1.235 (0.50), 1.667 (15.87), 1.678 (16.00), 3.315 (1.19), 5.746 (6.08), 5.856 (0.60), 5.868 (2.60), 5.879 (4.01), 5.891 (2.63), 5.902 (0.66), 7.485 (2.07), 7.493 (3.34), 7.499 (3.89), 7.508 (2.27), 7.977 (0.52), 7.991 (4.70), 7.994 (7.58), 8.000 (9.65), 8.001 (8.52), 8.250 (5.93), 8.417 (13.98), 8.650 (7.04), 8.654 (8.26), 8.689 (8.03), 8.693 (6.75), 8.714 (4.25), 8.722 (4.54), 9.363 (3.37), 9.374 (3.38). | LC-MS (method 2): R$_t$ = 2.08 min; MS (ESIpos): m/z = 441 [M + H]$^+$ |
| I-14 | | $^1$H-NMR (600 MHz, DMSO-d$_6$) δ [ppm]: 1.176 (0.66), 1.615 (15.97), 1.626 (16.00), 1.987 (1.29), 3.263 (0.41), 3.315 (0.51), 5.791 (0.59), 5.802 (2.57), 5.814 (4.00), 5.825 (2.57), 5.837 (0.59), 7.491 (2.08), 7.497 (2.21), 7.500 (3.44), 7.505 (3.13), 7.509 (2.04), 7.514 (2.28), 7.810 (4.28), 7.812 (7.22), 7.815 (4.75), 7.855 (3.79), 7.858 (6.96), 7.861 (3.74), 7.918 (4.95), 7.920 (7.75), 7.923 (4.24), 7.988 (0.89), 7.994 (8.67), 7.996 (8.91), 8.000 (5.21), 8.001 (6.08), 8.005 (3.83), 8.016 (0.54), 8.018 (0.56), 8.637 (7.14), 8.641 (8.55), 8.678 (8.07), 8.682 (6.82), 8.711 (4.30), 8.719 (3.83), 9.034 (3.10), 9.045 (3.03). | LC-MS (method 2): R$_t$ = 2.00 min; MS (ESIpos): m/z = 417 [M + H]$^+$ |

-continued

| Example | Structure | NMR Peaklist[1] | LC-MS[1] |
|---|---|---|---|
| I-15 | | $^1$H-NMR (600 MHz, DMSO-d₆) δ [ppm]: 1.651 (16.00), 1.663 (15.75), 5.848 (0.59), 5.859 (2.60), 5.870 (4.00), 5.882 (2.56), 5.893 (0.60), 7.490 (2.26), 7.496 (2.18), 7.498 (3.60), 7.504 (4.10), 7.513 (2.44), 7.981 (0.48), 7.983 (0.44), 7.994 (4.35), 7.997 (8.04), 7.999 (5.38), 8.003 (9.11), 8.005 (8.47), 8.372 (5.72), 8.482 (5.40), 8.501 (6.52), 8.649 (7.64), 8.653 (9.27), 8.688 (8.65), 8.692 (7.18), 8.714 (2.55), 8.716 (4.02), 8.718 (2.63), 8.722 (2.59), 8.724 (4.44), 8.726 (2.44), 9.259 (3.01), 9.271 (3.00). | LC-MS (method 2): R$_t$ = 1.76 min; MS (ESIpos): m/z = 398 [M + H]$^+$ |
| I-16 | | $^1$H-NMR (600 MHz, DMSO-d₆) δ [ppm]: 1.627 (16.00), 1.638 (15.98), 3.333 (0.59), 5.814 (0.65), 5.826 (2.66), 5.837 (4.06), 5.849 (2.65), 5.860 (0.64), 7.493 (1.95), 7.501 (4.53), 7.508 (4.09), 7.516 (2.10), 7.998 (9.23), 8.004 (8.64), 8.194 (8.12), 8.239 (7.61), 8.283 (6.64), 8.644 (6.77), 8.648 (7.90), 8.683 (7.82), 8.687 (6.51), 8.714 (4.26), 8.722 (4.12), 9.105 (3.47), 9.117 (3.43). | LC-MS (method 2): R$_t$ = 1.70 min; MS (ESIpos): m/z = 408 [M + H]$^+$ |
| I-17 | | $^1$H-NMR (600 MHz, DMSO-d₆) δ [ppm]: 1.165 (0.45), 1.177 (0.92), 1.188 (0.44), 1.629 (15.82), 1.640 (16.00), 1.988 (1.74), 4.026 (0.42), 4.038 (0.41), 5.746 (6.75), 5.804 (0.59), 5.815 (2.59), 5.827 (4.02), 5.838 (2.61), 5.850 (0.64), 7.488 (2.03), 7.495 (4.73), 7.503 (4.39), 7.510 (2.25), 7.712 (5.20), 7.818 (5.00), 7.994 (8.73), 8.000 (8.39), 8.016 (0.41), 8.062 (7.78), 8.642 (6.99), 8.646 (8.48), 8.682 (8.08), 8.686 (6.86), 8.709 (4.30), 8.717 (4.12), 9.108 (3.27), 9.120 (3.24). | LC-MS (method 1): R$_t$ = 1.41 min; MS (ESIneg): m/z = 465 [M – H]$^-$ |
| I-18 | | $^1$H-NMR (600 MHz, DMSO-d₆) δ [ppm]: 1.628 (16.00), 1.639 (15.97), 2.069 (1.26), 5.818 (0.59), 5.830 (2.62), 5.841 (4.05), 5.853 (2.58), 5.864 (0.59), 7.493 (1.95), 7.500 (4.36), 7.508 (4.56), 7.515 (2.06), 7.999 (8.43), 8.005 (8.43), 8.101 (4.27), 8.104 (7.40), 8.107 (4.82), 8.168 (9.80), 8.171 (12.01), 8.173 (7.05), 8.644 (6.83), 8.647 (8.14), 8.683 (7.76), 8.687 (6.55), 8.715 (4.16), 8.722 (4.13), 9.104 (3.26), 9.116 (3.20). | LC-MS (method 2): R$_t$ = 1.66 min; MS (ESIpos): m/z = 364 [M + H]$^+$ |

-continued

| Example | Structure | NMR Peaklist[1] | LC-MS[1] |
|---|---|---|---|
| I-19 | | $^1$H-NMR (400 MHz, DMSO-d6) δ [ppm]: 1.194 (0.58), 1.212 (0.85), 1.232 (0.72), 1.609 (15.85), 1.626 (16.00), 5.732 (0.58), 5.749 (2.62), 5.766 (4.07), 5.783 (2.60), 5.800 (0.58), 7.799 (4.69), 7.803 (7.59), 7.807 (5.41), 7.869 (3.44), 7.873 (6.35), 7.878 (3.59), 7.908 (5.81), 7.912 (8.48), 7.916 (4.65), 8.011 (5.17), 8.033 (7.67), 8.118 (5.24), 8.124 (5.28), 8.139 (3.58), 8.145 (3.68), 8.651 (7.67), 8.657 (9.43), 8.706 (8.85), 8.712 (7.48), 8.765 (4.95), 8.771 (5.11), 9.069 (3.61), 9.086 (3.54) | LC-MS (method 2): $R_t$ = 2.31 min; MS (ESIpos): m/z = 451 [M + H]$^+$ |
| I-20 | | $^1$H-NMR (600 MHz, DMSO-d6) δ [ppm]: 1.216 (0.60), 1.227 (0.87), 1.234 (0.72), 1.245 (0.60), 1.658 (16.00), 1.669 (15.93), 2.069 (0.82), 5.818 (0.62), 5.829 (2.57), 5.841 (3.92), 5.852 (2.52), 5.863 (0.58), 8.015 (5.54), 8.029 (7.55), 8.101 (4.24), 8.105 (4.26), 8.115 (3.15), 8.119 (3.16), 8.252 (5.88), 8.409 (14.23), 8.658 (6.95), 8.662 (7.94), 8.713 (7.80), 8.717 (6.88), 8.758 (6.16), 8.762 (6.02), 9.367 (2.85), 9.378 (2.80). | LC-MS (method 2): $R_t$ = 2.35 min; MS (ESIpos): m/z = 475 [M + H]$^+$ |
| I-21 | | $^1$H-NMR (600 MHz, DMSO-d6) δ [ppm]: 1.626 (16.00), 1.637 (15.99), 5.769 (0.58), 5.780 (2.57), 5.792 (3.96), 5.803 (2.54), 5.814 (0.56), 7.676 (5.20), 7.714 (4.74), 7.913 (4.69), 7.916 (7.41), 7.918 (4.64), 8.017 (5.45), 8.031 (7.34), 8.110 (4.45), 8.114 (4.46), 8.124 (3.31), 8.128 (3.39), 8.653 (7.22), 8.657 (8.26), 8.708 (8.09), 8.712 (7.12), 8.759 (5.93), 8.763 (5.87), 9.110 (2.89), 9.121 (2.85). | LC-MS (method 2): $R_t$ = 2.35 min; MS (ESIpos): m/z = 457 [M + H]$^+$ |
| I-22 | | $^1$H-NMR (400 MHz, DMSO-d6) δ [ppm]: 1.216 (0.58), 1.233 (0.42), 1.622 (15.91), 1.639 (16.00), 5.745 (0.56), 5.762 (2.64), 5.779 (4.12), 5.796 (2.63), 5.813 (0.57), 7.704 (5.28), 7.838 (4.31), 8.013 (5.33), 8.035 (8.08), 8.053 (5.39), 8.056 (8.42), 8.060 (4.84), 8.114 (5.28), 8.120 (5.29), 8.135 (3.59), 8.142 (3.70), 8.655 (7.76), 8.661 (9.44), 8.709 (9.06), 8.715 (7.49), 8.763 (5.15), 8.769 (5.19), 9.143 (3.66), 9.160 (3.59). | LC-MS (method 10): $R_t$ = 1.25 min; MS (ESIpos): m/z = 501 [M + H]$^+$ |

-continued

| Example | Structure | NMR Peaklist[1] | LC-MS[1] |
|---|---|---|---|
| I-23 | | $^1$H-NMR (400 MHz, DMSO-d6) δ [ppm]: 1.222 (0.48), 1.622 (15.80), 1.639 (16.00), 5.760 (0.72), 5.777 (2.77), 5.794 (4.21), 5.811 (2.77), 5.828 (0.72), 8.018 (4.95), 8.039 (7.41), 8.100 (7.91), 8.119 (4.92), 8.125 (4.58), 8.140 (3.40), 8.146 (3.25), 8.169 (8.87), 8.193 (5.25), 8.658 (7.08), 8.664 (7.86), 8.711 (8.07), 8.717 (6.76), 8.771 (5.53), 8.777 (5.28), 9.141 (4.22), 9.158 (4.12). | LC-MS (method 2): $R_t$ = 1.99 min; MS (ESIpos): m/z = 398 [M + H]+ |
| I-24 | | $^1$H-NMR (400 MHz, DMSO-d6) δ [ppm]: 1.634(15.88), 1.651 (16.00), 5.767 (0.58), 5.784 (2.66), 5.801 (4.12), 5.818 (2.64), 5.835 (0.58), 8.013 (5.56), 8.023 (5.26), 8.034 (8.30), 8.063 (6.66), 8.113 (9.71), 8.119 (9.48), 8.134 (3.48), 8.141 (3.55), 8.657 (7.52), 8.664 (9.19), 8.712 (8.82), 8.718 (7.33), 8.766 (5.04), 8.772 (5.09), 9.228 (3.56), 9.245 (3.49). | LC-MS (method 2): $R_t$ = 2.30 min; MS (ESIpos): m/z = 441 [M + H]+ |
| I-25 | | $^1$H-NMR (400 MHz, DMSO-d6) δ [ppm]: 1.219 (0.60), 1.231 (0.79), 1.644 (15.24), 1.661 (15.33), 2.711 (0.43), 5.792 (0.62), 5.809 (2.65), 5.826 (4.14), 5.844 (2.64), 5.860 (0.61), 8.020 (5.44), 8.041 (8.14), 8.116 (4.90), 8.122 (4.84), 8.137 (3.17), 8.143 (3.18), 8.373 (7.12), 8.503 (16.00), 8.664 (7.35), 8.669 (8.67), 8.716 (8.93), 8.722 (7.07), 8.772 (6.98), 8.778 (6.80), 9.296 (3.82), 9.313 (3.68). | LC-MS (method 2): $R_t$ = 2.06 min; MS (ESIpos): m/z = 432 [M + H]+ |

-continued

| Example | Structure | NMR Peaklist[1] | LC-MS[1] |
|---------|-----------|-----------------|----------|
| I-26 | | $^1$H-NMR (600 MHz, DMSO-d6) δ [ppm]: 1.654 (6.27), 1.665 (6.20), 3.912 (16.00), 5.935 (1.05), 5.947 (1.60), 5.959 (1.03), 7.571 (1.34), 7.575 (1.35), 7.585 (1.44), 7.590 (1.43), 7.999 (2.61), 8.014 (2.42), 8.257 (2.49), 8.424 (2.68), 8.429 (2.94), 8.436 (6.04), 8.606 (2.38), 8.609 (3.20), 8.628 (3.16), 8.632 (2.34), 9.354 (1.50), 9.365 (1.46). | LC-MS (method 10): R$_t$ = 3.56 min; MS (ESIneg): m/z = 469 [M − H]$^-$ |
| I-27 | | $^1$H-NMR (600 MHz, DMSO-d6) δ [ppm]: 1.617 (5.72), 1.628 (5.69), 3.918 (16.00), 5.881 (0.95), 5.893 (1.46), 5.904 (0.94), 7.574 (1.30), 7.579 (1.32), 7.589 (1.41), 7.594 (1.40), 7.726 (1.93), 7.822 (1.85), 7.998 (2.38), 8.013 (2.20), 8.076 (2.85), 8.420 (2.32), 8.425 (2.29), 8.598 (2.31), 8.602 (3.10), 8.622 (2.98), 8.625 (2.21), 9.095 (1.31), 9.107 (1.26). | LC-MS (method 10): R$_t$ = 3.60 min; MS (ESIneg): m/z = 495 [M − H]$^-$ |
| I-28 | | $^1$H-NMR (600 MHz, DMSO-d6) δ [ppm]: 1.616 (6.36), 1.628 (6.32), 3.917 (16.00), 5.882 (1.07), 5.894 (1.62), 5.905 (1.05), 7.573 (1.40), 7.578 (1.35), 7.588 (1.49), 7.592 (1.43), 7.699 (2.58), 7.716 (2.34), 7.939 (3.18), 7.997 (2.59), 8.012 (2.41), 8.419 (2.59), 8.424 (2.51), 8.597 (2.61), 8.601 (3.24), 8.621 (3.27), 8.624 (2.43), 9.088 (1.56), 9.100 (1.52). | LC-MS (method 10): R$_t$ = 3.53 min; MS (ESIneg): m/z = 451 [M − H]$^-$ |
| I-29 | | $^1$H-NMR (600 MHz, DMSO-d6) δ [ppm]: 1.631 (6.01), 1.642 (5.95), 3.917 (16.00), 5.904 (1.01), 5.916 (1.52), 5.928 (0.98), 7.574 (1.30), 7.579 (1.34), 7.589 (1.41), 7.593 (1.42), 8.000 (2.51), 8.009 (2.43), 8.014 (2.83), 8.086 (2.64), 8.138 (2.53), 8.424 (2.40), 8.429 (2.38), 8.601 (2.34), 8.604 (3.17), 8.625 (3.01), 8.628 (2.33), 9.183 (1.39), 9.194 (1.35). | LC-MS (method 2): R$_t$ = 2.15 min; MS (ESIpos): m/z = 437 [M + H]$^+$ |

Example I-30                          Example I-31

(rac)-Methyl 6-(3-{1-[3,5-bis(trifluoromethyl)ben-
zamido]ethyl}pyrazin-2-yl)pyridine-3-carboxylate (rac)-6-(3-{1-[3,5-Bis(trifluoromethyl)benzamido]
ethyl}pyrazin-2-yl)pyridine-3-carboxylic acid (rac) 6-{3-[1-aminoethyl]pyrazin-2-yl}pyridine-3-car-
boxylate (intermediate 25A, 130 mg, 503 µmol), 3,5-bis
(trifluoromethyl)benzoic acid (169 mg, 654 µmol) and
DIPEA (260 µl, 1.5 mmol) were dissolved in DMF (3.0 mL).
The solution was cooled on an ice-water bath to 0° C. and
HATU (287 mg, 755 µmol) was added. The cooling bath was
removed and mixture was stirred for 30 min. Then water was
added. The precipitated product was collected on a filter
funnel, dried under vacuum and eventually purified by
preparative HPLC (RP-C18, water-acetonitril gradient with
0.1% TFA). A yield of 260 mg (71% of theory) of the title
compound was isolated.

LC-MS (method 2): $R_t$=2.18 min; MS (ESIpos): m/z=499
[M+H]$^+$ $^1$H-NMR (400 MHz, DMSO-d6) δ[ppm]: −0.008 (1.26),
0.008 (1.63), 1.685 (5.98), 1.702 (6.07), 2.733 (0.41), 2.892
(0.53), 3.363 (0.90), 3.369 (0.69), 3.375 (0.65), 3.381 (0.53),
3.925 (16.00), 5.803 (1.02), 5.820 (1.55), 5.837 (1.02),
8.101 (2.16), 8.103 (2.16), 8.121 (2.48), 8.123 (2.44), 8.259
(2.16), 8.361 (5.21), 8.424 (1.99), 8.429 (1.99), 8.444 (1.75),
8.450 (1.79), 8.695 (3.13), 8.701 (3.83), 8.752 (3.66), 8.758
(3.05), 9.180 (2.04), 9.182 (2.20), 9.186 (2.20), 9.187 (1.99),
9.354 (1.47), 9.371 (1.42).

(rac)-Methyl 6-(3-{1-[3,5-bis(trifluoromethyl)ben-
zamido]ethyl}pyrazin-2-yl)pyridine-3-carboxylate (ex-
ample I-30, 185 mg, 371 µmol) was suspended in methanol
(3.0 mL) and a previously prepared solution of sodium
hydroxide (104 mg, 2.61 mmol) in water (1.0 mL) was
added at ambient temperature. The mixture was stirred for
30 min. The reaction mixture was then diluted with water,
acidified with 1 M hydrochloric acid and extracted with
three portions of ethyl acetate. The combined organic
extracts were washed with brine, dried over anhydrous
sodium sulfate, evaporated and eventually purified by pre-
parative HPLC (RP-C18, water-acetonitril gradient with
0.1% TFA). A yield of 153 mg (100% purity, 85% of theory)
of the title compound was isolated.

LC-MS (method 2): $R_t$=1.84 min; MS (ESIpos): m/z=485
[M+H]$^+$ $^1$H-NMR (600 MHz, DMSO-d6) δ[ppm]: 1.687 (15.76),
1.698 (15.70), 5.823 (0.66), 5.834 (2.72), 5.846 (4.10),
5.857 (2.70), 5.869 (0.62), 8.096 (5.83), 8.110 (6.33), 8.244
(6.75), 8.376 (16.00), 8.413 (4.03), 8.416 (4.25), 8.426
(3.80), 8.430 (4.02), 8.690 (6.82), 8.693 (7.94), 8.743 (7.63),
8.747 (6.99), 9.167 (6.59), 9.169 (6.90), 9.352 (4.20), 9.364
(4.09), 13.492 (0.90).

Example I-32

(rac)-6-(3-{1-[3,5-Bis(trifluoromethyl)benzamido]
ethyl}pyrazin-2-yl)-N-(cyclopropylmethyl)-N-meth-
ylpyridine-3-carboxamide (rac)-6-(3-{1-[3,5-bis(trifluoromethyl)benzamido]
ethyl}pyrazin-2-yl)pyridine-3-carboxylic acid (70.0 mg,
145 μmol) was dissolved in DMF (2.0 mL). 1-cyclopropyl-
N-methylmethanamine hydrogen chloride (26.4 mg, 217
μmol) and DIPEA (130 μl, 720 μmol) were added. The
mixture was stirred at ambient temperature for 1 h, then it
was charged upon a preparative HPLC device and purified
directly (RP-C18 column, water-acetonitril gradient with
0.1% TFA) to yield 67.0 mg (100% purity, 84% yield) of the
title compound.

LC-MS (method 2): R$_t$=2.11 min; MS (ESIpos): m/z=552
[M+H]$^+$ $^1$H-NMR (500 MHz, DMSO-d6) δ[ppm]: 0.2 (s, 1H), 0.32
(s, 1H), 0.4-0.51 (m, 2H), 0.93-1.12 (m, 1H), 1.68 (d, 3H),
2.95 (m, 2H), 3.11 (m, 3H), 3.39 (m, 1H), 5.92 (m, 1H), 8.02
(m, 2H), 8.25 (s, 1H), 8.40 (s, 2H), 8.68-8.73 (m, 3H) 9.38
(d, 1H).

Compounds Prepared in Analogy:

| Example | Structure<br>IUPAC-Name<br>LC-MS (method): Retention time; Mass found<br>$^1$H-NMR |
|---|---|
| I-33 | <br><br>(rac)-3-Bromo-5-cyano-N-[1-{3-[5-(morpholine-4-carbonyl)pyridin-2-yl]pyrazin-2-yl}ethyl]benzamide<br>LC-MS (method 2): R$_t$ = 1.49 min; MS (ESIpos): m/z = 521 [M + H]$^+$<br>$^1$H-NMR (600 MHz, DMSO-d6) δ [ppm]: 1.107 (12.00), 1.627 (16.00), 1.639 (15.94), 3.078 (3.84), 3.384 (1.05), 3.655 (2.72), 5.842 (0.61), 5.854 (2.62), 5.865 (3.99), 5.876 (2.57), 5.888 (0.58), 8.032 (1.82), 8.035 (1.71), 8.045 (6.33), 8.048 (6.56), 8.056 (8.96), 8.069 (2.37), 8.181 (8.64), 8.223 (5.07), 8.225 (8.06), 8.288 (6.54), 8.671 (7.32), 8.675 (8.45), 8.714 (8.41), 8.718 (7.11), 8.739 (6.54), 9.106 (3.20), 9.117 (3.13). |

-continued

| Example | Structure<br>IUPAC-Name<br>LC-MS (method): Retention time; Mass found<br>¹H-NMR |
| --- | --- |

I-34

(rac)-N-[1-{3-[5-(morpholine-4-carbonyl)pyridin-2-yl]pyrazin-2-yl}ethyl]-3,5-
bis(trifluoromethyl)benzamide LC-MS (method 2): R$_t$ = 1.84 min; MS (ESIpos): m/z = 554 [M + H]$^+$ ¹H-NMR (600 MHz, DMSO-d6) δ [ppm]: 1.665 (15.64), 1.676 (15.49), 3.661
(3.07), 5.887 (0.68), 5.899 (2.66), 5.910 (3.98), 5.922 (2.57), 5.933 (0.64), 8.035
(2.40), 8.038 (2.30), 8.048 (5.90), 8.051 (5.91), 8.066 (8.11), 8.080 (3.12), 8.259
(6.74), 8.412 (16.00), 8.449 (0.47), 8.678 (7.24), 8.682 (8.01), 8.721 (8.12), 8.725
(6.88), 8.744 (7.20), 9.377 (3.72), 9.389 (3.61).

I-35

(rac)-6-(3-{1-[3,5-Bis(trifluoromethyl)benzamido]ethyl}pyrazin-2-yl)-N-
ethylpyridine-3-carboxamide LC-MS (method 2): R$_t$ = 1.89 min; MS (ESIpos): m/z = 512 [M + H]$^+$ ¹H-NMR (400 MHz, DMSO-d6) δ [ppm]: 1.145 (7.27), 1.163 (16.00), 1.181
(7.52), 1.679 (10.42), 1.696 (10.42), 1.989 (0.73), 2.329 (0.73), 2.368 (0.97),
2.672 (0.73), 2.712 (0.97), 3.286 (2.42), 3.294 (2.67), 3.357 (10.42), 5.850 (1.70),
5.867 (2.67), 5.885 (1.70), 8.087 (3.88), 8.108 (4.61), 8.264 (4.36), 8.355 (3.15),
8.361 (3.15), 8.376 (2.67), 8.381 (2.67), 8.418 (9.94), 8.678 (5.58), 8.685 (6.79),
8.727 (6.55), 8.733 (5.33), 8.753 (1.21), 8.766 (2.42), 8.780 (1.21), 9.123 (4.61),
9.127 (4.36), 9.413 (2.67), 9.430 (2.42).

-continued

| Example | Structure<br>IUPAC-Name<br>LC-MS (method): Retention time; Mass found<br><sup>1</sup>H-NMR |
|---|---|

I-36

(rac)-6-(3-{1-[3-Chloro-5-(trifluoromethoxy)benzamido]ethyl}pyrazin-2-yl)-
N-ethyl-N-methylpyridine-3-carboxamide LC-MS (method 2): $R_t$ = 1.97 min; MS (ESIpos): m/z = 508 [M + H]$^+$ <sup>1</sup>H-NMR (600 MHz, DMSO-d6) δ [ppm]: 1.078 (3.41), 1.171 (3.17), 1.630
(15.54), 1.642 (16.00), 2.914 (4.26), 2.997 (4.99), 3.216 (1.87), 3.509 (1.97),
5.877 (1.95), 7.677 (7.26), 7.712 (6.92), 7.915 (7.31), 8.009 (1.99), 8.038 (8.23),
8.051 (3.61), 8.671 (7.79), 8.675 (10.08), 8.714 (10.13), 8.718 (10.14), 9.101
(4.23), 9.113 (4.35).

I-37

(rac)-N-[1-{3-[5-(Pyrrolidine-1-carbonyl)pyridin-2-yl]pyrazin-2-yl}ethyl]-3,5-
bis(trifluoromethyl)benzamide LC-MS (method 2): $R_t$ = 1.95 min; MS (ESIpos): m/z = 538 [M + H]$^+$ <sup>1</sup>H-NMR (600 MHz, DMSO-d6) δ [ppm]: 1.664 (15.80), 1.676 (16.00), 1.799
(2.20), 1.810 (3.60), 1.816 (3.79), 1.822 (3.31), 1.826 (3.25), 1.868 (1.87), 1.878
(4.82), 1.890 (5.89), 1.901 (3.65),1.912 (1.27), 2.572 (0.75), 2.613 (0.44), 3.362
(4.40), 3.374 (8.60), 3.385 (4.60), 3.497 (4.83), 3.509 (8.41), 3.520 (4.92), 3.627
(3.65), 5.896 (0.68), 5.907 (2.72), 5.918 (4.18), 5.930 (2.79), 5.941 (0.78), 8.038
(5.11), 8.052 (7.38), 8.108 (4.91), 8.112 (4.69), 8.122 (3.45), 8.126 (3.34), 8.255
(6.49), 8.405 (15.49), 8.682 (6.98), 8.686 (7.84), 8.724 (7.95), 8.728 (6.66), 8.813
(6.74), 8.814 (6.94), 8.816 (6.89), 9.356 (4.15), 9.367 (4.09).

-continued

|  |
| --- |
| Structure |
| IUPAC-Name |
| LC-MS (method): Retention time; Mass found |
| Example | ¹H-NMR |

I-38

(rac)-6-(3-{1-[3,5-Bis(trifluoromethyl)benzamido]ethyl}pyrazin-2-yl)-N,N-
dimethylpyridine-3-carboxamide LC-MS (method 2): $R_t$ = 1.85 min; MS (ESIpos): m/z = 512 [M + H]⁺

¹H-NMR (600 MHz, DMSO-d6) δ [ppm]: 1.65 (d, 3H), 2.92 (s, 3H), 3.04 (s, 3H),
5.92 (m, 1H), 8.04 (m, 2H), 8.26 (s, 1H), 8.43 (s, 2H), 8.68-8.72 (m, 3H), 9.39 (d,
1H).

I-39

(rac)-6-(3-{1-[3,5-Bis(trifluoromethyl)benzamido]ethyl}pyrazin-2-yl)-N-
(cyanomethyl)-N-methylpyridine-3-carboxamide LC-MS (method 2): $R_t$ = 1.91 min; MS (ESIpos): m/z = 537 [M + H]⁺

¹H-NMR (600 MHz, DMSO-d6) δ [ppm]: 1.67 (d, 3H), 3.05 (s, 3H), 3.60 (s, 2H),
5.92 (m, 1H), 8.10 (m, 2H), 8.25 (s, 1H), 8.41 (s, 2H), 8.69 (s, 1H, 8.72 (s, 1H),
8.80 (m, 1H), 9.39 (d, 1H).

-continued

Structure
IUPAC-Name
LC-MS (method): Retention time; Mass found

Example
<sup>1</sup>H-NMR

I-40

(rac)-3-Chloro-5-cyano-N-[1-{3-[5-(trifluoromethyl)pyridin-2-yl]pyrazin-2-yl}ethyl]benzamide LC-MS (method 11): $R_t$ = 1.04 min; MS (ESIpos): m/z = 432 [M + H]$^+$ <sup>1</sup>H-NMR (600 MHz, DMSO-d6) δ [ppm]: 1.222 (0.56), 1.649 (16.00), 1.661 (16.00), 2.731 (0.42), 2.889 (0.44), 3.876 (0.67), 5.769 (2.94), 5.780 (4.21), 5.791 (2.94), 8.063 (8.07), 8.129 (8.76), 8.168 (7.82), 8.178 (5.77), 8.192 (5.69), 8.379 (4.55), 8.391 (4.07), 8.702 (8.00), 8.761 (8.00), 9.095 (7.85), 9.110 (5.01), 9.121 (4.62).

I-41

(rac)-3-Cyano-5-(trifluoromethyl)-N-[1-{3-[5-(trifluoromethyl)pyridin-2-yl]pyrazin-2-yl}ethyl]benzamide LC-MS (method 11): $R_t$ = 1.08 min; MS (ESIpos): m/z = 466 [M + H]$^+$ <sup>1</sup>H-NMR (600 MHz, DMSO-d6) δ [ppm]: 1.671 (16.00), 1.682 (15.93), 5.790 (0.66), 5.802 (2.71), 5.813 (4.13), 5.824 (2.68), 5.836 (0.65), 8.175 (4.55), 8.189 (5.24), 8.326 (6.99), 8.367 (3.36), 8.370 (3.48), 8.381 (2.99), 8.384 (3.02), 8.463 (7.69), 8.482 (6.74), 8.707 (7.26), 8.711 (8.21), 8.768 (7.95), 8.772 (7.23), 9.091 (5.74), 9.256 (3.82), 9.267 (3.76).

-continued

| Example | Structure<br>IUPAC-Name<br>LC-MS (method): Retention time; Mass found<br>$^1$H-NMR |
|---|---|

I-42

(rac)-3-Bromo-5-cyano-N-[1-{3-[5-(trifluoromethyl)pyridin-2-yl]pyrazin-2-yl}ethyl]benzamide LC-MS (method 11): R$_t$ = 1.06 min; MS (ESIneg): m/z = 474 [M − H]$^-$ $^1$H-NMR (600 MHz, DMSO-d6) δ [ppm]: 1.222 (0.44), 1.647 (16.00), 1.658 (15.99), 2.731 (0.65), 2.889 (0.70), 5.756 (0.73), 5.767 (2.76), 5.778 (4.14), 5.790 (2.72), 5.801 (0.70), 8.156 (8.75), 8.179 (4.91), 8.193 (5.97), 8.202 (8.46), 8.279 (7.31), 8.381 (3.83), 8.392 (3.33), 8.700 (7.17), 8.703 (7.82), 8.761 (7.85), 8.765 (7.12), 9.095 (6.55), 9.113 (4.21), 9.124 (4.06).

I-43

(rac)-3-Bromo-5-chloro-N-[1-{3-[5-(trifluoromethyl)pyridin-2-yl]pyrazin-2-yl}ethyl]benzamide LC-MS (method 11): R$_t$ = 1.19 min; MS (ESIpos): m/z = 485 [M + H]$^+$ $^1$H-NMR (600 MHz, DMSO-d6) δ [ppm]: 1.636 (15.83), 1.648 (16.00), 2.732 (1.16), 2.890 (1.24), 3.257 (0.64), 5.733 (0.76), 5.745 (2.75), 5.756 (4.11), 5.768 (2.75), 5.778 (0.78), 7.767 (8.13), 7.852 (7.54), 7.878 (8.57), 8.175 (4.71), 8.189 (5.35), 8.383 (4.00), 8.395 (3.54), 8.694 (7.14), 8.697 (7.85), 8.756 (7.63), 8.760 (7.33), 9.042 (4.17), 9.053 (4.14), 9.091 (6.77).

-continued

| Example | Structure<br>IUPAC-Name<br>LC-MS (method): Retention time; Mass found<br>$^1$H-NMR |
| --- | --- |

I-44

(rac)-3-Bromo-5-(trifluoromethoxy)-N-[1-{3-[5-(trifluoromethyl)pyridin-2-
yl]pyrazin-2-yl}ethyl]benzamide LC-MS (method 11): R$_t$ = 1.22 min; MS (ESIpos): m/z = 535 [M + H]$^+$ $^1$H-NMR (600 MHz, DMSO-d6) δ [ppm]: 1.647 (16.00), 1.658 (15.91), 5.748 (0.64),
5.759 (2.69), 5.771 (4.12), 5.782 (2.65), 5.793 (0.64), 7.660 (6.16), 7.810 (5.89),
8.013 (8.21), 8.170 (4.66), 8.183 (5.32), 8.366 (3.44), 8.370 (3.44), 8.380 (3.07),
8.384 (3.01), 8.698 (7.19), 8.702 (7.87), 8.760 (7.81), 8.764 (6.97), 9.081 (5.98),
9.103 (3.96), 9.114 (3.84).

I-45

(rac)-3,5-Bis(trifluoromethyl)-N-[1-{3-[5-(trifluoromethyl)pyridin-2-yl]pyrazin-2-
yl}ethyl]benzamide LC-MS (method 2): R$_t$ = 2.36 min; MS (ESIpos): m/z = 509 [M + H]$^+$ $^1$H-NMR (600 MHz, DMSO-d6) δ [ppm]: 1.685 (14.25), 1.696 (14.26), 2.893 (0.44),
5.806 (0.59), 5.818 (2.40), 5.829 (3.66), 5.841 (2.38), 5.852 (0.58), 8.166 (4.11),
8.180 (4.77), 8.248 (5.76), 8.353 (3.27), 8.356 (3.40), 8.368 (16.00), 8.712 (6.52),
8.716 (7.16), 8.774 (7.08), 8.778 (6.34), 9.078 (5.22), 9.345 (3.42), 9.356 (3.34).

-continued

| Example | Structure<br>IUPAC-Name<br>LC-MS (method): Retention time; Mass found<br>$^1$H-NMR |
|---|---|

I-46

(rac)-3-Chloro-5-(trifluoromethyl)-N-[1-{3-[5-(trifluoromethyl)pyridin-2-yl]pyrazin-2-yl}ethyl]benzamide LC-MS (method 2): R$_t$ = 2.34 min; MS (ESIpos): m/z = 475 [M + H]$^+$ $^1$H-NMR (600 MHz, DMSO-d6) δ [ppm]: 1.663 (15.84), 1.674 (16.00), 5.771 (0.65), 5.783 (2.67), 5.794 (4.07), 5.806 (2.67), 5.817 (0.64), 8.001 (6.36), 8.017 (7.24), 8.079 (6.91), 8.171 (4.52), 8.184 (5.17), 8.367 (3.33), 8.371 (3.39), 8.381 (3.00), 8.384 (2.98), 8.704 (7.38), 8.708 (8.16), 8.766 (7.96), 8.770 (7.20), 9.087 (5.64), 9.189 (3.68), 9.201 (3.65).

I-47

(rac)-3-Chloro-5-(trifluoromethoxy)-N-[1-{3-[5-(trifluoromethyl)pyridin-2-yl]pyrazin-2-yl}ethyl]benzamide LC-MS (method 2): R$_t$ = 2.38 min; MS (ESIpos): m/z = 491 [M + H]$^+$ $^1$H-NMR (600 MHz, DMSO-d6) δ [ppm]: 1.651 (15.98), 1.662 (16.00), 5.750 (0.62), 5.761 (2.67), 5.773 (4.10), 5.784 (2.66), 5.796 (0.61), 7.633 (5.77), 7.708 (5.38), 7.873 (5.35), 7.876 (7.86), 8.170 (4.46), 8.184 (5.14), 8.368 (3.20), 8.371 (3.30), 8.382 (2.88), 8.385 (2.89), 8.701 (7.55), 8.705 (8.45), 8.763 (8.15), 8.767 (7.32), 9.084 (5.57), 9.098 (3.75), 9.110 (3.63).

-continued

| Example | Structure<br>IUPAC-Name<br>LC-MS (method): Retention time; Mass found<br>$^1$H-NMR |
|---|---|
| I-48 | <br>(rac)-3-Bromo-N-{1-[3-(5-chloropyridin-2-yl)pyrazin-2-yl]ethyl}-5-cyanobenzamide<br>LC-MS (method 2): R$_t$ = 2.02 min; MS (ESIpos): m/z = 442 [M + H]$^+$<br>$^1$H-NMR (400 MHz, DMSO-d6) δ [ppm]: 1.142 (0.45), 1.159 (0.45), 1.240 (0.68), 1.257 (0.54), 1.619 (15.85), 1.636 (16.00), 2.368 (0.41), 2.711 (0.41), 5.756 (0.64), 5.772 (2.69), 5.789 (4.16), 5.807 (2.65), 5.823 (0.61), 8.017 (4.84), 8.038 (7.22), 8.118 (4.98), 8.125 (5.02), 8.140 (3.40), 8.146 (3.49), 8.193 (8.90), 8.231 (5.20), 8.235 (8.37), 8.239 (5.24), 8.298 (4.33), 8.301 (6.14), 8.657 (6.72), 8.663 (8.03), 8.711 (8.19), 8.717 (6.88), 8.770 (5.91), 8.776 (5.81), 9.141 (3.84), 9.158 (3.76). |

Example I-49

(rac)-Methyl 2-(3-{1-[3,5-bis(trifluoromethyl)ben-zamido]ethyl}pyrazin-2-yl)-1,3-thiazole-5-carboxy-late (rac)-Methyl 2-{3-[1-aminoethyl]pyrazin-2-yl}-1,3-thi-azole-5-carboxylate (intermediate 28A, 300 mg, 1.14 mmol) and DIPEA (400 μL, 2.3 mmol) were dissolved in THF (15.0 mL) and cooled to 0° C. A solution of 3,5-bis(trifluorom-ethyl)benzoyl chloride (377 mg, 1.36 mmol) in THF (1.0 mL) was added and stirring was maintained for 30 min. The solvent was distilled, the residue was washed with tert-butylmethyl ether to give 480 mg (84% yield) of the title compound.

LC-MS (method 1): R$_t$=1.53 min; MS (ESIpos): m/z=505 [M+H]$^+$ $^1$H-NMR (600 MHz, DMSO-d6) δ[ppm]: 1.107 (1.29), 1.260 (1.91), 1.357 (1.65), 1.615 (7.46), 1.626 (7.32), 1.760 (0.75), 2.422 (0.62), 2.651 (0.56), 3.078 (0.46), 3.602 (0.74), 3.910 (16.00), 6.508 (1.21), 6.520 (1.86), 6.530 (1.24), 8.291 (3.48), 8.438 (1.85), 8.474 (0.78), 8.520 (7.94), 8.697 (8.88), 8.783 (3.57), 8.853 (1.55), 9.542 (1.75), 9.553 (1.77).

Example I-50

(rac)-2-(3-{1-[3,5-Bis(trifluoromethyl)benzamido]ethyl}pyrazin-2-yl)-1,3-thiazole-5-carboxylic acid (rac)-Methyl 2-(3-{1-[3,5-bis(trifluoromethyl)ben-zamido]ethyl}pyrazin-2-yl)-1,3-thiazole-5-carboxylate (ex-ample I-49, 570 mg, 1.13 mmol) was suspended in a mixture of methanol (15.0 mL), THF (5.0 mL) and water (5.0 mL). sodium hydroxide (300 μl, 50% in water, 5.7 mmol) was added and the mixture was stirred at 50° C. for 3 h. The solvents were distilled, the residue was diluted with water, acidified with 1M hydrochloric acid and the precipitate was collected by suction and dried under vacuum. Yield: 510 mg (86% purity, 79% yield) of the title compound.

LC-MS (method 1): $R_t$=1.32 min; MS (ESIpos): m/z=491 [M+H]⁺

¹H-NMR (600 MHz, DMSO-d6) δ[ppm]: 1.61 (d, 3H), 6.52 (m, 1H), 8.38 (s, 1H), 8.53 (s, 2H), 8.60 (s, 1H), 8.69 (s, 1H), 8.78 (s, 1H), 9.57 (d, 1H), 13.75 (br s, 1H).

Example I-51

(rac)-2-(3-{1-[3,5-Bis(trifluoromethyl)benzamido]ethyl}pyrazin-2-yl)-N-(cyclopropylmethyl)-N-methyl-1,3-thiazole-5-carboxamide (rac)-2-(3-{1-[3,5-Bis(trifluoromethyl)benzamido]ethyl}pyrazin-2-yl)-1,3-thiazole-5-carboxylic acid (example I-50, 100 mg, 204 μmol) was dissolved in DMF (3.6 mL). 1-cyclopropyl-N-methylmethanamine hydrogen chloride (49.6 mg, 408 μmol) and DIPEA (180 μl, 1.0 mmol) were added and the mixture was stirred at room temperature for 30 min. Then it was directly charged upon a preparative HPLC device and chromatographed (RP C-18 10 μm column, water-acetonitrile gradient with 0.1% TFA) to give 39.0 mg (100% purity, 34% yield) of the LC-MS (method 2): $R_t$=2.31 min; MS (ESIpos): m/z=558 [M+H]⁺

¹H-NMR (500 MHz, DMSO-d6) δ[ppm]: −0.006 (3.66), 0.006 (3.09), 0.116 (0.40), 0.284 (1.32), 0.503 (1.76), 0.511 (5.29), 0.514 (5.29), 0.527 (5.55), 0.539 (1.59), 1.079 (1.50), 1.234 (0.48), 1.617 (15.96), 1.631 (16.00), 2.362 (0.71), 2.636 (0.84), 3.115 (0.75), 3.386 (6.52), 3.400 (6.39), 6.517 (0.66), 6.530 (2.82), 6.544 (4.32), 6.557 (2.78), 6.571 (0.66), 8.309 (6.70), 8.448 (0.66), 8.539 (15.21), 8.675 (8.42), 8.679 (9.12), 8.745 (9.30), 8.749 (8.20), 9.559 (4.28), 9.573 (4.14).

By Analogy, the Following Compounds were Synthesized:

| Example | Structure<br>IUPAC-Name<br>LC-MS (method): Retention time; Mass found<br>¹H-NMR |
|---|---|
| I-52 | <br>(rac)-3-Chloro-N-{1-[3-(1,3-thiazol-2-yl)pyrazin-2-yl]ethyl}-5-(trifluoromethoxy)benzamide<br>LC-MS (method 2): $R_t$ = 2.28 min; MS (ESIpos): m/z = 429 [M + H]⁺<br>¹H-NMR (600 MHz, DMSO-d6) δ [ppm]: 1.233 (0.67), 1.581 (16.00), 1.592 (15.98), 3.318 (0.60), 5.744 (0.74), 6.485 (0.61), 6.496 (2.63), 6.507 (4.04), 6.519 (2.57), 6.530 (0.62), 7.748 (4.87), 7.783 (5.25), 8.006 (7.67), 8.011 (8.16), 8.037 (5.04), 8.040 (7.45), 8.043 (4.58), 8.138 (8.33), 8.144 (7.52), 8.634 (7.43), 8.638 (8.44), 8.687 (8.17), 8.691 (7.08), 9.250 (3.30), 9.262 (3.25). |

-continued

| Example | Structure<br>IUPAC-Name<br>LC-MS (method): Retention time; Mass found<br>$^1$H-NMR |
| --- | --- |

I-53

(rac)-3-Bromo-N-{1-[3-(1,3-thiazol-2-yl)pyrazin-2-yl]ethyl}-5-
(trifluoromethoxy)benzamide
LC-MS (method 2): R$_t$ = 2.32 min; MS (ESIpos): m/z = 473 [M + H]$^+$
$^1$H-NMR (600 MHz, DMSO-d6) δ [ppm]: 1.576 (1.82), 1.588 (1.81), 3.284
(16.00), 3.311 (0.42), 6.502 (0.46), 7.806 (0.67), 7.851 (0.64), 8.003 (0.81),
8.008 (0.84), 8.135 (0.86), 8.140 (0.78), 8.175 (0.91), 8.631 (0.81), 8.635
(0.86), 8.684 (0.89), 8.687 (0.73), 9.252 (0.43), 9.263 (0.41).

I-54

(rac)-3-Bromo-5-chloro-N-{1-[3-(1,3-thiazol-2-yl)pyrazin-2-
yl]ethyl}benzamide
LC-MS (method 2): R$_t$ = 2.24 min; MS (ESIpos): m/z = 423 [M + H]$^+$
$^1$H-NMR (600 MHz, DMSO-d6) δ [ppm]: 1.250 (0.80), 1.261 (0.92), 1.275
(0.65), 1.570 (15.91), 1.581 (16.00), 2.071 (3.00), 2.734 (4.08), 2.892 (4.73),
6.469 (0.60), 6.480 (2.60), 6.492 (4.00), 6.503 (2.62), 6.515 (0.61), 7.892
(3.53), 7.895 (7.35), 7.898 (4.72), 7.917 (5.02), 7.920 (7.44), 7.923 (4.37),
7.954 (0.68), 8.005 (7.37), 8.010 (8.22), 8.030 (4.87), 8.033 (7.89), 8.035
(4.76), 8.139 (8.13), 8.145 (7.66), 8.632 (7.18), 8.636 (8.30), 8.687 (7.84),
8.691 (7.01), 9.183 (3.27), 9.195 (3.23).

I-55

(rac)-3-Bromo-5-cyano-N-{1-[3-(1,3-thiazol-2-yl)pyrazin-2-
yl]ethyl}benzamide

-continued

| Example | Structure<br>IUPAC-Name<br>LC-MS (method): Retention time; Mass found<br>¹H-NMR |
| --- | --- |

LC-MS (method 2): $R_t$ = 1.96 min; MS (ESIpos): m/z = 414 [M + H]$^+$

¹H-NMR (400 MHz, DMSO-d6) δ [ppm]: 1.571 (15.98), 1.588 (16.00), 2.366
(0.68), 2.709 (0.74), 3.276 (1.09), 5.752 (1.97), 6.479 (0.54), 6.496 (2.66),
6.513 (4.16), 6.530 (2.64), 6.547 (0.60), 8.014 (9.57), 8.022 (10.90), 8.143
(11.26), 8.152 (9.97), 8.298 (4.90), 8.301 (9.97), 8.305 (6.37), 8.328 (4.04),
8.332 (7.81), 8.336 (5.25), 8.346 (7.25), 8.350 (8.51), 8.354 (3.92), 8.638
(8.82), 8.644 (10.87), 8.689 (10.00), 8.695 (8.08), 9.275 (3.34), 9.293 (3.32).

I-56

(rac)-3-Cyano-N-{1-[3-(1,3-thiazol-2-yl)pyrazin-2-yl]ethyl}-5-
(trifluoromethyl)benzamide LC-MS (method 2): $R_t$ = 1.99 min; MS (ESIpos): m/z = 404 [M + H]$^+$ ¹H-NMR (600 MHz, DMSO-d6) δ [ppm]: 1.397 (1.68), 1.601 (16.00), 1.612
(16.00), 3.314 (1.12), 6.534 (0.56), 6.546 (2.61), 6.557 (4.00), 6.569 (2.62),
6.580 (0.61), 8.011 (8.01), 8.017 (8.82), 8.146 (8.77), 8.151 (8.21), 8.483
(5.99), 8.518 (5.69), 8.604 (6.75), 8.642 (7.52), 8.646 (8.88), 8.691 (8.24),
8.695 (7.31), 9.406 (3.22), 9.417 (3.15).

I-57

(rac)-3-Chloro-5-cyano-N-{1-[3-(1,3-thiazol-2-yl)pyrazin-2-
yl]ethyl}benzamide

LC-MS (method 2): $R_t$ = 1.93 min; MS (ESIpos): m/z = 370 [M + H]$^+$

¹H-NMR (600 MHz, DMSO-d6) δ [ppm]: 1.579 (15.97), 1.590 (16.00), 2.423
(0.41), 2.652 (0.41), 3.167 (1.39), 3.176 (1.48), 3.254 (0.42), 3.312 (1.50),
3.895 (0.66), 4.058 (0.40), 5.745 (0.77), 6.497 (0.60), 6.508 (2.59), 6.520
(4.01), 6.531 (2.60), 6.543 (0.62), 8.008 (7.66), 8.014 (8.41), 8.141 (8.22),
8.147 (7.66), 8.208 (13.45), 8.210 (14.69), 8.271 (5.11), 8.274 (8.36), 8.638
(7.42), 8.642 (8.42), 8.689 (8.14), 8.693 (7.17), 9.249 (3.27), 9.260 (3.28).

-continued

| Example | Structure<br>IUPAC-Name<br>LC-MS (method): Retention time; Mass found<br>$^1$H-NMR |
| --- | --- |

I-58

(rac)-N-[1-{3-[5-(Morpholine-4-carbonyl)-1,3-thiazol-2-yl]pyrazin-2-
yl}ethyl]-3,5-bis(trifluoromethyl)benzamide
LC-MS (method 2): R$_t$ = 2.05 min; MS (ESIpos): m/z = 560 [M + H]$^+$
$^1$H-NMR (600 MHz, DMSO-d6) δ [ppm]: 1.617 (5.74), 1.629 (5.71), 3.674
(16.00), 6.527 (0.99), 6.539 (1.49), 6.550 (0.97), 8.296 (2.32), 8.376 (5.09),
8.537 (5.51), 8.672 (2.67), 8.676 (2.81), 8.745 (2.84), 8.748 (2.55), 9.540 (1.35),
9.551 (1.30).

I-59

(rac)-3-Chloro-N-[1-{3-[5-(morpholine-4-carbonyl)-1,3-thiazol-2-yl]pyrazin-
2-yl}ethyl]-5-(trifluoromethyl)benzamide
LC-MS (method 9): R$_t$ = 1.07 min; MS (ESIpos): m/z = 526 [M + H]$^+$
$^1$H-NMR (600 MHz, DMSO-d6) δ [ppm]: 1.593 (5.50), 1.604 (5.46), 3.671
(16.00), 6.484 (0.93), 6.496 (1.42), 6.507 (0.91), 8.048 (2.21), 8.185 (2.58),
8.232 (2.44), 8.368 (4.79), 8.665 (2.33), 8.669 (2.60), 8.740 (2.54), 8.744 (2.38),
9.366 (1.30), 9.377 (1.28).

I-60

-continued

| Example | Structure<br>IUPAC-Name<br>LC-MS (method): Retention time; Mass found<br>$^1$H-NMR |
|---|---|

(rac)-3-Chloro-N-[1-{3-[5-(morpholine-4-carbonyl)-1,3-thiazol-2-yl]pyrazin-2-yl}ethyl]-5-(trifluoromethoxy)benzamide LC-MS (method 2): $R_t$ = 2.07 min; MS (ESIpos): m/z = 542 [M + H]$^+$ $^1$H-NMR (600 MHz, DMSO-d6) δ [ppm]: 1.583 (5.83), 1.594 (5.80), 3.670 (16.00), 6.463 (0.98), 6.474 (1.51), 6.485 (0.96), 7.754 (1.80), 7.788 (1.96), 8.040 (1.83), 8.042 (2.80), 8.045 (1.71), 8.364 (5.87), 8.664 (2.90), 8.668 (3.11), 8.739 (3.04), 8.743 (2.80), 9.273 (1.17), 9.285 (1.12).

I-61

(rac)-3-Bromo-N-[1-{3-[5-(morpholine-4-carbonyl)-1,3-thiazol-2-yl]pyrazin-2-yl}ethyl]-5-(trifluoromethoxy)benzamide LC-MS (method 2): $R_t$ = 2.10 min; MS (ESIpos): m/z = 586 [M + H]$^+$ $^1$H-NMR (600 MHz, DMSO-d6) δ [ppm]: 1.582 (5.82), 1.593 (5.83), 3.670 (16.00), 6.460 (0.98), 6.471 (1.51), 6.483 (0.97), 7.813 (1.91), 7.862 (1.77), 8.177 (1.80), 8.180 (2.92), 8.182 (1.75), 8.364 (6.26), 8.664 (3.04), 8.668 (3.29), 8.739 (3.15), 8.743 (2.84), 9.278 (1.16), 9.289 (1.13).

I-62

(rac)-2-(3-{1-[3,5-Bis(trifluoromethyl)benzamido]ethyl}pyrazin-2-yl)-1,3-thiazole-5-carboxamide LC-MS (method 2): $R_t$ = 1.87 min; MS (ESIpos): m/z = 490 [M + H]$^+$ $^1$H-NMR (600 MHz, DMSO-d6) δ [ppm]: 1.358 (1.12), 1.612 (16.00), 1.624 (15.98), 1.761 (0.72), 2.071 (0.56), 3.603 (0.66), 6.501 (0.60), 6.512 (2.73), 6.524 (4.25), 6.535 (2.74), 6.547 (0.65), 7.740 (2.06), 8.248 (2.10), 8.292 (6.46), 8.527 (15.21), 8.579 (15.25), 8.674 (7.50), 8.678 (8.10), 8.742 (8.12), 8.745 (7.26), 9.526 (3.61), 9.538 (3.55).

-continued

|  | Structure<br>IUPAC-Name<br>LC-MS (method): Retention time; Mass found |
| Example | ¹H-NMR |

I-63

(rac)-2-(3-{1-[3,5-Bis(trifluoromethyl)benzamido]ethyl}pyrazin-2-yl)-N-
(cyclopropylmethyl)-N-(propan-2-yl)-1,3-thiazole-5-carboxamide
LC-MS (method 2): $R_t$ = 2.50 min; MS (ESIpos): m/z = 586 [M + H]⁺
¹H-NMR (600 MHz, DMSO-d6) δ [ppm]: 0.282 (3.92), 0.505 (5.40), 0.517
(5.34), 1.084 (1.30), 1.262 (16.00), 1.623 (10.72), 1.634 (10.35), 3.913 (0.44),
4.325 (1.58), 6.539 (2.01), 6.550 (2.75), 6.561 (1.90), 8.296 (6.06), 8.309 (6.32),
8.541 (11.36), 8.674 (5.33), 8.742 (5.31), 9.541 (3.26), 9.551 (3.18).

I-64

(rac)-N-[1-{3-[5-(Piperidine-1-carbonyl)-1,3-thiazol-2-yl]pyrazin-2-
yl}ethyl]-3,5-bis(trifluoromethyl)benzamide
LC-MS (method 1): $R_t$ = 1.53 min; MS (ESIpos): m/z = 558 [M + H]⁺
¹H-NMR (600 MHz, DMSO-d6) δ [ppm]: 1.583 (9.99), 1.590 (8.25), 1.616
(16.00), 1.628 (15.83), 1.642 (2.76), 1.652 (4.76), 1.660 (4.61), 2.423 (0.48),
3.603 (8.88), 3.611 (12.02), 3.620 (8.46), 3.910 (2.19), 6.518 (0.77), 6.529
(2.64), 6.540 (3.91), 6.552 (2.61), 6.563 (0.71), 8.294 (7.02), 8.307 (12.92),
8.521 (1.34), 8.535 (15.01), 8.579 (0.57), 8.666 (6.67), 8.670 (7.41), 8.697
(1.31), 8.737 (7.12), 8.741 (6.75), 8.783 (0.54), 9.536 (4.07), 9.547 (4.03).

I-65

-continued

| | Structure<br>IUPAC-Name<br>LC-MS (method): Retention time; Mass found |
| --- | --- |
| Example | $^1$H-NMR |

| | (rac)-2-(3-{1-[3,5-Bis(trifluoromethyl)benzamido]ethyl}pyrazin-2-yl)-N-<br>methyl-N-(2,2,2-trifluoroethyl)-1,3-thiazole-5-carboxamide<br>LC-MS (method 2): R$_t$ = 2.29 min; MS (ESIpos): m/z = 586 [M + H]$^+$<br>$^1$H-NMR (500 MHz, DMSO-d6) δ [ppm]: 1.620 (14.96), 1.634 (14.41), 2.363<br>(1.15), 2.636 (0.81), 3.395 (3.44), 4.432 (3.11), 4.449 (2.96), 6.527 (2.67), 6.541<br>(4.00), 6.554 (2.56), 8.309 (6.89), 8.538 (16.00), 8.687 (7.41), 8.691 (8.44),<br>8.763 (7.85), 8.767 (7.63), 9.564 (4.22), 9.578 (4.11). |
| --- | --- |

I-66

(rac)-N-[1-(3-{5-[(cis)-2,6-Dimethylmorpholine-4-carbonyl]-1,3-thiazol-2-yl}pyrazin-2-yl)ethyl]-3,5-bis(trifluoromethyl)benzamide
LC-MS (method 2): R$_t$ = 2.29 min; MS (ESIpos): m/z = 588 [M + H]$^+$
$^1$H-NMR (500 MHz, DMSO-d6) δ [ppm]: -0.120 (0.68), -0.006 (6.91), 0.006
(4.28), 0.117 (0.68), 1.125 (8.79), 1.617 (14.87), 1.630 (14.72), 2.362 (1.05),
2.636 (1.20), 3.613 (2.55), 6.510 (0.53), 6.523 (2.33), 6.537 (3.61), 6.551 (2.33),
6.564 (0.53), 8.311 (6.31), 8.382 (16.00), 8.443 (1.05), 8.539 (14.65), 8.581
(2.48), 8.675 (7.81), 8.680 (8.56), 8.746 (8.49), 8.750 (7.44), 9.563 (4.13), 9.576
(3.98), 11.287 (0.98).

I-67

(rac)-2-(3-{1-[3,5-Bis(trifluoromethyl)benzamido]ethyl}pyrazin-2-yl)-N-
(cyanomethyl)-N-methyl-1,3-thiazole-5-carboxamide
LC-MS (method 2): R$_t$ = 2.09 min; MS (ESIpos): m/z = 543 [M + H]$^+$
$^1$H-NMR (500 MHz, DMSO-d6) δ [ppm]: -0.120 (0.55), 0.006 (4.26), 0.117
(0.55), 1.033 (2.06), 1.045 (1.92), 1.621 (14.76), 1.634 (14.63), 2.073 (0.82),
2.363 (0.89), 2.636 (0.96), 3.422 (0.62), 3.484 (0.41), 4.643 (3.64), 6.515 (0.62),
6.529 (2.54), 6.542 (3.98), 6.556 (2.54), 6.570 (0.62), 8.310 (6.25), 8.540
(16.00), 8.691 (7.35), 8.695 (8.10), 8.765 (8.03), 8.770 (7.14), 9.569 (3.98),
9.583 (3.85).

-continued

| Example | Structure<br>IUPAC-Name<br>LC-MS (method): Retention time; Mass found<br>¹H-NMR |
| --- | --- |

I-68

(rac)-N-[1-{3-[5-(1,4-Oxazepane-4-carbonyl)-1,3-thiazol-2-yl]pyrazin-2-
yl}ethyl]-3,5-bis(trifluoromethyl)benzamide
LC-MS (method 2): $R_t$ = 2.08 min; MS (ESIpos): m/z = 574 [M + H]⁺
¹H-NMR (400 MHz, DMSO-d6) δ [ppm]: -0.149 (0.67), -0.008 (6.02), 0.008
(7.76), 0.146 (0.72), 1.614 (15.57), 1.632 (15.71), 1.907 (3.33), 2.074 (0.87),
2.329 (0.43), 2.368 (0.67), 2.672 (0.48), 2.712 (0.67), 3.714 (5.93), 3.761 (8.24),
6.509 (0.58), 6.526 (2.51), 6.543 (3.90), 6.560 (2.51), 6.578 (0.58), 8.310 (6.94),
8.383 (5.30), 8.542 (16.00), 8.676 (9.83), 8.682 (11.23), 8.745 (10.55), 8.751
(9.11), 9.564 (4.29), 9.581 (4.14).

I-69

(rac)-2-(3-{1-[3,5-Bis(trifluoromethyl)benzamido]ethyl}pyrazin-2-yl)-N,N-
dimethyl-1,3-thiazole-5-carboxamide
LC-MS (method 1): $R_t$ = 1.40 min; MS (ESIpos): m/z = 518 [M + H]⁺
¹H-NMR (600 MHz, DMSO-d6) δ [ppm]: 1.620 (15.33), 1.631 (15.11), 2.071
(16.00), 3.053 (2.63), 3.239 (2.71), 6.521 (0.64), 6.532 (2.60), 6.544 (3.94),
6.555 (2.51), 6.566 (0.57), 8.294 (6.07), 8.417 (13.65), 8.535 (14.33), 8.670
(7.18), 8.674 (7.42), 8.741 (7.63), 8.745 (6.58), 9.535 (3.91), 9.546 (3.73).

I-70

-continued

| Example | Structure<br>IUPAC-Name<br>LC-MS (method): Retention time; Mass found<br>¹H-NMR |
|---|---|

(rac)-N-[1-{3-[5-(3,3-Dimethyl-1,3-azasilinane-1-carbonyl)-1,3-thiazol-2-yl]pyrazin-2-yl}ethyl]-3,5-bis(trifluoromethyl)benzamide LC-MS (method 1): $R_t$ = 1.63 min; MS (ESIpos): m/z = 602 [M + H]⁺

¹H-NMR (600 MHz, DMSO-d6) δ [ppm]: 0.108 (16.00), 0.811 (2.90), 0.822 (4.07), 0.833 (3.05), 1.616 (12.01), 1.627 (11.88), 1.841 (2.10), 2.423 (0.40), 3.237 (0.82), 3.261 (7.11), 3.323 (0.45), 3.536 (2.82), 6.521 (0.45), 6.532 (2.02), 6.544 (3.10), 6.555 (2.00), 6.567 (0.45), 8.274 (5.59), 8.294 (4.89), 8.535 (11.28), 8.664 (5.54), 8.668 (6.02), 8.734 (6.12), 8.737 (5.49), 9.535 (3.17), 9.547 (3.05).

I-71

(rac)-N-[1-{3-[5-(Pyrrolidine-1-carbonyl)-1,3-thiazol-2-yl]pyrazin-2-yl}ethyl]-3,5-bis(trifluoromethyl)benzamide LC-MS (method 1): $R_t$ = 1.46 min; MS (ESIpos): m/z = 544 [M + H]⁺

¹H-NMR (600 MHz, DMSO-d6) δ [ppm]: 1.619 (16.00), 1.631 (15.85), 1.864 (0.87), 1.875 (3.03), 1.886 (5.12), 1.898 (4.10), 1.909 (1.40), 1.952 (1.49), 1.963 (3.99), 1.974 (4.86), 1.985 (2.85), 1.997 (0.76), 2.424 (0.42), 3.520 (8.26), 3.532 (9.50), 3.543 (5.39), 3.781 (3.05), 3.792 (5.34), 3.803 (2.76), 6.521 (0.65), 6.533 (2.74), 6.544 (4.16), 6.555 (2.67), 6.567 (0.57), 8.294 (6.10), 8.513 (15.56), 8.532 (14.40), 8.673 (7.59), 8.677 (8.16), 8.744 (8.08), 8.748 (7.25), 9.534 (4.04), 9.545 (3.85).

I-72

(rac)-2-(3-{1-[3,5-Bis(trifluoromethyl)benzamido]ethyl}pyrazin-2-yl)-N-ethyl-N-methyl-1,3-thiazole-5-carboxamide LC-MS (method 1): $R_t$ = 1.45 min; MS (ESIpos): m/z = 532 [M + H]⁺

¹H-NMR (600 MHz, DMSO-d6) δ [ppm]: 1.188 (2.83), 1.619 (15.88), 1.631 (16.00), 2.071 (0.78), 2.610 (0.55), 2.653 (0.44), 3.019 (0.91), 3.217 (1.11), 3.262 (0.94), 3.320 (1.18), 3.516 (4.03), 3.528 (4.06), 5.746 (1.28), 6.520 (0.65), 6.532 (2.62), 6.543 (4.04), 6.555 (2.69), 6.566 (0.74), 8.294 (6.25), 8.395 (0.61), 8.535 (14.34), 8.671 (7.92), 8.675 (8.48), 8.741 (8.30), 8.745 (7.44), 9.535 (3.80), 9.546 (3.75).

-continued

| Example | Structure<br>IUPAC-Name<br>LC-MS (method): Retention time; Mass found<br>$^1$H-NMR |
|---|---|

I-73

(rac)-2-(3-{1-[3,5-Bis(trifluoromethyl)benzamido]ethyl}-5-methylpyrazin-2-
yl)-N-(cyclopropylmethyl)-N-methyl-1,3-thiazole-5-carboxamide
LC-MS (method 1): $R_t$ = 1.58 min; MS (ESIpos): m/z = 572 [M + H]$^+$
$^1$H-NMR (600 MHz, DMSO-d6) δ [ppm]: 0.270 (1.55), 0.505 (1.76), 0.514
(5.50), 0.528 (5.43), 0.535 (1.47), 1.074 (1.51), 1.601 (16.00), 1.612 (15.96),
2.424 (0.46), 2.653 (0.52), 3.387 (5.90), 3.399 (5.79), 6.483 (0.66), 6.495 (2.82),
6.507 (4.30), 6.518 (2.78), 6.530 (0.62), 8.293 (6.75), 8.368 (0.56), 8.521
(15.53), 8.551 (11.97), 9.492 (4.25), 9.504 (4.06).

I-74

(rac)-2-(3-{1-[3,5-Bis(trifluoromethyl)benzamido]ethyl}-5-methylpyrazin-2-
yl)-N-(cyanomethyl)-N-methyl-1,3-thiazole-5-carboxamide
LC-MS (method 1): $R_t$ = 1.45 min; MS (ESIpos): m/z = 557 [M + H]$^+$
$^1$H-NMR (600 MHz, DMSO-d6) δ [ppm]: 1.604 (16.00), 1.615 (15.85), 2.070
(1.26), 2.424 (0.48), 2.653 (0.51), 3.252 (0.63), 3.261 (0.63), 3.330 (4.15), 4.636
(4.11), 6.484 (0.59), 6.496 (2.82), 6.507 (4.26), 6.519 (2.72), 6.530 (0.63), 8.294
(6.43), 8.501 (2.82), 8.522 (15.41), 8.568 (12.29), 9.502 (4.22), 9.513 (4.09).

I-75

-continued

| Example | Structure<br>IUPAC-Name<br>LC-MS (method): Retention time; Mass found<br>¹H-NMR |
| --- | --- |

(rac)-2-(3-{1-[3-Bromo-5-(trifluoromethoxy)benzamido]ethyl}pyrazin-2-yl)-
N-(cyanomethyl)-N-methyl-1,3-thiazole-5-carboxamide
LC-MS (method 1): R$_t$ = 1.41 min; MS (ESIneg): m/z = 567 [M – H]$^-$
¹H-NMR (600 MHz, DMSO-d6) δ [ppm]: 1.589 (16.00), 1.600 (15.62), 2.069
(3.62), 2.423 (0.63), 2.652 (0.52), 3.256 (1.62), 3.326 (4.39), 4.640 (4.08), 6.456
(0.68), 6.468 (2.77), 6.479 (4.15), 6.491 (2.64), 6.502 (0.63), 7.814 (6.06), 7.860
(5.88), 8.180 (8.06), 8.528 (2.61), 8.679 (6.83), 8.683 (7.43), 8.758 (7.60), 8.762
(6.69), 9.283 (4.23), 9.294 (4.07).

I-76

(rac)-2-(3-{1-[3-Bromo-5-(trifluoromethoxy)benzamido]ethyl}pyrazin-2-yl)-
N-(cyclopropylmethyl)-N-methyl-1,3-thiazole-5-carboxamide
LC-MS (method 1): R$_t$ = 1.54 min; MS (ESIpos): m/z = 584 [M + H]$^+$
¹H-NMR (600 MHz, DMSO-d6) δ [ppm]: 0.276 (1.53), 0.507 (1.83), 0.516
(5.63), 0.527 (5.75), 0.537 (1.50), 1.077 (1.54), 1.585 (16.00), 1.596 (15.87),
2.423 (0.49), 2.575 (0.47), 2.652 (0.45), 3.387 (8.11), 3.399 (7.52), 6.457 (0.68),
6.469 (2.79), 6.480 (4.20), 6.492 (2.75), 6.503 (0.64), 7.813 (6.51), 7.858 (6.20),
8.179 (8.90), 8.181 (5.83), 8.391 (0.53), 8.663 (7.46), 8.667 (8.05), 8.737 (7.95),
8.741 (7.32), 9.273 (4.26), 9.284 (4.18).

I-77

(rac)-2-(3-{1-[3-Chloro-5-(methanesulfonyl)benzamido]ethyl}pyrazin-2-yl)-
N-(cyanomethyl)-N-methyl-1,3-thiazole-5-carboxamide
LC-MS (method 1): R$_t$ = 1.10 min; MS (ESIneg): m/z = 517 [M – H]$^-$
¹H-NMR (600 MHz, DMSO-d6) [ppm]: 1.606 (15.93), 1.618 (16.00), 2.424
(0.42), 3.374 (1.20), 3.724 (1.52), 4.642 (4.37), 5.744 (6.55), 5.746 (6.39), 6.491
(0.72), 6.502 (2.81), 6.514 (4.24), 6.525 (2.72), 6.536 (0.66), 8.125 (3.89), 8.128
(7.39), 8.130 (6.62), 8.132 (3.48), 8.261 (4.22), 8.263 (7.89), 8.266 (7.29), 8.342
(4.48), 8.344 (8.91), 8.346 (7.92), 8.536 (2.82), 8.686 (6.69), 8.688 (7.02), 8.690
(7.42), 8.692 (6.64), 8.766 (6.91), 8.767 (7.35), 8.770 (6.78), 8.771 (5.97), 9.402
(4.60), 9.413 (4.42).

-continued

|  | Structure<br>IUPAC-Name<br>LC-MS (method): Retention time; Mass found |
| Example | <sup>1</sup>H-NMR |

I-78

(rac)-2-(3-{1-[3,5-Bis(trifluoromethyl)benzamido]ethyl}-5-methylpyrazin-2-
yl)-1,3-thiazole-5-carboxylic acid
LC-MS (method 2): R$_t$ = 2.09 min; MS (ESIpos): m/z = 505 [M + H]$^+$
$^1$H-NMR (600 MHz, DMSO-d6) δ [ppm]: 1.234 (0.65), 1.595 (16.00), 1.607
(15.84), 2.384 (0.72), 2.423 (0.93), 2.612 (0.62), 2.652 (0.88), 6.475 (2.78),
6.487 (4.25), 6.498 (2.73), 8.289 (6.15), 8.509 (14.50), 8.555 (12.26), 8.568
(12.11), 9.495 (4.12), 9.507 (3.96).

I-79

(rac)-Methyl 2-(3-{1-[3,5-bis(trifluoromethyl)benzamido]ethyl}-5-
methylpyrazin-2-yl)-1,3-thiazole-5-carboxylate
LC-MS (method 1): R$_t$ = 1.60 min; MS (ESIneg): m/z = 519 [M + H]$^+$
$^1$H-NMR (600 MHz, DMSO-d6) δ [ppm]: 1.595 (7.27), 1.607 (7.17), 3.901
(16.00), 6.473 (1.24), 6.484 (1.86), 6.495 (1.21), 8.290 (3.00), 8.507 (7.15),
8.577 (5.22), 8.658 (5.52), 9.501 (1.88), 9.512 (1.82).

I-80

(rac)-2-(3-{1-[3-Chloro-5-(methanesulfonyl)benzamido]ethyl}pyrazin-2-yl)-
1,3-thiazole-5-carboxylic acid -continued

| Example | Structure<br>IUPAC-Name<br>LC-MS (method): Retention time; Mass found<br>$^1$H-NMR |
|---|---|
| | LC-MS (method 1): R$_t$ = 1.01 min; MS (ESIpos): m/z = 467 [M + H]$^+$<br>$^1$H-NMR (600 MHz, DMSO-d6) δ [ppm]: 1.596 (5.83), 1.608 (5.77), 2.068<br>(0.59), 3.246 (0.56), 3.317 (16.00), 6.485 (1.00), 6.496 (1.51), 6.508 (0.96),<br>8.120 (1.60), 8.123 (2.83), 8.126 (1.77), 8.253 (1.85), 8.256 (2.90), 8.259 (1.84),<br>8.334 (2.03), 8.336 (3.24), 8.338 (1.89), 8.596 (4.74), 8.688 (2.80), 8.692 (3.04),<br>8.771 (2.90), 8.775 (2.65), 9.398 (1.55), 9.409 (1.52). |
| I-81 | <br>(rac)-2-(3-{1-[3-Bromo-5-(trifluoromethoxy)benzamido]ethyl}pyrazin-2-yl)-<br>1,3-thiazole-5-carboxylic acid<br>LC-MS (method 2): R$_t$ = 1.97 min; MS (ESIpos): m/z = 517 [M + H]$^+$<br>$^1$H-NMR (600 MHz, DMSO-d6) δ [ppm]: 1.561 (16.00), 1.573 (15.73), 2.385<br>(0.64), 2.424 (0.78), 2.574 (0.49), 2.652 (0.63), 6.461 (2.83), 6.473 (4.12), 6.484<br>(2.63), 7.815 (6.92), 7.848 (6.63), 8.121 (3.72), 8.179 (8.60), 8.624 (7.62), 8.659<br>(7.18), 9.234 (4.24), 9.245 (4.01). |

Example I-82

(rac)-N-{1-[3-(5-Cyano-1,3-thiazol-2-yl)pyrazin-2-yl]ethyl}-3,5-bis(trifluoromethyl)benzamide (rac)-2-(3-{1-[3,5-bis(trifluoromethyl)benzamido]ethyl}pyrazin-2-yl)-1,3-thiazole-5-carboxamide (example I-62, 75.0 mg, 153 μmol) was dissolved in THF (3.1 mL) Burgess reagent (CAS RN 29684-56-8, 38.3 mg, 161 μmol) was added and the mixture was reacted at ambient temperature for 1 h. More Burgess reagent (18.3 mg, 76.6 μmol) was added and stirring was maintained for another 30 min. The mixture was directly charged onto a preparative HPLC device and chromatographed (RP C-18 10 μm column, water acetonitrile gradient with 0.1% TFA to give 36.0 mg (100% purity, 50% yield) of the title compound.

LC-MS (method 2): R$_t$=2.29 min; MS (ESIpos): m/z=472 [M+H]$^+$ $^1$H-NMR (600 MHz, DMSO-d6) δ[ppm]: −0.022 (0.44), 1.193 (0.46), 1.234 (1.85), 1.611 (15.63), 1.623 (15.64), 2.069 (2.30), 2.423 (0.51), 2.652 (0.43), 3.261 (1.29), 3.910 (0.99), 6.469 (0.68), 6.481 (2.58), 6.492 (3.94), 6.503 (2.58), 8.294 (6.79), 8.522 (16.00), 8.712 (6.84), 8.715 (7.27), 8.823 (7.21), 8.827 (7.00), 8.938 (11.11), 9.557 (3.60), 9.569 (3.49).

Example I-83

(rac)-2-{3-[1-{[3,5-Bis(trifluoromethyl)benzoyl]
(cyclopropylmethyl)amino}ethyl]pyrazin-2-yl}-N-
ethyl-N-methyl-1,3-thiazole-5-carboxamide (rac)-2-(3-{1-[3,5-bis(trifluoromethyl)benzamido]
ethyl}pyrazin-2-yl)-N-ethyl-N-methyl-1,3-thiazole-5-car-
boxamide (example 72, 196 mg, 369 μmol) was dissolved in
DMF (4.0 mL) and sodium hydride (22.1 mg, 60% in
paraffin, 553 μmol) was added. The mixture was stirred at
RT for 20 min, then bromomethyl)cyclopropane (110 μl, 1.1
mmol) was added and heated to 60° C. for 3 h. The mixture
was directly charged onto a preparative HPLC device and
chromatographed (RP C-18 10 μm column, water acetoni-
trile gradient with 0.1% TFA to give 66.0 mg (100% purity,
31% yield) of the title compound.

LC-MS (method 1): $R_t$=1.55 min; MS (ESIpos): m/z=586
[M+H]$^+$ $^1$H-NMR (600 MHz, DMSO-d6) δ[ppm]: 0.517 (1.85),
1.162 (8.17), 1.688 (6.60), 2.422 (1.07), 2.652 (1.07), 3.480
(6.56), 6.327 (0.76), 7.582 (1.66), 7.835 (1.46), 8.700 (9.40),
8.803 (16.00), 8.807 (13.58).

Examples I-84 and I-85—Separation of Enantiomers 2-(3-{(1R)-1-[3,5-bis(trifluoromethyl)benzamido]
ethyl}pyrazin-2-yl)-N-ethyl-N-methyl-1,3-thiazole-
5-carboxamide and 2-(3-{(1S)-1-[3,5-bis(trifluorom-
ethyl)benzamido]ethyl}pyrazin-2-yl)-N-ethyl-N-
methyl-1,3-thiazole-5-carboxamide -continued (rac)-2-(3-{1-[3,5-bis(trifluoromethyl)benzamido]
ethyl}pyrazin-2-yl)-N-ethyl-N-methyl-1,3-thiazole-5-car-
boxamide (example I-72, 400 mg, 0.82 mmol) was submit-
ted to chiral HPLC at 40° C., using Daicel Chiralpak ID, 5
μm 250*20 mm as stationary phase and a mixture of
n-heptane/2-propanol (1:1) at 18 mL/min as eluent. Two
fractions were eluted at 5.16 and 7.09 min, respectively
which were freeze-dried to give

Example I-84

Yield: 121 mg (30%) eluting at 5.16 min in the prepara-
tive HPLC.
Analytical chiral HPLC (method 7) $R_t$=4.99 min
Optical rotation (method 8): $[\alpha]_D^{20}$=−88.8° (c=0.48,
CHCl$_3$).

Example I-85

Yield: 122 mg (31%) eluting at 7.09 min in the prepara-
tive HPLC.
Analytical chiral HPLC (method 7) $R_t$=6.25 min
Optical rotation (method 8): $[\alpha]_D^{20}$=85.5° (c=0.49,
CHCl$_3$).

Example I-86

(rac)-Ethyl 1-(3-{1-[3,5-bis(trifluoromethyl)ben-
zamido]ethyl}pyrazin-2-yl)-1H-pyrazole-4-carboxy-
late (rac)-Ethyl 1-{3-[1-aminoethyl]pyrazin-2-yl}-1H-pyrazole-4-carboxylate (intermediate 37A, 330 mg, 1.26 mmol), 3,5-bis(trifluoromethyl)benzoic acid (424 mg, 1.64 mmol) and DIPEA (660 μl, 3.8 mmol) were dissolved in DMF (5.0 mL). The solution was cooled on an ice-water bath to 0° C. and HATU (720 mg, 1.89 mmol) was added. The cooling bath was removed and mixture was stirred for 1 h. Then water was added. The precipitated product was collected on a filter funnel, dried under vacuum. 558 mg (100% purity, 88% yield) of the title compound were obtained.

LC-MS (method 2): $R_t$=2.27 min; MS (ESIpos): m/z=502 [M+H]$^+$ $^1$H-NMR (600 MHz, DMSO-d6) δ[ppm]: 1.291 (7.96), 1.303 (16.00), 1.315 (7.97), 1.637 (12.36), 1.648 (12.24), 2.694 (0.72), 2.737 (1.30), 2.895 (1.44), 4.254 (0.47), 4.263 (1.69), 4.272 (4.12), 4.275 (4.39), 4.284 (4.14), 4.287 (4.18), 4.295 (1.57), 4.299 (1.38), 4.305 (0.43), 5.722 (0.52), 5.734 (2.11), 5.745 (3.17), 5.756 (2.05), 5.768 (0.49), 8.259 (9.18), 8.273 (5.29), 8.448 (12.45), 8.591 (5.52), 8.594 (5.87), 8.803 (5.61), 8.807 (5.64), 8.883 (9.31), 9.436 (3.22), 9.447 (3.13).

Example I-87

(rac)-1-(3-{1-[3,5-Bis(trifluoromethyl)benzamido]ethyl}pyrazin-2-yl)-1H-pyrazole-4-carboxylic acid (rac)-Ethyl 1-(3-{1-[3,5-bis(trifluoromethyl)benzamido]ethyl}pyrazin-2-yl)-1H-pyrazole-4-carboxylate (example I-86, 555 mg, 1.11 mmol) was suspended in a mixture of THF (4.0 mL), ethanol (4.0 mL) and water (1.0 mL). sodium hydroxide (443 mg, 50% in water, 5.53 mmol was added and the mixture was heated to 35° C. Another 80 mg (2.0 mmol) of neat sodium hydroxide were added and stirring was maintained for 30 min at room temperature. The mixture was poured into water, acidified with 4 M hydrochloric acid and the precipitate was collected by suction and eventually dried under vacuum. 435 mg (97% purity, 81% yield) of the title compound were isolated.

LC-MS (method 2): $R_t$=1.83 min; MS (ESIpos): m/z=474 [M+H]$^+$ $^1$H-NMR (600 MHz, DMSO-d6) δ[ppm]: 1.177 (0.41), 1.326 (0.41), 1.338 (0.83), 1.498 (0.65), 1.510 (0.61), 1.636 (16.00), 1.648 (15.89), 1.989 (0.77), 5.736 (0.66), 5.748 (2.89), 5.759 (4.09), 5.770 (2.66), 5.782 (0.63), 8.218 (12.06), 8.273 (6.27), 8.461 (14.68), 8.555 (0.59), 8.583 (7.81), 8.586 (8.12), 8.786 (7.92), 8.790 (7.73), 8.831 (12.37), 9.457 (4.05), 9.468 (3.92), 12.750 (2.03).

Example I-88

(rac)-1-(3-{1-[3,5-Bis(trifluoromethyl)benzamido]ethyl}pyrazin-2-yl)-N,N-dimethyl-1H-pyrazole-4-carboxamide (rac)-1-(3-{1-[3,5-bis(trifluoromethyl)benzamido]ethyl}pyrazin-2-yl)-1H-pyrazole-4-carboxylic acid (example I-87,105 mg, 222 μmol), N-methylmethanamine hydrogen chloride (27.1 mg, 333 μmol) and DIPEA (190 μl, 1.1 mmol) were dissolved in DMF (2.0 mL). HATU (143 mg, 377 μmol) was added and the mixture was stirred at room temperature for 1 h. When it was diluted with water, a precipitate formed which was collected by suction and dried under vacuum to give 66.0 mg (98% purity, 58% yield) of the title compound.

LC-MS (method 2): $R_t$=1.89 min; MS (ESIpos): m/z=501 [M+H]$^+$ $^1$H-NMR (600 MHz, DMSO-d6) δ[ppm]: 1.337 (0.63), 1.497 (0.52), 1.509 (0.53), 1.643 (16.00), 1.654 (15.80), 2.734 (1.18), 2.892 (1.45), 2.994 (3.46), 3.168 (3.46), 5.811 (0.70), 5.822 (2.70), 5.834 (4.09), 5.845 (2.63), 5.856 (0.63), 8.141 (11.32), 8.276 (6.41), 8.468 (15.04), 8.556 (0.62), 8.567 (7.42), 8.571 (7.75), 8.739 (11.86), 8.756 (7.64), 8.760 (7.40), 9.445 (4.02), 9.456 (3.90).

By Analogous Procedures, the Following Example Compounds were Obtained:

| Example | Structure<br>IUPAC-Name<br>LC-MS (method): Retention time; Mass found<br>$^1$H-NMR |
| --- | --- |
| I-89 | <br>(rac)-1-(3-{1-[3,5-Bis(trifluoromethyl)benzamido]ethyl}pyrazin-2-yl)-N-ethyl-N-methyl-1H-pyrazole-4-carboxamide<br>LC-MS (method 2): $R_t$ = 1.97 min; MS (ESIpos): m/z = 515 [M + H]$^+$<br>$^1$H-NMR (600 MHz, DMSO-d6) δ [ppm]: 1.133 (3.06), 1.642 (15.83), 1.653 (16.00), 2.072 (0.66), 2.963 (0.93), 3.141 (1.58), 3.466 (4.14), 3.478 (4.21), 5.824 (1.83), 5.835 (2.72), 5.846 (1.90), 8.131 (1.05), 8.276 (6.53), 8.469 (14.78), 8.571 (7.62), 8.575 (7.93), 8.719 (0.87), 8.758 (8.07), 8.761 (7.82), 9.441 (3.99), 9.452 (4.02). |
| I-90 | <br>N-[(rac)-1-{3-[4-(Morpholine-4-carbonyl)-1H-pyrazol-1-yl]pyrazin-2-yl}ethyl]-3,5-bis(trifluoromethyl)benzamide<br>LC-MS (method 2): $R_t$ = 1.86 min; MS (ESIpos): m/z = 543 [M + H]$^+$<br>$^1$H-NMR (600 MHz, DMSO-d6) δ [ppm]: 1.642 (12.72), 1.654 (12.88), 2.072 (0.65), 3.333 (16.00), 5.804 (0.51), 5.815 (2.18), 5.827 (3.31), 5.838 (2.18), 5.849 (0.57), 8.127 (9.63), 8.282 (4.65), 8.473 (10.90), 8.569 (6.68), 8.573 (6.88), 8.755 (10.27), 8.760 (7.13), 8.764 (6.64), 9.457 (3.14), 9.468 (3.08). |

| Example | Structure<br>IUPAC-Name<br>LC-MS (method): Retention time; Mass found<br>$^1$H-NMR |
|---|---|

I-91

N-[(rac)-1-{3-[4-(Pyrrolidine-1-carbonyl)-1H-pyrazol-1-yl]pyrazin-2-
yl}ethyl]-3,5-bis(trifluoromethyl)benzamide LC-MS (method 2): R$_t$ = 1.96 min; MS (ESIpos): m/z = 527 [M + H]$^+$ $^1$H-NMR (600 MHz, DMSO-d6) δ [ppm]: 1.642 (15.90), 1.653 (16.00), 1.822
(0.79), 1.832 (3.02), 1.844 (5.40), 1.855 (4.57), 1.866 (1.75), 1.883 (0.51), 1.895
(1.38), 1.903 (2.96), 1.913 (3.50), 1.924 (2.39), 3.465 (4.07), 3.476 (7.42), 3.487
(4.08), 3.630 (0.67), 3.647 (1.84), 3.658 (2.92), 3.668 (2.80), 3.680 (3.03), 3.691
(1.77), 3.696 (1.49), 3.707 (0.64), 5.805 (0.62), 5.816 (2.71), 5.827 (4.11), 5.839
(2.72), 5.850 (0.67), 8.198 (12.79), 8.279 (6.28), 8.465 (14.84), 8.577 (7.23),
8.581 (7.81), 8.759 (13.40), 8.766 (8.00), 8.770 (7.76), 9.435 (4.05), 9.446
(4.00).

I-92

(rac)-3,5-Bis(trifluoromethyl)-N-[1-{3-[4-(trifluoromethyl)-1H-pyrazol-1-
yl]pyrazin-2-yl}ethyl]benzamide LC-MS (method 1): R$_t$ = 1.56 min; MS (ESIpos): m/z = 498 [M + H]$^+$ $^1$H-NMR (600 MHz, DMSO-d6) δ [ppm]: 1.649 (15.82), 1.660 (16.00), 2.423
(0.49), 2.571 (1.42), 3.240 (0.56), 3.322 (3.29), 3.340 (0.86), 5.675 (0.67), 5.686
(2.68), 5.697 (4.03), 5.708 (2.77), 5.720 (0.76), 8.275 (6.35), 8.332 (9.68), 8.441
(14.99), 8.601 (7.38), 8.605 (7.45), 8.821 (7.52), 8.825 (7.18), 9.081 (7.81),
9.420 (3.94), 9.431 (3.92).

-continued

| Example | Structure<br>IUPAC-Name<br>LC-MS (method): Retention time; Mass found<br>$^1$H-NMR |
| --- | --- |

I-93

(rac)-3-Chloro-5-(methanesulfonyl)-N-[1-{3-[4-(trifluoromethyl)-1H-
pyrazol-1-yl]pyrazin-2-yl}ethyl]benzamide
LC-MS (method 1): $R_t$ = 1.29 min; MS (ESIneg): m/z = 472 [M – H]$^-$
$^1$H-NMR (600 MHz, DMSO-d6) δ [ppm]: 1.626 (2.03), 1.637 (2.01), 3.290
(16.00), 3.299 (5.37), 5.672 (0.51), 8.106 (0.57), 8.109 (0.93), 8.112 (0.55),
8.184 (0.67), 8.186 (0.98), 8.189 (0.57), 8.274 (0.72), 8.276 (1.08), 8.279 (0.60),
8.355 (1.26), 8.594 (0.98), 8.598 (0.98), 8.816 (0.98), 8.820 (0.92), 9.108 (0.99),
9.333 (0.52), 9.344 (0.49).

I-94

(rac)-3-Bromo-5-(trifluoromethoxy)-N-[1-{3-[4-(trifluoromethyl)-1H-
pyrazol-1-yl]pyrazin-2-yl}ethyl]benzamide
LC-MS (method 9): $R_t$ = 24 min; MS (ESIpos): m/z = 524 [M + H]$^+$
$^1$H-NMR (600 MHz, DMSO-d6) δ [ppm]: 1.611 (16.00), 1.623 (15.91), 2.069
(0.59), 2.612 (0.46), 3.255 (0.50), 5.623 (0.73), 5.635 (2.74), 5.646 (3.98), 5.657
(2.68), 5.668 (0.71), 7.734 (4.96), 7.736 (5.43), 7.738 (4.73), 7.839 (5.08), 8.086
(5.52), 8.088 (8.06), 8.091 (4.67), 8.336 (9.21), 8.590 (8.11), 8.594 (8.38), 8.810
(8.11), 8.814 (7.69), 9.088 (7.22), 9.192 (3.78), 9.203 (3.72).

I-95

-continued

| Example | Structure<br>IUPAC-Name<br>LC-MS (method): Retention time; Mass found<br>$^1$H-NMR |
| --- | --- |

(rac)-3-Bromo-5-cyano-N-[1-{3-[4-(trifluoromethyl)-1H-pyrazol-1-
yl]pyrazin-2-yl}ethyl]benzamide LC-MS (method 9): $R_t$ = 1.09 min; MS (ESIpos): m/z = 465 [M + H]$^+$ $^1$H-NMR (600 MHz, DMSO-d6) δ [ppm]: 1.609 (16.00), 1.620 (15.91), 5.634
(0.63), 5.645 (2.70), 5.657 (4.03), 5.668 (2.65), 5.680 (0.61), 8.214 (8.36), 8.268
(7.87), 8.271 (4.82), 8.306 (6.97), 8.346 (9.92), 8.592 (7.18), 8.596 (7.39), 8.811
(7.43), 8.815 (7.15), 9.093 (7.91), 9.194 (3.96), 9.205 (3.82).

I-96

N-{(rac)-1-[3-(4-Chloro-1H-pyrazol-1-yl)pyrazin-2-yl]ethyl}-3,5-
bis(trifluoromethyl)benzamide LC-MS (method 1): $R_t$ = 1.54 min; MS (ESIpos): m/z = 464 [M + H]$^+$ $^1$H-NMR (600 MHz, DMSO-d6) δ [ppm]: 1.635 (16.00), 1.646 (15.83), 2.071
(0.47), 5.779 (0.62), 5.790 (2.65), 5.801 (3.99), 5.812 (2.59), 5.824 (0.56), 8.038
(11.03), 8.039 (10.33), 8.279 (6.04), 8.468 (14.31), 8.540 (7.57), 8.544 (7.88),
8.716 (11.28), 8.717 (10.48), 8.737 (7.69), 8.741 (7.46), 9.452 (3.71), 9.462
(3.55).

I-97

(rac)-3-Bromo-N-{1-[3-(4-chloro-1H-pyrazol-1-yl)pyrazin-2-yl]ethyl}-5-
(trifluoromethoxy)benzamide LC-MS (method 1): $R_t$ = 1.56 min; MS (ESIpos): m/z = 490 [M + H]$^+$ $^1$H-NMR (600 MHz, DMSO-d6) δ [ppm]: 1.234 (0.70), 1.598 (15.81), 1.609
(16.00), 2.519 (1.33), 3.310 (1.86), 5.725 (0.64), 5.736 (2.63), 5.748 (3.98),
5.759 (2.67), 5.770 (0.75), 7.757 (5.41), 7.759 (4.90), 7.844 (5.16), 8.034
(10.44), 8.035 (10.44), 8.110 (5.16), 8.112 (8.11), 8.115 (4.88), 8.531 (8.02),
8.535 (8.35), 8.712 (10.69), 8.713 (10.68), 8.729 (8.17), 8.733 (7.94), 9.206
(3.60), 9.217 (3.55).

-continued

| | Structure<br>IUPAC-Name<br>LC-MS (method): Retention time; Mass found<br>$^1$H-NMR |
|---|---|
| Example | |

I-98

(rac)-3-Bromo-N-{1-[3-(4-chloro-1H-pyrazol-1-yl)pyrazin-2-yl]ethyl}-5-
cyanobenzamide
LC-MS (method 2): R$_t$ = 2.06 min; MS (ESIpos): m/z = 431 [M + H]$^+$
$^1$H-NMR (600 MHz, DMSO-d6) δ [ppm]: 1.224 (0.49), 1.594 (16.00), 1.606
(15.70), 2.085 (2.58), 3.261 (0.44), 3.328 (0.58), 5.738 (0.76), 5.745 (7.26),
5.750 (2.82), 5.761 (4.05), 5.772 (2.60), 5.783 (0.60), 8.038 (11.09), 8.237
(8.40), 8.239 (4.85), 8.284 (4.62), 8.287 (7.87), 8.290 (4.91), 8.305 (5.38), 8.308
(6.80), 8.311 (3.40), 8.533 (7.45), 8.537 (7.56), 8.713 (11.27), 8.729 (7.52),
8.733 (7.25), 9.199 (3.76), 9.210 (3.62).

I-99

(rac)-3-Chloro-N-{1-[3-(4-chloro-1H-pyrazol-1-yl)pyrazin-2-yl]ethyl}-5-
(methanesulfonyl)benzamide
LC-MS (method 1): R$_t$ = 1.26 min; MS (ESIpos): m/z = 440 [M + H]$^+$
$^1$H-NMR (600 MHz, DMSO-d6) δ [ppm]: 1.612 (6.34), 1.624 (6.24), 2.069
(1.41), 3.307 (16.00), 5.768 (1.07), 5.779 (1.62), 5.791 (1.03), 8.044 (4.44),
8.107 (1.64), 8.110 (2.87), 8.113 (1.69), 8.201 (1.99), 8.204 (3.02), 8.207 (1.81),
8.287 (2.15), 8.290 (3.30), 8.292 (1.86), 8.536 (2.97), 8.540 (3.03), 8.721 (4.55),
8.735 (3.03), 8.739 (2.91), 9.329 (1.55), 9.340 (1.49).

I-100

-continued

| Example | Structure<br>IUPAC-Name<br>LC-MS (method): Retention time; Mass found<br>¹H-NMR |
| --- | --- |

N-{(rac)-1-[3-(4-Cyano-1H-pyrazol-1-yl)pyrazin-2-yl]ethyl}-3,5-
bis(trifluoromethyl)benzamide
LC-MS (method 2): $R_t$ = 2.09 min; MS (ESIpos): m/z = 455 [M + H]⁺
¹H-NMR (600 MHz, DMSO-d6) δ [ppm]: 1.647 (15.50), 1.658 (16.00), 2.695
(1.29), 2.736 (4.01), 2.895 (4.37), 5.625 (0.64), 5.636 (2.63), 5.647 (4.02), 5.659
(2.74), 5.670 (0.79), 7.957 (0.78), 8.280 (6.73), 8.450 (15.74), 8.482 (11.64),
8.587 (0.44), 8.611 (6.95), 8.615 (7.79), 8.839 (7.01), 8.842 (7.52), 9.322
(11.44), 9.470 (4.00), 9.481 (4.10).

I-101

(rac)-3-Chloro-N-{1-[3-(4-cyano-1H-pyrazol-1-yl)pyrazin-2-yl]ethyl}-5-
(cyclopropanesulfonyl)benzamide
LC-MS (method 2): $R_t$ = 1.73 min; MS (ESIpos): m/z = 457 [M + H]⁺
¹H-NMR (600 MHz, DMSO-d6) δ [ppm]: 1.078 (7.12), 1.088 (7.16), 1.176
(8.80), 1.624 (15.94), 1.635 (16.00), 2.425 (0.77), 2.653 (0.69), 2.993 (3.71),
5.611 (2.85), 5.623 (4.16), 5.633 (2.90), 8.084 (8.70), 8.201 (9.22), 8.239 (9.71),
8.483 (10.08), 8.608 (9.09), 8.838 (9.04), 9.323 (10.13), 9.368 (4.93), 9.378
(4.88).

I-102

(rac)-3-Bromo-N-{1-[3-(4-cyano-1H-pyrazol-1-yl)pyrazin-2-yl]ethyl}-5-
(trifluoromethoxy)benzamide
LC-MS (method 2): $R_t$ = 2.12 min; MS (ESIpos): m/z = 481 [M + H]⁺
¹H-NMR (600 MHz, DMSO-d6) δ [ppm]: 1.217 (0.46), 1.232 (0.47), 1.606
(16.00), 1.618 (15.96), 2.614 (0.54), 2.693 (2.15), 2.734 (3.18), 2.892 (3.55),
3.061 (0.65), 3.258 (0.55), 3.399 (0.80), 5.568 (0.74), 5.580 (2.76), 5.591 (4.06),
5.602 (2.75), 5.613 (0.80), 7.739 (6.44), 7.812 (0.59), 7.846 (6.09), 7.881 (0.46),
7.954 (0.74), 7.980 (0.51), 8.074 (0.68), 8.090 (8.45), 8.475 (10.84), 8.599
(7.97), 8.603 (7.61), 8.828 (7.97), 8.832 (7.18), 9.222 (4.16), 9.233 (4.09), 9.314
(11.18).

-continued

| Example | Structure<br>IUPAC-Name<br>LC-MS (method): Retention time; Mass found<br>$^1$H-NMR |
|---|---|

I-103

(rac)-3-Chloro-N-{1-[3-(4-cyano-1H-pyrazol-1-yl)pyrazin-2-yl]ethyl}-5-
(methanesulfonyl)benzamide
LC-MS (method 2): $R_t$ = 1.57 min; MS (ESIpos): m/z = 431 [M + H]$^+$
$^1$H-NMR (600 MHz, DMSO-d6) δ [ppm]: 1.622 (6.29), 1.633 (6.44), 2.692
(0.74), 2.733 (1.22), 2.892 (1.35), 3.306 (16.00), 3.349 (0.43), 3.356 (0.63),
3.397 (0.45), 5.609 (1.05), 5.620 (1.62), 5.631 (1.12), 8.114 (2.89), 8.187 (3.05),
8.272 (3.37), 8.486 (4.49), 8.605 (2.90), 8.609 (3.05), 8.835 (2.93), 8.839 (2.92),
9.323 (4.46), 9.351 (1.73), 9.362 (1.71).

I-104

(rac)-3-Chloro-N-{1-[3-(4-cyano-1H-pyrazol-1-yl)pyrazin-2-yl]ethyl}-5-
(trifluoromethoxy)benzamide
LC-MS (method 2): $R_t$ = 2.09 min; MS (ESIpos): m/z = 437 [M + H]$^+$
$^1$H-NMR (600 MHz, DMSO-d6) δ [ppm]: 1.606 (16.00), 1.618 (15.88), 2.070
(2.45), 5.570 (0.66), 5.581 (2.68), 5.593 (4.03), 5.604 (2.62), 5.615 (0.61), 7.711
(5.96), 7.741 (5.46), 7.952 (7.68), 8.474 (11.68), 8.599 (7.16), 8.603 (7.32),
8.827 (7.37), 8.831 (7.05), 9.215 (3.95), 9.226 (3.81), 9.313 (11.91).

I-105

(rac)-3-Chloro-N-{1-[3-(4-cyano-1H-pyrazol-1-yl)pyrazin-2-yl]ethyl}-5-
(trifluoromethyl)benzamide -continued

| Example | Structure<br>IUPAC-Name<br>LC-MS (method): Retention time; Mass found<br>$^1$H-NMR |
|---|---|

LC-MS (method 2): $R_t$ = 2.06 min; MS (ESIpos): m/z = 421 [M+H]$^+$ $^1$H-NMR (600 MHz, DMSO-d6) δ [ppm]: 1.617 (16.00), 1.628 (15.95), 2.690 (0.41), 2.731 (1.03), 2.890 (1.15), 5.588 (0.67), 5.600 (2.70), 5.611 (4.01), 5.622 (2.63), 5.633 (0.66), 8.031 (6.72), 8.096 (7.66), 8.150 (7.42), 8.477 (11.00), 8.600 (7.22), 8.604 (7.89), 8.829 (7.38), 8.832 (7.54), 9.307 (4.70), 9.314 (13.13).

I-106

(rac)-3,5-Dibromo-N-{1-[3-(4-cyano-1H-pyrazol-1-yl)pyrazin-2-yl]ethyl}benzamide

LC-MS (method 2): $R_t$ = 2.08 min; MS (ESIpos): m/z = 475 [M + H]$^+$ $^1$H-NMR (600 MHz, DMSO-d6) δ [ppm]: 1.591 (13.79), 1.602 (13.73), 2.733 (1.08), 2.892 (1.21), 3.260 (0.53), 5.553 (0.61), 5.564 (2.32), 5.575 (3.44), 5.587 (2.31), 5.598 (0.57), 7.977 (12.14), 7.979 (16.00), 7.993 (4.88), 7.996 (6.58), 8.477 (9.83), 8.595 (6.23), 8.598 (6.63), 8.824 (6.35), 8.828 (6.46), 9.158 (3.44), 9.168 (3.38), 9.311 (9.68).

I-107

(rac)-3-Bromo-5-cyano-N-{1-[3-(4-cyano-1H-pyrazol-1-yl)pyrazin-2-yl]ethyl}benzamide LC-MS (method 2): $R_t$ = 1.80 min; MS (ESIpos): m/z = 422 [M + H]$^+$ $^1$H-NMR (600 MHz, DMSO-d6) δ [ppm]: 1.601 (16.00), 1.612 (16.00), 2.069 (1.12), 2.732 (1.81), 2.890 (2.06), 5.582 (0.65), 5.593 (2.68), 5.604 (4.02), 5.616 (2.62), 5.627 (0.62), 8.220 (8.46), 8.222 (5.56), 8.266 (4.58), 8.268 (8.07), 8.271 (4.95), 8.306 (4.39), 8.309 (6.95), 8.312 (4.17), 8.479 (11.88), 8.600 (7.57), 8.604 (7.99), 8.826 (7.73), 8.831 (7.69), 9.221 (3.86), 9.232 (3.78), 9.312 (12.19).

-continued

| Example | Structure<br>IUPAC-Name<br>LC-MS (method): Retention time; Mass found<br>$^1$H-NMR |
|---|---|

I-108

(rac)-3-Cyano-N-{1-[3-(4-cyano-1H-pyrazol-1-yl)pyrazin-2-yl]ethyl}-5-fluorobenzamide LC-MS (method 2): $R_t$ = 1.64 min; MS (ESIpos): m/z = 362 [M + H]$^+$ $^1$H-NMR (600 MHz, DMSO-d6) δ [ppm]: 1.609 (15.74), 1.621 (16.00), 2.734 (0.59), 2.893 (0.68), 3.329 (0.67), 5.591 (0.60), 5.602 (2.63), 5.613 (3.98), 5.625 (2.71), 5.636 (0.75), 7.915 (2.04), 7.920 (2.90), 7.922 (2.54), 7.931 (2.29), 7.934 (2.86), 7.935 (2.93), 7.938 (2.53), 8.017 (2.12), 8.019 (2.55), 8.021 (2.73), 8.023 (2.41), 8.031 (2.35), 8.033 (2.69), 8.035 (2.73), 8.037 (2.38), 8.133 (5.69), 8.135 (8.52), 8.137 (5.62), 8.481 (10.90), 8.484 (2.12), 8.603 (7.45), 8.607 (8.45), 8.610 (1.40), 8.829 (7.48), 8.833 (8.03), 8.837 (1.38), 9.203 (3.70), 9.214 (3.76), 9.315 (11.15), 9.319 (1.97).

I-109

(rac)-3-Cyano-N-{1-[3-(4-cyano-1H-pyrazol-1-yl)pyrazin-2-yl]ethyl}-5-(propan-2-yl)benzamide LC-MS (method 2): $R_t$ = 1.90 min; MS (ESIpos): m/z = 386 [M + H]$^+$ 1H-NMR (600 MHz, DMSO-d6) δ [ppm]: 1.184 (0.54), 1.207 (15.02), 1.219 (16.00), 1.231 (1.56), 1.617 (8.60), 1.629 (8.44), 2.072 (0.64), 2.965 (0.57), 2.976 (1.38), 2.988 (1.81), 2.999 (1.38), 3.011 (0.59), 5.578 (1.45), 5.589 (2.15), 5.600 (1.41), 7.874 (4.12), 7.940 (4.18), 8.060 (2.80), 8.063 (4.40), 8.477 (6.44), 8.597 (4.03), 8.601 (4.15), 8.828 (4.03), 8.832 (3.95), 9.094 (2.15), 9.106 (2.08), 9.315 (6.40).

-continued

| Example | Structure<br>IUPAC-Name<br>LC-MS (method): Retention time; Mass found<br>$^1$H-NMR |
| --- | --- |

I-110

(rac)-3-tert-Butyl-5-cyano-N-{1-[3-(4-cyano-1H-pyrazol-1-yl)pyrazin-2-yl]ethyl}benzamide LC-MS (method 2): R$_t$ = 1.99 min; MS (ESIpos): m/z = 400 [M + H]$^+$ $^1$H-NMR (600 MHz, DMSO-d6) δ [ppm]: 1.296 (16.00), 1.625 (2.15), 1.636 (2.13), 2.072 (0.56), 5.594 (0.54), 7.988 (1.05), 7.991 (0.76), 8.039 (0.72), 8.041 (1.10), 8.044 (0.72), 8.090 (1.16), 8.476 (1.56), 8.599 (1.01), 8.603 (1.05), 8.830 (1.01), 8.834 (0.99), 9.133 (0.57), 9.143 (0.55), 9.318 (1.57).

I-111

(rac)-N-{1-[3-(4-cyano-1H-pyrazol-1-yl)pyrazin-2-yl]ethyl}-3-fluoro-5-(pentafluoro-lambda$^6$-sulfanyl)benzamide LC-MS (method 2): R$_t$ = 2.01 min; MS (ESIpos): m/z = 463 [M + H]$^+$ $^1$H-NMR (600 MHz, DMSO-d6) δ [ppm]: 1.295 (0.41), 1.626 (16.00), 1.638 (15.91), 2.070 (6.39), 3.258 (0.88), 3.340 (0.62), 5.590 (0.63), 5.602 (2.66), 5.613 (4.00), 5.624 (2.61), 5.635 (0.61), 7.977 (3.20), 7.991 (3.09), 8.106 (3.44), 8.109 (2.30), 8.120 (3.43), 8.124 (2.17), 8.146 (7.36), 8.474 (11.53), 8.604 (7.68), 8.608 (7.74), 8.831 (7.67), 8.835 (7.26), 9.314 (11.60), 9.352 (4.01), 9.363 (3.89).

I-112

-continued

| Example | Structure<br>IUPAC-Name<br>LC-MS (method): Retention time; Mass found<br>¹H-NMR |
|---|---|

(rac)-3-Bromo-N-{1-[3-(4-cyano-1H-pyrazol-1-yl)pyrazin-2-yl]ethyl}-5-
iodobenzamide LC-MS (method 2): R$_t$ = 2.11 min; MS (ESIpos): m/z = 523 [M + H]$^+$ ¹H-NMR (600 MHz, DMSO-d6) δ [ppm]: 1.586 (16.00), 1.597 (15.83), 2.071
(1.00), 5.538 (0.76), 5.550 (2.75), 5.561 (4.04), 5.572 (2.65), 5.583 (0.65), 7.966
(8.26), 8.097 (7.61), 8.133 (8.72), 8.475 (11.33), 8.592 (7.53), 8.595 (7.05),
8.822 (7.72), 8.825 (6.68), 9.132 (4.25), 9.143 (4.06), 9.302 (0.82), 9.309
(11.61).

I-113

(rac)-3-Bromo-N-{1-[3-(4-cyano-1H-pyrazol-1-yl)pyrazin-2-yl]ethyl}-5-
(trifluoromethyl)benzamide LC-MS (method 2): R$_t$ = 2.06 min; MS (ESIpos): m/z = 465 [M + H]$^+$ ¹H-NMR (600 MHz, DMSO-d6) δ [ppm]: 1.617 (16.00), 1.628 (15.81), 2.573
(0.50), 2.734 (1.08), 2.892 (1.24), 3.319 (0.57), 5.586 (0.68), 5.598 (2.71), 5.609
(4.01), 5.620 (2.62), 5.631 (0.65), 8.126 (7.75), 8.137 (6.92), 8.291 (7.41), 8.478
(11.14), 8.601 (7.32), 8.605 (7.40), 8.830 (7.46), 8.834 (7.11), 9.306 (4.37),
9.314 (14.51).

I-114

(rac)-3-Chloro-N-{1-[3-(4-cyano-1H-pyrazol-1-yl)pyrazin-2-yl]ethyl}-5-
(trifluoromethanesulfonyl)benzamide LC-MS (method 2): R$_t$ = 2.02 min; MS (ESIpos): m/z = 485 [M + H]$^+$ ¹H-NMR (600 MHz, DMSO-d6) δ [ppm]: 1.629 (4.21), 1.633 (4.96), 1.640
(4.23), 1.644 (3.97), 3.284 (11.93), 3.287 (16.00), 5.641 (1.21), 8.363 (2.20),
8.432 (2.54), 8.474 (2.34), 8.477 (2.58), 8.495 (2.65), 8.609 (2.11), 8.612 (2.68),
8.616 (1.89), 8.836 (2.12), 8.840 (2.68), 8.844 (1.83), 9.312 (2.21), 9.316 (2.47),
9.524 (1.61).

-continued

Structure
IUPAC-Name
LC-MS (method): Retention time; Mass found

Example                                                ¹H-NMR

I-115

(rac)-3-Cyano-N-{1-[3-(4-cyano-1H-pyrazol-1-yl)pyrazin-2-yl]ethyl}-5-
(trifluoromethyl)benzamide LC-MS (method 2): R$_t$ = 1.81 min; MS (ESIpos): m/z = 412 [M + H]⁺

¹H-NMR (600 MHz, DMSO-d6) δ [ppm]: 1.629 (16.00), 1.641 (15.96), 2.071
(2.38), 5.620 (0.72), 5.632 (2.75), 5.643 (4.09), 5.654 (2.69), 5.665 (0.66), 8.405
(7.40), 8.483 (11.28), 8.511 (7.14), 8.529 (8.01), 8.609 (7.35), 8.613 (7.54),
8.644 (0.53), 8.834 (7.43), 8.838 (7.32), 9.317 (11.35), 9.366 (4.15), 9.377
(4.06), 11.188 (0.41).

I-116

(rac)-3-Cyano-N-{1-[3-(4-cyano-1H-pyrazol-1-yl)pyrazin-2-yl]ethyl}-5-
(trifluoromethoxy)benzamide LC-MS (method 2): R$_t$ = 1.86 min; MS (ESIpos): m/z = 428 [M + H]⁺

¹H-NMR (600 MHz, DMSO-d6) δ [ppm]: 1.618 (16.00), 1.629 (15.65), 2.071
(2.27), 5.602 (0.78), 5.613 (2.76), 5.624 (4.07), 5.635 (2.68), 5.647 (0.70), 8.034
(6.69), 8.190 (6.20), 8.332 (8.90), 8.404 (0.75), 8.478 (10.52), 8.607 (7.19),
8.610 (7.55), 8.832 (7.41), 8.836 (7.48), 9.280 (4.28), 9.291 (4.28), 9.315
(10.76), 11.092 (0.69).

-continued

| Example | Structure<br>IUPAC-Name<br>LC-MS (method): Retention time; Mass found<br>$^1$H-NMR |
| --- | --- |

I-117

(rac)-2-(3-{1-[3-Bromo-5-(trifluoromethyl)benzamido]ethyl}pyrazin-2-yl)-
1,3-thiazole-5-carboxylic acid
LC-MS (method 2): R$_t$ = 1.94 min; MS (ESIpos): m/z = 501 [M + H]$^+$
$^1$H-NMR (600 MHz, DMSO-d6) δ [ppm]: 1.572 (16.00), 1.583 (15.96), 6.472
(0.66), 6.484 (2.72), 6.495 (4.14), 6.507 (2.70), 6.518 (0.66), 8.113 (5.20), 8.141
(6.68), 8.214 (7.34), 8.377 (7.26), 8.621 (6.68), 8.625 (8.06), 8.658 (7.55), 8.662
(6.56), 9.326 (4.07), 9.337 (3.94).

I-118

(rac)-2-(3-{1-[3-Bromo-5-(trifluoromethyl)benzamido]ethyl}pyrazin-2-yl)-
N,N-dimethyl-1,3-thiazole-5-carboxamide
LC-MS (method 1): R$_t$ = 1.39 min; MS (ESIneg): m/z = 526 [M − H]$^-$
$^1$H-NMR (600 MHz, DMSO-d6) δ [ppm]: 1.594 (15.00), 1.605 (14.92), 2.070
(2.72), 2.572 (1.42), 3.052 (2.29), 3.240 (2.54), 3.258 (2.49), 3.322 (2.49), 6.476
(0.62), 6.488 (2.52), 6.499 (3.89), 6.510 (2.52), 6.522 (0.63), 8.151 (5.54), 8.210
(6.00), 8.374 (6.12), 8.410 (16.00), 8.663 (7.51), 8.667 (8.09), 8.737 (7.82),
8.741 (7.09), 9.363 (3.55), 9.374 (3.46).

I-119

| Example | Structure<br>IUPAC-Name<br>LC-MS (method): Retention time; Mass found<br>$^1$H-NMR |
|---|---|

(rac)-2-(3-{1-[3-Bromo-5-(trifluoromethyl)benzamido]ethyl}pyrazin-2-yl)-
N-(cyclopropylmethyl)-N-methyl-1,3-thiazole-5-carboxamide
LC-MS (method 1): R$_t$ = 1.52 min; MS (ESIpos): m/z = 568 [M + H]$^+$
$^1$H-NMR (600 MHz, DMSO-d6) δ [ppm]: 0.278 (1.70), 0.507 (1.86), 0.514
(5.77), 0.528 (6.14), 0.537 (2.00), 1.077 (1.63), 1.107 (1.14), 1.595 (15.79),
1.606 (16.00), 2.069 (0.47), 2.423 (0.42), 2.572 (2.51), 2.652 (1.00), 3.253
(1.47), 3.271 (3.77), 3.334 (5.79), 3.352 (3.07), 3.388 (8.42), 3.399 (8.16), 6.490
(2.72), 6.501 (4.14), 6.512 (2.70), 6.524 (0.72), 8.150 (6.93), 8.210 (7.65), 8.373
(7.88), 8.665 (7.60), 8.669 (7.53), 8.738 (7.93), 8.742 (6.84), 9.362 (4.40), 9.373
(4.14).

I-120

(rac)-3-Bromo-N-[1-(3-{5-[(cis)-2,6-dimethylmorpholine-4-carbonyl]-1,3-
thiazol-2-yl}pyrazin-2-yl)ethyl]-5-(trifluoromethyl)benzamide
LC-MS (method 1): R$_t$ = 1.51 min; MS (ESIpos): m/z = 598 [M + H]$^+$
$^1$H-NMR (600 MHz, DMSO-d6) δ [ppm]: 1.124 (8.17), 1.595 (14.32), 1.606
(14.07), 2.069 (14.35), 2.073 (1.28), 2.573 (0.49), 2.652 (0.49), 3.249 (0.60),
3.322 (0.60), 3.610 (2.29), 6.472 (0.54), 6.484 (2.25), 6.495 (3.36), 6.507 (2.20),
6.518 (0.48), 8.153 (5.82), 8.210 (6.30), 8.368 (16.00), 8.372 (6.98), 8.666
(6.86), 8.670 (7.75), 8.740 (7.35), 8.744 (6.94), 9.365 (3.77), 9.377 (3.57).

I-121

(rac)-3-Chloro-5-cyano-N-{1-[3-(4-cyano-1H-pyrazol-1-yl)pyrazin-2-
yl]ethyl}benzamide
LC-MS (Method 2): R$_t$ = 1.73 min; MS (ESIpos): m/z = 378 [M + H]$^+$
$^1$H-NMR (600 MHz, DMSO-d6) δ [ppm]: 1.605 (16.00), 1.616 (15.64), 1.686
(0.61), 1.697 (0.62), 3.174 (1.13), 3.890 (0.79), 5.590 (0.72), 5.602 (2.74), 5.613
(4.01), 5.624 (2.57), 5.635 (0.62), 5.745 (1.57), 8.133 (7.75), 8.197 (12.89),
8.325 (0.40), 8.481 (11.00), 8.602 (7.28), 8.606 (7.30), 8.829 (7.51), 8.832
(7.47), 9.193 (0.47), 9.217 (4.19), 9.228 (3.99), 9.313 (11.40).

-continued

| Example | Structure<br>IUPAC-Name<br>LC-MS (method): Retention time; Mass found<br>¹H-NMR |
|---------|---------------------------------------------------------------------------------|

I-122

(rac)-3-Chloro-N-{1-[3-(4-cyano-1-pyrazol-1-yl)pyrazin-2-yl]ethyl}-5-
(ethanesulfonyl)benzamide LC-MS (Method 2): R$_t$ = 1.65 min; MS (ESIpos): m/z = 445 [M + H]$^+$ ¹H-NMR (600 MHz, DMSO-d6) δ [ppm]: 1.101 (7.94), 1.113 (16.00), 1.125
(8.80), 1.149 (1.09), 1.162 (1.17), 1.173 (0.82), 1.623 (13.18), 1.635 (13.21),
1.684 (0.56), 1.695 (0.50), 3.387 (4.50), 3.399 (8.58), 3.411 (8.20), 3.423 (3.27),
3.466 (0.80), 3.478 (0.69), 5.597 (0.71), 5.608 (2.35), 5.619 (3.43), 5.630 (2.36),
8.062 (6.26), 8.209 (6.89), 8.232 (7.46), 8.311 (0.46), 8.361 (0.40), 8.481 (8.73),
8.606 (6.09), 8.609 (6.25), 8.837 (6.28), 8.840 (6.06), 9.319 (8.77), 9.358 (3.81),
9.369 (3.73).

I-123

(rac)-2-(3-{1-[3,5-Bis(trifluoromethyl)benzamido]ethyl}-6-methylpyrazin-2-
yl)-1,3-thiazole-5-carboxylic acid LC-MS (Method 1): R$_t$ = 1.40 min; MS (ESIpos): m/z = 505 [M + H]$^+$ ¹H-NMR (600 MHz, DMSO-d6) δ [ppm]: 1.359 (0.56), 1.596 (7.27), 1.607
(7.21), 1.751 (0.91), 1.757 (1.21), 1.762 (2.57), 1.767 (1.21), 1.772 (0.94), 2.572
(16.00), 3.592 (1.00), 3.603 (2.36), 3.614 (0.96), 6.482 (1.22), 6.493 (1.86),
6.505 (1.23), 8.284 (3.11), 8.518 (7.32), 8.579 (6.48), 8.656 (5.41), 9.498 (2.00),
9.510 (1.93).

-continued

Structure
IUPAC-Name
LC-MS (method): Retention time; Mass found
Example | <sup>1</sup>H-NMR

I-124

(rac)-2-(3-{1-[3,5-Bis(trifluoromethyl)benzamido]ethyl}-6-methylpyrazin-2- yl)-N-(cyanomethyl)-N-methyl-1,3-thiazole-5-carboxamide

LC-MS (Method 2): $R_t$ = 2.16 min; MS (ESIpos): m/z = 557 [M + H]$^+$ $^1$H-NMR (600 MHz, DMSO-d6) δ [ppm]: 1.107 (16.00), 1.601 (5.22), 1.612

(5.12), 2.570 (11.24), 3.078 (5.09), 3.306 (13.03), 4.642 (1.69), 6.497 (0.89), 6.509 (1.35), 6.520 (0.87), 8.288 (2.36), 8.526 (6.09), 8.650 (3.84), 9.500 (1.47), 9.512 (1.42).

I-125

(rac)-2-(3-{1-[3,5-Bis(trifluoromethyl)benzamido]ethyl}-6-methylpyrazin-2- yl)-N-(cyclopropylmethyl)-N-methyl-1,3-thiazole-5-carboxamide

LC-MS (Method 2): $R_t$ = 2.41 min; MS (ESIpos): m/z = 572 [M + H]$^+$ $^1$H-NMR (600 MHz, DMSO-d6) δ [ppm]: 0.273 (0.67), 0.506 (0.81), 0.514

(2.41), 0.527 (2.46), 0.536 (0.62), 1.076 (0.73), 1.107 (16.00), 1.598 (6.69), 1.610 (6.58), 2.563 (14.77), 3.078 (5.29), 3.391 (2.61), 3.403 (2.52), 6.498

(1.13), 6.510 (1.71), 6.521 (1.12), 8.288 (2.86), 8.526 (6.63), 8.629 (4.99), 9.492

(1.83), 9.503 (1.75).

-continued

Structure
IUPAC-Name
LC-MS (method): Retention time; Mass found
Example | ¹H-NMR

I-126

(rac)-N-[1-(3-{5-[cis-2,6-Dimethylmorpholine-4-carbonyl]-1,3-thiazol-2-yl}-
5-methylpyrazin-2-yl)ethyl]-3,5-bis(trifluoromethyl)benzamide
LC-MS (Method 2): $R_t$ = 2.37 min; MS (ESIpos): m/z = 602 [M + H]⁺
¹H-NMR (600 MHz, DMSO-d6) δ [ppm]: 1.107 (16.00), 1.125 (3.15), 1.598
(4.27), 1.609 (4.28), 2.562 (9.68), 3.078 (5.05), 3.607 (0.82), 6.489 (0.68), 6.501
(1.03), 6.512 (0.67), 8.290 (1.89), 8.354 (3.82), 8.525 (4.42), 8.630 (3.27), 9.496
(1.22), 9.507 (1.17).

I-127

(rac)-N-[1-(3-{5-[cis-2,6-dimethylmorpholine-4-carbonyl]-1,3-thiazol-2-yl}-
6-methylpyrazin-2-yl)ethyl]-3,5-bis(trifluoromethyl)benzamide
LC-MS (Method 2): $R_t$ = 2.38 min; MS (ESIpos): m/z = 602 [M + H]⁺
¹H-NMR (600 MHz, DMSO-d6) δ [ppm]: 1.122 (10.12), 1.599 (15.67), 1.611
(15.44), 2.384 (0.44), 2.424 (0.60), 2.573 (1.13), 2.612 (0.56), 2.652 (0.63),
3.267 (0.44), 3.339 (1.48), 3.607 (2.66), 5.745 (3.04), 6.478 (0.58), 6.489 (2.59),
6.501 (3.88), 6.512 (2.47), 6.523 (0.58), 8.294 (6.10), 8.334 (16.00), 8.520
(14.21), 8.552 (11.96), 9.495 (4.17), 9.507 (3.98).

-continued

Structure
IUPAC-Name
LC-MS (method): Retention time; Mass found
Example
¹H-NMR

I-128

(rac)-3-Chloro-N-{1-[3-(4-cyano-1H-pyrazol-1-yl)pyrazin-2-yl]ethyl}-5-(4-
fluorobenzene-1-sulfonyl)benzamide
LC-MS (Method 2): R$_t$ = 1.96 min; MS (ESIpos): m/z = 511 [M + H]$^+$
¹H-NMR (600 MHz, DMSO-d6) δ [ppm]: 1.611 (15.79), 1.622 (16.00), 2.384
(0.46), 2.423 (0.53), 2.612 (1.31), 2.652 (1.06), 3.242 (0.47), 3.256 (1.47), 3.330
(2.42), 5.572 (0.73), 5.583 (2.77), 5.594 (4.12), 5.605 (2.83), 5.616 (0.84), 7.469
(4.82), 7.483 (9.70), 7.498 (5.33), 8.107 (5.10), 8.115 (5.69), 8.122 (5.82), 8.130
(5.32), 8.170 (8.12), 8.185 (7.92), 8.280 (8.59), 8.469 (10.92), 8.598 (7.27),
8.602 (7.68), 8.821 (7.39), 8.825 (7.31), 9.313 (10.97), 9.353 (4.48), 9.364
(4.48).

I-129

(rac)-1-{3-[1-{[1-methyl-5-(trifluoromethyl)-1H-pyrazole-3-
carbonyl]amino}ethyl]pyrazin-2-yl}-1H-pyrazole-4-carboxylic acid
LC-MS (Method 2): R$_t$ = 1.43 min; MS (ESIpos): m/z = 410 [M + H]$^+$
¹H-NMR (600 MHz, DMSO-d6) δ [ppm]: 1.164 (1.96), 1.175 (3.69), 1.187
(1.80), 1.522 (9.36), 1.533 (9.16), 1.750 (0.41), 1.755 (0.46), 1.760 (1.17), 1.766
(0.45), 1.771 (0.41), 1.988 (6.79), 3.591 (0.44), 3.602 (1.01), 3.613 (0.41), 3.996
(0.48), 4.013 (1.05), 4.022 (16.00), 4.036 (1.75), 4.048 (0.66), 5.765 (1.57),
5.776 (2.30), 5.788 (1.52), 7.210 (5.84), 8.250 (6.82), 8.545 (2.31), 8.557 (2.23),
8.595 (4.86), 8.599 (4.93), 8.795 (4.81), 8.799 (4.60), 8.830 (7.17).

-continued

| Example | Structure<br>IUPAC-Name<br>LC-MS (method): Retention time; Mass found<br>¹H-NMR |
| --- | --- |

I-130

(rac)-1-{3-[1-{[1-Ethyl-5-(trifluoromethyl)-1H-pyrazole-3-carbonyl]amino}ethyl]pyrazin-2-yl}-1H-pyrazole-4-carboxylic acid LC-MS (Method 2): $R_t$ = 1.59 min; MS (ESIpos): m/z = 424 [M + H]⁺

¹H-NMR (600 MHz, DMSO-d6) δ [ppm]: 1.171 (0.52), 1.208 (7.98), 1.220 (16.00), 1.232 (7.86), 1.357 (1.35), 1.557 (13.29), 1.568 (13.16), 4.393 (2.33), 4.405 (6.35), 4.417 (6.24), 4.428 (2.16), 5.735 (0.60), 5.746 (2.32), 5.757 (3.45), 5.769 (2.23), 5.781 (0.54), 7.382 (9.58), 8.226 (9.82), 8.590 (6.24), 8.594 (5.67), 8.782 (6.31), 8.785 (5.46), 8.860 (10.04), 9.108 (3.67), 9.120 (3.49).

I-131

(rac)-1-(3-{1-[3,5-Bis(trifluoromethyl)benzamido]ethyl}pyrazin-2-yl)-N-(cyclopropylmethyl)-N-methyl-1H-pyrazole-4-carboxamide LC-MS (Method 2):$R_t$ = 2.09 min; MS (ESIpos): m/z = 541 [M + H]⁺

¹H-NMR (600 MHz, DMSO-d6) δ [ppm]: 0.268 (1.37), 0.470 (2.20), 0.477 (6.39), 0.479 (6.48), 0.490 (6.69), 0.500 (1.92), 1.035 (1.56), 1.234 (0.51), 1.642 (15.25), 1.654 (15.18), 3.050 (0.92), 3.219 (1.86), 3.321 (0.69), 3.345 (5.17), 3.356 (5.18), 5.808 (0.70), 5.819 (2.82), 5.830 (4.23), 5.841 (2.74), 5.853 (0.66), 8.144 (0.96), 8.276 (7.13), 8.472 (16.00), 8.571 (7.73), 8.575 (8.04), 8.759 (8.14), 8.762 (7.85), 9.448 (4.01), 9.458 (3.94).

-continued

| Example | Structure<br>IUPAC-Name<br>LC-MS (method): Retention time; Mass found<br>$^1$H-NMR |
|---|---|

I-132

(rac)-1-(3-{1-[3-Chloro-5-(trifluoromethyl)benzamido]ethyl}pyrazin-2-yl)-
N-(cyclopropylmethyl)-N-methyl-1H-pyrazole-4-carboxamide LC-MS (Method 2): $R_t$ = 2.04 min; MS (ESIpos): m/z = 507 [M + H]$^+$ $^1$H-NMR (600 MHz, DMSO-d6) δ [ppm]: 0.269 (1.44), 0.473 (2.29), 0.481
(6.87), 0.494 (6.92), 0.502 (1.93), 1.036 (1.52), 1.233 (0.76), 1.616 (16.00),
1.628 (15.84), 2.122 (0.43), 2.199 (0.64), 2.209 (0.64), 3.052 (0.91), 3.223
(1.92), 3.259 (1.10), 3.347 (5.50), 3.357 (5.50), 5.773 (0.73), 5.784 (2.89), 5.795
(4.36), 5.807 (2.85), 5.818 (0.71), 8.028 (7.36), 8.120 (8.76), 8.170 (7.91), 8.564
(7.59), 8.567 (7.66), 8.753 (8.04), 8.756 (7.70), 9.279 (4.38), 9.289 (4.28).

I-133

(rac)-1-(3-{1-[3-Chloro-5-(trifluoromethoxy)benzamido]ethyl}pyrazin-2-yl)-
N-(cyclopropylmethyl)-N-methyl-1H-pyrazole-4-carboxamide LC-MS (Method 2): $R_t$ = 2.09 min; MS (ESIpos): m/z = 523 [M + H]$^+$ $^1$H-NMR (600 MHz, DMSO-d6) δ [ppm]: 0.270 (1.38), 0.474 (2.04), 0.481
(6.03), 0.483 (6.45), 0.494 (6.58), 0.496 (6.59), 0.504 (2.26), 1.039 (1.41), 1.235
(0.44), 1.606 (15.67), 1.618 (16.00), 2.184 (1.17), 2.195 (1.21), 3.052 (0.84),
3.227 (1.73), 3.319 (1.03), 3.349 (5.26), 3.359 (5.32), 5.753 (0.67), 5.765 (2.88),
5.776 (4.47), 5.787 (2.99), 5.799 (0.81), 7.734 (13.33), 7.824 (0.42), 7.974
(8.07), 8.002 (0.65), 8.144 (0.96), 8.562 (7.97), 8.566 (8.66), 8.594 (0.47), 8.610
(0.41), 8.751 (8.28), 8.755 (8.44), 9.190 (4.18), 9.201 (4.16).

-continued

| | Structure<br>IUPAC-Name<br>LC-MS (method): Retention time; Mass found |
| Example | $^1$H-NMR |

I-134

(rac)-1-(3-{1-[3-Bromo-5-(trifluoromethoxy)benzamido]ethyl}pyrazin-2-yl)-
N-(cyclopropylmethyl)-N-methyl-1H-pyrazole-4-carboxamide
LC-MS (Method 2): $R_t$ = 2.12 min; MS (ESIpos): m/z = 567 [M + H]$^+$
$^1$H-NMR (600 MHz, DMSO-d6) δ [ppm]: 0.273 (1.23), 0.474 (2.17), 0.481
(6.32), 0.484 (6.27), 0.488 (3.22), 0.495 (6.60), 0.497 (6.20), 0.504 (1.90), 1.039
(1.31), 1.234 (0.68), 1.605 (16.00), 1.617 (15.90), 2.071 (0.47), 2.184 (0.90),
2.195 (0.90), 3.052 (0.76), 3.228 (1.59), 3.243 (1.12), 3.349 (5.07), 3.360 (5.04),
5.750 (0.68), 5.762 (2.95), 5.773 (4.45), 5.784 (2.90), 5.796 (0.65), 7.735 (0.40),
7.759 (6.43), 7.842 (6.23), 8.111 (8.94), 8.143 (0.89), 8.562 (8.62), 8.566 (8.88),
8.751 (8.69), 8.755 (8.34), 9.195 (4.26), 9.206 (4.10).

I-135

(rac)-1-{3-[1-(3-Cyano-5-fluorobenzamido)ethyl]pyrazin-2-yl}-N-
(cyclopropylmethyl)-N-methyl-1H-pyrazole-4-carboxamide
LC-MS (Method 9): $R_t$ = 0.92 min; MS (ESIpos): m/z = 448 [M + H]$^+$
$^1$H-NMR (500 MHz, DMSO-d6) δ [ppm]: 0.197 (1.04), 0.284 (2.10), 0.476
(2.21), 0.486 (6.98), 0.502 (7.15), 0.511 (2.00), 1.042 (1.64), 1.263 (0.42), 1.614
(16.00), 1.628 (16.00), 3.048 (1.42), 3.244 (3.21), 3.361 (5.21), 5.768 (0.65),
5.781 (2.41), 5.795 (3.59), 5.808 (2.40), 5.821 (0.65), 7.555 (0.83), 7.569 (0.71),
7.575 (0.63), 7.607 (0.86), 7.621 (0.83), 7.630 (1.28), 7.646 (0.74), 7.935 (3.66),
7.954 (3.65), 8.031 (3.40), 8.048 (3.37), 8.160 (10.63), 8.571 (7.40), 8.575
(8.13), 8.758 (8.49), 8.762 (8.72), 9.198 (4.88), 9.211 (4.77).

-continued

Structure
IUPAC-Name
LC-MS (method): Retention time; Mass found
Example                          ¹H-NMR

I-136

(rac)-1-(3-{1-[3,5-Bis(trifluoromethyl)benzamido]ethyl}pyrazin-2-yl)-N-
methyl-N-(propan-2-yl)-1H-pyrazole-4-carboxamide
LC-MS (Method 2): R_t = 2.05 min; MS (ESIpos): m/z = 529 [M + H]⁺
¹H-NMR (600 MHz, DMSO-d6) δ [ppm]: 1.154 (12.23), 1.643 (15.85), 1.655
(16.00), 2.967 (1.52), 3.260 (1.09), 3.330 (1.32), 3.343 (0.83), 5.846 (2.09),
8.118 (1.02), 8.278 (7.00), 8.472 (14.01), 8.570 (6.98), 8.572 (7.21), 8.698
(1.10), 8.756 (7.14), 8.758 (7.02), 9.443 (3.23), 9.454 (3.26).

I-137

(rac)-1-(3-{1-[3-Bromo-5-(trifluoromethoxy)benzamido]ethyl}pyrazin-2-yl)-
N-methyl-N-(propan-2-yl)-1H-pyrazole-4-carboxamide
LC-MS (Method 2): R_t = 2.08 min; MS (ESIpos): m/z = 555 [M + H]⁺
¹H-NMR (600 MHz, DMSO-d6) δ [ppm]: 1.157 (15.23), 1.606 (16.00), 1.618
(15.76), 2.970 (1.74), 4.744 (0.41), 5.789 (2.46), 7.759 (6.81), 7.842 (6.83),
8.111 (8.43), 8.561 (7.62), 8.564 (7.55), 8.689 (1.34), 8.748 (7.82), 9.190 (3.95),
9.201 (3.79).

-continued

Structure
IUPAC-Name
LC-MS (method): Retention time; Mass found

Example
$^1$H-NMR

I-138

(rac)-N-[1-(3-{4-[(cis)-2,6-Dimethylmorpholine-4-carbonyl]-1H-pyrazol-1-
yl}pyrazin-2-yl)ethyl]-3,5-bis(trifluoromethyl)benzamide
LC-MS (Method 2): R$_t$ = 2.04 min; MS (ESIpos): m/z = 571 [M + H]$^+$
$^1$H-NMR (400 MHz, DMSO-d6) δ [ppm]: 1.102 (9.35), 1.640 (15.14), 1.657
(15.36), 2.368 (0.43), 2.672 (0.48), 2.712 (0.46), 2.894 (0.52), 3.545 (3.53),
3.923 (0.49), 4.356 (0.50), 5.742 (0.62), 5.760 (2.68), 5.776 (4.12), 5.793 (2.69),
5.810 (0.65), 8.124 (11.45), 8.296 (6.63), 8.468 (16.00), 8.582 (6.92), 8.587
(7.44), 8.745 (12.08), 8.771 (7.41), 8.776 (7.16), 9.479 (4.31), 9.496 (4.19).

I-139

(rac)-1-(3-{1-[3,5-Bis(trifluoromethyl)benzamido]ethyl}pyrazin-2-yl)-N-
cyclopropyl-N-methyl-1H-pyrazole-4-carboxamide
LC-MS (Method 2): R$_t$ = 1.99 min; MS (ESIpos): m/z = 527 [M + H]$^+$
$^1$H-NMR (600 MHz, DMSO-d6) δ [ppm]: 0.602 (1.81), 0.607 (2.05), 0.610
(1.79), 0.809 (1.23), 0.814 (1.38), 0.818 (1.36), 1.638 (4.79), 1.649 (4.71), 2.988
(8.08), 3.141 (0.41), 3.302 (16.00), 5.841 (0.80), 5.852 (1.20), 5.864 (0.77),
8.218 (2.49), 8.272 (1.97), 8.473 (4.57), 8.562 (2.40), 8.566 (2.41), 8.750 (2.43),
8.754 (2.27), 8.804 (2.60), 9.450 (1.23), 9.461 (1.19).

-continued

| Example | Structure<br>IUPAC-Name<br>LC-MS (method): Retention time; Mass found<br>¹H-NMR |
|---|---|

I-140

(rac)-N-(Cyclopropylmethyl)-2-(3-{1-[3-(methanesulfonyl)-5-
(trifluoromethoxy)benzamido]ethyl}pyrazin-2-yl)-N-methyl-1,3-thiazole-5-
carboxamide
LC-MS (Method 2): $R_t$ = 1.93 min; MS (ESIpos): m/z = 584 [M + H]⁺
¹H-NMR (600 MHz, DMSO-d6) δ [ppm]: 0.278 (0.81), 0.516 (2.74), 0.529
(2.79), 1.078 (0.82), 1.615 (6.77), 1.626 (6.68), 2.069 (0.93), 3.249 (0.52), 3.356
(16.00), 3.390 (3.12), 3.401 (2.99), 6.522 (1.18), 6.533 (1.78), 6.545 (1.16),
8.054 (2.90), 8.157 (3.02), 8.492 (3.88), 8.674 (3.08), 8.677 (3.32), 8.747 (3.29),
8.751 (3.12), 9.478 (1.98), 9.490 (1.91).

I-141

(rac)-2-(3-{1-[3,5-Bis(difluoromethyl)benzamido]ethyl}pyrazin-2-yl)-N-
(cyclopropylmethyl)-N-methyl-1,3-thiazole-5-carboxamide
LC-MS (Method 2): $R_t$ = 1.99 min; MS (ESIpos): m/z = 522 [M + H]⁺
¹H-NMR (600 MHz, DMSO-d6) δ [ppm]: 0.272 (1.72), 0.517 (6.04), 0.529
(6.05), 1.079 (1.77), 1.164 (1.19), 1.176 (2.37), 1.187 (1.21), 1.237 (0.64), 1.397
(0.52), 1.602 (16.00), 1.613 (15.70), 1.987 (4.41), 2.571 (0.42), 3.117 (0.76),
3.252 (1.11), 3.321 (1.90), 3.391 (6.64), 3.402 (6.51), 4.013 (0.41), 4.025 (1.13),
4.037 (1.09), 6.482 (0.71), 6.493 (2.74), 6.505 (4.16), 6.516 (2.69), 6.527 (0.66),
7.077 (5.60), 7.170 (11.42), 7.262 (5.30), 7.922 (6.84), 8.256 (15.25), 8.414
(0.60), 8.664 (7.12), 8.667 (8.00), 8.734 (7.69), 8.737 (7.42), 9.344 (4.43), 9.355
(4.26).

-continued

Structure
IUPAC-Name
LC-MS (method): Retention time; Mass found
Example                                                    ¹H-NMR

I-142

(rac)-N-(Cyanomethyl)-2-(3-{1-[3-cyclopropyl-5-
(difluoromethoxy)benzamido]ethyl}pyrazin-2-yl)-N-methyl-1,3-thiazole-5-
carboxamide
LC-MS (Method 2): R$_t$ = 1.92 min; MS (ESIpos): m/z = 513 [M + H]$^+$
¹H-NMR (600 MHz, DMSO-d6) δ [ppm]: 0.742 (0.69), 0.750 (0.86), 0.758
(3.86), 0.762 (2.29), 0.766 (4.46), 0.771 (4.46), 0.780 (3.58), 0.796 (0.69), 0.974
(0.40), 0.982 (0.81), 0.992 (6.15), 0.995 (6.38), 1.006 (6.44), 1.009 (6.06), 1.019
(0.56), 1.587 (16.00), 1.599 (15.83), 1.973 (0.87), 1.982 (1.76), 1.987 (1.88),
1.996 (3.21), 2.004 (1.76), 2.010 (1.58), 2.018 (0.72), 2.070 (2.12), 3.261 (0.65),
3.328 (4.10), 4.641 (3.79), 6.432 (0.63), 6.444 (2.72), 6.455 (4.16), 6.467 (2.67),
6.478 (0.61), 7.042 (6.35), 7.109 (3.52), 7.233 (7.05), 7.356 (3.41), 7.385 (6.20),
7.453 (8.11), 8.529 (2.45), 8.669 (7.74), 8.672 (8.33), 8.748 (8.06), 8.751 (7.29),
9.002 (4.28), 9.013 (4.08).

I-143

(rac)-2-(3-{1-[3,5-Bis(difluoromethoxy)benzamido]ethyl}pyrazin-2-yl)-N-
(cyclopropylmethyl)-N-methyl-1,3-thiazole-5-carboxamide
LC-MS (Method 2): R$_t$ = 2.06 min; MS (ESIpos): m/z = 554 [M + H]$^+$
¹H-NMR (600 MHz, DMSO-d6) δ [ppm]: 0.278 (1.42), 0.508 (1.66), 0.517
(5.20), 0.529 (5.25), 0.538 (1.46), 1.078 (1.44), 1.590 (16.00), 1.601 (15.83),
2.571 (0.42), 3.117 (0.64), 3.276 (1.70), 3.341 (1.20), 3.350 (0.53), 3.389 (6.21),
3.401 (6.19), 6.457 (0.68), 6.468 (2.74), 6.480 (4.18), 6.491 (2.72), 6.503 (0.63),
7.201 (7.56), 7.208 (7.11), 7.324 (14.13), 7.446 (6.69), 7.567 (14.92), 7.571
(14.83), 8.414 (0.50), 8.661 (7.49), 8.665 (8.23), 8.732 (7.99), 8.736 (7.36),
9.144 (4.30), 9.155 (4.19).

-continued

| Example | Structure<br>IUPAC-Name<br>LC-MS (method): Retention time; Mass found<br>¹H-NMR |
|---|---|

I-144

(rac)-Methyl 2-(3-{1-[3,5-Bis(difluoromethoxy)benzamido]ethyl}pyrazin-2-yl)-1,3-thiazole-5-carboxylate LC-MS (Method 1): R$_t$ = 1.42 min; MS (ESIpos): m/z = 501 [M + H]$^+$ ¹H-NMR (600 MHz, DMSO-d6) δ [ppm]: 1.585 (6.97), 1.596 (6.83), 3.910 (16.00), 6.448 (1.19), 6.459 (1.76), 6.471 (1.18), 7.197 (3.06), 7.206 (3.08), 7.320 (5.63), 7.442 (2.71), 7.557 (6.63), 7.560 (6.27), 8.688 (4.14), 8.691 (9.05), 8.774 (3.41), 8.778 (3.08), 9.157 (1.87), 9.168 (1.80).

I-145

(rac)-Methyl 2-(3-{1-[3-Cyclopropyl-5-(difluoromethoxy)benzamido]ethyl}pyrazin-2-yl)-1,3-thiazole-5-carboxylate LC-MS (Method 1): R$_t$ = 1.47 min; MS (ESIpos): m/z = 475 [M + H]$^+$ ¹H-NMR (600 MHz, DMSO-d6) delta [ppm]: 0.753 (1.82), 0.762 (2.35), 0.766 (2.41), 0.775 (1.71), 0.989 (2.89), 0.992 (3.00), 1.003 (3.01), 1.006 (2.83), 1.579 (7.01), 1.591 (6.82), 1.977 (0.78), 1.983 (0.89), 1.991 (1.40), 2.000 (0.82), 2.005 (0.70), 2.733 (1.18), 2.891 (1.32), 3.167 (14.19), 3.176 (14.37), 3.258 (0.86), 3.910 (16.00), 4.042 (1.48), 4.051 (4.11), 4.059 (3.96), 4.068 (1.30), 6.423 (1.20), 6.434 (1.79), 6.445 (1.15), 7.039 (3.00), 7.105 (1.37), 7.228 (2.78), 7.352 (1.39), 7.372 (2.98), 7.439 (3.69), 8.679 (3.40), 8.682 (3.70), 8.689 (5.79), 8.768 (3.35), 8.772 (3.14), 9.006 (1.86), 9.017 (1.80).

-continued

| Example | Structure<br>IUPAC-Name<br>LC-MS (method): Retention time; Mass found<br>$^1$H-NMR |
|---|---|

I-146

(rac)-2-(3-{1-[3,5-Bis(difluoromethoxy)benzamido]ethyl}pyrazin-2-yl)-1,3-thiazole-5-carboxylic acid LC-MS (Method 9): R$_t$ = 0.94 min; MS (ESIpos): m/z = 487 [M + H]$^+$ $^1$H-NMR (600 MHz, DMSO-d6) δ [ppm]: 1.358 (2.55), 1.575 (16.00), 1.586 (15.95), 2.185 (0.42), 2.466 (0.64), 3.911 (0.51), 6.448 (0.76), 6.459 (2.79), 6.470 (4.23), 6.482 (2.74), 6.493 (0.69), 7.200 (7.55), 7.207 (7.82), 7.329 (13.07), 7.451 (6.29), 7.569 (15.09), 7.572 (14.86), 8.274 (4.41), 8.639 (7.12), 8.643 (7.91), 8.689 (7.60), 8.693 (6.89), 9.121 (4.12), 9.133 (3.93).

I-147

(rac)-2-(3-{1-[3-Cyclopropyl-5-(difluoromethoxy)benzamido]ethyl}pyrazin-2-yl)-1,3-thiazole-5-carboxylic acid LC-MS (Method 1): R$_t$ = 1.28 min; MS (ESIpos): m/z = 461 [M + H]$^+$ $^1$H-NMR (600 MHz, DMSO-d6) δ [ppm]: 0.760 (4.13), 0.769 (5.26), 0.773 (5.36), 0.782 (3.91), 0.992 (7.00), 1.004 (6.96), 1.016 (0.68), 1.358 (0.70), 1.564 (16.00), 1.576 (15.64), 1.760 (0.64), 1.974 (0.95), 1.982 (1.84), 1.988 (2.10), 1.996 (3.23), 2.004 (1.97), 2.010 (1.63), 2.019 (0.76), 3.602 (1.09), 6.421 (0.69), 6.432 (2.76), 6.444 (4.10), 6.455 (2.69), 6.467 (0.64), 7.034 (7.00), 7.114 (3.15), 7.238 (6.26), 7.361 (3.11), 7.386 (6.93), 7.451 (8.54), 8.206 (5.40), 8.623 (6.90), 8.626 (7.90), 8.669 (7.48), 8.672 (6.83), 8.961 (4.35), 8.973 (4.14).

-continued

| Example | Structure IUPAC-Name LC-MS (method): Retention time; Mass found ¹H-NMR |
| --- | --- |

I-148

(rac)-2-(3-{1-[3,5-Bis(trifluoromethyl)benzamido]ethyl}-5-methylpyrazin-2-yl)-N-ethyl-N-methyl-1,3-thiazole-5-carboxamide LC-MS (Method 0): $R_t$ = 1.18 min; MS (ESIpos): m/z = 546 [M + H]$^+$ ¹H-NMR (600 MHz, DMSO-d6) δ [ppm]: 1.181 (2.85), 1.599 (16.00), 1.611 (15.71), 2.070 (1.15), 3.026 (0.83), 3.212 (1.03), 3.513 (3.81), 3.524 (3.64), 5.746 (0.97), 6.480 (0.65), 6.492 (2.72), 6.503 (4.18), 6.515 (2.63), 6.526 (0.60), 8.292 (6.69), 8.346 (0.56), 8.520 (15.15), 8.549 (11.74), 9.492 (4.01), 9.503 (3.78).

I-149

(rac)-Methyl 2-{3-[1-{[2,6-Bis(trifluoromethyl)pyridine-4-carbonyl]amino}ethyl]-5-methylpyrazin-2-yl}-1,3-thiazole-5-carboxylate LC-MS (Method 9): $R_t$ = 1.22 min; MS (ESIpos): m/z = 520 [M + H]$^+$ ¹H-NMR (600 MHz, DMSO-d6) δ [ppm]: 1.177 (0.42), 1.605 (6.83), 1.616 (6.72), 1.988 (0.88), 2.071 (1.49), 2.564 (14.75), 3.903 (16.00), 6.513 (1.18), 6.524 (1.79), 6.536 (1.16), 8.568 (10.28), 8.593 (5.04), 8.660 (5.83), 9.705 (1.70), 9.716 (1.65).

-continued

Structure
IUPAC-Name
LC-MS (method): Retention time; Mass found

Example $^1$H-NMR

I-150

(rac)-2-{3-[1-{[2,6-Bis(trifluoromethyl)pyridine-4-carbonyl]amino}ethyl]-5-
methylpyrazin-2-yl}-1,3-thiazole-5-carboxylic acid LC-MS (Method 1): R$_t$ = 1.37 min; MS (ESIpos): m/z = 506 [M + H]$^+$ $^1$H-NMR (400 MHz, DMSO-d6) δ [ppm]: 1.031 (0.95), 1.046 (0.89), 1.600
(7.10), 1.617 (7.14), 2.370 (0.53), 2.558 (16.00), 2.673 (0.41), 2.713 (0.61),
6.510 (1.22), 6.527 (1.91), 6.544 (1.25), 8.568 (6.46), 8.575 (11.96), 8.587
(5.91), 9.725 (1.90), 9.742 (1.90).

I-151

(rac)-N-[1-(3-{5-[Ethyl(methyl)carbamoyl]-1,3-thiazol-2-yl}-6-
methylpyrazin-2-yl)ethyl]-2,6-bis(trifluoromethyl)pyridine-4-carboxamide LC-MS (Method 2): R$_t$ = 2.21 min; MS (ESIpos): m/z = 547 [M + H]$^+$ $^1$H-NMR (400 MHz, DMSO-d6) δ [ppm]: 1.178 (2.13), 1.599 (9.80), 1.616
(9.91), 2.083 (0.55), 2.709 (0.44), 3.014 (0.74), 3.215 (1.12), 3.238 (1.05), 3.416
(0.49), 3.487 (1.07), 3.505 (2.52), 3.522 (2.46), 6.520 (1.72), 6.537 (2.66), 6.554
(1.69), 8.362 (0.46), 8.563 (7.75), 8.579 (16.00), 9.716 (2.44), 9.733 (2.40).

-continued

Structure
IUPAC-Name
LC-MS (method): Retention time; Mass found
Example                    ¹H-NMR

I-152

(rac)-2-(3-{1-[3,5-Bis(trifluoromethyl)benzamido]ethyl}-6-methylpyrazin-2-
yl)-N-ethyl-N-methyl-1,3-thiazole-5-carboxamide LC-MS (Method 1): $R_t$ = 1.52 min; MS (ESIpos): m/z = 546 [M + H]⁺

¹H-NMR (400 MHz, DMSO-d6) delta [ppm]: −0.149 (0.74), 0.146 (0.74), 1.183
(1.56), 1.592 (6.62), 1.609 (6.62), 2.073 (0.45), 2.367 (0.60), 2.561 (16.00),
2.711 (0.52), 3.029 (0.52), 3.209 (0.74), 3.513 (1.71), 3.532 (1.71), 6.487 (1.12),
6.504 (1.71), 6.521 (1.12), 8.304 (2.98), 8.530 (6.62), 8.630 (5.80), 9.518 (1.71),
9.536 (1.64).

I-153

(rac)-Methyl 2-(3-{1-[3,5-Bis(trifluoromethyl)benzamido]ethyl}-6-
methylpyrazin-2-yl)-1,3-thiazole-5-carboxylate LC-MS (Method 1): $R_t$ = 1.59 min; MS (ESIpos): m/z = 519 [M + H]⁺

¹H-NMR (600 MHz, DMSO-d6) δ [ppm]: 1.166 (1.66), 1.177 (3.31), 1.189
(1.73), 1.253 (0.65), 1.265 (0.73), 1.359 (1.22), 1.595 (6.91), 1.607 (6.93), 1.989
(6.24), 2.574 (15.20), 3.907 (16.00), 4.015 (0.58), 4.027 (1.62), 4.039 (1.56),
4.051 (0.56), 6.481 (1.19), 6.493 (1.77), 6.504 (1.19), 8.284 (2.89), 8.516 (6.71),
8.672 (5.97), 8.675 (6.77), 9.504 (1.81), 9.515 (1.77).

-continued

Structure
IUPAC-Name
LC-MS (method): Retention time; Mass found
Example ¹H-NMR

I-154

(−)-2-(3-{(1R)-1-[3,5-Bis(trifluoromethyl)benzamido]ethyl}-5-methylpyrazin-
2-yl)-N-ethyl-N-methyl-1,3-thiazole-5-carboxamide
LC-MS (Method 9): $R_t$ = 1.20 min; MS (ESIpos): m/z = 546 [M + H]⁺
$[\alpha]_D^{20}$ = −51.3° (c = 0.34, CHCl₃)
¹H-NMR (400 MHz, DMSO-d6) δ [ppm]: −0.149 (0.55), 0.146 (0.52), 1.185
(3.58), 1.284 (0.49), 1.595 (15.86), 1.612 (16.00), 2.368 (0.48), 2.711 (0.53),
3.022 (1.14), 3.216 (1.49), 3.509 (4.25), 3.527 (4.19), 6.470 (0.61), 6.488 (2.76),
6.505 (4.30), 6.522 (2.78), 6.539 (0.61), 8.307 (7.24), 8.526 (15.86), 8.554
(13.54), 9.520 (4.09), 9.537 (4.00).

I-155

(+)-2-(3-{(1S)-1-[3,5-Bis(trifluoromethyl)benzamido]ethyl}-5-
methylpyrazin-2-yl)-N-ethyl-N-methyl-1,3-thiazole-5-carboxamide
LC-MS (Method 9): $R_t$ = 1.20 min; MS (ESIpos): m/z = 546 [M + H]⁺
$[\alpha]_D^{20}$ = +52.5° (c = 0.31, CHCl₃)
¹H-NMR (400 MHz, DMSO-d6) δ [ppm]: −0.149 (0.71), 0.146 (0.70), 1.030
(0.42), 1.045 (0.43), 1.183 (3.50), 1.283 (0.60), 1.595 (15.82), 1.612 (16.00),
2.367 (0.81), 2.711 (0.85), 3.015 (1.09), 3.216 (1.40), 3.509 (4.17), 3.526 (4.19),
6.470 (0.57), 6.487 (2.72), 6.504 (4.22), 6.522 (2.71), 6.538 (0.62), 8.308 (6.75),
8.526 (15.31), 8.554 (12.58), 9.520 (4.08), 9.537 (3.96).

-continued

Structure

IUPAC-Name

LC-MS (method): Retention time; Mass found

Example

<sup>1</sup>H-NMR

I-156

(−)-2-(3-{(1R)-1-[3,5-bis(trifluoromethyl)benzamido]ethyl}-6-methylpyrazin-
2-yl)-N-ethyl-N-methyl-1,3-thiazole-5-carboxamide LC-MS (Method 9): $R_t$ = 1.17 min; MS (ESIpos): m/z = 546 [M + H]$^+$ $[\alpha]_D^{20}$ = −77.3° (c = 0.37, CHCl$_3$)

<sup>1</sup>H-NMR (600 MHz, DMSO-d6) δ [ppm]: 1.183 (1.41), 1.596 (7.21), 1.607 (7.16), 2.561 (16.00), 3.217 (0.50), 3.263 (0.62), 3.517 (1.73), 3.528 (1.70), 6.494 (1.21), 6.505 (1.84), 6.517 (1.17), 8.288 (3.05), 8.525 (6.99), 8.627 (5.38), 9.492 (1.87), 9.503 (1.80).

I-157

(+)-2-(3-{(1S)-1-[3,5-bis(trifluoromethyl)benzamido]ethyl}-6-methylpyrazin-
2-yl)-N-ethyl-N-methyl-1,3-thiazole-5-carboxamide LC-MS (Method 1): $R_t$ = 1.52 min; MS (ESIpos): m/z = 546 [M + H]$^+$ $[\alpha]_D^{20}$ = +77.5° (c = 0.39, CHCl$_3$)

<sup>1</sup>H-NMR (600 MHz, DMSO-d6) δ [ppm]: 1.182 (1.25), 1.596 (7.05), 1.607 (6.99), 2.561 (16.00), 3.213 (0.41), 3.517 (1.57), 3.528 (1.54), 6.494 (1.18), 6.505 (1.78), 6.517 (1.15), 8.286 (2.87), 8.525 (6.59), 8.626 (5.39), 9.492 (1.80), 9.503 (1.73).

-continued

Structure
IUPAC-Name
LC-MS (method): Retention time; Mass found
Example                                    ¹H-NMR

I-158

(−)-N-[(1R)-1-(3-{5-[Ethyl(methylcarbamoyl]-1,3-thiazol-2-yl)-6-
methylpyrazin-2-yl)ethyl]-2,6-bis(trifluoromethyl)pyridine-4-carboxamide
LC-MS (Method 2): $R_t$ = 2.20 min; MS (ESIpos): m/z = 547 [M + H]⁺
$[\alpha]_D^{20}$ = −41.3° (c = 0.26, CHCl₃)
¹H-NMR (600 MHz, DMSO-d6) δ [ppm]: 1.181 (2.37), 1.606 (10.72), 1.618
(11.07), 2.423 (0.41), 2.652 (0.85), 3.020 (0.78), 3.215 (0.99), 3.256 (1.33),
3.324 (2.22), 3.513 (2.86), 3.523 (2.90), 6.517 (0.50), 6.529 (1.84), 6.540 (2.81),
6.551 (1.95), 6.563 (0.55), 8.355 (0.50), 8.563 (7.96), 8.576 (16.00), 9.691
(2.81), 9.702 (2.77).

I-159

(+)-N-[(1S)-1-(3-(5-[ethyl(methyl)carbamoyl]-1,3-thiazol-2-yl)-6-
methylpyrazin-2-yl)ethyl]-2,6-bis(trifluoromethyl)pyridine-4-carboxamide
LC-MS (Method 2): $R_t$ = 2.20 min; MS (ESIpos): m/z = 547 [M + H]⁺
$[\alpha]_D^{20}$ = +38.8° (c = 0.26, CHCl₃)
¹H-NMR (600 MHz, DMSO-d6) δ [ppm]: 1.162 (1.51), 1.174 (1.78), 1.606
(10.61), 1.618 (10.42), 3.020 (0.53), 3.225 (0.64), 3.258 (1.39), 3.326 (0.55),
3.512 (2.19), 3.524 (2.13), 6.517 (0.45), 6.529 (1.87), 6.540 (2.83), 6.551 (1.80),
8.563 (7.99), 8.576 (16.00), 9.691 (2.51), 9.702 (2.44).

Example I-160

6-(3-{1-[3,5-Bis(trifluoromethyl)benzamido]
ethyl}pyrazin-2-yl)-N,N-diethylpyridine-3-carbox-
amide (Enantiomer 1)

enantiomer 1

To a solution of (rac)-6-{3-[1-Aminoethyl]pyrazin-2-yl}-N,N-diethylpyridine-3-carboxamide (intermediate 50A, 55 mg, 0.18 mmol), 3,5-bis(trifluoromethyl)benzoic acid (94 mg, 0.36 mmol) in N,N-dimethylformamide (6 mL) was added N,N-diisopropylethylamine (46.5 mg, 0.36 mmol) and HATU (47.5 mg, 0.25 mmol) respectively. After stirring at 25° C. for 2 h, the reaction mixture was purified via prep-HPLC [RP-C18, mobile Phase A: water (0.1% TFA), mobile Phase B: acetonitrile; gradient: 65% B to 75% B in 10 min] to give 70 mg of the mixture of enantiomers as a white solid.

The two enantiomers were separated by chiral HPLC [Column: CHIRALPAK IG, 2*25 cm, 5 um; mobile phase A: MTBE (0.5% 2 M ammonia in MeOH), Mobile Phase B: isopropanol; flow rate: 20 mL/min; Gradient: hold 5% B over 10.5 min; 254/220 nm; $R_t$ 1: 5.262 min; Rt 2: 8.757 min] to give the title compound as isomer 1 (24.6 mg (24% yield) as an off-white solid eluting at 5.262 min in chiral prep HPLC).

LC-MS (Method 12): $R_t$=1.14; MS (ESIpos): m/z 540 [M+H]⁺.

Chiral HPLC (Method 10): $R_t$=1.53 min

¹H-NMR (400 MHz, DMSO-d6 δ [ppm] 1.05-1.19 (m, 6H), 1.67 (d, 3H), 5.92 (m, 1H), 8.06 (m, 2H), 8.31 (s, 1H), 8.42 (s, 2H), 8.67-8.77 (m, 3H), 9.43 (br s, 1H).

Example I-161

6-(3-{1-[3,5-Bis(trifluoromethyl)benzamido]
ethyl}pyrazin-2-yl)-N,N-diethylpyridine-3-carbox-
amide (Enantiomer 2)

enantiomer 2

The title compound was obtained from the chiral chromatography described under example I-160 as the second isomer: 20 mg (20% yield) as an off-white solid (eluting at 8.757 min in chiral Prep HPLC).

Analytical chiral HPLC [Column: CHIRALPAK IG-3, 4.6*50 mm, 3 um; Mobile Phase A: MTBE (0.1% DEA): IPA=95:5, Mobile Phase B: IPA; Flow rate: 1 mL/min; Gradient: hold 5% B over 3.5 min] Rt=1.533 min.

Example I-162

6-(3-{1-[3,5-bis(trifluoromethyl)benzamido]
ethyl}pyrazin-2-yl)-N-(cyanomethyl)-N-methylpyri-
dine-3-carboxamide (Enantiomer 1)

enantiomer 1

To a solution of (rac)-6-(3-{1-[3,5-Bis(trifluoromethyl) benzamido]ethyl}pyrazin-2-yl)pyridine-3-carboxylic acid (example I-31, 80 mg, 0.17 mmol), 2-(methylamino)acetonitrile (18 mg, 0.25 mmol) in N,N-dimethylformamide (6 ml) was added N,N-diisopropylethylamine (107 mg, 0.83 mmol) and HATU (94 mg, 0.25 mmol) respectively. After stirring at 25° C. for 2 h, the reaction mixture was purified via prep-HPLC [mobile phase A: water (0.1% TFA), mobile phase B: acetonitrile; gradient: 65% B to 75% B in 10 min] to give 40 mg of the mixture of enantiomers as a white solid. The two enantiomers were separated by Chiral-HPLC [Column: CHIRALPAK IG, 2*25 cm, 5 um; Mobile Phase A: MTBE (0.5% 2 M NH₃-MeOH), Mobile Phase B: IPA; Flow rate: 20 mL/min; Gradient: hold 5% B in 8.5 min; 254/220 nm; R$_t$ 1: 4.457 min; R$_t$ 2: 6.687 min] to give the title compound isomer 1 (7.5 mg, 8% yield) as a pink solid (eluting at 4.457 min in chiral Prep HPLC).

Analytical chiral HPLC [Column: CHIRALPAK IG-3, 4.6*50 mm 3 um; Mobile Phase A: MtBE (0.1% diethylamine) isopropanol 98:2, Mobile Phase B: IPA; Flow rate: 1 mL/min; Gradient: 5% B to 5% B in 3 min] Rt=1.281 min. $[\alpha]_D^{23}$=46° (c=0.002, CHCl₃).

Example I-163

6-(3-{1-[3,5-bis(trifluoromethyl)benzamido] ethyl}pyrazin-2-yl)-N-(cyanomethyl)-N-methylpyridine-3-carboxamide (Enantiomer 2)

enantiomer 1

The title compound was obtained as the second isomer from the chiral chromatography described under example I-162 (16.9 mg, 19% yield) as a pink solid (eluting at 6.687 min in chiral prep HPLC).

Analytical chiral HPLC [Column: CHIRALPAK IG-3, 4.6*50 mm 3 um; Mobile Phase A: MtBE (0.1% diethylamine) isopropanol=98:2, Mobile Phase B: isopropanol; flow rate: 1 mL/min; gradient: 5% B to 5% B in 3 min] R$_t$=1.952 min $[\alpha]_D^{23}$=−60° (c=0.002, CHCl₃).

LC-MS (Method 12): R$_t$=1.08; MS (esiPos): m/z 537 [M+H]$^+$.

$^1$H-NMR (400 MHz, DMSO-d6 δ [ppm]: 1.67 (d, 3H), 3.06 (s, 3H), 4.64 (s, 2H), 5.92 (m, 1H), 8.10 (m, 2H), 8.28 (s, 1H), 8.41 (s, 2H), 8.67-8.77 (m, 3H), 9.46 (m, 1H).

Example I-164

6-(3-{1-[3,5-Bis(trifluoromethyl)benzamido] ethyl}pyrazin-2-yl)-N-(cyclopropylmethyl)-N-methylpyridine-3-carboxamide (Enantiomer 1)

enantiomer 1

To a solution of (rac)-6-(3-{1-[3,5-Bis(trifluoromethyl) benzamido]ethyl}pyrazin-2-yl)pyridine-3-carboxylic acid (example I-31, 80 mg, 0.17 mmol), cyclopropyl-N-methyl-methanamine (28 mg, 0.25 mmol) in N,N-dimethylformamide (6 ml) was added N,N-diisopropylethylamine (107 mg, 0.83 mmol) and HATU (94 mg, 0.25 mmol) respectively. After stirred at 25° C. for 2 h, the reaction mixture was purified via prep-HPLC [Mobile Phase A: Water (0.1% FA), Mobile Phase B: ACN; Gradient: 65% B to 75% B in 10 min] to give 30 mg of the mixture of enantiomers as a pink solid. The two enantiomers were separated by chiral HPLC [Column: CHIRALPAK IC, 2*25 cm, 5 um; mobile phase A: hexane:DCM=3:1 (0.5% 2 M ammonia in MeOH), mobile phase B: isopropanol; flow rate: 20 mL/min; gradient: hold 10% B in 22 min; 220/254 nm; Rt 1: 16.225; Rt 2: 19.408] to give the title compound as the first eluting isomer (10.7 mg (12% yield) as a pink solid (eluting at 16.225 min in chiral Prep HPLC).

Analytical chiral HPLC [Column: CHIRALPAK IC, 4.6*50 mm 3 um; Mobile Phase A: (Hexane:DCM=3:1) (0.1% DEA): IPA=90:10, Mobile Phase B: IPA; Flow rate: 1 mL/min; Gradient: 10% B to 10% B in 7 min] Rt=4.141 min.

Optical rotation: $[\alpha]_D^{23}$=20° (c=0.002, CHCl₃).

LC-MS (Method 12): R$_t$=1.17; MS (ESIpos): m/z 552 [M+H]$^+$.

$^1$H-NMR (400 MHz, DMSO-d6 δ [ppm] 0.1-0.7 (m, 4H), 0.81-1.20 (m, 1H), 1.67 (d, 3H), 2.96 (s, 2H), 3.10 (s, 3H), 5.94 (br s, 1H), 8.06 (m, 2H), 8.31 (s, 1H), 8.42 (s, 2H), 8.67-8.77 (m, 3H), 9.43 (br s, 1H).

Example I-165

6-(3-{1-[3,5-Bis(trifluoromethyl)benzamido]ethyl}pyrazin-2-yl)-N-(cyclopropylmethyl)-N-methylpyridine-3-carboxamide (Enantiomer 2)

enantiomer 2

The title compound was obtained as the second isomer from the chiral chromatography described under example I-164 (7.6 mg, 8% yield) as a pink solid (eluting at 19.408 min in chiral Prep HPLC).

Analytical chiral HPLC [Column: CHIRALPAK IC, 4.6*50 mm 3 um; Mobile Phase A: (Hexane:DCM=3:1) (0.1% DEA): IPA=90:10, Mobile Phase B: IPA; Flow rate: 1 mL/min; Gradient: 10% B to 10% B in 7 min] Rt=5.943 min.

Optical rotation: $[\alpha]_D^{23}$=−32° (c=0.002, CHCl$_3$).

LC-MS (Method 12): R$_t$=1.17; MS (ESIpos): m/z 552 [M+H]$^+$.

$^1$H-NMR (400 MHz, DMSO-d6 δ [ppm] 0.1-0.7 (m, 4H), 0.81-1.20 (m, 1H), 1.67 (d, 3H), 2.96 (s, 2H), 3.10 (s, 3H), 5.94 (br s, 1H), 8.06 (m, 2H), 8.31 (s, 1H), 8.42 (s, 2H), 8.67-8.77 (m, 3H), 9.43 (br s, 1H).

Example I-166

N-[1-(3-{5-[(cis)-2,6-Dimethylmorpholine-4-carbonyl]pyridin-2-yl}pyrazin-2-yl)ethyl]-3,5-bis(trifluoromethyl)benzamide (Enantiomer 1)

enantiomer 1

To a solution of (rac)-6-(3-{1-[3,5-Bis(trifluoromethyl)benzamido]ethyl}pyrazin-2-yl)pyridine-3-carboxylic acid (example I-31, 80 mg, 0.17 mmol), (cis)-2,6-dimethylmorpholine (28 mg, 0.25 mmol) in N,N-dimethylformamide (6 ml) was added N,N-diisopropylethylamine (107 mg, 0.83 mmol) and HATU (94 mg, 0.25 mmol) respectively. After stirred at 25° C. for 2 h, the reaction mixture was purified via prep-HPLC [Mobile Phase A: Water (0.1% FA), Mobile Phase B: ACN; Gradient: 65% B to 75% B in 10 min] to give 67 mg of the mixture of enantiomers as an off-white solid. The two enantiomers were separated by chiral HPLC [Column: CHIRALPAK IG, 2*25 cm, 5 um; mobile phase A: MTBE (0.5% 2 M ammonia in MeOH), mobile phase B: isopropanol; flow rate: 20 mL/min; gradient: hold 5% B in 9 min; 254/220 nm; Rt 1: 4.59 min; Rt 2: 7.081 min] to give the title compound (16.1 mg 16% yield) as an off-white solid (eluting at 4.59 min in chiral prep HPLC).

Analytical chiral HPLC [Column: CHIRALPAK IG-3, 4.6*50 mm, 3.0 um; Mobile Phase A: MTBE (0.1% DEA): IPA=95:5, Mobile Phase B: IPA; Flow rate: 1 mL/min; 5% B to 5% B in 3.5 min] Rt=1.031 min.

Optical rotation: $[\alpha]_D^{23}$=+103° (c=0.003, CHCl$_3$).

LC-MS (Method 12): R$_t$=1.14; MS (ESIpos): m/z 582 [M+H]$^+$.

$^1$H-NMR (400 MHz, DMSO-d6 δ [ppm] 0.9-1.3 (m, 6H), 1.66 (d, 3H), 2.81-2.95 (m, 1H), 3.40-3.50 (m, 3H), 4.42 (br s, 1H), 5.94 (br s, 1H), 8.06 (m, 2H), 8.31 (s, 1H), 8.42 (s, 2H), 8.67-8.77 (m, 3H), 9.43 (br s, 1H).

Example I-167

N-[1-(3-{5-[(cis)-2,6-Dimethylmorpholine-4-carbonyl]pyridin-2-yl}pyrazin-2-yl)ethyl]-3,5-bis(trifluoromethyl)benzamide (Enantiomer 2)

enantiomer 2

The title compound was obtained as the second isomer from the chiral chromatography described under example I-166 (19.5 mg 20% yield) as an off-white solid (eluting at 7.081 min in chiral Prep HPLC).

Analytical chiral HPLC [Column: CHIRALPAK IG-3, 4.6*50 mm, 3.0 urn; Mobile Phase A: MTBE (0.1% DEA):

IPA=95:5, Mobile Phase B: IPA; Flow rate: 1 mL/min; 5% B to 5% B in 3.5 min] Rt=1.324 min.

Optical rotation: $[\alpha]_D^{23}$=−90° (c=0.003, CHCl$_3$).

LC-MS (Method 12): R$_t$=1.14; MS (ESIpos): m/z 582 [M+H]$^+$.

$^1$H-NMR (400 MHz, DMSO-d6 δ [ppm] 0.9-1.3 (m, 6H), 1.66 (d, 3H), 2.81-2.95 (m, 1H), 3.40-3.50 (m, 3H), 4.42 (br s, 1H), 5.94 (br s, 1H), 8.06 (m, 2H), 8.31 (s, 1H), 8.42 (s, 2H), 8.67-8.77 (m, 3H), 9.43 (br s, 1H).

| Example | Structure<br>IUPAC-Name<br>LC-MS (method): Retention time; Mass found<br>$^1$H-NMR |
|---|---|
| I-168 | <br>(rac)-Methyl 1-{3-[1-{[1-Methyl-5-(trifluoromethyl)-1H-pyrazole-3-carbonyl]amino}ethyl]pyrazin-2-yl}-1H-pyrazole-4-carboxylate<br>LC-MS (Method 2): R$_t$ = 1.77 min; MS (ESIpos): m/z = 424 [M + H]$^+$<br>$^1$H-NMR (400 MHz, DMSO-d6) δ [ppm]: −0.149 (0.41), 1.106 (0.52), 1.515 (5.91), 1.532 (5.89), 2.073 (2.45), 3.820 (16.00), 3.996 (0.47), 4.019 (11.07), 5.722 (0.98), 5.740 (1.54), 5.757 (0.92), 7.206 (4.21), 8.315 (5.07), 8.555 (1.35), 8.573 (1.32), 8.602 (3.10), 8.608 (3.30), 8.809 (3.14), 8.815 (3.00), 8.918 (5.18). |
| I-169 | <br>(rac)-Methyl 1-{3-[1-{[1-Ethyl-5-(trifluoromethyl)-1H-pyrazole-3-carbonyl]amino}ethyl]pyrazin-2-yl}-1H-pyrazole-4-carboxylate<br>LC-MS (Method 2): R$_t$ = 1.93 min; MS (ESIpos): m/z = 438 [M + H]$^+$<br>$^1$H-NMR (400 MHz, DMSO-d6) δ [ppm]: 1.198 (3.76), 1.216 (8.26), 1.234 (3.82), 1.244 (0.90), 1.259 (0.75), 1.274 (0.49), 1.550 (5.92), 1.567 (5.97), 3.813 (16.00), 4.381 (0.95), 4.399 (2.89), 4.417 (2.88), 4.435 (0.93), 5.706 (0.99), 5.723 (1.57), 5.740 (0.99), 7.370 (4.39), 8.290 (5.04), 8.600 (3.07), 8.606 (3.29), 8.799 (3.19), 8.805 (3.06), 8.949 (5.12), 9.096 (1.37), 9.113 (1.35). |

-continued

Structure
IUPAC-Name
LC-MS (method): Retention time; Mass found
Example                                    ¹H-NMR

I-170

(−)-2-(3-{1-[3-(Difluoromethyl)-5-(trifluoromethyl)benzamido]ethyl}pyrazin-2-
yl)-N-ethyl-N-methyl-1,3-thiazole-5-carboxamide
$[\alpha]_D^{20}$ = −82.6° (c = 0.19, CHCl₃)
LC-MS (Method 2): R$_t$ = 2.03 min; MS (ESIpos): m/z = 514 [M + H]⁺
¹H-NMR (400 MHz, DMSO-d6) δ [ppm]: −0.149 (1.17), 0.146 (1.04), 1.185 (3.58),
1.356 (0.75), 1.606 (15.89), 1.623 (16.00), 2.071 (0.87), 2.086 (1.38), 2.133 (0.95),
2.367 (0.87), 2.711 (0.86), 3.021 (1.31), 3.225 (1.66), 3.512 (4.67), 3.530 (4.67),
3.547 (1.85), 5.754 (2.67), 6.486 (0.62), 6.503 (2.70), 6.520 (4.19), 6.537 (2.68),
6.554 (0.66), 7.060 (3.36), 7.198 (6.96), 7.336 (3.14), 8.107 (6.67), 8.386 (7.44),
8.429 (7.29), 8.669 (8.11), 8.675 (9.67), 8.738 (9.19), 8.744 (8.18), 9.478 (3.98),
9.496 (3.99).

I-171

(+)-2-(3-{1-[3-(Difluoromethyl)-5-(trifluoromethyl)benzamido]ethyl}pyrazin-2-
yl)-N-ethyl-N-methyl-1,3-thiazole-5-carboxamide
$[\alpha]_D^{20}$ = +88.2° (c = 0.22, CHCl₃)
LC-MS (Method 2): R$_t$ = 2.03 min; MS (ESIpos): m/z = 514 [M + H]⁺
¹H-NMR (400 MHz, DMSO-d6) δ [ppm]: −0.149 (0.76), −0.008 (5.50), 0.146 (0.75),
1.188 (3.68), 1.606 (15.90), 1.623 (16.00), 2.071 (0.59), 2.133 (0.63), 2.367 (0.63),
2.711 (0.67), 3.024 (1.28), 3.224 (1.68), 3.494 (1.88), 3.512 (4.82), 3.530 (4.76),
3.546 (1.84), 5.754 (0.49), 6.486 (0.61), 6.503 (2.65), 6.520 (4.10), 6.537 (2.68),
6.554 (0.61), 7.060 (3.26), 7.198 (6.56), 7.336 (3.04), 8.106 (6.36), 8.386 (7.47),
8.428 (7.24), 8.669 (7.05), 8.675 (8.47), 8.738 (8.18), 8.744 (7.36), 9.478 (4.05),
9.495 (3.99).

-continued

Structure
IUPAC-Name
LC-MS (method): Retention time; Mass found

Example                                    ¹H-NMR

I-172

(+)-N-[(1S)-1-(3-{5-[Ethyl(methyl)carbamoyl]-1,3-thiazol-2-yl}pyrazin-2-
yl)ethyl]-2,6-bis(trifluoromethyl)pyridine-4-carboxamide $[\alpha]_D^{20}$ = +78.3° (c = 0.20, CHCl₃)

LC-MS (Method 2): R_t = 2.09 min; MS (ESIpos): m/z = 533 [M + H]⁺

¹H-NMR (600 MHz, DMSO-d6) δ [ppm]: 1.171 (1.33), 1.621 (10.69), 1.633 (10.44),
2.068 (1.03), 2.082 (0.76), 2.152 (0.41), 2.420 (0.57), 2.649 (0.48), 3.007 (0.70),
3.224 (0.97), 3.284 (2.34), 3.348 (0.83), 3.511 (2.13), 3.522 (2.03), 6.555 (0.41),
6.567 (1.78), 6.578 (2.71), 6.590 (1.70), 8.587 (16.00), 8.685 (5.42), 8.688 (5.72),
8.750 (5.76), 8.754 (4.95), 9.759 (2.51), 9.770 (2.30).

I-173

(+)-2-(3-{(1S)-1-[3-Chloro-5-(difluoromethoxy)benzamido]ethyl}pyrazin-2-yl)-N-
ethyl-N-methyl-1,3-thiazole-5-carboxamide $[\alpha]_D^{20}$ = +91.4° (c = 0.23, CHCl₃)

LC-MS (Method 2): R_t = 2.01 min; MS (ESIpos): m/z = 496 [M + H]⁺

¹H-NMR (600 MHz, DMSO-d6) δ [ppm]: 1.172 (2.21), 1.581 (16.00), 1.593 (15.73),
2.054 (0.59), 2.108 (0.65), 3.014 (1.03), 3.226 (1.28), 3.514 (4.81), 3.525 (4.12),
6.447 (0.65), 6.459 (2.70), 6.470 (4.07), 6.482 (2.59), 6.493 (0.57), 7.212 (3.56),
7.334 (7.15), 7.362 (0.55), 7.456 (3.41), 7.501 (3.79), 7.504 (6.61), 7.508 (3.91),
7.608 (6.16), 7.862 (5.16), 7.865 (7.87), 8.413 (0.45), 8.663 (7.82), 8.667 (8.33),
8.736 (8.29), 8.740 (7.38), 9.200 (3.98), 9.211 (3.81).

-continued

| Example | Structure<br>IUPAC-Name<br>LC-MS (method): Retention time; Mass found<br>$^1$H-NMR |
|---|---|

I-174

(+)-2-(3-{(1S)-1-[3-Cyclopropyl-5-(trifluoromethoxy)benzamido]ethyl}pyrazin-2-
yl)-N-ethyl-N-methyl-1,3-thiazole-5-carboxamide $[\alpha]_D^{20}$ = +105.2° (c = 0.20, CHCl$_3$)

LC-MS (Method 2): R$_t$ = 2.23 min; MS (ESIpos): m/z = 520 [M + H]$^+$

$^1$H-NMR (600 MHz, DMSO-d6) δ [ppm]: 0.755 (0.93), 0.758 (0.81), 0.763 (0.88),
0.767 (0.97),0.771 (0.75), 0.774(0.87), 0.779(0.83),0.787 (3.77), 0.791(2.52),
0.795 (5.67), 0.799 (5.46), 0.803 (2.50), 0.807 (3.56), 0.814 (0.82), 0.819 (0.51),
0.823 (0.63), 1.001 (0.54), 1.010 (1.58), 1.019 (7.08), 1.023 (6.99), 1.033 (7.14),
1.036 (6.35), 1.046 (0.92), 1.054 (0.50), 1.101 (0.65), 1.174 (2.08), 1.587 (16.00),
1.598 (15.82), 2.025 (1.00), 2.034 (1.95), 2.039 (2.12), 2.048 (3.70), 2.056 (1.93),
2.062 (1.78), 2.070 (0.88), 2.074 (1.20), 2.095 (1.04), 3.018 (0.89), 3.224 (1.13),
3.307 (0.89), 3.373 (0.72), 3.513 (3.21), 3.525 (3.14), 6.440 (0.61), 6.451 (2.54),
6.463 (3.87), 6.474 (2.48), 6.486 (0.54), 7.048 (0.79), 7.108 (0.57), 7.260 (5.06),
7.551 (5.04), 7.595 (5.03), 7.597 (7.77), 8.414 (0.42), 8.658 (9.27), 8.662 (9.85),
8.731 (9.25), 8.735 (8.29), 9.122 (3.70), 9.133 (3.53).

I-175

(+)-2-(3-{(1S)-1-[3-Bromo-5-(trifluoromethoxy)benzamido]ethyl}pyrazin-2-yl)-N-
ethyl-N-methyl-1,3-thiazole-5-carboxamide $[\alpha]_D^{20}$ = +100.3° (c = 0.21, CHCl$_3$)

LC-MS (Method 2): R$_t$ = 2.23 min; MS (ESIpos): m/z = 558 [M + H] $^+$

$^1$H-NMR (600 MHz, DMSO-d6) δ [ppm]: 1.177 (2.34), 1.584 (16.00), 1.596 (15.65),
2.055 (0.57), 2.109 (0.64), 3.014 (1.04), 3.223 (1.33), 3.514 (3.69), 3.525 (3.56),
6.456 (0.68), 6.467 (2.68), 6.479 (4.04), 6.490 (2.57), 6.501 (0.59), 7.816 (5.75),
7.870 (5.47), 8.185 (8.13), 8.328 (0.41), 8.414 (0.48), 8.667 (7.64), 8.670 (7.98),
8.739 (8.21), 8.743 (7.21), 9.297 (4.05), 9.308 (3.81).

-continued

Structure
IUPAC-Name
LC-MS (method): Retention time; Mass found

Example
$^1$H-NMR

I-176

(+)-N-Ethyl-2-(3-{(1S)-1-[3-(methanesulfonyl)-5-
(trifluoromethoxy)benzamido]ethyl}pyrazin-2-yl)-N-methyl-1,3-thiazole-5-
carboxamide $[\alpha]_D^{20}$ = +109.7° (c = 0.20, CHCl$_3$)

LC-MS (Method 2): R$_t$ = 1.81 min; MS (ESIpos): m/z = 558 [M + H]$^+$ $^1$H-NMR (600 MHz, DMSO-d6) δ [ppm]: 1.611 (2.42), 1.623 (2.38), 3.308 (16.00),
3.312 (7.55), 3.358 (5.45), 3.514 (0.47), 3.525 (0.47), 6.528 (0.56), 8.059 (0.81),
8.157 (0.82), 8.493 (1.13), 8.674 (1.10), 8.678 (1.15), 8.747 (1.11), 8.751 (0.96),
9.498 (0.62), 9.509 (0.60).

I-177

(+)-2-{3-[(1S)-1-(3,5-Dibromobenzamido)ethyl]pyrazin-2-yl}-N-ethyl-N-methyl-
1,3-thiazole-5-carboxamide LC-MS (Method 2): R$_t$ = 2.18 min; MS (ESIpos): m/z = 552 [M + H]$^+$ $[\alpha]_D^{20}$ = +110.6° (c = 0.22, CHCl$_3$)

$^1$H-NMR (600 MHz, DMSO-d6) δ [ppm]: 1.176 (1.67), 1.568 (13.23), 1.580 (12.92),
2.047 (0.88), 2.071 (3.41), 2.084 (0.61), 2.102 (1.00), 3.012 (0.79), 3.224 (0.99),
3.285 (1.18), 3.349 (0.55), 3.356 (0.59), 3.512 (2.55), 3.523 (2.50), 6.434 (0.54),
6.445 (2.16), 6.457 (3.26), 6.468 (2.08), 6.479 (0.46), 8.013 (3.53), 8.016 (7.07),
8.019 (4.23), 8.059 (16.00), 8.062 (13.86), 8.661 (6.84), 8.664 (7.30), 8.735 (7.09),
8.739 (6.30), 9.222 (3.19), 9.233 (3.02).

-continued

Structure
IUPAC-Name
LC-MS (method): Retention time; Mass found
Example
¹H-NMR

I-178

(+)-2-(3-{(1S)-1-[3-(2-Cyanopropan-2-yl)-5-
(trifluoromethoxy)benzamido]ethyl}pyrazin-2-yl)-N-ethyl-N-methyl-1,3-thiazole-
5-carboxamide
$[\alpha]_D^{20}$ = +84.4° (c = 0.21, CHCl₃)
LC-MS (Method 2): R$_t$ = 2.05 min; MS (ESIpos): m/z = 547 [M + H] $^+$
¹H-NMR (600 MHz, DMSO-d6) δ [ppm]: 1.186 (0.79), 1.610 (5.42), 1.621 (5.32),
1.736 (16.00), 1.738 (15.30), 2.517 (0.46), 2.520 (0.46), 3.218 (0.48), 3.277 (0.60),
3.514 (1.22), 3.525 (1.19), 6.487 (0.88), 6.499 (1.30), 6.510 (0.85), 7.660 (2.04),
7.861 (1.95), 8.049 (2.68), 8.668 (2.72), 8.672 (2.84), 8.738 (2.88), 8.742 (2.51),
9.304 (1.31), 9.316 (1.25).

I-179

(+)-2-(3-{(1S)-1-[3-(1-Cyanocyclopropyl)-5-
(trifluoromethoxy)benzamido]ethyl}pyrazin-2-yl)-N-ethyl-N-methyl-1,3-thiazole-
5-carboxamide
$[\alpha]_D^{20}$ = +89.0° (c = 0.22, CHCl₃)
LC-MS (Method 2): R$_t$ = 2.00 min; MS (ESIpos): m/z = 545 [M + H] $^+$
¹H-NMR (600 MHz, DMSO-d6) δ [ppm]: 1.178 (2.17), 1.601 (16.00), 1.612 (15.66),
1.636 (0.82), 1.644 (2.56), 1.647 (2.38), 1.654 (8.37), 1.658 (9.17), 1.664 (2.22),
1.667 (2.48), 1.676 (0.59), 1.695 (0.44), 1.814 (0.60), 1.824 (3.37), 1.832 (10.52),
1.837 (9.48), 1.845 (2.76), 2.109 (0.47), 2.518 (0.87), 3.017 (1.00), 3.224 (1.25),
3.283 (1.11), 3.347 (0.96), 3.514 (3.44), 3.526 (3.35), 6.466 (0.62), 6.478 (2.64),
6.490 (3.97), 6.501 (2.56), 6.512 (0.58), 7.476 (5.74), 7.782 (5.57), 7.857 (7.99),
8.416 (0.47), 8.666 (8.04), 8.670 (8.55), 8.736 (8.54), 8.740 (7.61), 9.284 (3.94),
9.295 (3.76).

-continued

Structure

IUPAC-Name

LC-MS (method): Retention time; Mass found

Example                           ¹H-NMR

I-180

(+)-2-(3-{(1S)-1-[3-(Difluoromethanesulfonyl)-5-
(trifluoromethoxy)benzamido]ethyl}pyrazin-2-yl)-N-ethyl-N-methyl-1,3-thiazole-
5-carboxamide $[\alpha]_D^{20}$ = +81.7° (c = 0.20, CHCl₃)

LC-MS (Method 2): R$_t$ = 2.01 min; MS (ESIpos): m/z = 594 [M + H] $^+$

¹H-NMR (600 MHz, DMSO-d6) δ [ppm]: 1.179 (2.25), 1.616 (16.00), 1.627 (15.75),
2.387 (0.60), 2.426 (0.59), 2.467 (1.32), 2.615 (0.45), 2.654 (0.44), 3.017 (1.20),
3.226 (1.46), 3.515 (3.57), 3.526 (3.52), 6.515 (0.67), 6.526 (2.70), 6.538 (4.10),
6.549 (2.67), 6.560 (0.62), 7.347 (2.97), 7.433 (5.74), 7.520 (2.53), 8.102 (5.77),
8.404 (6.33), 8.530 (8.19), 8.679 (7.48), 8.683 (8.23), 8.749 (8.04), 8.753 (7.34),
9.647 (4.05), 9.658 (3.92).

I-181

(+)-2-(3-{(1S)-1-[3,5-Bis(trifluoromethyl)benzamido]ethyl}pyrazin-2-yl)-N-ethyl-
1,3-thiazole-5-carboxamide $[\alpha]_D^{20}$ = +100.4° (c = 0.28, CHCl₃)

LC-MS (Method 2): R$_t$ = 2.08 min; MS (ESIpos): m/z = 518 [M + H] $^+$

¹H-NMR (600 MHz, DMSO-d6) δ [ppm]: 1.150 (8.59), 1.162 (15.53), 1.174 (8.39),
1.233 (0.97), 1.610 (14.28), 1.621 (14.06), 2.074 (6.47), 6.514 (2.67), 6.526 (3.79),
6.537 (2.62), 8.303 (7.15), 8.529 (16.00), 8.558 (9.56), 8.677 (7.41), 8.744 (7.45),
8.798 (4.56), 9.541 (4.47), 9.553 (4.25).

-continued

| Structure |
| --- |
| IUPAC-Name |
| LC-MS (method): Retention time; Mass found |
| $^1$H-NMR |

Example

I-182

(+)-N-[(1S)-1-(3-{5-[(cis)-2,6-dimethylmorpholine-4-carbonyl]-1,3-thiazol-2-
yl}pyrazin-2-yl)ethyl]-3,5-bis(trifluoromethyl)benzamide $[\alpha]_D^{20}$ = +93.5° (c = 0.26, CHCl$_3$)

LC-MS (Method 2): R$_t$ = 2.27 min; MS (ESIpos): m/z = 588 [M + H] $^+$ $^1$H-NMR (600 MHz, DMSO-d6) δ [ppm]: 1.125 (6.79), 1.617 (14.43), 1.628 (14.20),
2.468 (0.82), 2.515 (1.01), 2.518 (1.02), 2.521 (0.89), 2.612 (0.50), 2.652 (0.41),
3.263 (0.52), 3.276 (1.50), 3.279 (1.39), 3.339 (0.41), 3.609 (2.14), 6.514 (0.60),
6.525 (2.21), 6.536 (3.30), 6.548 (2.12), 6.559 (0.47), 8.303 (5.50), 8.378 (16.00),
8.536 (12.76), 8.673 (7.84), 8.677 (8.17), 8.743 (8.09), 8.747 (7.11), 9.556 (3.93),
9.567 (3.67).

I-183

(+)-3-Cyclopropyl-N-[(1S)-1-(3-{5-[(cis)-2,6-dimethylmorpholine-4-carbonyl]-1,3-
thiazol-2-yl}pyrazin-2-yl)ethyl]-5-(trifluoromethoxy)benzamide $[\alpha]_D^{20}$ = +111.4° (c = 0.26, CHCl$_3$)

LC-MS (Method 2): R$_t$ = 2.32 min; MS (ESIpos): m/z = 576 [M + H] $^+$ $^1$H-NMR (600 MHz, DMSO-d6) δ [ppm]: 0.768 (0.64), 0.784 (3.68), 0.792 (5.29),
0.795 (5.22), 0.803 (3.57), 0.818 (0.60), 0.999 (0.52), 1.008 (1.29), 1.017 (6.75),
1.021 (6.63), 1.031 (7.13), 1.035 (6.27), 1.043 (1.11), 1.053 (0.59), 1.123 (7.85),
1.585 (15.36), 1.597 (15.08), 2.023 (0.93), 2.031 (1.77), 2.037 (1.95), 2.045 (3.25),
2.053 (1.78), 2.059 (1.64), 2.067 (0.76), 2.384 (0.46), 2.423 (0.43), 2.515 (1.17),
2.518 (1.12), 2.521 (1.09), 2.573 (0.61), 2.612 (0.57), 2.652 (0.43), 3.259 (0.51),
3.272 (0.87), 3.278 (1.07), 3.343 (1.20), 3.608 (2.44), 6.433 (0.57), 6.444 (2.29),
6.456 (3.48), 6.467 (2.24), 6.479 (0.54), 7.258 (5.62), 7.546 (5.57), 7.592 (8.07),
8.367 (16.00), 8.658 (7.80), 8.662 (8.38), 8.731 (8.27), 8.735 (7.41), 9.122 (4.35),
9.133 (4.12).

-continued

| Structure |
| IUPAC-Name |
| LC-MS (method): Retention time; Mass found |
| Example | ¹H-NMR |

I-184

(+)-3-Bromo-N-[(1S)-1-(3-{5-[(cis)-2,6-dimethylmorpholine-4-carbonyl]-1,3-
thiazol-2-yl}pyrazin-2-yl)ethyl]-5-(trifluoromethoxy)benzamide $[\alpha]_D^{20}$ = +109.5° (c = 0.25, CHCl₃)

LC-MS (Method 2): $R_t$ = 2.32 min; MS (ESIpos): m/z = 614 [M+H] ⁺

IH-NMR (600 MHz, DMSO-d6) 5 [ppm]: 1.123 (8.48), 1.395 (1.03), 1.583 (16.00),
1.594 (15.67), 2.384 (0.51), 2.423 (0.49), 2.518 (1.06), 2.573 (0.55), 2.612 (0.64),
2.652 (0.47), 2.992 (0.43), 3.271 (0.89), 3.281 (1.39), 3.342 (0.83), 3.608 (2.62),
6.449 (0.64), 6.461 (2.47), 6.472 (3.67), 6.484 (2.39), 6.495 (0.60), 7.813 (6.07),
7.869 (5.89), 8.182 (8.50), 8.368 (15.70), 8.666 (7.82), 8.670 (8.16), 8.739 (8.32),
8.743 (7.35), 9.297 (4.53), 9.308 (4.24).

I-185

(+)-3-Bromo-N-[(1S)-1-(3-(5-[(2R,6S)-2,6-dimethylmorpholine-4-carbonyl]-1,3-
thiazol-2-yl}pyrazin-2-yl)ethyl]-5-(trifluoromethyl)benzamide $[\alpha]_D^{20}$ = +107.2° (c = 0.27, CHCl₃)

LC-MS (Method 2): $R_t$ = 2.28 min; MS (ESIpos): m/z = 598 [M + H] ⁺

¹H-NMR (600 MHz, DMSO-d6) δ [ppm]: 1.124 (6.54), 1.231 (0.44), 1.395 (1.20),
1.592 (12.36), 1.604 (12.05), 2.384 (0.40), 2.466 (0.43), 2.521 (0.93), 2.571 (0.80),
2.612 (0.51), 3.264 (0.40), 3.276 (1.82), 3.342 (2.74), 3.348 (0.64), 3.609 (2.04),
6.470 (0.49), 6.481 (1.90), 6.493 (2.85), 6.504 (1.84), 6.515 (0.45), 8.160 (5.28),
8.212 (5.76), 8.372 (16.00), 8.668 (5.75), 8.672 (6.24), 8.740 (6.14), 8.744 (5.65),
9.385 (3.46), 9.396 (3.31).

-continued

| Structure |
| IUPAC-Name |
| LC-MS (method): Retention time; Mass found |
| Example     $^1$H-NMR |

I-186

(+)-3,5-Dibromo-N-[(lS)-l-(3-{5-[(cis)-2,6-dimethylmorpholine-4-carbonyl]-l,3-thiazol-2-yl}pyrazin-2-yl)ethyl]benz amide $[a]_D^{20}$ = +116.9° (c = 0.26, CHCl₃)

LC-MS (Method 2): R$_t$ = 2.29 min; MS (ESIpos): m/z = 608 [M + H] $^+$

$^1$H-NMR (600 MHz, DMSO-d6) δ [ppm]: 1.126 (7.80), 1.232 (0.48), 1.398 (1.03), 1.572 (14.11), 1.583 (13.78), 2.387 (0.42), 2.521 (1.05), 2.577 (0.42), 2.615 (0.56), 3.284 (1.56), 3.350 (0.51), 3.609 (2.40), 6.432 (0.57), 6.443 (2.18), 6.454 (3.26), 6.466 (2.11), 6.477 (0.51), 8.019 (6.89), 8.060 (16.00), 8.062 (13.33), 8.368 (13.30), 8.665 (6.69), 8.669 (7.01), 8.740 (7.16), 8.744 (6.27), 9.226 (4.01), 9.237 (3.79).

I-187

(+)-3-(1-Cyanocyclopropyl)-N-[(1S)-1-(3-{5-[(cis)-2,6-dimethylmorpholine-4-carbonyl]-l,3-thiazol-2-yl}pyrazin-2-yl)ethyl]-5-(trifluoromethoxy)benzamide $[\alpha]_D^{20}$ = +99.6° (c = 0.25, CHCl₃)

LC-MS (Method 2): R$_t$ = 2.12 min; MS (ESIpos): m/z = 601 [M + H] $^+$

$^1$H-NMR (600 MHz, DMSO-d6) δ [ppm]: 1.126 (8.50), 1.176 (0.74), 1.235 (0.65), 1.602 (16.00), 1.613 (15.80), 1.635 (0.64), 1.643 (2.33), 1.653 (9.70), 1.658 (9.89), 1.666 (2.60), 1.674 (0.47), 1.798 (0.43), 1.825 (3.99), 1.833 (10.53), 1.838 (9.35), 1.846 (3.19), 1.989 (0.45), 2.386 (0.46), 2.426 (0.45), 2.468 (1.05), 2.571 (0.51), 2.615 (0.61), 2.655 (0.41), 3.276 (2.11), 3.341 (0.97), 3.612 (2.63), 6.462 (0.61), 6.474 (2.46), 6.485 (3.74), 6.496 (2.46), 6.508 (0.61), 7.475 (6.22), 7.781 (6.09), 7.858 (8.39), 8.373 (15.96), 8.668 (7.68), 8.672 (8.35), 8.739 (8.22), 8.743 (7.52), 9.287 (4.58), 9.298 (4.40).

-continued

| Example | Structure<br>IUPAC-Name<br>LC-MS (method): Retention time; Mass found<br>$^1$H-NMR |
|---|---|

I-188

(+)-3-(2-Cyanopropan-2-yl)-N-[(1S)-1-(3-{5-[(cis)-2,6-dimethylmorpholine-4-
carbonyl]-1,3-thiazol-2-yl}pyrazin-2-yl)ethyl]-5-(trifluoromethoxy)benzamide

[a]20 = +96.2° (c = 0.25, CHCl$_3$)

LC-MS (Method 2): R = 2.17 min; MS (ESIpos): m/z = 603 [M+H] $^+$

IH-NMR (600 MHz, DMSO-d6) 5 [ppm]: 1.127 (2.88), 1.612 (4.72), 1.623 (4.67),
1.738 (16.00), 2.468 (0.42), 3.278 (0.90), 3.615 (0.88), 6.486 (0.77), 6.497 (1.12),
6.509 (0.72), 7.662 (1.99), 7.862 (1.96), 8.050 (2.51), 8.377 (4.33), 8.670 (2.28),
8.674 (2.27), 8.742 (2.43), 8.745 (2.04), 9.310 (1.40), 9.322 (1.31).

I-189

(rac)-1-Ethyl-N-[1-(3-{4-[ethyl(methyl)carbamoyl]-1H-pyrazol-1-yl}pyrazin-2-
yl) ethyl]-5-(trifluoromethyl)-1H-pyrazole-3-carboxamide LC-MS (Method 2): R$_t$ = 1.78 min; MS (ESIpos): m/z = 465 [M + H] $^+$ $^1$H-NMR (600 MHz, DMSO-d6) δ [ppm]: 1.128 (1.88), 1.207 (7.87), 1.219 (16.00),
1.231 (7.55), 1.567 (12.16), 1.579 (11.96), 2.958 (0.89), 3.150 (1.44), 3.469 (2.74),
3.480 (2.65), 4.396 (1.96), 4.408 (5.37), 4.420 (5.26), 4.432 (1.78), 5.787 (0.44),
5.798 (1.53), 5.809 (2.28), 5.821 (1.50), 7.387 (7.75), 8.144 (0.65), 8.578 (5.77),
8.582 (5.85), 8.755 (6.55), 8.759 (6.19), 9.097 (3.10), 9.109 (2.97).

-continued

Structure
IUPAC-Name
LC-MS (method): Retention time; Mass found
<sub>Example</sub> ¹H-NMR

I-190

(rac)-N-[1-(3-{4-[Ethyl(methyl)carbamoyl]-1H-pyrazol-1-yl}pyrazin-2-yl)ethyl]-
1-methyl-5-(trifluoromethyl)-1H-pyrazole-3-carboxamide LC-MS (Method 2): R$_t$ = 1.62 min; MS (ESIpos): m/z = 451 [M + H] $^+$
¹H-NMR (600 MHz, DMSO-d6) δ [ppm]: 1.129 (1.16), 1.527 (8.80), 1.538 (8.63),
2.962 (0.61), 3.163 (0.95), 3.486 (2.18), 4.006 (0.40), 4.023 (16.00), 5.849 (0.81),
5.861 (1.17), 5.872 (0.80), 7.210 (5.83), 8.174 (0.46), 8.528 (2.16), 8.540 (2.11),
8.585 (4.14), 8.589 (4.25), 8.768 (4.56), 8.772 (4.34).

I-191

(+)-2-(3-{(1S)-1-[3,5-Bis(trifluoromethyl)benzamido]ethyl}pyrazin-2-yl)-N,N-
dimethyl-1,3-thiazole-5-carboxamide

[a]$_D^{20}$ = +184.9° (c = 0.25, methanol)

LC-MS (Method 2): R$_t$ = 2.07 min; MS (ESIpos): m/z = 518 [M + H] $^+$
¹H-NMR (600 MHz, DMSO-d6) δ [ppm]: 1.620 (16.00), 1.632 (15.76), 3.052 (3.87),
3.246 (3.97), 3.352 (0.49), 3.361 (0.51), 6.522 (0.69), 6.533 (2.79), 6.545 (4.14),
6.556 (2.68), 6.568 (0.59), 8.304 (6.54), 8.424 (14.08), 8.445 (0.44), 8.540 (15.47),
8.673 (7.14), 8.677 (7.73), 8.744 (7.71), 8.748 (6.93), 9.556 (4.29), 9.568 (4.08).

-continued

| Example | Structure<br>IUPAC-Name<br>LC-MS (method): Retention time; Mass found<br>$^1$H-NMR |
| --- | --- |

I-192

(+)-N-[(1S)-1-{3-[5-(Dimethylcarbamoyl)-1,3-thiazol-2-yl]pyrazin-2-yl}ethyl]-2,6-
bis(trifluoromethyl)pyridine-4-carboxamide $[a]_D^{20}$ = +147.5° (c = 0.27, methanol)

LC-MS (Method 2): R$_t$ = 1.98 min; MS (ESIpos): m/z = 519 [M + H] $^+$ $^1$H-NMR (600 MHz, DMSO-d6) δ [ppm]: 1.624 (10.33), 1.635 (10.30), 2.463 (0.53),
2.689 (1.82), 3.048 (2.45), 3.242 (2.60), 3.275 (1.65), 3.342 (1.32), 6.559 (0.44),
6.570 (1.79), 6.581 (2.70), 6.593 (1.73), 8.422 (9.60), 8.590 (16.00), 8.685 (4.75),
8.689 (5.16), 8.752 (5.08), 8.756 (4.55), 9.762 (2.67), 9.773 (2.52).

I-193

(+)-2-(3-{(1S)-1-[3-cyclopropyl-5-(trifluoromethoxy)benzamido]ethyl}pyrazin-2-
yl)-N,N-dimethyl-1,3-thiazole-5-carboxamide $[α]_D^{20}$ = +186.4° (c = 0.28, methanol)

LC-MS (Method 2): R$_t$ = 2.12 min; MS (ESIpos): m/z = 506 [M + H] $^+$ $^1$H-NMR (600 MHz, DMSO-d6) δ [ppm]: 0.767 (0.71), 0.783 (3.87), 0.792 (5.53),
0.795 (5.64), 0.804 (3.87), 0.820 (0.70), 0.998 (0.46), 1.006 (0.99), 1.016 (6.47),
1.019 (6.76), 1.030 (6.86), 1.033 (6.33), 1.043 (0.72), 1.584 (16.00), 1.596 (15.73),
2.022 (0.92), 2.030 (1.75), 2.036 (1.96), 2.044 (3.24), 2.052 (1.84), 2.058 (1.58),
2.067 (0.73), 2.688 (0.41), 3.048 (3.78), 3.239 (3.91), 3.278 (1.70), 6.437 (0.69),
6.448 (2.79), 6.459 (4.17), 6.471 (2.68), 6.482 (0.64), 7.257 (6.09), 7.547 (6.03),
7.594 (8.22), 8.409 (14.47), 8.654 (7.19), 8.658 (7.93), 8.727 (7.80), 8.731 (7.14),
9.120 (4.40), 9.131(4.19).

-continued

| Structure |
| IUPAC-Name |
| LC-MS (method): Retention time; Mass found |
| Example                                  ¹H-NMR |

I-194

(+)-2-(3-{(1S)-1-[3-(Methanesulfonyl)-5-
(trifluoromethoxy)benzamido]ethyl}pyrazin-2-yl)-N,N-dimethyl-1,3-thiazole-5-
carboxamide
$[\alpha]_D^{20}$ = +161.1° (c = 0.27, methanol)
LC-MS (Method 2): R$_t$ = 1.69 min; MS (ESIpos): m/z = 544 [M + H] $^+$
¹H-NMR (600 MHz, DMSO-d6) δ [ppm]: 1.612 (6.45), 1.623 (6.36), 3.049 (1.70),
3.242 (1.89), 3.359 (16.00), 6.517 (1.12), 6.528 (1.69), 6.540 (1.11), 8.059 (2.53),
8.158 (2.62), 8.419 (5.68), 8.446 (0.56), 8.493 (3.56), 8.673 (2.89), 8.677 (3.16),
8.747 (3.12), 8.750 (2.86), 9.498 (1.82), 9.509 (1.77).

I-195

(+)-2-(3-{(1S)-1-[3-Chloro-5-(cyclopropanesulfonyl)benzamido]ethyl}pyrazin-2-
yl)-N,N-dimethyl-1,3-thiazole-5-carboxamide
$[\alpha]_D^{20}$ = +168.1° (c = 0.27, methanol)
LC-MS (Method 2): R$_t$ = 1.70 min; MS (ESIpos): m/z = 520 [M + H] $^+$
¹H-NMR (600 MHz, DMSO-d6) δ [ppm]: 1.070 (1.07), 1.078 (4.09), 1.083 (4.87),
1.091 (4.84),1.096 (4.46), 1.104 (1.26), 1.160 (0.81), 1.175 (3.42), 1.181 (5.52),
1.187 (5.86), 1.195 (3.13), 1.211 (0.46), 1.573 (0.51), 1.585 (0.75), 1.600 (16.00),
1.612 (15.65), 1.986 (0.67), 2.515 (0.73), 2.689 (0.93), 2.990 (1.16), 2.998 (2.23),
3.004 (2.56), 3.011 (3.96), 3.019 (2.71), 3.024 (2.77), 3.033 (2.62), 3.048 (3.89),
3.245 (4.01), 3.280 (0.87), 3.341 (0.48), 3.344 (1.32), 3.903(4.73), 6.488 (0.70),
6.500 (2.81), 6.511 (4.24), 6.523 (2.72), 6.534 (0.64), 8.101 (7.64), 8.283 (7.87),
8.312 (8.52), 8.418 (14.89), 8.653 (1.72), 8.670 (7.44), 8.674 (7.99), 8.746 (7.95),
8.749 (7.23), 9.436 (4.45), 9.448 (4.23).

-continued

Structure
IUPAC-Name
LC-MS (method): Retention time; Mass found
Example
¹H-NMR

I-196

(+)-2-(3-{(1S)-1-[3-(1-Cyanocyclopropyl)-5-
(trifluoromethoxy)benzamido]ethyl}pyrazin-2-yl)-N,N-dimethyl-1,3-thiazole-5-
carboxamide
$[\alpha]_D^{20}$ = +168.2° (c = 0.28, methanol)
LC-MS (Method 2): R$_t$ = 1.92 min; MS (ESIpos): m/z = 531 [M + H] $^+$
¹H-NMR (600 MHz, DMSO-d6) δ [ppm]: 1.601 (16.00), 1.612 (15.71), 1.653 (8.84),
1.658 (9.05), 1.664 (3.12), 1.676 (0.78), 1.795 (0.42), 1.813 (0.70), 1.824 (3.46),
1.832 (10.37), 1.836 (8.95), 1.844 (2.63), 1.856 (1.14), 1.989 (0.42), 2.426 (0.42),
2.733 (0.97), 2.892 (1.07), 3.049 (3.99), 3.242 (4.12), 3.281 (2.59), 6.465 (0.75),
6.477 (2.83), 6.488 (4.21), 6.500 (2.68), 6.511 (0.61), 7.476 (6.34), 7.506 (0.50),
7.741 (0.58), 7.781 (6.30), 7.856 (8.19), 7.966 (0.67), 8.415 (14.31), 8.665 (7.53),
8.668 (7.67), 8.736 (8.03), 8.739 (6.90), 9.284 (4.44), 9.295 (4.27).

I-197

(+)-2-(3-{(1S)-1-[3-(2-Cyanopropan-2-yl)-5-
(trifluoromethoxy)benzamido]ethyl}pyrazin-2-yl)-N,N-dimethyl-1,3-thiazole-5-
carboxamide
$[\alpha]_D^{20}$ = +168.6° (c = 0.26, methanol)
LC-MS (Method 2): R$_t$ = 1.97 min; MS (ESIpos): m/z = 533 [M + H] $^+$
¹H-NMR (600 MHz, DMSO-d6) δ [ppm]: 1.608 (5.24), 1.620 (5.19), 1.735 (16.00),
3.048 (1.30), 3.240 (1.33), 3.266 (0.52), 3.278 (0.75), 6.485 (0.93), 6.497 (1.39),
6.508 (0.89), 7.657 (2.06), 7.859 (2.02), 8.047 (2.66), 8.415 (5.03), 8.664 (2.45),
8.668 (2.63), 8.736 (2.62), 8.740 (2.36), 9.303 (1.45), 9.314 (1.39).

Biological Examples

*Rhipicephalus* (*Boophilus*) *microplus*—In-Vitro Contact Tests Larval Cattle Tick (Strain Parkhurst, Resistant Against Synthetic Pyrethroids)

9 mg compound is solved in 1 mL acetone and diluted with acetone to the desired concentration. 250 of the test solution is filled in 25 mL glass test tubes and homogeneously distributed on the inner walls by rotation and tilting on a shaking device (2 h at 30 rpm). With a compound concentration of 900 ppm, an inner surface of 44.7 cm² and a homogeneous distribution, a dose of 5 μg/cm² is achieved.

After the solvent has evaporated, each test tube is filled with 20-50 cattle tick larvae (*Rhipicephalus microplus*), closed with a perforated lid and incubated in a horizontal position at 85% relative humidity and 27° C. in an incubator. After 48 hours efficacy is determined. The larvae are patted on the ground of the tubes and negative geotactic behaviour is recorded. Larvae that climb back to the top of the vial in a manner comparable to untreated control larvae are marked as alive, larvae not climbing back up comparable to untreated control larvae but are moving uncoordinatedly or only twitching their legs are marked as moribund, tick larvae remaining on the bottom and not moving at all are counted as dead.

A compound shows a good efficacy against *Rhipicephalus microplus*, if at a compound concentration of 5 μg/cm² an efficacy of at least 80% is monitored. An efficacy of 100% means all larvae are dead or moribund; 0% means no larvae are dead or moribund.

In this test, for example, the following compounds from the preparation examples showed good activity of 100% at an application rate of 5 μg/cm² (=500 g/ha): I-5, I-7, I-8, I-9, I-11, I-13, I-20, I-32, I-33, I-34, I-35, I-37, I-38, I-46, I-59, I-61, I-64, I-65, I-66, I-68, I-69, I-72, I-76, I-82, I-83, I-85, I-88, I-89, I-90, I-91, I-92, I-93, I-94, I-100, I-113, I-115, I-116, I-118, I-119, I-120, I-124, I-125, I-126, I-127, I-131, I-132, I-133, I-134, I-136, I-137, I-138, I-139.

In this test, for example, the following compounds from the preparation examples showed good activity of 90% at an application rate of 5 μg/cm² (=500 g/ha): I-17, I-24, I-26, I-29, I-51, I-54, I-58, I-75, I-102, I-103, I-114, I-141, I-143.

In this test, for example, the following compounds from the preparation examples showed good activity of 80% at an application rate of 5 μg/cm² (=500 g/ha): I-6, I-10, I-14, I-15, I-27, I-28, I-128.

In this test, for example, the following compounds from the preparation examples showed good activity of 100% at an application rate of 1 μg/cm² (=100 g/ha): I-1, I-5, I-7, I-8, I-9, I-13, I-20, I-32, I-34, I-35, I-37, I-38, I-46, I-58, I-59, I-61, I-64, I-65, I-66, I-68, I-69, I-72, I-76, I-82, I-83, I-85, I-88, I-89, I-90, I-91, I-92, I-93, I-94, I-100, I-113, I-115, I-118, I-119, I-120, I-124, I-125, I-126, I-127, I-131, I-132, I-133, I-134, I-136, I-137, I-138, I-139, I-141, I-143.

In this test, for example, the following compounds from the preparation examples showed good activity of 90% at an application rate of 1 μg/cm² (=100 g/ha): I-10, I-14, I-24, I-27, I-28, I-33, I-51, I-75, I-102, I-103, I-114, I-116, I-122, I-128.

In this test, for example, the following compounds from the preparation examples showed good activity of 80% at an application rate of 1 μg/cm² (=100 g/ha): I-6, I-15, I-17.

*Rhipicephalus* (*Boophilus*) *microplus*—Injection Test

Solvent: dimethyl sulfoxide

To produce a suitable preparation of active compound, 10 mg of active compound are dissolved in 0.5 mL solvent, and the concentrate is diluted with solvent to the desired concentration.

Five adult engorged female ticks (*Rhipicephalus microplus*) are injected with 1 μL compound solution into the abdomen. The ticks are transferred into replica plates and incubated in a climate chamber.

After 7 days egg deposition of fertile eggs is monitored. Eggs where fertility is not visible are stored in a climate chamber till hatching after about 42 days. An efficacy of 100% means all eggs are infertile; 0% means all eggs are fertile.

In this test, for example, the following compounds from the preparation examples showed good activity of 100% at an application rate of 4 μg/animal: I-2, I-3, I-7, I-8, I-9, I-10, I-17, I-23, I-24, I-56, I-63, I-64.

In this test, for example, the following compounds from the preparation examples showed good activity of 80% at an application rate of 4 μg/animal: I-5, I-13, I-14, I-15, I-20, I-21, I-25, I-53, I-65, I-66.

*Ctenocephalides felis*—In-Vitro Contact Tests Adult Cat Flea 9 mg compound is solved in 1 ml acetone and diluted with acetone to the desired concentration. 250 μL of the test solution is filled in 25 mL glass test tubes and homogeneously distributed on the inner walls by rotation and tilting on a shaking device (2 h at 30 rpm). With a compound concentration of 900 ppm, an inner surface of 44.7 cm² and a homogeneous distribution, a dose of 5 μg/cm² is achieved.

After the solvent has evaporated, each test tube is filled with 5-10 adult cat fleas (*Ctenocephalides felis*), closed with a perforated lid and incubated in a lying position at room temperature and relative humidity. After 48 hours efficacy is determined. The fleas are patted on the ground of the tubes and are incubated on a heating plate at 45-50° C. for at most 5 minutes Immotile or uncoordinated moving fleas, which are not able to escape the heat by climbing upwards, are marked as dead or moribund.

A compound shows a good efficacy against *Ctenocephalides felis*, if at a compound concentration of 5 μg/cm² an efficacy of at least 80% is monitored. An efficacy of 100% means all fleas are dead or moribund; 0% means no fleas are dead or moribund.

In this test, for example, the following compounds from the preparation examples showed good activity of 100% at an application rate of 5 μg/cm² (=500 g/ha): I-32, I-33, I-35, I-61, I-64, I-65, I-66, I-68, I-82, I-83, I-85, I-132, I-133, I-134, I-141.

In this test, for example, the following compounds from the preparation examples showed good activity of 90% at an application rate of 5 μg/cm² (=500 g/ha): I-34, I-118, I-119, I-140.

In this test, for example, the following compounds from the preparation examples showed good activity of 80% at an application rate of 5 μg/cm² (=500 g/ha): I-10, I-19, I-27, I-103.

In this test, for example, the following compounds from the preparation examples showed good activity of 100% at an application rate of 1 μg/cm² (=100 g/ha): I-33, I-61, I-64, I-65, I-66, I-68, I-82, I-83, I-85, I-132, I-133, In this test, for example, the following compounds from the preparation examples showed good activity of 90% at an application rate of 1 μg/cm² (=100 g/ha): I-7, I-38.

In this test, for example, the following compounds from the preparation examples showed good activity of 80% at an application rate of 1 μg/cm² (=100 g/ha): I-27, I-34, I-35, I-134.

*Ctenocephalides felis*—Oral Test

Solvent: dimethyl sulfoxide

To produce a suitable preparation of active compound, 10 mg of active compound are dissolved in 0.5 mL solvent, and the concentrate is diluted with citrated cattle blood to the desired concentration.

Approximately 20 adult unfed cat fleas (*Ctenocephalides felis*) are placed in a flea chamber whose top and bottom is covered with gauze. A chamber whose bottom is sealed with parafilm, is filled with the blood-compound solution and placed on top of the flea chamber, so that the fleas can suck the blood. The blood chamber is heated to 37° C. whereas the flea chamber is kept at room temperature.

After 2 days mortality in % is determined. 100% means all the fleas have been killed; 0% means none of the fleas have been killed.

In this test, for example, the following compounds from the preparation examples showed good activity of 100% at an application rate of 100 ppm: I-7, I-8, I-10, I-12, I-14, I-15, I-16, I-17, I-23, I-24, I-55.

In this test, for example, the following compounds from the preparation examples showed good activity of 90% at an application rate of 100 ppm: I-1, I-2, I-3, I-5, I-11, I-13, I-25.

In this test, for example, the following compounds from the preparation examples showed good activity of 80% at an application rate of 100 ppm: I-9, I-65.

*Rhipicephalus sanguineus*—In-Vitro Contact Tests with Adult Brown Dog Ticks 9 mg compound is solved in 1 mL acetone and diluted with acetone to the desired concentration. 250 of the test solution is filled in 25 mL glass test tubes and homogeneously distributed on the inner walls by rotation and tilting on a shaking device (2 h at 30 rpm). With a compound concentration of 900 ppm, an inner surface of 44.7 cm² and a homogeneous distribution, a dose of 5 μg/cm² is achieved.

After the solvent has evaporated, each test tube is filled with 5-10 adult brown dog ticks (*Rhipicephalus sanguineus*), closed with a perforated lid and incubated in a lying position at room temperature and relative humidity. After 48 hours efficacy is determined. The ticks are patted on the ground of the tubes and are incubated on a heating plate at 45-50° C. for at most 5 minutes Immotile or uncoordinated moving ticks, which are not able to escape the heat by climbing upwards, are marked as dead or moribund.

A compound shows a good efficacy against *Rhipicephalus sanguineus*, if at a compound concentration of 5 μg/cm² an efficacy of at least 80% is monitored. An efficacy of 100% means all ticks are dead or moribund; 0% means no ticks are dead or moribund.

In this test, for example, the following compounds from the preparation examples showed good activity of 100% at an application rate of 5 μg/cm² (=500 g/ha): I-2, I-7, I-59, I-64, I-68, I-85, I-132, I-133, I-134, I-138.

In this test, for example, the following compounds from the preparation examples showed good activity of 80% at an application rate of 5 μg/cm² (=500 g/ha): I-9, I-10, I-16, I-34, I-48, I-54, I-65, I-66, I-72, I-83, I-93, I-94, I-103, I-131.

In this test, for example, the following compounds from the preparation examples showed good activity of 100% at an application rate of 1 μg/cm² (=100 g/ha): I-132, I-133, I-134, I-138.

In this test, for example, the following compounds from the preparation examples showed good activity of 80% at an application rate of 1 μg/cm² (=100 g/ha): I-131, I-132.

*Meloidogyne incognita*—Test

Solvent: 125.0 parts by weight of acetone

To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate and the seedlings grow. Galls develop in the roots.

After 14 days the nematicidal activity is determined based on the percentage of gall formation. 100% means no galls were found and 0% means the number of galls found on the roots of the treated plants was equal to that in untreated control plants.

In this test, for example, the following compounds from the preparation examples showed good activity of 100% at an application rate of 20 ppm: I-55, I-82.

In this test, for example, the following compounds from the preparation examples showed good activity of 90% at an application rate of 20 ppm: I-17, I-52, I-54, I-63.

*Diabrotica balteata*—Spray Test

Solvent: 78.0 parts by weight of acetone 1.5 parts by weight of dimethylformamide Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Soaked wheat seeds (*Triticum aestivum*) are placed in a multiple well plate filled with agar and some water and are incubated for 1 day to germinate (5 seeds per well). The germinated wheat seeds are sprayed with a test solution containing the desired concentration of the active ingredient. Afterwards each unit is infected with 10-20 larvae of the banded cucumber beetle (*Diabrotica* balteata).

After 7 days efficacy in % is determined. 100% means all the seedlings have grown up like in the untreated, uninfected control; 0% means none of the seedlings have grown.

In this test, for example, the following compounds from the preparation examples showed good activity of 100% at an application rate of 100 g/ha (=32 μg/well): I-1, I-3, I-10, I-12, I-15, I-16, I-17, I-18, I-19, I-20, I-21, I-22, I-24, I-25, I-26, I-27, I-29, I-36, I-39, I-40, I-44, I-46, I-76, I-82, I-83, I-85, I-88, I-89, I-48, I-51, I-52, I-53, I-54, I-56, I-59, I-63, I-66, I-67, I-68, I-69, I-70, I-71, I-72, I-75, I-76, I-77, I-82, I-83, I-85, I-88, I-89, I-90, I-92, I-93, I-94, I-96, I-97, I-98, I-100, I-102, I-103, I-104, I-105, I-106, I-112, I-113, I-114, I-115, I-116, I-118, I-119, I-120, I-121, I-124, I-126, I-131, I-132, I-133, I-134, I-138, I-141, I-142, I-143, I-152, I-155.

In this test, for example, the following compounds from the preparation examples showed good activity of 80% at an application rate of 100 g/ha (=32 μg/well): I-5, I-13, I-14, I-28, I-34, I-43, I-139.

In this test, for example, the following compounds from the preparation examples showed good activity of 100% at an application rate of 20 g/ha (=6.4 μg/well): I-8, I-10, I-12, I-13, I-17, I-19, I-21, I-22, I-24, I-25, I-26, I-28, I-29, I-41, I-51, I-52, I-56, I-63, I-66, I-69, I-71, I-72, I-76, I-83, I-85, I-88, I-89, I-92, I-93, I-96, I-98, I-100, I-102, I-103, I-104, I-106, I-113, I-115, I-116, I-118, I-119, I-124, I-131, I-132, I-133, I-134, I-143, I-152, I-155.

In this test, for example, the following compounds from the preparation examples showed good activity of 80% at an application rate of 20 g/ha (=6.4 μg/well): I-3, I-14, I-20, I-48, I-53, I-57.

*Myzus persicae*—Oral Test

Solvent: 100 parts by weight acetone

To produce a suitable preparation of active compound, 1 part by weight of active compound is mixed with the stated amount of solvent, and the concentrate is diluted with water to the desired concentration.

50 μL compound solution is filled in microtiter plates and 150 μL IPL41 insect medium (33%+15% sugar) is added to obtain a total volume of 200 μL per well. Afterwards the plates are sealed with parafilm through which a mixed population of the green peach aphid (*Myzus persicae*) can suck on the compound preparation.

After 5 days mortality in % is determined. 100% means all aphids have been killed and 0% means none of the aphids have been killed.

In this test, for example, the following compounds from the preparation examples showed good activity of 100% at an application rate of 4 ppm: I-34.

In this test, for example, the following compounds from the preparation examples showed good activity of 90% at an application rate of 4 ppm: I-20.

In this test, for example, the following compounds from the preparation examples showed good activity of 100% at an application rate of 0.8 ppm: I-8.

In this test, for example, the following compounds from the preparation examples showed good activity of 90% at an application rate of 0.8 ppm: I-10.

*Myzus persicae*—Spray Test

Solvent: 78.0 parts by weight acetone 1.5 parts by weight dimethylformamide

Emulsifier: alkylarylpolyglycol ether

To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks infected with all instars of the green peach aphid (*Myzus persicae*), are sprayed with a preparation of the active ingredient of the desired concentration.

After 5 days mortality in % is determined. 100% means all aphids have been killed and 0% means none of the aphids have been killed.

In this test, for example, the following compounds from the preparation examples showed good activity of 100% at an application rate of 100 g/ha: I-8, I-10.

In this test, for example, the following compounds from the preparation examples showed good activity of 90% at an application rate of 100 g/ha: I-28, I-38, I-84, I-85, I-88, I-160, I-164, I-166.

*Nezara viridula*—Spray Test

Solvent: 78.0 parts by weight of acetone 1.5 parts by weight of dimethylformamide Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Barley plants (*Hordeum vulgare*) infested with larvae of the southern green stink bug (*Nezara viridula*) are sprayed with a test solution containing the desired concentration of the active ingredient.

After 4 days mortality in % is determined. 100% means all the stink bugs have been killed; 0% means none of the stink bugs have been killed.

In this test, for example, the following compounds from the preparation examples showed good activity of 100% at an application rate of 500 g/ha: I-83, I-93, I-99, I-131, I-132, I-133, I-134, I-139, I-141, I-155.

In this test, for example, the following compounds from the preparation examples showed good activity of 90% at an application rate of 100 g/ha: I-9.

*Nilaparvata lugens*—Spray Test

Solvent: 78.0 parts by weight of acetone 1.5 parts by weight of dimethylformamide Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Rice plants (*Oryza sativa*) are sprayed with a preparation of the active ingredient of the desired concentration and the plants are infested with the brown planthopper (*Nilaparvata lugens*).

After 4 days mortality in % is determined. 100% means all planthoppers have been killed and 0% means none of the planthoppers have been killed.

In this test, for example, the following compounds from the preparation examples showed good activity of 100% at an application rate of 500 g/ha: I-83, I-85, I-132, I-134, I-140, I-141.

In this test, for example, the following compounds from the preparation examples showed good activity of 100% at an application rate of 100 g/ha: I-8.

*Spodoptera fruaiperda*—Spray Test

Solvent: 78.0 parts by weight acetone 1.5 parts by weight dimethylformamide

Emulsifier: alkylarylpolyglycol ether

To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Maize (*Zea mays*) leaf sections are sprayed with a preparation of the active ingredient of the desired concentration. Once dry, the leaf sections are infested with fall armyworm larvae (*Spodoptera frugiperda*).

After 7 days mortality in % is determined. 100% means all caterpillars have been killed and 0% means none of the caterpillars have been killed.

In this test, for example, the following compounds from the preparation examples showed good activity of 100% at an application rate of 100 g/ha: I-1, I-8, I-10, I-13, I-19, I-20, I-21, I-22, I-23, I-24, I-25, I-32, I-36, I-38, I-39, I-45, I-46, I-47, I-48, I-51, I-56, I-58, I-63, I-65, I-66, I-67, I-69, I-72, I-73, I-75, I-76, I-77, I-83, I-85, I-88, I-89, I-90, I-92, I-93, I-94, I-98, I-100, I-101, I-102, I-103, I-105, I-106, I-113, I-114, I-115, I-116, I-118, I-119, I-120, I-122, I-124, I-125, I-128, I-131, I-132, I-133, I-134, I-136, I-137, I-138, I-139, I-140, I-141 I-142, I-143, I-148, I-151, I-152, I-155, I-157, I-159, I-160, I-164, I-166.

In this test, for example, the following compounds from the preparation examples showed good activity of 83% at an application rate of 100 g/ha: I-12, I-17, I-41, I-59, I-60.

*Aedes aegypti* Test (AEDSAE Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/ml/RME 2000 ppm). This solution is pipetted onto a glazed tile and after evaporation of the acetone, adult mosquitoes of the species *Aedes aegypti* strain MONHEIM are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 80-100% at a surface concentration of 20 mg/m$^2$: I-7, I-8, I-9, I-10, I-85.

The following examples showed in this test efficacy of 80-100% at a surface concentration of 4 mg/m$^2$: I-7, I-8, I-9, I-10.

*Anopheles funestus* Test (ANPHFU Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/ml/RME 2000 ppm). This solution is pipetted onto a glazed tile and after evaporation of the acetone, adult mosquitoes of the species *Anopheles funestus* strain FUMOZ-R (Hunt et al., Med. Vet. Entomol. 2005 Sep. 19(3): 271-275) are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 80-100% at a surface concentration of 20 mg/m$^2$: I-7, I-8, I-9, I-10, I-85.

The following examples showed in this test efficacy of 80-100% at a surface concentration of 4 mg/m$^2$: I-9.

*Musca domestica* Test (MUSCDO Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/ml/RME 2000 ppm). This solution is pipetted onto a glazed tile and after evaporation of the acetone, adult flies of the species *Musca domestica* strain WHO-N are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 80-100% at a surface concentration of 20 mg/m$^2$: I-8, I-10, I-85.

The following examples showed in this test efficacy of 80-100% at a surface concentration of 4 mg/m$^2$: I-7, I-8.

*Blattella germanica* Test (BLTTGE Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/ml/RME 2000 ppm). This solution is pipetted onto a glazed tile and after evaporation of the acetone, adult animals of the species *Blattella germanica* strain PAULINIA are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 80-100% at a surface concentration of 20 mg/m$^2$: I-7, I-8, I-10.

The invention claimed is:

1. A compound of formula (I)

(I)

wherein,

R$^1$ is hydrogen, in each case optionally substituted C$_1$-C$_6$alkyl, C$_3$-C$_6$cycloalkyl, C$_3$-C$_6$cycloalkylC$_1$-C$_6$alkyl, C$_2$-C$_6$alkenyl, C$_2$-C$_6$haloalkenyl, C$_2$-C$_6$alkynyl, or C$_2$-C$_6$haloalkynyl;

or phenyl-C$_1$-C$_6$alkyl, in which phenyl is optionally substituted with 1 to 5 substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, C$_1$-C$_6$alkyl, C$_3$-C$_6$cycloalkyl, C$_3$-C$_6$cycanocycloalkyl, C$_3$-C$_6$halocycloalkyl, C$_3$-C$_6$cycloalkyl-C$_1$-C$_6$alkyl, C$_1$-C$_3$haloalkyl, C$_1$-C$_3$cyanoalkyl, C$_1$-C$_4$alkoxy, C$_1$-C$_3$haloalkoxy, C$_1$-C$_3$cyanoalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, C$_1$-C$_3$cyanoalkylthio, C$_1$-C$_3$cyanoalkylsulfinyl, or C$_1$-C$_3$cyanoalkylsulfonyl;

or heterocyclyl-C$_1$-C$_6$alkyl, wherein the heterocyclyl is selected from the group consisting of saturated or partially unsaturated 3- to 10-membered heterocyclyl, 5-membered heteroaryl, 6-membered heteroaryl, 9-membered heteroaryl and 10-membered heteroaryl and the heterocyclyl is optionally substituted with 1 to 5 substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, C$_1$-C$_6$alkyl, C$_3$-C$_6$cycloalkyl, C$_3$-C$_6$cycanocycloalkyl, C$_3$-C$_6$halocycloalkyl, C$_3$-C$_6$cycloalkyl-C$_1$-C$_6$alkyl, C$_1$-C$_6$haloalkyl, C$_1$-C$_3$cyanoalkyl, C$_1$-C$_4$alkoxy, C$_1$-C$_3$haloalkoxy, C$_1$-C$_3$cyanoalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, C$_1$-C$_3$cyanoalkylthio, C$_1$-C$_3$cyanoalkylsulfinyl, and C$_1$-C$_3$cyanoalkylsulfo-nyl;

R$^2$ is phenyl or a 5- or 6-membered heteroaryl, each of which is optionally substituted with 1, 2 or 3 substituents independently selected from the group consisting of halogen, hydroxy, —CN, —COOH, —NO$_2$, —NH$_2$, —SF$_5$;

in each case optionally substituted C$_1$-C$_6$alkyl, C$_2$-C$_6$alkenyl, C$_2$-C$_6$alkynyl, C$_3$-C$_6$cycloalkyl, C$_1$-C$_6$haloalkyl, C$_1$-C$_6$alkoxy, C$_3$-C$_6$cycloalkoxy, C$_1$-C$_6$haloalkoxy, hydroxy-C$_1$-C$_6$alkyl, —CO$_2$C$_1$-C$_6$alkyl, —NH (C$_1$-C$_6$alkyl), —N(C$_1$-C$_6$alkyl)$_2$, S-C$_1$-C$_6$alkylsulfinimidoyl, S-C$_3$-C$_6$cycloalkylsulfinimidoyl, S-C$_2$-C$_6$alkenylsulfinimidoyl, S-C$_2$-C$_6$alkinylsulfinimidoyl, S-phenylsulfinimidoyl, S-heterocyclylsulfinimidoyl, S-heteroarylsulfinimi-doyl, S-C$_1$-C$_6$alkylsulfonimidoyl, S-C$_3$-C$_6$cycloalkylsulfonimidoyl, S-C$_2$-C$_6$alkenylsulfonimidoyl, S-C$_2$-C$_6$alkinylsulfonimidoyl, S-phenylsulfonimidoyl, S-heterocyclylsulfonimidoyl, S-heteroarylsulfonimi-doyl, —C(=NOC$_1$-C$_6$alkyl) H, —C(=NOC$_1$-C$_6$alkyl)-C$_1$-C$_6$alkyl, (C$_1$-C$_6$alkyl) 3-silyl;

and the substructures S1-S9, in which the bond to the phenyl or 5- or 6-membered heteroaryl is marked with a # and Z is CO or CS and Y is independently selected from CO or SO$_2$;

S1

S2

S3

S4

S5

S6

S7

S8

-continued

S9

R$^{21}$ is hydrogen or in each case optionally substituted C$_1$-C$_6$alkyl, C$_1$-C$_6$haloalkyl, C$_3$-C$_6$cycloalkyl, —C$_1$-C$_6$alkyl-C$_3$-C$_6$cycloalkyl, phenyl, heteroaryl or hetero-cyclyl;

R$^{22}$ is hydrogen or in each case optionally substituted C$_1$-C$_6$alkyl, C$_1$-C$_6$haloalkyl, —C$_1$-C$_6$alkyl-C$_3$-C$_6$cycloalkyl or C$_3$-C$_6$cycloalkyl;

R$^{23}$ is independently selected from in each case optionally substituted C$_1$-C$_6$alkyl, C$_1$-C$_6$haloalkyl, C$_3$-C$_6$cycloalkyl or phenyl;

R$^{24}$ is in each case optionally substituted C$_1$-C$_6$alkyl, C$_2$-C$_6$alkenyl, C$_2$-C$_6$alkynyl, C$_1$-C$_6$haloalkyl, C$_3$-C$_6$cycloalkyl, phenyl, heteroaryl or heterocyclyl;

or

R$^{21}$ and R$^{22}$ together with the nitrogen atom to which they are attached, represent a monocyclic or poly-cyclic optionally substituted 3- to 12-membered saturated or unsaturated heterocyclyl which may contain further heteroatoms;

and 3- to 6-membered heterocyclyl or a 5- to 6-mem-bered heteroaryl each containing 1 or 2 heteroatoms selected from the group consisting of N, O, and S, wherein the 3- to 6-membered heterocyclyl or the 5- to 6-membered heteroaryl substituent may optionally carry 1, 2, 3 or 4 substituents independently selected from the group consisting of halogen, hydroxy, CN, —COOH, —CONH$_2$, —CSNH$_2$, —NO$_2$, —Si (CH$_3$)$_3$, SF$_5$, —NH$_2$, C$_1$-C$_6$alkyl, C$_3$-C$_6$cycloalkyl, C$_3$-C$_6$cycanocycloalkyl, C$_3$-C$_6$halocycloalkyl, C$_3$-C$_6$cycloalkyl-C$_1$-C$_6$alkyl, C$_1$-C$_3$haloalkyl, C$_1$-C$_3$cyanoalkyl, C$_3$-C$_6$cyanocycloalkyl, C$_1$-C$_4$alkoxy, C$_1$-C$_3$haloalkoxy, C$_1$-C$_3$cyanoalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, C$_1$-C$_3$cyanoalkylthio, C$_1$-C$_3$cyanoalkylsulfinyl, and C$_1$-C$_3$cyanoalkylsulfonyl;

R$^3$ is hydrogen or C$_1$-C$_6$alkyl optionally substituted with 1 to 3 substituents selected from the group consisting of halogen, C$_3$-C$_6$-cycloalkyl and C$_1$-C$_6$-alkoxy;

R$^4$ is a monocyclic heterocycle selected from the group consisting of a 5-membered heteroaryl, a 6-membered heteroaryl and a 3-6 membered heterocyclyl, each of which containing 1 or 2 heteroatoms selected from the group consisting of N, O, and S, and each of which is optionally substituted by 1, 2, 3 or 4 substituents independently selected from the group consisting of halogen, hydroxy, —CN, —COOH, —NO$_2$, —NH$_2$, —SF$_5$;

in each case optionally substituted C$_1$-C$_6$alkyl, C$_2$-C$_6$alkenyl, C$_2$-C$_6$alkynyl, C$_3$-C$_6$cycloalkyl, C$_1$-C$_6$alkyl-C$_3$-C$_6$cycloalkyl, C$_1$-C$_6$haloalkyl, C$_3$-C$_6$halocycloalkyl, C$_1$-C$_6$alkoxy, C$_3$-C$_6$cycloalkoxy, C$_1$-C$_6$haloalkoxy, hydroxy-C$_1$-C$_6$alkyl, —NH(C$_1$-C$_6$alkyl), —NH(C$_1$-C$_6$alkyl-C$_3$-C$_6$cycloalkyl), —N(C$_1$-C$_6$alkyl)$_2$, —N(C$_1$-C$_6$alkyl) (C$_1$-C$_6$alkyl-C$_3$-C$_6$cycloalkyl), —CO$_2$C$_1$-C$_6$alkyl, S-C$_1$-C$_6$alkylsulfinimidoyl, S-C$_3$-C$_6$cycloalkylsulfinimidoyl, S-C$_2$-C$_6$alkenylsulfinimidoyl, S-C$_2$-C$_6$alkinylsulfinimi-- doyl, S-phenylsulfinimidoyl, S-heterocyclylsul-finimidoyl, S-heteroarylsulfinimidoyl, S-C$_1$-C$_6$alkylsulfonimidoyl, S-C$_3$-C$_6$cycloalkylsulfo-nimidoyl, S-C$_2$-C$_6$alkenylsulfonimidoyl, S-C$_2$-C$_6$alkinylsulfonimidoyl, S-phenylsulfonimidoyl, S-heterocyclylsulfonimidoyl, S-heteroarylsulfonimi-doyl, —C(═NOC$_1$-C$_6$alkyl) H, —C(═NOC$_1$-C$_6$alkyl)-C$_1$-C$_6$alkyl;

3- to 6-membered heterocyclyl containing 1 or 2 het-eroatoms selected from the group consisting of N, O, and S, wherein the 3- to 6-membered heterocyclyl substituent may optionally carry 1, 2, 3 or 4 sub-stituents independently selected from the group con-sisting of halogen, hydroxy, —CN, —COOH, —CONH$_2$, —CSNH$_2$, —NO$_2$, —Si(CH$_3$)$_3$, —SF$_5$, —NH$_2$, C$_1$-C$_6$alkyl, C$_3$-C$_6$cycloalkyl, C$_3$-C$_6$cycanocycloalkyl, C$_3$-Chalocycloalkyl, C$_3$-C$_6$cycloalkyl-C$_1$-C$_6$alkyl, C$_1$-C$_3$haloalkyl, C$_1$-C$_3$cyanoalkyl, C$_1$-C$_4$alkoxy, C$_1$-C$_3$haloalkoxy, C$_1$-C$_3$cyanoalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, C$_1$-C$_3$cyanoalkylthio, C$_1$-C$_3$cyanoalkylsulfinyl, and C$_1$-C$_3$cyanoal-kylsulfonyl;

and the following substructures S10-S18, in which the bond to the 5-membered heteroaryl, the 6-membered heteroaryl or the 3-6 membered heterocyclyl is marked with a # and Z is CO or CS and Y is independently selected from CO or SO$_2$:

S10

S11

S12

S13

S14

S15

S16

-continued

S17

S18

R$^{41}$ is hydrogen or in each case optionally substituted C$_1$-C$_6$alkyl, C$_1$-C$_6$haloalkyl, C$_3$-C$_6$cycloalkyl, —C$_1$-C$_6$alkyl-C$_3$-C$_6$cycloalkyl, phenyl, heteroaryl or hetero-cyclyl;

R$^{42}$ is hydrogen or in each case optionally substituted C$_1$-C$_6$alkyl, C$_1$-C$_6$haloalkyl or C$_3$-C$_6$cycloalkyl;

R$^{43}$ is independently selected from in each case optionally substituted C$_1$-C$_6$alkyl, C$_1$-C$_6$haloalkyl, C$_3$-C$_6$cycloalkyl or phenyl;

R$^{44}$ is in each case optionally substituted C$_1$-C$_6$alkyl, C$_2$-C$_6$alkenyl, C$_2$-C$_6$alkynyl, C$_1$-C$_6$haloalkyl, C$_3$-C$_6$cycloalkyl, phenyl, heteroaryl or heterocyclyl;

or

R$^{41}$ and R$^{42}$ together with the nitrogen atom to which they are attached, represent a monocyclic or polycyclic optionally substituted 3- to 12-membered saturated or unsaturated heterocyclyl which may contain further heteroatoms;

R$^5$ is hydrogen, halogen, —CN, or in each case optionally substituted C$_1$-C$_3$-alkyl, C$_1$-C$_3$-haloalkyl, C$_1$-C$_3$cyanoalkyl, C$_3$-C$_4$-cycloalkyl, C$_3$-C$_4$halocycloalkyl, C$_3$-C$_6$cyanocycloalkyl, C$_1$-C$_3$alkoxy, C$_1$-C$_3$haloalkoxy, C$_1$-C$_3$cyanoalkoxy, —CO$_2$ (C$_1$-C$_3$alkyl), —CH-(C$_1$-C$_3$alkoxy) 2, —CONH(C$_1$-C$_4$alkyl), —CON(C$_1$-C$_4$alkyl)$_2$, —NHCO-C$_1$-C$_4$alkyl, —N(C$_1$-C$_4$alkyl)CO-C$_1$-C$_4$alkyl, —C(═NOC$_1$-C$_4$alkyl) H, or —C(═NOC$_1$-C$_4$alkyl)-C$_1$-C$_4$alkyl, —NH$_2$, —NH(C$_1$-C$_3$alkyl), —N(C$_1$-C$_3$alkyl)$_2$, C$_1$-C$_3$alkylthio, C$_1$-C$_3$alkylsulfinyl, C$_1$-C$_3$alkylsulfonyl, C$_3$-C$_6$cycloalkylthio, C$_3$-C$_6$cycloalkylsulfinyl, or C$_3$-C$_6$cycloalkylsulfonyl;

R$^6$ is hydrogen, halogen, —CN, or in each case optionally substituted C$_1$-C$_3$-alkyl, C$_1$-C$_3$-haloalkyl, C$_3$-C$_4$cycloalkyl, C$_3$-C$_4$halocycloalkyl, C$_1$-C$_3$alkoxy, C$_1$-C$_3$haloalkoxy, —CO$_2$ (C$_1$-C$_3$alkyl), —CH-(C$_1$-C$_3$alkoxy) 2, —CONH(C$_1$-C$_4$alkyl), —CON(C$_1$-C$_4$alkyl)$_2$, —NHCO-C$_1$-C$_4$alkyl, —N(C$_1$-C$_4$alkyl)CO-C$_1$-C$_4$alkyl, —C(═NOC$_1$-C$_4$alkyl) H, or —C(═NOC$_1$-C$_4$alkyl)-C$_1$-C$_4$alkyl, —NH$_2$, —NH(C$_1$-C$_3$alkyl), —N(C$_1$-C$_3$alkyl)$_2$, C$_1$-C$_3$alkylthio, C$_1$-C$_3$alkylsulfinyl, C$_1$-C$_3$alkylsulfonyl, C$_3$-C$_6$cycloalkylthio, C$_3$-C$_6$cycloalkylsulfinyl, or C$_3$-C$_6$cycloalkylsulfonyl;

and/or a salt and/or a N-oxide thereof.

2. The compound of claim 1, wherein

R$^1$ is hydrogen; or in each case optionally substituted C$_1$-C$_6$alkyl, C$_3$-C$_6$cycloalkylC$_1$-C$_6$alkyl, C$_2$-C$_6$alkenyl, C$_2$-C$_6$alkynyl, C$_1$-C$_6$alkoxyC$_1$-C$_6$alkyl, C$_1$-C$_6$alkylthioC$_1$-C$_6$alkyl, C$_1$-C$_6$alkylsulfinylC$_1$-C$_6$alkyl, or C$_1$-C$_6$alkylsulfonylC$_1$-C$_6$alkyl, wherein the aforementioned optionally substituted radicals are optionally substituted with up to 3 substituents inde-pendently selected from the group consisting of halo-gen, hydroxy, —CN, —NO$_2$, —Si(CH$_3$)$_3$, —NH$_2$ and C$_1$-C$_6$alkyl;

or phenyl-$C_1$-$C_6$alkyl, in which phenyl is optionally substituted with 1 to 5 substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cyanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, and $C_1$-$C_3$cyanoalkylsulfonyl;

or heterocyclyl-$C_1$-$C_3$alkyl, wherein the heterocyclyl is selected from the group consisting of tetrahydropyranyl, tetrahydrofuranyl, oxetanyl and azetidinyl, or heteroaryl, wherein the heteroaryl is selected from the group consisting of pyridyl, pyrimidinyl, pyrazyl, pyridazinyl, thiophenyl, furanyl, pyrazolyl, imidazolyl, triazolyl, thiazolyl, and oxazolyl, and wherein the heteroaryl or the heterocyclyl is optionally substituted with 1 to 3 substituents, each independently selected from the group consisting of halogen, hydroxy, —CN, —COOH, —CONH$_2$, —CSNH$_2$, —NO$_2$, —Si(CH$_3$)$_3$, SF$_5$, —NH$_2$, $C_1$-$C_6$alkyl, $C_3$-$C_6$cycloalkyl, $C_3$-$C_6$cycanocycloalkyl, $C_3$-$C_6$halocycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$cyanoalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, $C_1$-$C_3$cyanoalkylthio, $C_1$-$C_3$cyanoalkylsulfinyl, and $C_1$-$C_3$cyanoalkylsulfonyl;

$R^2$ is selected from the group consisting of phenyl, pyridine, pyrimidine, pyrazine, pyridazine, pyrazole, pyrrole, thiazole, oxazole and thiophene, each of which is optionally substituted by 1, 2 or 3 substituents independently selected from the group consisting of halogen, hydroxy, —CN, —COOH, —NO$_2$, —NH$_2$, —SF$_5$;

in each case optionally substituted $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_1$-$C_4$alkoxy, $C_3$-$C_6$cycloalkoxy, $C_1$-$C_3$haloalkoxy, hydroxy-$C_1$-$C_4$alkyl, —CO$_2$$C_1$-$C_4$alkyl, —NH($C_1$-$C_4$alkyl), —N($C_1$-$C_4$alkyl)$_2$, —C(=NO$C_1$-$C_4$alkyl) H, —C(=NO$C_1$-$C_4$alkyl)-$C_1$-$C_4$alkyl and ($C_1$-$C_4$alkyl) 3-silyl, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$, $C_1$-$C_3$alkyl, $C_1$-$C_3$haloalkyl, $C_3$-$C_4$cycloalkyl, $C_3$-$C_4$halocycloalkyl, $C_1$-$C_3$alkylsulfonyl, $C_3$-$C_4$cycloalkylsulfonyl, $C_1$-$C_3$haloalkylthio and $C_1$-$C_3$haloalkylsulfonyl;

and the substructures S1, S4, S7, S8 or S9, in which the bond to the aforementioned phenyl, pyridine, pyrimidine, pyrazine, pyridazine, pyrazole, pyrrole, thiazole, oxazole or thiophene is marked with a # and Z is CO or CS;

S1

-continued

S4

S7

S8

S9

$R^{21}$ is hydrogen or in each case optionally substituted $C_1$-$C_4$alkyl, $C_1$-$C_4$haloalkyl, $C_3$-$C_6$cycloalkyl, —$C_1$-$C_4$alkyl-$C_3$-$C_6$cycloalkyl or 3- to 6-membered heterocyclyl;

$R^{22}$ is hydrogen or in each case optionally substituted $C_1$-$C_4$alkyl, $C_1$-$C_4$haloalkyl, —$C_1$-$C_4$alkyl-$C_3$-$C_6$cycloalkyl or $C_3$-$C_6$cycloalkyl;

$R^{24}$ is in each case optionally substituted $C_1$-$C_4$alkyl, $C_2$-$C_6$alkenyl, $C_2$-$C_6$alkynyl, $C_1$-$C_4$haloalkyl, $C_3$-$C_6$cycloalkyl, phenyl, heteroaryl or 3- to 6-membered heterocyclyl;

wherein the aforementioned optionally substituted radicals in the definitions of $R^{21}$, $R^{22}$ and $R^{24}$ are optionally substituted with up to 3 substituents independently selected from the group consisting of halogen, hydroxy, —CN, —NO$_2$, —Si(CH$_3$)$_3$, —NH$_2$, $C_1$-$C_3$alkyl, $C_1$-$C_3$haloalkyl, $C_3$-$C_4$cycloalkyl, $C_3$-$C_4$halocycloalkyl, $C_1$-$C_4$alkoxy, $C_1$-$C_4$haloalkoxy, $C_1$-$C_3$alkylsulfonyl, $C_3$-$C_4$cycloalkylsulfonyl, $C_1$-$C_3$haloalkylthio and $C_1$-$C_3$haloalkylsulfonyl;

or $R^{21}$ and $R^{22}$ together with the nitrogen atom to which they are attached, represent a 4- to 12-membered saturated or unsaturated heterocyclyl which may contain up to two further heteroatoms selected from the group of oxygen, nitrogen and sulfur and which is optionally substituted with one to three substituents selected from the group consisting of halogen, =O (oxo), =S (thiono), hydroxy, —CN, —NO$_2$, —SF$_5$, —NH$_2$;

$C_1$-$C_4$alkyl, $C_3$-$C_6$cycloalkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_3$-$C_6$cycloalkylsulfanyl, $C_3$-$C_6$cycloalkylsulfinyl, $C_3$-$C_6$cycloalkylsulfonyl, $C_1$-$C_4$haloalkylthio, $C_1$-$C_4$haloalkylsulfinyl, $C_1$-$C_4$haloalkylsulfonyl;

and 3- to 6-membered heterocyclyl or a 5- to 6-membered heteroaryl each containing 1 or 2 heteroatoms selected from the group consisting of N, O, and S, wherein the 3- to 6-membered heterocyclyl or the 5- to 6-membered heteroaryl substituent may optionally carry 1, 2 or 3 substituents independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl;

$R^3$ is hydrogen or $C_1$-$C_6$alkyl optionally substituted with halogen, cyano, $C_3$-$C_6$cycloalkyl or $C_1$-$C_4$alkoxy;

$R^4$ is selected from the group consisting of pyridine, pyrimidine, pyrazine, pyridazine, thiazole, pyrazole, pyrrole, oxazole, isothiazole, isoxazole, thiophene and imidazole, each of which is optionally substituted by 1, 2 or 3 substituents independently selected from the group consisting of halogen, hydroxy, —CN, —COOH, —NO$_2$, —NH$_2$, —SF$_5$;

in each case optionally substituted $C_1$-$C_6$alkyl, $C_2$-$C_6$alkenyl, $C_2$-$C_6$alkynyl, $C_3$-$C_6$cycloalkyl, $C_1$-$C_3$haloalkyl, $C_1$-$C_4$alkoxy, $C_3$-$C_6$cycloalkoxy, $C_1$-$C_3$haloalkoxy, hydroxy-$C_1$-$C_4$alkyl, —CO$_2$C$_1$-$C_4$alkyl, —NH($C_1$-$C_4$alkyl), —N($C_1$-$C_4$alkyl)$_2$, —C(=NOC$_1$-$C_4$alkyl) H, —C(=NOC$_1$-$C_4$alkyl)-$C_1$-$C_4$alkyl and ($C_1$-$C_4$alkyl) 3-silyl, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$, $C_1$-$C_3$alkyl, $C_1$-$C_3$haloalkyl, $C_3$-$C_4$cycloalkyl, $C_3$-$C_4$halocycloalkyl, $C_1$-$C_4$alkoxy, $C_1$-$C_4$haloalkoxy, $C_1$-$C_3$alkylsulfonyl, $C_3$-$C_4$cycloalkylsulfonyl, $C_1$-$C_3$haloalkylthio and $C_1$-$C_3$haloalkylsulfonyl;

and the substructures S10, S11, S13, S14, S16, S17 and S18, in which the bond to the aforementioned pyridine, pyrimidine, pyrazine, pyridazine, thiazole, pyrazole, pyrrole, oxazole, isothiazole, isoxazole, thiophene or imidazole is marked with a # and Z is CO or CS;

S10

S11

S13

S14

S16

S17

-continued

S18

$R^{41}$ is hydrogen or in each case optionally substituted $C_1$-$C_4$alkyl, $C_1$-$C_4$haloalkyl, $C_3$-$C_6$cycloalkyl, —$C_1$-$C_4$alkyl-$C_3$-$C_6$cycloalkyl or 3- to 6-membered heterocyclyl;

$R^{42}$ is hydrogen or in each case optionally substituted $C_1$-$C_4$alkyl, $C_1$-$C_4$haloalkyl, —$C_1$-$C_4$alkyl-$C_3$-$C_6$cycloalkyl or $C_3$-$C_6$cycloalkyl;

$R^{43}$ is independently selected from in each case optionally substituted $C_1$-$C_4$alkyl, $C_1$-$C_4$haloalkyl or $C_3$-$C_6$cycloalkyl;

$R^{44}$ is in each case optionally substituted $C_1$-$C_4$alkyl, $C_1$-$C_4$haloalkyl, $C_3$-$C_6$cycloalkyl, phenyl, heteroaryl or 3- to 6-membered heterocyclyl;

wherein the aforementioned optionally substituted radicals in the definitions of $R^{41}$, $R^{42}$, $R^{43}$ and $R^{24}$ are optionally substituted with up to 3 substituents independently selected from the group consisting of halogen, hydroxy, —CN, —NO$_2$, —Si(CH$_3$)$_3$, —NH$_2$, $C_1$-$C_3$alkyl, $C_1$-$C_3$haloalkyl, $C_3$-$C_4$cycloalkyl, $C_3$-$C_4$halocycloalkyl, $C_1$-$C_4$alkoxy, $C_1$-$C_4$haloalkoxy, $C_1$-$C_3$alkylsulfonyl, $C_3$-$C_4$cycloalkylsulfonyl, $C_1$-$C_3$haloalkylthio and $C_1$-$C_3$haloalkylsulfonyl;

or $R^{41}$ and $R^{42}$ together with the nitrogen atom to which they are attached, represent a 4- to 12-membered saturated or unsaturated heterocyclyl which may contain up to two further heteroatoms selected from the group of oxygen, nitrogen, sulfur and silicon and which is optionally substituted with one to three substituents selected from the group consisting of halogen, =O (oxo), =S (thiono), hydroxy, —CN, —NO$_2$, —SF$_5$, —NH$_2$; $C_1$-$C_4$alkyl, $C_3$-$C_6$cycloalkyl, $C_3$-$C_6$cycloalkyl-$C_1$-$C_6$alkyl, $C_1$-$C_4$haloalkyl, $C_1$-$C_4$alkoxy, $C_1$-$C_4$haloalkoxy, $C_1$-$C_4$alkoxy-$C_1$-$C_6$alkyl, $C_1$-$C_4$alkylthio, $C_1$-$C_4$alkylsulfinyl, $C_1$-$C_4$alkylsulfonyl, $C_3$-$C_6$cycloalkylsulfanyl, $C_3$-$C_6$cycloalkylsulfinyl, $C_3$-$C_6$cycloalkylsulfonyl, $C_1$-$C_4$haloalkylthio, $C_1$-$C_4$haloalkylsulfinyl, $C_1$-$C_4$haloalkylsulfonyl;

and 3- to 6-membered heterocyclyl or a 5- to 6-membered heteroaryl each containing 1 or 2 heteroatoms selected from the group consisting of N, O, and S, wherein the 3- to 6-membered heterocyclyl or the 5- to 6-membered heteroaryl substituent may optionally carry 1, 2 or 3 substituents independently selected from the group consisting of halogen, hydroxy, —CN, —COOH, —CONH$_2$, —CSNH$_2$, —NO$_2$, —Si(CH$_3$)$_3$, —SF$_5$, —NH$_2$, $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_3$cyanoalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, and $C_1$-$C_3$haloalkylsulfonyl;

$R^5$ is hydrogen, halogen, —CN, NH$_2$, or in each case optionally substituted $C_1$-$C_3$-alkyl, $C_3$-$C_4$-cycloalkyl, $C_1$-$C_3$alkoxy, —CO$_2$ ($C_1$-$C_3$alkyl), —CH-($C_1$-$C_3$alkoxy) 2, —CONH($C_1$-$C_4$alkyl), —CON($C_1$-$C_4$alkyl)$_2$, —NHCO-$C_1$-$C_4$alkyl, —N($C_1$-$C_4$alkyl)CO- $C_1$-$C_4$alkyl, —C(=NOC$_1$-$C_4$alkyl) H,-C(=NOC$_1$-$C_4$alkyl)-$C_1$-$C_4$alkyl, NH($C_1$-$C_3$alkyl), N($C_1$-$C_3$alkyl)$_2$, $C_1$-$C_3$alkylthio, or $C_3$-$C_6$cycloalkylthio, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$ and $C_1$-$C_3$alkyl;

$R^6$ is hydrogen, halogen, —CN, NH$_2$, or in each case optionally substituted $C_1$-$C_3$-alkyl, $C_3$-$C_4$-cycloalkyl, $C_1$-$C_3$alkoxy, —CO$_2$ ($C_1$-$C_3$alkyl), —CH-($C_1$-$C_3$alkoxy) 2, —CONH($C_1$-$C_4$alkyl), —CON($C_1$-$C_4$alkyl)$_2$, —NHCO-$C_1$-$C_4$alkyl, —N($C_1$-$C_4$alkyl)CO-$C_1$-$C_4$alkyl, —C(=NOC$_1$-$C_4$alkyl) H,-C(=NOC$_1$-$C_4$alkyl)-$C_1$-$C_4$alkyl, NH($C_1$-$C_3$alkyl), N($C_1$-$C_3$alkyl)$_2$, $C_1$-$C_3$alkylthio, or $C_3$-$C_6$cycloalkylthio, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$ and $C_1$-$C_3$alkyl;

and/or a salt and/or a N-oxide thereof.

3. The compound of claim 1, wherein $R^1$ is hydrogen; or $C_1$-$C_6$alkyl, $C_3$-$C_6$cycloalkyl$C_1$-$C_6$alkyl, $C_2$-$C_6$alkenyl, $C_2$-$C_6$haloalkenyl, $C_2$-$C_6$alkynyl, $C_2$-$C_6$haloalkynyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl, $C_1$-$C_6$haloalkyl, $C_1$-$C_6$cyanoalkyl;

$R^2$ is selected from the group consisting of pyrazole, phenyl, pyridine, pyrimidine, pyrazine, and pyridazine, each of which is optionally substituted by a total of 1, 2 or 3 substituents, wherein 1, 2 or 3 of the optional substituents are independently selected from group A consisting of halogen, hydroxy, —CN, —COOH, —NO$_2$, —NH$_2$, —SF$_5$;

$C_1$-$C_4$alkyl, $C_1$-$C_3$haloalkyl, $C_1$-$C_3$cyanoalkyl, $C_3$-$C_4$cycloalkyl, $C_3$-$C_4$halocycloalkyl, $C_3$-$C_4$cyanocycloalkyl, $C_1$-$C_3$alkoxy, $C_1$-$C_3$haloalkoxy, $C_3$-$C_4$cycloalkoxy, $C_1$-$C_3$cyanoalkoxy, —CO$_2$$C_1$-$C_4$alkyl and ($C_1$-$C_3$alkyl) 3-silyl; and optionally 1 of the optional substituents may be selected from group B consisting of the substructures S1, S4, S7, S8 and S9, in which the bond to the phenyl, pyridine, pyrimidine, pyrazine, or pyridazine is marked with a # and Z is CO;

-continued

S9

$R^{21}$ is hydrogen or in each case optionally substituted $C_1$-$C_3$alkyl, $C_1$-$C_3$haloalkyl, or $C_3$-$C_4$cycloalkyl;

$R^{22}$ is hydrogen or in each case optionally substituted $C_1$-$C_3$alkyl, $C_1$-$C_3$haloalkyl or $C_3$-$C_4$cycloalkyl;

$R^{24}$ is in each case optionally substituted $C_1$-$C_3$alkyl, $C_1$-$C_3$haloalkyl, $C_3$-$C_4$cycloalkyl or phenyl;

wherein the aforementioned optionally substituted radicals in the definitions of $R^{21}$, $R^{22}$ and $R^{24}$ are optionally substituted with up to 3 substituents independently selected from the group consisting of halogen, —CN, —NO$_2$, —Si(CH$_3$)$_3$, $C_1$-$C_3$alkyl, and $C_1$-$C_3$haloalkyl;

$R^3$ is hydrogen or $C_1$-$C_6$alkyl;

$R^4$ is a 5-membered heteroaryl or 6-membered heteroaryl selected from the group consisting of pyridine, pyrimidine, pyrazine, pyridazine, pyrazole, pyrrole, thiazole, oxazole, isothiazole, isoxazole, thiophene and imidazole, wherein the aforementioned 6-membered heteroaryl are each optionally substituted by 1, 2 or 3 substituents and the aforementioned 5-membered heteroaryl are each optionally substituted by 1 or 2 substituents, wherein in each case up to all of the optional substituents are independently selected from group D consisting of halogen, hydroxy, —CN, —COOH, —NO$_2$, —NH$_2$, —SF$_5$;

$C_1$-$C_3$alkyl, $C_3$-$C_4$cycloalkyl, $C_1$-$C_3$haloalkyl, $C_1$-$C_3$cyanoalkyl, $C_3$-$C_4$cyanocycloalkyl, $C_1$-$C_3$alkoxy, $C_3$-$C_4$cycloalkoxy, $C_1$-$C_3$haloalkoxy, $C_1$-$C_3$cyanoalkoxy, hydroxy-$C_1$-$C_3$alkyl, —CO$_2$$C_1$-$C_3$alkyl, —NH($C_1$-$C_3$alkyl), —N($C_1$-$C_3$alkyl)$_2$, —C(=NOC$_1$-$C_3$alkyl) H, —C(=NOC$_1$-$C_3$alkyl)-$C_1$-$C_3$alkyl and ($C_1$-$C_3$alkyl) 3-silyl;

and optionally 1 of the optional substituents may be selected from group E consisting of the substructures S10, S13, S16, S17 and S18, in which the bond to the aforementioned pyridine, pyrimidine, pyrazine, pyridazine, pyrazole, pyrrole, thiazole, oxazole, isothiazole, isoxazole, thiophene or imidazole is marked with a # and Z is CO;

S1

S4

S7

S8

S10

S13

S16

S17

-continued

S18

$$R^{44}\diagdown \underset{\overset{\|}{O}}{\overset{S}{\big|}}\diagup^{\#}\diagdown O$$

$R^{41}$ is hydrogen or in each case optionally substituted $C_1$-$C_3$alkyl, $C_1$-$C_5$haloalkyl, $C_3$-$C_4$cycloalkyl, —$C_1$-$C_2$alkyl-$C_3$-$C_4$cycloalkyl or 3- to 6-membered hetero-cyclyl containing 1 heteroatom selected from the group consisting of N, O, and S;

$R^{42}$ is hydrogen or in each case optionally substituted $C_1$-$C_3$alkyl, $C_1$-$C_3$haloalkyl, —$C_1$-$C_2$alkyl-$C_3$-$C_4$cycloalkyl or $C_3$-$C_4$cycloalkyl;

$R^{44}$ is in each case optionally substituted $C_1$-$C_3$alkyl, $C_1$-$C_3$haloalkyl, or $C_3$-$C_4$cycloalkyl;

wherein the aforementioned optionally substituted radicals defined for $R^{41}$, $R^{42}$ and $R^{44}$ are optionally substituted with up to 2 substituents independently selected from the group consisting of halogen, —CN, —NO$_2$, —Si(CH$_3$)$_3$, $C_1$-$C_3$alkyl, and $C_1$-$C_3$haloalkyl; or $R^{41}$ and $R^{42}$ together with the nitrogen atom to which they are attached, represent a monocyclic 4- to 8-membered saturated heterocyclyl which may contain up to one further heteroatom selected from the group of oxygen, nitrogen, sulfur and silicon and which is optionally substituted with one to three substituents selected from the group consisting of halogen, =O (oxo), =S (thiono), hydroxy, —CN, —NO$_2$, —NH$_2$;

$C_1$-$C_3$alkyl, $C_3$-$C_4$cycloalkyl, $C_1$-$C_3$haloalkyl, $C_1$-$C_3$alkoxy, and $C_1$-$C_3$haloalkoxy;

$R^5$ is hydrogen, halogen, —CN, $C_1$-$C_3$-alkyl, $C_1$-$C_3$-haloalkyl, $C_3$-$C_4$-cycloalkyl, $C_1$-$C_3$alkoxy, or $C_1$-$C_3$haloalkoxy;

$R^6$ is hydrogen, halogen, —CN, $C_1$-$C_3$-alkyl, $C_1$-$C_3$-haloalkyl, $C_3$-$C_4$cycloalkyl, $C_1$-$C_3$alkoxy, or $C_1$-$C_3$haloalkoxy;

and/or a salt and/or a N-oxide thereof.

4. The compound of claim 1, wherein $R^1$ is hydrogen, methyl, ethyl, n-propyl, isopropyl, cyanomethyl, cyclopropylmethyl, methoxymethyl, ethoxymethyl, methylthiomethyl, ethylthiomethyl, methylthioethyl, ethylthioethyl, methylsulfonylethyl, or ethylsulfonylethyl;

$R^2$ is selected from the group consisting of pyrazole, phenyl and pyridine each of which is optionally substituted by 1 or 2 substituents independently selected from the group consisting of fluorine, chlorine, bromine, iodine, hydroxy, —CN, —COOH, —CONH$_2$, —NO$_2$, —NH$_2$, —SF$_5$, methyl, ethyl, n-propyl, isopropyl, butyl, tert-butyl, cyclopropyl, cyclobutyl, 1-cyanocyclopropyl, difluoromethyl, trifluoromethyl, pentafluoroethyl, cyanomethyl, 1-cyano-1-methyleth-1-yl, methoxy, ethoxy, difluoromethoxy, trifluoromethoxy, cyanomethoxy, methylthio, methylsulfinyl, methylsulfonyl, ethylsulfonyl, cyclopropylsulfonyl, difluoromethylthio, trifluoromethylthio, difluoromethylsulfinyl, trifluoromethylsulfinyl, difluoromethylsulfonyl, trifluoromethylsulfonyl, (CH$_3$) 3-silyl, or phenylsulfonyl which may carry a fluorine, chlorine or methyl substituent;

$R^3$ is hydrogen, methyl, ethyl, n-propyl, or isopropyl;

$R^4$ is selected from the group consisting of pyridin-2-yl, pyrimidin-2-yl, pyrimidin-4-yl, pyrazin-3-yl, and 1,3- thiazol-2-yl, 1,3-oxazol-2-yl, 1,2-oxazol-3-yl, 1,2-thi-azol-3-yl, 1H-pyrazol-1-yl, 1H-pyrazol-3-yl, and 1H-imidazol-4-yl, each of which is optionally substituted by 1 substituent selected from the group consisting of fluorine, chlorine, bromine, —CN, —COOH, methyl, ethyl, n-propyl, isopropyl, cyclopropyl, cyclobutyl, difluoromethyl, trifluoromethyl, pentafluoroethyl, cyanomethyl, methoxy, ethoxy, difluoromethoxy, trifluoromethoxy, cyanomethoxy, methylthio, methylsulfinyl, methylsulfonyl, ethylsulfonyl, cyclopropylsulfonyl, difluoromethylthio, trifluoromethylthio, difluoromethylsulfinyl, trifluoromethylsulfinyl, difluoromethylsulfonyl, trifluoromethylsulfonyl, —COOCH$_3$, —COOCH$_2$CH$_3$, and the substructures S13, in which the bond to the aforementioned pyridin-2-yl, pyrimidin-2-yl, pyrimidin-4-yl, pyrazin-3-yl, and 1,3-thiazol-2-yl, 1,3-oxazol-2-yl, 1,2-oxazol-3-yl, 1,2-thiazol-3-yl, 1H-pyrazol-1-yl, 1H-pyrazol-3-yl, 1H-imidazol-4-yl, is marked with a # and Z is CO;

S13

$$R^{42}\diagdown \underset{\overset{|}{R^{41}}}{N}\diagdown Z\diagup^{\#}$$

$R^{41}$ is hydrogen, methyl, ethyl, n-propyl, propane-2-yl, butane-2-yl, 2,2,2-trifluoroethyl, 2-trifluoromethoxy-ethyl, cyanomethyl, cyclopropyl, cyclopropylmethyl, or 2-methyl-n-propyl;

$R^{42}$ is hydrogen, methyl, ethyl, n-propyl, propane-2-yl, butane-2-yl, 2,2,2-trifluoroethyl, 2-trifluoromethoxy-ethyl, cyanomethyl, cyclopropyl, cyclo-propylmethyl, or 2-methyl-n-propyl;

$R^{41}$ and $R^{42}$ together with the nitrogen atom to which they are attached, represent pyrrolidine, piperidine, azepane, morpholine, oxazepane, azasilolidine, azasilinane, azasilepane each of which is optionally substituted with 1 or 2 methyl groups;

$R^5$ is hydrogen, fluorine, chlorine, bromine, iodine, —CN, methyl, ethyl, n-propyl, isopropyl, butyl, tert-butyl, difluoromethyl, trifluoromethyl, pentafluoroethyl, cyanomethyl, cyclopropyl, cyclobutyl, methoxy, ethoxy, difluoromethoxy, trifluoromethoxy or cyanomethoxy;

$R^6$ is hydrogen, fluorine, chlorine, bromine, iodine, —CN, methyl, ethyl, n-propyl, isopropyl, butyl, tert-butyl, difluoromethyl, trifluoromethyl, pentafluoroethyl, cyanomethyl, cyclopropyl, cyclobutyl, methoxy, ethoxy, difluoromethoxy, trifluoromethoxy or cyanomethoxy;

and/or a salt and/or a N-oxide thereof.

5. The compound of claim 1, wherein $R^1$ is hydrogen, or cyclopropylmethyl;

$R^2$ is selected from the group consisting of pyrazol, phenyl and pyridine, each of which is optionally substituted by 1 or 2 substituents independently selected from the group consisting of fluorine, chlorine, bromine, iodine, —CN, —SF$_5$, methyl, ethyl, n-propyl, isopropyl, tert-butyl, 1-cyano-1-methyleth-1-yl, cyclopropyl, 1-cyanocyclopropyl, difluoromethyl, trifluoromethyl, methoxy, ethoxy, difluoromethoxy, difluoromethoxy, trifluoromethoxy, methylsulfonyl, ethylsulfonyl, cyclopropylsulfonyl, trifluoromethylsulfonyl, 4-fluorophenyl-sulfonyl, or difluoromethylsulfonyl;

$R^3$ is methyl;

$R^4$ is selected from the group consisting of pyridine-2-yl, pyrimidin-2-yl, 1,3-thiazol-2-yl, and 1H-pyrazol-1-yl each of which is optionally substituted by 1 substituent selected from the group consisting of fluorine, chlorine, bromine, —CN, methyl, ethyl, trifluoromethyl, methoxy, ethoxy, —COOH, —COOCH$_3$, —COOCH$_2$CH$_3$, and the substructure S13, in which the bond marked with # is connected to the C-5-position of the aforementioned pyridin-2-yl, pyrimidin-2-yl, 1,3-thiazol-2-yl-, or to the C-4-position in the above mentioned 1H-pyrazol-1-yl, and Z is CO;

S13

$R^{41}$ is hydrogen, methyl, ethyl, propane-2-yl, 2,2,2-trifluoroethyl, cyanomethyl, cyclopropylmethyl, 2-methyl-n-propyl, or cyclopropyl;

$R^{42}$ is hydrogen, methyl, ethyl, propane-2-yl, 2,2,2-trifluoroethyl, cyanomethyl, cyclopropylmethyl, or 2-methyl-n-propyl;

$R^{41}$ and $R^{42}$ together with the nitrogen atom to which they are attached, represent pyrrolidine, piperidine, morpholine, 2,6-dimethylmorpholine, oxazepane, or (Si,Si-dimethyl) azasilinane;

$R^5$ is hydrogen or methyl;

$R^6$ is hydrogen or methyl;

and/or a salt and/or a N-oxide thereof.

6. The compound of claim 1, wherein $R^2$ is selected from the group consisting of phenyl, pyridyl, thiophene, pyrazole and imidazole;

and/or a salt and/or a N-oxide thereof.

7. The compound of claim 1, wherein $R^4$ is selected from the group consisting of pyridine, pyrimidine pyrazine, and pyridazine;

and/or a salt and/or a N-oxide thereof.

8. The compound of claim 1, wherein $R^4$ is selected from the group consisting of thiazole, pyrazole, pyrrole, oxazole, isothiazole, isoxazole, thiophene and imidazole;

and/or a salt and/or a N-oxide thereof.

9. The compound of claim 1, wherein $R^2$ is the substructure Q1 wherein the bond to the C=O-group is marked with a #:

Q1 wherein $R^{25}$ is hydroxy, —NH$_2$, —SO$_2$NH$_2$, C$_4$-C$_6$alkyl, C$_4$alkoxy, C$_1$-C$_3$cyanoalkyl, C$_3$-C$_6$cycloalkyl, C$_3$-C$_6$halocycloalkyl, C$_3$-C$_6$cyanocycloalkyl, C$_1$-C$_3$alkylthio, C$_1$-C$_3$alkylsulfinyl, C$_1$-C$_3$alkylsulfonyl, C$_3$-C$_6$cycloalkylsulfanyl, C$_3$-C$_6$cycloalkylsulfinyl, C$_3$-C$_6$cycloalkylsulfonyl, C$_1$-C$_3$haloalkylsulfinyl, C$_1$-C$_3$haloalkylsulfonyl, C$_1$-C$_3$cyanoalkoxy, hydroxy-C$_1$-C$_4$alkyl, —NH(C$_1$-C$_4$alkyl), —N(C$_1$-C$_4$alkyl)$_2$, —NHCO-C$_1$-C$_4$alkyl, NHCO-C$_3$-C$_6$cycloalkyl, —NHSO$_2$ (C$_1$-C$_4$alkyl), —N(C$_1$-C$_4$alkyl)CO-C$_1$-C$_4$alkyl, —N(C$_1$-C$_4$alkyl)CO-C$_3$-C$_6$cyclolkyl, —N(C$_1$-C$_4$alkyl) SO$_2$C$_1$-C$_4$alkyl, —N(SO$_2$C$_1$-C$_4$alkyl)$_2$, —CO$_2$C$_1$-C$_4$alkyl, —CONH (C$_1$-C$_4$alkyl), —CONH(C$_3$-C$_6$cycloalkyl), —CONH-phenyl, —CON(C$_1$-C$_4$alkyl)$_2$, —CON(C$_1$-C$_4$alkyl) (C$_3$-C$_6$cycloalkyl), —CON(C$_1$-C$_4$alkyl)-phenyl, —C(=NOC$_1$-C$_4$alkyl) H, —C(=NOC$_1$-C$_4$alkyl)-C$_1$-C$_4$alkyl, (C$_1$-C$_4$alkyl) 3-silyl, —SO$_2$NH(C$_1$-C$_4$alkyl), phenylsulfonyl, or 3- to 6-membered heterocyclyl containing 1 or 2 heteroatoms selected from the group consisting of N, O, and S, wherein phenyl groups of the aforementioned substituents and the 3- to 6-membered heterocyclyl substituent may optionally carry 1, 2 or 3 substituents independently selected from the group consisting of halogen, CN, C$_1$-C$_6$alkyl, C$_1$-C$_6$haloalkyl and C$_1$-C$_3$cyanoalkyl; and $R^{26}$ is halogen, —CN, —COOH, —CONH$_2$, —NO$_2$, —SF$_5$, C$_1$-C$_3$alkyl, C$_1$-C$_3$haloalkyl, C$_1$-C$_3$alkoxy, C$_1$-C$_3$haloalkoxy, C$_1$-C$_3$haloalkylthio, C$_1$-C$_3$alkylthio, C$_1$-C$_3$alkylsulfinyl, C$_1$-C$_3$alkylsulfonyl, C$_1$-C$_3$haloalkylsulfinyl, C$_1$-C$_3$haloalkylsulfonyl, C$_3$-C$_6$cycloalkylsulfanyl, C$_3$-C$_6$cycloalkylsulfinyl, C$_3$-C$_6$cycloalkylsulfonyl, C$_3$-C$_6$cycloalkyl, C$_1$-C$_3$cyanoalkyl, or C$_3$-C$_6$cyanocycloalkyl.

10. The compound of claim 1, comprising a structure according to formulae (I-vii)-(I-xix)

(I-vii)

(I-viii)

(I-ix)

311
-continued

312
-continued (I-x)

(I-xi)

(I-xii)

(I-xiii)

(I-xiv)

(I-xv)

(I-xvi)

(I-xvii)

(I-xviii)

(I-xix)

wherein $R^7$ are the same or different and have the meaning of the substituents on the phenyl or 5- or 6-membered heteroaryl as defined for $R^2$;

$R^8$ are the same or different and have the meaning of the substituents on the monocyclic heterocycle as defined for $R^4$;

$R^{81}$ represents in each case optionally substituted $C_1$-$C_6$alkyl, $C_2$-$C_6$alkenyl, $C_2$-$C_6$alkynyl, $C_3$-$C_6$cycloalkyl, $C_1$-$C_3$haloalkyl, hydroxy-$C_2$-$C_4$alkyl, —$CO_2C_1$-$C_4$ alkyl, —C(=NO$C_1$-$C_4$alkyl) H, or —C(=NOC$_1$-C$_4$alkyl)-C$_1$-C$_4$alkyl, wherein the aforementioned optionally substituted radicals are optionally substituted with up to 3 substituents independently selected from the group consisting of halogen, hydroxy, —CN, —NO$_2$, —Si(CH$_3$)$_3$, —NH$_2$, C$_1$-C$_3$alkyl, C$_1$-C$_3$haloalkyl, C$_3$-C$_4$cycloalkyl, C$_3$-C$_4$halocycloalkyl, C$_1$-C$_4$alkoxy, C$_1$-C$_4$haloalkoxy, C$_1$-C$_3$alkylsulfonyl, C$_3$-C$_4$cycloalkylsulfonyl, C$_1$-C$_3$haloalkylthio and C$_1$-C$_3$haloalkylsulfonyl;

or R$^{81}$ represents 3- to 6-membered heterocyclyl containing 1 or 2 heteroatoms selected from the group consisting of N, O, and S, wherein the 3- to 6-membered heterocyclyl may optionally carry 1, 2, 3 or 4 substituents independently selected from the group consisting of halogen, hydroxy, CN, —COOH, —CONH$_2$, —CSNH$_2$, —NO$_2$, —Si(CH$_3$)$_3$, —SF$_5$, —NH$_2$, C$_1$-C$_6$alkyl, C$_3$-C$_6$cycloalkyl, C$_3$-C$_6$cyanocycloalkyl, C$_3$-C$_6$halocycloalkyl, C$_3$-C$_6$cycloalkyl-C$_1$-C$_6$alkyl, C$_1$-C$_3$haloalkyl, C$_1$-C$_3$cyanoalkyl, C$_1$-C$_4$alkoxy, C$_1$-C$_3$haloalkoxy, C$_1$-C$_3$cyanoalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, C$_1$-C$_3$cyanoalkylthio, C$_1$-C$_3$cyanoalkylsulfinyl, and C$_1$-C$_3$cyanoalkylsulfonyl;

n represents an integer of 0, 1 or 2;

m represents an integer of 1 or 2;

and/or a salt and/or a N-oxide thereof.

* * * * *